United States Patent
Kopka et al.

(10) Patent No.: US 7,405,221 B2
(45) Date of Patent: Jul. 29, 2008

(54) SUBSTITUTED PYRIMIDINES

(75) Inventors: Ihor E. Kopka, Warren, NJ (US); Bing Li, Towaco, NJ (US); William K. Hagmann, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/527,561

(22) PCT Filed: Sep. 23, 2003

(86) PCT No.: PCT/US03/30161

§ 371 (c)(1),
(2), (4) Date: Mar. 11, 2005

(87) PCT Pub. No.: WO2004/029204

PCT Pub. Date: Apr. 8, 2004

(65) Prior Publication Data
US 2005/0245554 A1    Nov. 3, 2005

Related U.S. Application Data

(60) Provisional application No. 60/414,144, filed on Sep. 27, 2002.

(51) Int. Cl.
| | |
|---|---|
| C07D 239/28 | (2006.01) |
| C07D 239/34 | (2006.01) |
| C07D 239/48 | (2006.01) |
| C07D 239/52 | (2006.01) |
| A61K 31/505 | (2006.01) |
| A61K 31/506 | (2006.01) |
| A61P 25/18 | (2006.01) |
| A61P 25/28 | (2006.01) |

(52) U.S. Cl. .............. 514/272; 514/275; 544/309; 544/310; 544/323; 544/324

(58) Field of Classification Search ............ 544/309, 544/310, 323, 324; 514/269, 272, 275
See application file for complete search history.

(56) References Cited

U.S. PATENT DOCUMENTS

| | | | | |
|---|---|---|---|---|
| 4,438,117 A | * | 3/1984 | Cherkofsky | 514/274 |
| 5,366,982 A | * | 11/1994 | Dereu et al. | 514/340 |
| 5,462,960 A | | 10/1995 | Barth et al. | |
| 5,624,941 A | | 4/1997 | Barth et al. | |
| 5,684,011 A | | 11/1997 | Fitzjohn et al. | |
| 6,096,753 A | * | 8/2000 | Spohr et al. | 514/269 |
| 2002/0004600 A1 | | 1/2002 | Meyer et al. | |
| 2004/0259887 A1 | | 12/2004 | Dow | |
| 2005/0043315 A1 | * | 2/2005 | Tsutsumi et al. | 514/252.02 |

FOREIGN PATENT DOCUMENTS

| | | |
|---|---|---|
| EP | 0 576 357 | 3/1997 |
| EP | 0 656 354 | 6/1997 |
| WO | WO 98/32441 | 7/1998 |
| WO | WO 98/37061 | 8/1998 |
| WO | WO 01/58450 | 8/2001 |
| WO | WO 03/002114 | 1/2003 |
| WO | WO 03/006007 | 1/2003 |
| WO | WO 03/000787 | 3/2003 |
| WO | WO 03/027076 | 4/2003 |
| WO | WO 03/051850 | 6/2003 |
| WO | WO 03/051851 | 6/2003 |
| WO | WO 03/084935 A2 | * 10/2003 |
| WO | WO 03/084943 | 10/2003 |
| WO | WO 2004009560 A1 | * 1/2004 |
| WO | WO 2004/012671 | 2/2004 |
| WO | WO 2004016605 A1 | * 2/2004 |
| WO | WO 2004/018433 | 3/2004 |
| WO | WO 2004/035566 | 4/2004 |
| WO | WO 2004/037823 | 5/2004 |
| WO | WO 2004/052864 | 6/2004 |
| WO | WO 2004/094421 | 11/2004 |
| WO | WO 2004/105699 | 12/2004 |

(Continued)

OTHER PUBLICATIONS

Petrocellis et al., British Journal of Pharmacology, 141, 765-774, 2004.*

(Continued)

*Primary Examiner*—Venkataraman Balasubramanian
(74) *Attorney, Agent, or Firm*—Baerbel R. Brown; Catherine D. Fitch

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, the treatment of obesity or eating disorders, as well as the treatment of asthma, constipation, chronic intestinal pseudo-obstruction, and cirrhosis of the liver

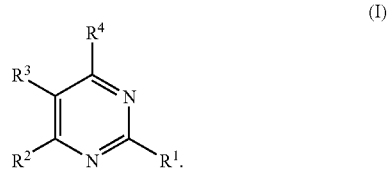

14 Claims, No Drawings

FOREIGN PATENT DOCUMENTS

| | | |
|---|---|---|
| WO | WO 2004/110453 | 12/2004 |
| WO | WO 2004/111033 | 12/2004 |
| WO | WO 2004/111034 | 12/2004 |
| WO | WO 2004/111038 | 12/2004 |
| WO | WO 2004/111039 | 12/2004 |
| WO | WO 2005/000817 | 1/2005 |
| WO | WO 2005/009479 | 2/2005 |
| WO | WO 2005/016286 | 2/2005 |
| WO | WO 2005/020992 | 3/2005 |

OTHER PUBLICATIONS

Black, Curr. Opin.. Investig. Drugs 5(4): 389-394, 2004.*
Cecil Textbook of Medicine, edited by Bennet, J.C., and Plum F., 20th edition, vol. 1, 1004-1010, 1996.*
Olivera et al., Tetrahedron 58(15):3021-3037, 2002.*
Gaodeng Xuexiao Huaxue Xuebao 16(11): 1740-1743, 1995. CA 124: 317095,1996.*
DD 294255, CA 116: 128952,1992.*
Chemistry of Natural Compounds (Translation of Khimya Prirodnykh Soedinenii) 37(4): 307-310, 2001, CA 137: 78805, 2002.*
Khimya Geterotsiklicheskikh Soedinenii, 11: 1542-1550, 1985, CA 105: 208819, 1986.*
Tanaka et al., Chemical & Pharmaceutical Bulletin 42(9), 1828-1834, 1994; CA123:9410, 1995.*
Le Foll et al., J. Pharm. & Exper. Ther., vol. 312 (2005), pp. 875-883, "Cannabinoid CB1 receptor antagonists as promising new medications for drug dependence".
Lange et al., J. Med. Chem., Bioisosteric replacements of the pyrazole moiety of rimonabant . . . 48(6), 1823-1839, 2005.
Piomelli et al., Trends in Pharma. Sci., vol. 21 (2000), pp. 218-224, "The endocannabinoid system as a target for therapeutic drugs".
Goya et al., Exp. Opin. Ther. Patents, vol. 10 (2000), pp. 1529-1538, "Recent advances in cannabinoid receptor agonists and antagonists".
Xiang et al., Ann. Reports in Med. Chem., vol. 34 (1999), pp. 199-208, "Chap. 20. Pharmacology of cannabinoid receptor agonists and antagonists".
Barth, Exp. Opin. Ther. Patents, vol. 8 (1998), pp. 301-313, "Cannabinoid receptor agonists and antagonists".
Rinaldi-Carmona et al., Life Sciences, vol. 56 (1995), pp. 1941-1947, "Biochemical and pharmacological characterisation of SR141716A, the first potent and selective brain cannabinoid receptor antagonist".
Rinaldi-Carmona et al., FEBS Letters, vol. 350 (1994), pp. 250-244, "SR141716A, a potent and selective antagonist of the brain cannabinoid receptor".
Hetzheim et al., Pharmazie, vol. 40(1) (1985), pp. 17-20, "Ringtransformation von O,N-heterocyclen".

* cited by examiner

SUBSTITUTED PYRIMIDINES

CROSS-REFERENCE TO RELATED APPLICATIONS

This application is a U.S. National Phase application under 35 U.S.C. §371 of PCT Application No. PCT/US03/30161, filed Sep. 23, 2003, which claims priority under 35 U.S.C. §119 from U.S. Provisional Application No. 60/414,144, filed Sep. 27, 2002.

BACKGROUND OF THE INVENTION

Marijuana (*Cannabis sativa L.*) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

The genes for the respective cannabinoid receptors have each been disrupted in mice. The CB1$^{-/-}$ receptor knockout mice appeared normal and fertile. They were resistant to the effects of $\Delta^9$-THC and demonstrated a strong reduction in the reinforcing properties of morphine and the severity of withdrawal syndrome. They also demonstrated reduced motor activity and hypoalgesia. The CB2$^{-/-}$ receptor knockout mice were also healthy and fertile. They were not resistant to the central nervous system mediated effects of administered $\Delta^9$-THC. There were some effects on immune cell activation, reinforcing the role for the CB2 receptor in immune system functions.

Excessive exposure to $\Delta^9$-THC can lead to overeating, psychosis, hypothermia, memory loss, and sedation. Specific synthetic ligands for the cannabinoid receptors have been developed and have aided in the characterization of the cannabinoid receptors: CP55,940 (J. Pharmacol. Exp. Ther. 1988, 247, 1046-1051); WIN55212-2 (J. Pharmacol. Exp. Ther. 1993, 264, 1352-1363); SR141716A (FEBS Lett. 1994, 350, 240-244; Life Sci. 1995, 56, 1941-1947); and SR144528 (J. Pharmacol. Exp. Ther. 1999, 288, 582-589). The pharmacology and therapeutic potential for cannabinoid receptor ligands has been reviewed (Exp. Opin. Ther. Patents 1998, 8, 301-313; Ann. Rep. Med. Chem., A. Doherty, Ed.; Academic Press, NY 1999, Vol. 34, 199-208; Exp. Opin. Ther. Patents 2000, 10, 1529-1538; Trends in Pharma. Sci. 2000, 21, 218-224). There is at least one CB1 modulator characterized as an inverse agonist or an antagonist, N-(1-piperidinyl)-5-(4-chlorophenyl)-1-(2,4-dichlorophenyl)-4-methylpyrazole-3-carboxamide (SR141716A), in clinical trials for treatment of eating disorders at this time. There still remains a need for potent low molecular weight CB1 modulators that have pharmacokinetic and pharmacodynamic properties suitable for use as human pharmaceuticals.

Treatment of asthma with CB1 receptor modulators (such as CB1 inverse agonists) is supported by the finding that presynaptic cannabinoid CB1 receptors mediate the inhibition of noradrenaline release (in the guinea pig lung) (Europ. J. of Pharmacology, 2001, 431 (2), 237-244).

Treatment of cirrhosis of the liver with CB1 receptor modulators is supported by the finding that a CB1 receptor modulator will reverse the low blood pressure observed in rats with carbon tetrachloride-induced liver cirrhosis and will lower the elevated mesenteric blood flow and portal vein pressure (Nature Medicine, 2001, 7 (7), 827-832).

U.S. Pat. Nos. 5,624,941 and 6,028,084, PCT Application Nos. WO98/43636 and WO98/43635, and EPO Application No. EP-658546 disclose substituted pyrazoles having activity against the cannabinoid receptors.

PCT Application Nos. WO98/31227 and WO98/41519 also disclose substituted pyrazoles having activity against the cannabinoid receptors.

PCT Application Nos. WO98/37061, WO00/10967, and WO00/10968 disclose diaryl ether sulfonamides having activity against the cannabinoid receptors.

PCT Application Nos. WO97/29079 and WO99/02499 disclose alkoxy-isoindolones and alkoxy-quinolones as having activity against the cannabinoid receptors.

U.S. Pat. No. 5,532,237 discloses N-benzoyl-indole derivatives having activity against the cannabinoid receptors.

U.S. Pat. Nos. 4,973,587, 5,013,837, 5,081,122, and 5,112,820, 5,292,736 disclose aminoalkylindole derivatives as having activity against the cannabinoid receptors.

PCT publication WO 01/58869 discloses pyrazoles, pyrroles and imidazole cannabinoid receptor modulatorsuseful for treating respiratory and non-respiratory leukocyte activation-associated disorders.

PCT publications WO 01/64632, 01/64633, and 01/64634 assigned to Aventis are directed to azetidine derivatives as cannabinoid antagonists.

The compounds of the present invention are modulators of the Cannabinoid-1 (CB1) receptor and are useful in the treatment, prevention and suppression of diseases mediated by the Cannabinoid-1 (CB1) receptor. In particular, compounds of the present invention are antagonists or inverse agonists of the CB1 receptor. The invention is concerned with the use of these compounds to modulate the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of eating disorders by inhibiting excessive food intake and the resulting obesity and complications associated therewith. The compounds are also useful for the treatment of constipation and chronic intestinal pseudo-obstruction, as well as for the treatment of asthma, and cirrhosis of the liver.

SUMMARY OF THE INVENTION

The present invention is concerned with novel substituted pyrimidines of general Formula I:

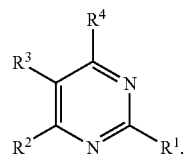

and pharmaceutically acceptable salts thereof which are antagonists and/or inverse agonists of the Cannabinoid-1 (CB1) receptor and are useful in the treatment, prevention and suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine, including smoking cessation. The compounds are also useful for the treatment of obesity or eating disorders associated with excessive food intake and complications associated therewith. The compounds are also useful for the treatment of constipation and chronic intestinal pseudo-obstruction. The compounds are also useful for the treatment of cirrhosis of the liver. The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with novel compounds of structural formula I.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds used in the methods of the present invention are represented by the compound of structural formula I:

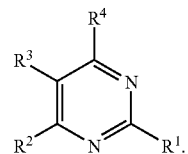

or a pharmaceutically acceptable salt thereof.

In one embodiment of the present invention, $R^1$ is selected from:
(1) hydrogen,
(2) $C_{1-10}$alkyl,
(3) —$OR^a$,
(4) —$NR^aR^b$,
(5) —$NR^bC(O)R^a$,
(6) —$CO_2R^a$,
(7) —$C(O)NR^aR^b$,
(8) cyano,
(9) —$SR^b$, and
(10) —$SO_2R^b$.

In one class of this embodiment, $R^1$ is selected from:
(1) $C_{1-6}$alkyl,
(2) —OH,
(3) —$OC_{1-6}$alkyl, unsubstituted or substituted with one to three $R^e$ substituents,
(4) cycloalkyloxy-, unsubstituted or substituted with one to three $R^e$ substituents,
(5) cycloalkyl-$C_{1-4}$alkyloxy-, unsubstituted or substituted with one to thee $R^e$ substituents,
(6) cycloheteroalkyloxy-, unsubstituted or substituted with one to three $R^e$ substituents,
(7) cycloheteroalkyl-$C_{1-4}$ alkyloxy, unsubstituted or substituted with one to three $R^e$ substituents,
(8) phenyloxy, unsubstituted or substituted with one to three $R^e$ substituents,
(9) heteroaryloxy, unsubstituted or substituted with one to three $R^e$ substituents,
(10) phenyl-$C_{1-4}$alkyloxy, unsubstituted or substituted with one to three $R^e$ substituents,
(11) heteroaryl-$C_{1-4}$alkyloxy, unsubstituted or substituted with one to three $R^e$ substituents,
(12) —$NR^aR^b$,
(13) —$NR^bC(O)R^a$,
(14) —$CO_2H$,
(15) $C_{1-6}$alkyloxycarbonyl-, unsubstituted or substituted with one to three $R^e$ substituents,
(16) cycloalkyloxycarbonyl-, unsubstituted or substituted with one to three $R^e$ substituents,
(17) cycloalkyl-$C_{1-4}$alkyloxycarbonyl-, unsubstituted or substituted with one to three $R^e$ substituents,
(18) phenyloxycarbonyl, unsubstituted or substituted with one to three $R^e$ substituents,
(19) heteroaryloxycarbonyl, unsubstituted or substituted with one to three $R^e$ substituents,
(20) phenyl-$C_{1-4}$alkyloxycarbonyl, unsubstituted or substituted with one to three $R^e$ substituents,

(21) heteroaryl-$C_{1-4}$alkyloxycarbonyl, unsubstituted or substituted with one to three $R^c$ substituents,
(22) —C(O)$NR^aR^b$,
(23) cyano,
(24) —$SC_{1-6}$alkyl, unsubstituted or substituted with one to three $R^c$ substituents, and
(25) —$SO_2C_{1-6}$alkyl, unsubstituted or substituted with one to three $R^c$ substituents.

In one subclass, $R^1$ is selected from:
(1) $C_{1-6}$alkyl,
(2) —OH,
(3) —$OC_{1-6}$alkyl, unsubstituted or substituted with one to three $R^c$ substituents,
(4) $C_{4-7}$cycloalkyloxy-, unsubstituted or substituted with one to two $R^c$ substituents,
(5) cycloalkyl-$C_{1-3}$alkyloxy-, unsubstituted or substituted with one to two $R^c$ substituents,
(6) phenyloxy, unsubstituted or substituted with one to two $R^c$ substituents,
(7) pyridyloxy, unsubstituted or substituted with one or two $R^c$ substituents,
(8) phenyl-$C_{1-3}$alkyloxy, unsubstituted or substituted with one or two $R^c$ substituents,
(9) pyridyl-$C_{1-3}$alkyloxy, unsubstituted or substituted with one or two $R^c$ substituents,
(10) —$NR^aR^b$,
(11) —$NR^bC(O)R^a$,
(12) —$CO_2H$,
(13) $C_{1-6}$alkyloxycarbonyl-, unsubstituted or substituted with one to three $R^c$ substituents,
(14) —C(O)$NR^aR^b$,
(15) cyano,
(16) —$SC_{1-6}$alkyl, unsubstituted or substituted with one to three $R^c$ substituents, and
(17) —$SO_2C_{1-6}$alkyl, unsubstituted or substituted with one to three $R^c$ substituents.

In another subclass, $R^1$ is selected from:
(1) methyl, ethyl, propyl, isopropyl, n-butyl, sec-butyl, isobutyl, tert.-butyl, n-pentyl, or 2,2-dimethylpropyloxy,
(2) —OH,
(3) methoxy, ethyloxy, isopropyloxy, n-butyloxy, sec-butyloxy, isobutyloxy, tert.-butyloxy, n-pentyloxy, or 2,2-dimethylpropyloxy, unsubstituted or substituted with one to three halo, hydroxy, or methoxy substituents,
(4) cyclopropyloxy, cyclobutyloxy, cyclopentyloxy, cyclohexyloxy, or cycloheptyloxy,
(5) cyclopropylmethoxy, cyclobutylmethoxy, cyclopentylmethoxy, cyclohexylmethoxy, or cycloheptylmethoxy,
(6) 4-fluorophenyloxy, 4-chlorophenyloxy, 4-methoxyphenyloxy, 3-fluorophenyloxy, 3-chlorophenyloxy, 3,4-difluorophenyloxy, 3,4-dichlorophenyloxy, 3,5-difluorophenyloxy, 3,5-dichlorophenyloxy or phenyloxy,
(7) 4-pyridyloxy, 3-pyridyloxy, 2-pyridyloxy, 6-chloro-3-pyridyloxy, or 5-chloro-3-pyridyloxy,
(8) benzyloxy, 3-fluorobenzyloxy, 3-chlorobenzyloxy, 4-fluorobenzyloxy, 4-chlorobenzyloxy, 3,4-difluorobenzyloxy, 3,4-dichlorobenzyloxy, 3,5-difluorobenzyloxy, 3,5-dichlorobenzyloxy, 2,4-difluorobenzyloxy, 2,4-dichlorobenzyloxy, alpha-methyl-4-fluorobenzyloxy, alpha-methyl-4-chlorobenzyloxy, alpha,alphadiethyl-4-fluorobenzyloxy, or alpha,alpha-dimethyl-4-chlorobenzyloxy,
(9) 2-pyridylmethyloxy 3,-pyridylmethyloxy, or 4-pyridylmethyloxy,

(10) amino, N-methylamino, N,N-dimethyamino, N,N-diisopropylamino, or —N(CH$_3$)CH$_2$CH$_2$N(CH$_3$)$_2$, or N-containing heterocycloalkyl bonded via nitrogen selected from: morpholinyl, thiomorpholinyl, pyrrolidnyl, piperidinyl, and [2.2.1]azabicycloheptyl,
(12) —NHCOR$^a$ wherein R$^a$ is selected from:
(a) hydrogen,
(b) C$_{1-4}$alkyl,
(c) C$_{4-6}$cycloalkyl, and
(d) phenyl, 4-fluorophenyl, 4-chlorophenyl, 3,4-difluorophenyl, or 3,4-dichlorophenyl,
(13) —CO$_2$H,
(14) —C(O)NH$_2$,
(15) —CN,
(16) —SCH$_3$, and
(17) —SO$_2$CH$_3$.

In one embodiment of the present invention, R$^2$ is selected from:
(1) hydrogen,
(2) C$_{1-10}$alkyl,
(3) —OR$^a$,
(4) —NR$^a$R$^b$,
(5) —NR$^a$C(O)R$^b$,
(6) —CO$_2$R$^a$,
(7) —C(O)NR$^a$R$^b$,
(8) cyano,
(9) —SR$^a$, and
(10) —SO$_2$R$^a$, In one class of this embodiment, R$^2$ is selected from:
(1) hydrogen,
(2) C$_{1-6}$alkyl,
(3) —OH,
(4) —OC$_{1-6}$alkyl, unsubstituted or substituted with one to three R$^c$ substituents,
(5) cycloalkyloxy-, unsubstituted or substituted with one to three R$^c$ substituents,
(6) cycloalkyl-C$_{1-4}$alkyloxy-, unsubstituted or substituted with one to three R$^c$ substituents,
(7) cycloheteroalkyloxy-, unsubstituted or substituted with one to three R$^c$ substituents,
(8) cycloheteroalkyl-C$_{1-4}$ alkyloxy, unsubstituted or substituted with one to three R$^c$ substituents,
(9) phenyloxy, unsubstituted or substituted with one to three R$^c$ substituents,
(10) heteroaryloxy, unsubstituted or substituted with one to three R$^c$ substituents,
(11) phenyl-C$_{1-4}$alkyloxy, unsubstituted or substituted with one to three R$^c$ substituents,
(12) heteroaryl-C$_{1-4}$alkyloxy, unsubstituted or substituted with one to three R$^c$ substituents,
(13) —NR$^a$R$^b$,
(14) —NR$^b$C(O)R$^a$,
(15) —CO$_2$H,
(16) C$_{1-6}$alkyloxycarbonyl-, unsubstituted or substituted with one to three R$^c$ substituents,
(17) cycloalkyloxycarbonyl-, unsubstituted or substituted with one to three R$^c$ substituents,
(18) cycloalkyl-C$_{1-4}$alkyloxycarbonyl-, unsubstituted or substituted with one to three R$^c$ substituents,
(19) phenyloxycarbonyl, unsubstituted or substituted with one to three R$^c$ substituents,
(20) heteroaryloxycarbonyl, unsubstituted or substituted with one to three R$^c$ substituents,
(21) phenyl-C$_{1-4}$alkyloxycarbonyl, unsubstituted or substituted with one to three R$^c$ substituents,

(22) heteroaryl-$C_{1-4}$alkyloxycarbonyl, unsubstituted or substituted with one to three $R^c$ substituents,
(23) —C(O)$NR^aR^b$,
(24) cyano,
(25) —$SC_{1-6}$alkyl, unsubstituted or substituted with one to three $R^c$ substituents, and
(26) —$SO_2C_{1-6}$alkyl, unsubstituted or substituted with one to three $R^c$ substituents.

In one subclass, $R^2$ is selected from:
(1) hydrogen,
(2) $C_{1-6}$alkyl,
(3) —OH,
(4) —$OC_{1-6}$alkyl, unsubstituted or substituted with one to three $R^c$ substituents,
(5) $C_{4-7}$cycloalkyloxy-, unsubstituted or substituted with one to two $R^c$ substituents,
(6) $C_{4-7}$cycloalkyl-$C_{1-3}$alkyloxy-, unsubstituted or substituted with one to two $R^c$ substituents,
(7) phenyloxy, unsubstituted or substituted with one to two $R^c$ substituents,
(8) pyridyloxy, unsubstituted or substituted with one to two $R^c$ substituents, phenyl-$C_{1-3}$alkyloxy, unsubstituted or substituted with one to two $R^c$ substituents,
(9) pyridyl-$C_{1-3}$alkyloxy, unsubstituted or substituted with one to two $R^c$ substituents,
(10) —$NR^aR^b$,
(12) —NHC(O)$R^a$,
(13) cyano, and
(14) —$SO_2C_{1-16}$alkyl, unsubstituted or substituted with one to three $R^c$ substituents.

In another subclass, $R^2$ is selected from:
(1) hydrogen,
(2) methyl, ethyl, propyl, isopropyl, n-butyl, sec-butyl, isobutyl, tert.-butyl, n-pentyl, or 2,2-dimethylpropyloxy,
(3) —OH,
(4) methoxy, ethyloxy, isopropyloxy, n-butyloxy, sec-butyloxy, isobutyloxy, tert.-butyloxy, n.-pentyloxy, or 2,2-dimethylpropyloxy, unsubstituted or substituted with one to three halo, hydroxy, or methoxy substituents,
(5) cyclopropyloxy, cyclobutyloxy, cyclopentyloxy, cyclohexyloxy, or cycloheptyloxy,
(6) cyclopropylmethoxy, cyclobutylinethoxy, cyclopentylmethoxy, cyclohexylmethoxy, or cycloheptylmethoxy,
(7) 4-fluorophenyloxy, 4-chlorophenyloxy, 3-fluorophenyloxy, 3-chlorophenyloxy, 3-cyanophenyloxy, 3,4-difluorophenyloxy, 3,4-dichlorophenyloxy, 3,5-difluorophenyloxy, 3,5-dichlorophenyloxy, or phenyloxy,
(8) benzyloxy, 3-fluorobenzyloxy, 3-chlorobenzyloxy, 4-fluorobenzyloxy, 4-chlorobenzyloxy, 3,4-difluorobenzyloxy, 3,4-dichlorobenzyloxy, 3,5-difluorobenzyloxy, 3,5dichlorobenzyloxy, 2,4-fluorobenzyloxy, or 2,4-dichlorobenzyloxy,
(9) 4-pyridyloxy, 3-pyridyloxy, 2-pyridyloxy, 6-chloro-3-pyridyloxy, or 5-chloro-3-pyridyloxy,
(10) amino, N-methylamino, N-ethylamino, N,N-dimethyamino, N,N-diethylamino,N,N-diisopropylamino, or N-containing heterocycloallkyl bonded via nitrogen selected from: pyrrolidinyl, and piperidinyl,
(11) —NHCO$R^a$ wherein $R^a$ is selected from:
  (a) hydrogen, and
  (b) $C_{1-4}$alkyl,
(12) —CN, and
(13) —$SO_2CH_3$.

In one embodiment of the present invention, $R^3$ is selected from:
(1) aryl,
(2) heteroaryl, wherein each aryl and heteroaryl is optionally substituted with one to four substituents independently selected from $R^g$.

In one class of this embodiment, $R^3$ is selected from:
(1) phenyl,
(2) pyridyl, wherein each phenyl and pyridyl is optionally substituted with one to three substituents independently selected from $R^g$.

In one subclass of this class, $R^3$ is selected from:

(1)

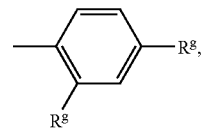

(2)

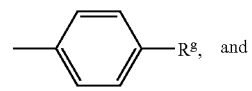

(3)

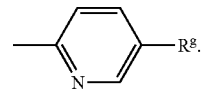

In one subclass, $R^3$ is selected from:
(1) phenyl,
(2) pyridyl, wherein each phenyl and pyridyl is optionally substituted with one or two substituents independently selected from halogen and —S—$C_{1-4}$alkyl.

In another subclass, $R^3$ is selected from:
(1) 4-chlorophenyl,
(2) 4-fluorophenyl,
(3) 4-methoxyphenyl,
(4) 4-trifluoromethylphenyl,
(5) 3-chlorophenyl,
(6) 3-methoxyphenyl,
(7) 2,4-dichlorophenyl, and
(8) 2-chloro-4-methylthiophenyl.

In still another subclass, $R^3$ is 4-chlorophenyl.

In one embodiment of the present invention, $R^4$ is selected from:
(1) aryl,
(2) heteroaryl, wherein each aryl and heteroaryl is optionally substituted with one to four substituents independently selected from $R^g$.

In one class of this embodiment, $R^4$ is selected from:
(1) phenyl,
(2) pyridyl, wherein each phenyl and pyridyl is optionally substituted with one to three substituents independently selected from $R^g$.

In one subclass of this class, $R^4$ is selected from:

(1) 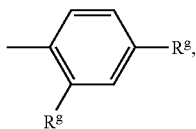

(2) 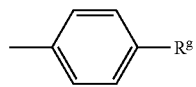

(3) 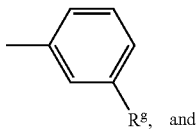

(4) 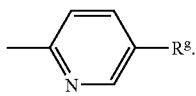

In one subclass of this class, $R^4$ is selected from:
(1) phenyl, and
(2) pyridyl, wherein each phenyl and pyridyl is optionally substituted with one or two substituents independently selected from halogen and —S—$C_{1-4}$alkyl.

In another subclass, $R^4$ is selected from:
(1) 4-chlorophenyl,
(2) 2,4-dichlorophenyl, and
(3) 2-chloro-4-methylthiophenyl.

In still another subclass, $R^4$ is 2,4-dichlorophenyl.

In one embodiment of the present invention, each $R^a$ is independently selected from:
(1) hydrogen,
(2) $C_{1-10}$alkyl,
(3) $C_{2-10}$alkenyl,
(4) cycloalkyl,
(5) cycloalkyl-$C_{1-10}$alkyl;
(6) cycloheteroalkyl,
(7) cycloheteroalkyl-$C_{1-10}$alkyl;
(8) aryl,
(9) heteroaryl,
(10) aryl-$C_{1-10}$alkyl, and
(11) heteroaryl-$C_{1-10}$alkyl; and each $R^b$ is independently selected from:
(1) hydrogen,
(2) $C_{1-10}$alkyl,
(3) $C_{2-10}$alkenyl,
(4) cycloalkyl,
(5) cycloalkyl-$C_{1-10}$alkyl;
(6) cycloheteroalkyl,
(7) cycloheteroalkyl-$C_{1-10}$alkyl;
(8) aryl,
(9) heteroaryl,
(10) aryl-$C_{1-10}$alkyl, and
(11) heteroaryl-$C_{1-10}$alkyl, or $R^a$ and $R^b$ together with the nitrogen atom to which they are attached form a bridged or unbridged heterocyclic ring of 4 to 7 members containing 0-2 additional heteroatoms independently selected from oxygen, sulfur and N—$R^d$, each $R^a$ and $R^b$ may be unsubstituted or substituted with one to three substituents selected from $R^c$.

In one class of this embodiment of the present invention, each $R^a$ and $R^b$ is independently selected from:
(1) hydrogen,
(2) $C_{1-6}$alkyl, unsubstituted or substituted with one to three $R^c$ substituents,
(3) cycloalkyl, unsubstituted or substituted with one to three $R^c$ substituents,
(4) cycloalkyl-$C_{1-4}$alkyl, unsubstituted or substituted with one to three $R^c$ substituents,
(5) phenyl, unsubstituted or substituted with one to three $R^c$ substituents,
(6) heteroaryl, unsubstituted or substituted with one to three $R^c$ substituents,
(7) phenyl-$C_{1-4}$alkyl, unsubstituted or substituted with one to three $R^c$ substituents,
(8) heteroaryl-$C_{1-4}$alkyl, unsubstituted or substituted with one to three $R^c$ substituents, or $R^a$ and $R^b$ together with the nitrogen atom to which they are attached form a bridged or unbridged heterocyclic ring of 4 to 7 members containing 0-2 additional heteroatoms independently selected from oxygen, sulfur and N—$R^d$, unsubstituted or substituted on carbon with one to three $R^c$ substitutents, In a subclass of this class, $R^a$ and $R^b$ are each independently selected from:
(1) hydrogen,
(2) $C_{1-6}$alkyl, unsubstituted or substituted with one to three $R^c$ substituents,
(3) cycloalkyl, unsubstituted or substituted with one to three $R^c$ substituents,
(4) cycloalkyl-$C_{1-4}$alkyl, unsubstituted or substituted with one to three $R^c$ substituents,
(5) phenyl, unsubstituted or substituted with one to three $R^c$ substituents,
(6) heteroaryl, unsubstituted or substituted with one to three $R^c$ substituents,
(7) phenyl-$C_{1-4}$alkyl, unsubstituted or substituted with one to three $R^c$ substituents,
(8) heteroaryl-$C_{1-4}$alkyl, unsubstituted or substituted with one to three $R^c$ substituents.

In another subclass, $R^a$ is selected from:
(1) hydrogen,
(2) $C_{1-6}$alkyl, unsubstituted or substituted with one to three $R^c$ substituents,
(3) cycloalkyl, unsubstituted or substituted with one to two $R^c$ substituents,
(4) cycloalkyl-$C_{1-4}$alkyl, unsubstituted or substituted with one to two $R^c$ substituents,
(5) phenyl, unsubstituted or substituted with one to two $R^c$ substituents,
(6) heteroaryl, unsubstituted or substituted with one to two $R^c$ substituents,
(7) benzyl, unsubstituted or substituted with one to two $R^c$ substituents, and $R^b$ is selected from:
(1) hydrogen,
(2) $C_{1-6}$alkyl, unsubstituted or substituted with one to three $R^c$ substituents, or $R^a$ and $R^b$ together with the nitrogen atom to which they are attached form a bridged or unbridged heterocyclic ring of 4 to 7 members containing 0-2 additional heteroatoms independently selected from oxygen, sulfur and N—$R^d$, unsubstituted or substituted on carbon with one to two $R^c$ substitutents.

In another subclass, $R^a$ is selected from:
(1) hydrogen,
(2) $C_{1-6}$alkyl, unsubstituted or substituted with one to three $R^c$ substituents,
(3) cycloalkyl, unsubstituted or substituted with one to two $R^c$ substituents,
(4) cycloalkyl-$C_{1-4}$alkyl, unsubstituted or substituted with one to two $R^c$ substituents,
(5) phenyl, unsubstituted or substituted with one to two $R^c$ substituents,
(6) pyridyl, unsubstituted or substituted with one to three $R^c$ substituents,
(7) benzyl, unsubstituted or substituted with one to two $R^c$ substituents,
(8) pyridylmethyl-, unsubstituted or substituted with one to three $R^c$ substituents.

In still another subclass, $R^a$ is selected from:
(1) hydrogen,
(2) $C_{1-4}$alkyl,
(3) $C_{4-6}$cycloalkyl, and
(4) phenyl, 4-fluorophenyl, 4-chlorophenyl, 3,4-difluorophenyl, or 3,4-dichlorophenyl.

In yet another subclass, $R^a$ is selected from:
(1) hydrogen, and
(2) $C_{1-6}$allyl, unsubstituted or substituted with one to three $R^c$ substituents.

In an additional subclass, $R^a$ is selected from:
(1) hydrogen, and
(2) $C_{1-4}$alkyl.

In another subclass, $R^b$ is selected from:
(1) hydrogen, and
(2) $C_{1-6}$alkyl, unsubstituted or substituted with one to three $R^c$ substituents.

In another subclass of the present invention, $R^a$ and $R^b$ together with the nitrogen atom to which they are attached form a bridged or unbridged heterocyclic ring of 4 to 7 members, unsubstituted or substituted on carbon with one to two $R^c$ substitutents.

In still another subclass of the present invention, $R^a$ and $R^b$ together with the nitrogen atom to which they are attached form a heterocyclic ring selected from: morpholinyl, thiomorpholinyl, pyrrolidnyl, piperidinyl, and [2.2.1]azabicycloheptyl.

In one embodiment of the present invention, each $R^c$ is independently selected from:
(1) $C_{1-10}$alkyl,
(2) —$OR^d$,
(3) —$NR^eS(O)_mR^d$,
(4) halogen,
(5) —$SR^d$,
(6) —$S(O)_mNR^dR^e$,
(7) —$NR^dR^e$,
(8) —$C(O)R^d$,
(9) —$CO_2R^d$,
(10) —CN,
(11) —$C(O)NR^dR^e$,
(12) —$NR^eC(O)R^d$,
(13) —$NR^eC(O)ORd^e$,
(14) —$NR^eC(O)NR^dR^e$,
(15) —$CF_3$,
(16) —$OCF_3$,
(17) cycloheteroalkyl,
(18) aryl,
(19) aryl$C_{1-4}$alkyl,
(20) heteroaryl, and
(21) heteroaryl$C_{1-4}$alkyl.

In one class of this embodiment, each $R^c$ is independently selected from:
(1) $C_{1-6}$alkyl,
(2) —$OR^d$,
(3) —$NHS(O)_2R^d$,
(4) halogen,
(5) —$SR^d$,
(6) —$S(O)_2NR^dR^e$,
(7) —$NR^dR^e$,
(8) —$C(O)R^d$,
(9) —$CO_2R^d$,
(10) —CN,
(11) —$C(O)NR^dR^e$,
(12) —$NHC(O)R^d$,
(13) —$NHC(O)ORd^e$,
(14) —$NHC(O)NR^dR^e$,
(15) —$CF_3$,
(16) —$OCF_3$,
(17) cycloheteroalkyl,
(18) phenyl,
(19) phenyl$C_{1-3}$alkyl,
(20) heteroaryl, and
(21) heteroaryl$C_{1-2}$alkyl.

In one subclass of this class, each $R^c$ is independently selected from:
(1) $C_{1-3}$alkyl,
(2) hydroxy,
(3) —$OC_{1-3}$alkyl,
(4) halogen,
(5) —$SCH_3$,
(6) —SH,
(7) —$NR^dR^e$,
(8) —$C(O)C_{1-3}$alkyl,
(9) —$CO_2C_{1-3}$alkyl,
(10) —$CO_2H$,
(11) —CN,
(12) —$CF_3$,
(13) —$OCF_3$,
(14) cycloheteroalkyl,
(15) phenyl,
(16) benzyl, and
(17) pyridyl.

In another subclass, each $R^c$ is independently selected from:
(1) hydroxy,
(2) methyloxy,
(3) amino,
(4) N,N-dimethylamino,
(5) trifluoromethyl,
(6) halogen, and
(7) cyano.

In one embodiment of the present invention, $R^d$ and $R^e$ are independently selected from:
(1) hydrogen,
(2) $C_{1-10}$alkyl,
(3) $C_{2-10}$alkenyl,
(4) cycloalkyl,
(5) cycloalkyl-$C_{1-10}$alkyl;
(6) cycloheteroalkyl,
(7) cycloheteroalkyl-$C_{1-10}$alkyl;
(8) aryl, (9) heteroaryl,
(10) aryl-$C_{1-10}$alkyl, and
(11) heteroaryl-$C_{1-10}$alkyl, or $R^d$ and $R^e$ together with the nitrogen atom to which they are attached form a bridged or unbridged heterocyclic ring of 4 to 7 members containing 0-2 additional heteroatoms independently selected from oxygen, sulfur and N—$R^f$, each $R^d$ and $R^e$ may be unsubstituted or substituted with one to three substituents selected from $R^f$.

In one class of this embodiment, $R^d$ and $R^e$ are independently selected from:
(1) hydrogen,
(2) $C_{1-6}$alkyl,
(3) cycloalkyl,
(4) cycloalkyl-$C_{1-4}$alkyl;
(5) cycloheteroalkyl,
(6) cycloheteroalkyl-$C_{1-4}$ alkyl;
(7) phenyl,
(8) pyridyl,
(9) phenyl-$C_{1-4}$alkyl, and
(10) pyridyl-$C_{1-4}$alkyl, or $R^d$ and $R^e$ together with the nitrogen atom to which they are attached form an unbridged heterocyclic ring of 4 to 7 members optionally containing an additional heteroatom independently selected from oxygen, sulfur and N—$R^f$, each $R^d$ and $R^e$ may be unsubstituted or substituted with one to three substituents selected from $R^f$.

In one subclass, $R^d$ and $R^e$ together with the nitrogen atom to which they are attached form a heterocyclic ring selected from: morpholinyl, thiomorpholinyl, pyrrolidinyl, and piperidinyl, unsubstituted or substituted on a carbon atom with an $R^f$ substituent.

In one subclass of this embodiment, each $R^d$ is independently selected from:
(1) hydrogen,
(2) $C_{1-6}$alkyl,
(3) cycloalkyl,
(4) cycloheteroalkyl,
(5) phenyl,
(6) pyridyl,
(7) phenyl-$C_{1-4}$alkyl, and
(8) pyridyl-$C_{1-4}$alkyl, or each $R^d$ may be unsubstituted or substituted with one to three substituents selected from $R^f$.

In one subclass, each $R^e$ is independently selected from:
(1) hydrogen, and
(2) $C_{1-6}$alkyl.

In another subclass, $R^d$ and $R^e$ are each independently selected from hydrogen and $C_{1-4}$ alkyl.

In one embodiment of the present invention, each $R^f$ is independently selected from:
(1) halogen,
(2) $C_{1-10}$alkyl,
(3) —O—$C_{1-4}$alkyl,
(4) —S—$C_{1-4}$alkyl,
(5) —CN,
(6) —$CF_3$, and
(7) —$OCF_3$.

In one class of this embodiment, each $R^f$ is independently selected from:
(1) halogen,
(2) methyl,
(3) methyloxy,
(4) methylthio,
(5) —CN,
(6) —$CF_3$, and
(7) —$OCF_3$.

In one subclass of this class, each $R^f$ is independently selected from chloro and fluoro. In one embodiment of the present invention, each $R^g$ is independently selected from:
(1) halogen,
(2) $C_{1-10}$alkyl,
(3) —O—$C_{1-4}$alkyl,
(4) —S—$C_{1-4}$alkyl,
(5) —CN,
(6) —$CF_3$, and
(7) —$OCF_3$.

In one class of this embodiment, each $R^g$ is independently selected from:
(1) halogen,
(2) $C_{1-4}$alkyl,
(3) —O—$C_{1-2}$alkyl,
(4) —S—$C_{1-2}$alkyl,
(5) —CN,
(6) —$CF_3$, and
(7) —$OCF_3$.

In one embodiment of the present invention, m is selected from 1 and 2. In one class of the present invention, m is 2.

Particular novel compounds which may be employed in the methods, uses and compositions of the present invention, include:
(1) 2-(4-fluorobenzyloxy)-4-(2,4-chlorophenyl)-5-(4-chlorophenyl)pyrimidine;
(2) 2-(4-fluorobenzyloxy)-4-(2-chloro-4-methylthiophenyl)-5-(4-chlorophenyl)pyrimidine;
(3) 2-(3,4-difluorobenzyloxy)-4-(2,4-dichlorophenyl)-5-(4-chlorophenyl)pyrimidine;
(4) 2-(3,4-difluorobenzyloxy)-4-(2-chloro-4-methylthiophenyl)-5-(4-chlorophenyl)pyrimidine;
(5) 2-(4-chlorobenzyloxy)-4-(2,4-dichlorophenyl)-5-(4-chlorophenyl)pyrimidine;
(6) 2-(4-chlorobenzyloxy)-4-(2-chloro-4-methylthio-phenyl)-5-(4-chlorophenyl)pyrimidine;
(7) 2-(3,4-dichlorobenzyloxy)-4-(2,4-dichlorophenyl)-5-(4-chlorophenyl)pyrimidine;
(8) 2-(3,4-dichlorobenzyloxy)-4-(2-chloro-4-methylthiophenyl)-5-(4-chlorophenyl)pyrimidine;
(9) 2-(3-fluorobenzyloxy)-4-(2,4-dichlorophenyl)-5-(4-chlorophenyl)pyrimidine;
(10) 2-(3-fluorobenzyloxy)-4-(2-chloro-4-methylthiophenyl)-5-(4-chlorophenyl)pyrimidine;
(11) 2-(3-chlorobenzylamino)-4-(2,4-dichlorophenyl)-5-(4-chlorophenyl)pyrimidine;
(12) 2-(n,n-dimethylamino)-4-(2,4-dichlorophenyl)-5-(4-chlorophenyl)pyrimidine;
(13) 2-amino-4-(2,4-dichlorophenyl)-5-(4-chlorophenyl)pyrimidine;
(14) 2-carboxy-4-(2,4-dichlorophenyl)-5-(4-chlorophenyl)pyrimidine;
(15) 2-methylthio-4-(3,4-difluorobenzyloxy)-5-(4-chlorophenyl)-6-(2,4-dichlorophenyl)pyrimidine;
(16) 2-methylthio-4-hydroxy-5-(4-chlorophenyl)-6-(2,4-dichlorophenyl)pyrimidine;2-methoxy-4-hydroxy-5-(4-chlorophenyl)-6-(2,4-dichlorophenyl)pyrimidine;
(18) 2,4-dihydroxy-5-(4-chlorophenyl)-6-(2,4-dichlorophenyl)pyrimidine;
(19) 2-methylthio-4-hydroxy-5-(4-chlorophenyl)-6-(2,4-dichlorophenyl)pyrimidine;

(20) 2-(3,4-difluorobenzyloxy)-4-hydroxy-5-(4-chlorophenyl)-6-(2,4-dichlorophenyl)pyrimidine;
(21) 2-(3,4-difluorobenyloxy)-4-hydroxy-5-(4-chlorophenyl)-6-(2,4-dichlorophenyl)pyrimidine;
(22) 2,4-bis-(3,4-difluorobenyloxy)-5-(4-chlorophenyl)-6-(2,4-dichlorophenyl)pyrimidine;
(23) 2,4-dimethoxy-5-(4-chlorophenyl)-6-(2,4-dichlorophenyl)pyrimidine;
(24) 2,4-diethoxy-5-(4-chlorophenyl)-6-(2,4-dichlorophenyl)pyrimidine;
(25) 2,4-diisopropoxy-5-(4-chlorophenyl)-6-(2,4-dichlorophenyl)pyrimidine;
(26) 2-methylsulfonyl-4-(3,4-difluorophenoxy)-5-(4-chlorophenyl)-6-(2,4-dichlorophenyl)pyrimidine;
(27) 2,4-bis(3,4-difluorophenoxy)-5-(4-chlorophenyl)-6-(2,4-dichlorophenyl)pyrimidine;
(28) 2-cyano-4-(3,4-difluorophenoxy)-5-(4-chlorophenyl)-6-(2,4-dichlorophenyl)pyrimidine;
(29) 2-(3,4-difluorobenzyloxy)-4-cyano-5-(4-chlorophenyl)-6-(2,4-dichlorophenyl)pyrimidine;
(30) 2-cyano-4-(3,4-difluorobenzyloxy)-5-(4-chlorophenyl)-6-(2,4-dichlorophenyl)pyrimidine;
(31) 2,4-bis(cyano)-5-(4-chlorophenyl)-6-(2,4-dichlorophenyl)pyrimidine;
(32) 2-(3,4-difluorophenoxy)-4-methyl-5-(4-chlorophenyl)-6-(2,4-dichlorophenyl)pyrimidine;
(33) 2-ethyl-4-(3,4-difluorophenoxy)-5-(4-chlorophenyl)-6-(2,4-dichlorophenyl)pyrimidine;
(34) 2-isopropy-4-(3,4-difluorophenoxy)-5-(4-chlorophenyl)-6-(2,4-dichlorophenyl)pyrimidine;
(35) 2-(3,4-difluorobenzyloxy)-4-methyl-5-(4-chlorophenyl)-6-(2,4-dichlorophenyl)pyrimidine;
(36) 2-(3,4-difluorobenzyloxy)-4-ethyl-5-(4-chlorophenyl)-6-(2,4-dichlorophenyl)pyrimidine;
(37) 2-(3,4-difluorobenzyloxy)-4-(n-methylamino)-5-(4-chlorophenyl)-6-(2,4-dichlorophenyl)pyrimidine;
(38) 2-(3,4-difluorophenoxy)-4-amino-5-(4-chlorophenyl)-6-(2,4-dichlorophenyl)pyrimidine;
(39) 2-(3,4-difluorobenzyloxy)-4-(amino)-5-(4-chlorophenyl)-6-(2,4-dichlorophenyl)pyrimidine;
(40) 2-(3,4-difluorophenoxy)-4-(acetylamino)-5-(4-chlorophenyl)-6-(2,4-dichlorophenyl)pyrimidine;
(41) 2-(3,4-difluorobenzyloxy)-4-(acetylamino)-5-(4-chlorophenyl)-6-(2,4-dichlorophenyl)pyrimidine;
(42) 2-(3,4-difluorophenoxy)-4-(n-pyrrolidinyl)-5-[4-chlorophenyl]-6-[2,4-dichlorophenyl]pyrimidine;
(43) 2-(cyclopropylmethoxy)-4-(n-pyrrolidinyl)-5-[4-chlorophenyl]-6-[2,4-dichlorophenyl]pyrimidine;
(44) 2-(n,n-diethylamino)-4-(3,4-difluorobenzyloxy)-5-(4-chlorophenyl)-6-(2,4-dichlorophenyl)pyrimidine;
(45) 2-(n,n-diisopropylamino)-4-(3,4-difluorobenzyloxy)-5-(4-chlorophenyl)-6-(2,4-dichlorophenyl)pyrimidine;
(46) 2-(n-pyrrolidyl)-4-(3,4-difluorobenzyloxy)-5-(4-chlorophenyl)-6-(2,4-dichlorophenyl)pyrimidine;
(47) 2-(n-piperidyl)-4-(3,4-difluorobenzyloxy)-5-(4-chlorophenyl)-6-(2,4-dichlorophenyl)pyrimidine;
(48) 2-(n-morpholinyl)-4-(3,4-difluorobenzyloxy)-5-(4-chlorophenyl)-6-(2,4-dichlorophenyl)pyrimidine;
(49) 2-(7-n-[2.2.1]-azabicycloheptyl)-4-(3,4-difluorophenoxy)-5-(4-chlorophenyl)-6-(2,4-dichlorophenyl)pyrimidine;
(50) 2-(n-propionyl)-4-(3,4-difluorophenoxy)-5-(4-chlorophenyl)-6-(2,4-dichlorophenyl)pyrimidine;
(51) 2-(n-(2-methyl)propionyl)-4-(3,4-difluorophenoxy)-5-(4-chlorophenyl)-6-(2,4-dichlorophenyl)pyrimidine;
(52) 2-(n-(3-methyl)butyryl)-4-(3,4-difluorophenoxy)-5-(4-chlorophenyl)-6-(2,4-dichlorophenyl)pyrimidine;
(53) 2-(aminocarbonyl)-4-(3,4-difluorophenoxy)-5-(4-chlorophenyl)-6-(2,4-dichlorophenyl)pyrimidine;
(54) 2-(carboxy)-4-(3,4-difluorophenoxy)-5-(4-chlorophenyl)-6-(2,4-dichlorophenyl)pyrimidine;
(55) 2-(2-hydroxyethyleneoxy)-4-(3,4-difluorophenoxy)-5-(4-chlorophenyl)-6-(2,4-dichlorophenyl)pyrimidine;
(56) 2-(2-methoxyethyleneoxy)-4-(3,4-difluorophenoxy)-5-(4-chlorophenyl)-6-(2,4-dichlorophenyl)pyrimidine;
(57) 2-(cyclohexylmethyloxy)-4-isopropoxy-5-(4-chlorophenyl)-6-(2,4-dichlorophenyl)pyrimidine;
(58) 2-cyclohexyloxy-4-isopropoxy-5-(4-chlorophenyl)-6-(2,4-dichlorophenyl)pyrimidine;
(59) 2-(3,4-difluorophenoxy)-4-cyclohexyloxy-5-(4-chlorophenyl)-6-(2,4-dichlorophenyl)pyrimidine;
(60) 2-(3,4-difluorobenzyloxy)-4-cyclohexyloxy-5-(4-chlorophenyl)-6-(2,4-dichlorophenyl)pyrimidine;
(61) 2,4-bis(cyclopropylmethyloxy)-5-(4-chlorophenyl)-6-(2,4-dichlorophenyl)pyrimidine;
(62) 2-cyclopropyloxy-4-(3-pyridyloxy)-5-(4-chlorophenyl)-6-(2,4-dichlorophenyl)pyrimidine;
(63) 2-(n-pyrrolidinyl)-4-cyclopropyloxy-5-(4-chlorophenyl)-6-(2,4-dichlorophenyl)pyrimidine;
(64) 2,4-bis(isopropyloxy)-5-(4-chlorophenyl)-6-(2,4-dichlorophenyl)pyrimidine;
(65) 2-(3,4-difluorobenzyloxy)-4-(4-chlorophenyl)-5-(2,4-chlorophenyl)pyrimidine;
(66) 2-(4-chlorobenzyloxy)-4-(4-chlorophenyl)-5-(2,4-dichlorophenyl)pyrimidine;
(67) 2-(3-fluorobenzyloxy)-4-(4-chlorophenyl)-5-(2,4-dichlorophenyl)pyrimidine;
(68) 2-(3-chlorobenzyloxy)-4-(4-chlorophenyl)-5-(2,4-dichlorophenyl)pyrimidine;
(69) 2-(4-fluorobenzyloxy)-4-(4-chlorophenyl)-5-(2,4-dichlorophenyl)pyrimidine;
(70) 2-(α-methyl-4-fluorobenzyloxy-)-4-(4-chlorophenyl)-5-(2,4-dichlorophenyl)pyrimidine;
(71) 2-(α-methyl-4-fluorobenzyloxy)-4-(2,4-dichlorophenyl)-5-(4-chlorophenyl)pyrimidine;
(72) 2-(3-pyridylmethoxy)-4-(2,4-dichlorophenyl)-5-(4-chlorophenyl)pyrimidine;
(73) 2-(n-butyloxy)-4-(2,4-dichlorophenyl)-5-(4-chlorophenyl)pyrimidine;
(74) 2-(2,4-dichlorobenzyloxy)-4-(2,4-chlorophenyl)-5-(4-chlorophenyl)pyrimidine;
(75) 2-(cyclohexylmethoxy)-4-(2,4-dichlorophenyl)-5-(4-chlorophenyl)pyrimidine;
(76) 2-(3,5-dichlorobenzyloxy)-4-(2,4-dichlorophenyl)-5-(4-chlorophenyl)pyrimidine;
(77) 2-(6-chloro-3-pyridylmethoxy)-4-(2,4-dichlorophenyl)-5-(4-chlorophenyl)pyrimidine;
(78) 2-(α,α-dimethyl-4-fluorobenzyloxy)-4-(2,4-dichlorophenyl)-5-(4-chlorophenyl)pyrimidine;
(79) 2-(4-fluorophenyloxy)-4-(2,4-dichlorophenyl)-5-(4-chlorophenyl)pyrimidine;
(80) 2-(3-fluorophenyloxy)-4-(2,4-dichlorophenyl)-5-(4-chlorophenyl)pyrimidine;
(81) 2-(3,4-difluorophenyloxy)-4-(2,4-dichlorophenyl)-5-(4-chlorophenyl)pyrimidine;
(82) 2-(3-chlorophenyloxy)-4-(2,4-dichlorophenyl)-5-(4-chlorophenyl)pyrimidine;
(83) 2-(4-methoxyphenyloxy)-4-(2,4-dichlorophenyl)-5-(4-chlorophenyl)pyrimidine;
(84) 2-(3-pyridyloxy)-4-(2,4-dichlorophenyl)-5-(4-chlorophenyl)pyrimidine;

(85) 2-(5-chloro-3-pyridyloxy)-4-(2,4-dichlorophenyl)-5-(4-chlorophenyl)pyrimidine;
(86) 2-(n-(4-fluorobenzamido))-4-(2,4-dichlorophenyl)-5-(4-chlorophenyl)pyrimidine;
(87) 2-(n-(cyclohexylcarboxamido))-4-(2,4-dichlorophenyl)-5-(4-chlorophenyl)pyrimidine;
(88) 2,4-bis(cyclobutylmethoxy)-5-(4-chlorophenyl)-6-(2,4-dichlorophenyl)pyrimidine;
(89) 2-cyclobutylmethoxy-4-(6-fluoro-3-pyridyloxy)-5-(4-chlorophenyl)-6-(2,4-dichlorophenyl)pyrimidine;
(90) 2-cyclobutylmethoxy-4-(5-chloro-3-pyridyloxy)-5-(4-chlorophenyl)-6-(2,4-dichlorophenyl)pyrimidine;
(91) 2-methylsulfonyl-4-(3-pyridyloxy)-5-(4-chlorophenyl)-6-(2,4-dichlorophenyl)pyrimidine;
(92) 2-cyclobutylmethoxy-4-(3-pyridyloxy)-5-(4-chlorophenyl)-6-(2,4-dichlorophenyl)pyrimidine;
(93) 2-(2,2-dimethylpropyloxy)-4-(3-pyridyloxy)-5-(4-chlorophenyl)-6-(2,4-dichlorophenyl)pyrimidine;
(94) 2-(2-t-butyloxy)-4-(3-pyridyloxy)-5-(4-chlorophenyl)-6-(2,4-dichlorophenyl)pyrimidine;
(95) 2-(2-cyclobutyloxy)-4-(3-pyridyloxy)-5-(4-chlorophenyl)-6-(2,4-dichlorophenyl)pyrimidine;
(96) 2-(n-propyloxy)-4-(3-pyridyloxy)-5-(4-chlorophenyl)-6-(2,4-dichlorophenyl)pyrimidine;
(97) 2-(n-butyloxy)-4-(3-pyridyloxy)-5-(4-chlorophenyl)-6-(2,4-dichlorophenyl)pyrimidine;
(98) 2-(sec-butyloxy)-4-(3-pyridyloxy)-5-(4-chlorophenyl)-6-(2,4-dichlorophenyl)pyrimidine;
(99) 2-(iso-butyloxy)-4-(3-pyridyloxy)-5-(4-chlorophenyl)-6-(2,4-dichlorophenyl)pyrimidine;
(100) 2-(isopropyloxy)-4-(3-pyridyloxy)-5-(4-chlorophenyl)-6-(2,4-dichlorophenyl)pyrimidine;
(101) 2-(n-pentyloxy)-4-(3-pyridyloxy)-5-(4-chlorophenyl)-6-(2,4-dichlorophenyl)pyrimidine;
(102) 2-cyclopropyloxy-4-(4-pyridyloxy)-5-(4-chlorophenyl)-6-(2,4-dichlorophenyl)pyrimidine;
(103) 2,4-bis-(4-pyridyloxy)-5-(4-chlorophenyl)-6-(2,4-dichlorophenyl)pyrimidine;
(104) 2-(isobutyloxy)-4-(3,4-difluorophenoxy)-5-(4-chlorophenyl)-6-(2,4-dichlorophenyl)pyrimidine;
(105) 2-(cyclopropylmethoxy)-4-(3,4-difluorophenoxy)-5-(4-chlorophenyl)-6-(2,4-dichlorophenyl)pyrimidine;
(106) 2-(isopropyloxy)-4-(3,4-difluorophenoxy)-5-(4-chlorophenyl)-6-(2,4-dichlorophenyl)pyrimidine;
(107) 2-ethoxy-4-(3,4-difluorophenoxy)-5-(4-chlorophenyl)-6-(2,4-dichlorophenyl)pyrimidine;
(108) 2-(n-pyrrolidinyl)-4-(3,4-difluorophenoxy)-5-(4-chlorophenyl)-6-(2,4-dichlorophenyl)pyrimidine;
(109) 2-(n,n',n'-trimethyl-ethylenediamino)-4-(3,4-difluorophenoxy)-5-(4-chlorophenyl)-6-(2,4-dichlorophenyl)pyrimidine;
(110) 2-(n-piperidyl)-4-(3,4-difluorophenoxy)-5-(4-chlorophenyl)-6-(2,4-dichlorophenyl)pyrimidine;
(111) 2-(n-morpholinyl)-ethylenediamino-4-(3,4-difluorophenoxy)-5-(4-chlorophenyl)-6-(2,4-dichlorophenyl)pyrimidine;
(112) 2-dimethylamino-4-(3,4-difluorophenoxy)-5-(4-chlorophenyl)-6-(2,4-dichlorophenyl)pyrimidine;
(113) 2-(n-pyrrolidinyl)-4-(3-pyridyloxy)-5-(4-chlorophenyl)-6-(2,4-dichlorophenyl)pyrimidine;
(114) 2-methylsulfonyl-4-(2-pyridyloxy)-5-(4-chlorophenyl)-6-(2,4-dichlorophenyl)pyrimidine;
(115) 2-(2-isopropyloxy)-4-(2-pyridyloxy)-5-(4-chlorophenyl)-6-(2,4-dichlorophenyl)pyrimidine;
(116) 2-(2-trimethyldiaimoloxy)-4-(2-pyridyloxy)-5-(4-chlorophenyl)-6-(2,4-dichlorophenyl)pyrimidine;
(117) 2-(2-pyrrolindyl)-4-(2-pyridyloxy)-5-(4-chlorophenyl)-6-(2,4-dichlorophenyl)pyrimidine;
(118) 2-(methylsulfonyl)-4-methoxy-5-(4-chlorophenyl)-6-(2,4-dichlorophenyl)pyrimidine;
(119) 2-methoxy-4-(methylsulfonyl)-5-(4-chlorophenyl)-6-(2,4-dichlorophenyl)pyrimidine;
(120) 2-(3,4-difluorophenyloxy)-4-methoxy-5-(4-chlorophenyl)-6-(2,4-dichlorophenyl)pyrimidine;
(121) 2-methoxy-4-(3,4-difluorophenyloxy)-5-(4-chlorophenyl)-6-(2,4-dichlorophenyl)pyrimidine;
(122) 2-(3-fluorophenyloxy)-4-methoxy-5-(4-chlorophenyl)-6-(2,4-dichlorophenyl)pyrimidine;
(123) 2-methoxy-4-(3-fluorophenyloxy)-5-(4-chlorophenyl)-6-(2,4-dichlorophenyl)pyrimidine;
(124) 2-methoxy-4-(2-pyridyloxy)-5-(4-chlorophenyl)-6-(2,4-dichlorophenyl)pyrimidine;
(125) 2-(2-pyridyloxy)-4-methoxy-5-(4-chlorophenyl)-6-(2,4-dichlorophenyl)pyrimidine;
(126) 2-(5-chloro-3-pyridyloxy)-4-methoxy-5-(4-chlorophenyl)-6-(2,4-dichlorophenyl)pyrimidine;
(127) 2-methoxy-4-(5-chloro-3-pyridyloxy)-5-(4-chlorophenyl)-6-(2,4-dichlorophenyl)pyrimidine;
(128) 2-(3-pyridyloxy)-4-methoxy-5-(4-chlorophenyl)-6-(2,4-dichlorophenyl)pyrimidine;
(129) 2-methoxy-4-(3-pyridyloxy)-5-(4-chlorophenyl)-6-(2,4-dichlorophenyl)pyrimidine;
(130) 2-methoxy-4-(4-fluorophenyloxy)-5-(4-chlorophenyl)-6-(2,4-dichlorophenyl)pyrimidine;
(131) 2-methoxy-4-(3,5-difluorophenyloxy)-5-(4-chlorophenyl)-6-(2,4-dichlorophenyl)pyrimidine;
(132) 2-methoxy-4-(3-cyanophenyloxy)-5-(4-chlorophenyl)-6-(2,4-dichlorophenyl)pyrimidine;
(133) 2-(3,4-difluorobenzyloxy)-4-methoxy-5-(4-chlorophenyl)-6-(2,4-dichlorophenyl)pyrimidine;
(134) 2-methoxy-4-(3,4-difluorobenzyloxy)-5-(4-chlorophenyl)-6-(2,4-dichlorophenyl)pyrimidine;
(135) 2-(methylsulfonyl)-4-ethoxy-5-(4-chlorophenyl)-6-(2,4-dichlorophenyl)pyrimidine;
(136) 2-ethoxy-4-(methylsulfonyl)-5-(4-chlorophenyl)-6-(2,4-dichlorophenyl)pyrimidine;
(137) 2-(3,4-difluorobenzyloxy)-4-ethoxy-5-(4-chlorophenyl)-6-(2,4-dichlorophenyl)pyrimidine;
(138) 2-ethoxy-4-(3,4-difluorophenyloxy)-5-(4-chlorophenyl)-6-(2,4-dichlorophenyl)pyrimidine;
(139) 2-(methylsulfonyl)-4-isopropyloxy-5-(4-chlorophenyl)-6-(2,4-dichlorophenyl)pyrimidine;
(140) 2-isopropyloxy-4-(methylsulfonyl)-5-(4-chlorophenyl)-6-(2,4-dichlorophenyl)pyrimidine;
(141) 2-(3,4-difluorobenzyloxy)-4-isopropyloxy-5-(4-chlorophenyl)-6-(2,4-dichlorophenyl)pyrimidine;
(142) 2-isopropyloxy-4-(3,4-difluorophenyloxy)-5-(4-chlorophenyl)-6-(2,4-dichlorophenyl)pyrimidine;
(143) 2-(3,4-difluorobenzyloxy)-4-pyrrolidinyl-5-(4-chlorophenyl)-6-(2,4-dichlorophenyl)pyrimidine;
(144) 2-(3,4-difluorobenzyloxy)-4-diethylamino-5-(4-chlorophenyl)-6-(2,4-dichlorophenyl)pyrimidine; and
(145) 2-(3,4-difluorobenzyloxy)-4-dimethylamino-5-(4-chlorophenyl)-6-(2,4-dichlorophenyl)pyrimidine;
(146) 2-(3,4-difluorophenoxy)-4-methoxy-5-(4-fluorophenyl)-6-[2,4-dichlorophenyl]pyrimidine;
(147) 2-(3,4-difluorophenoxy)-4-methoxy-5-(4-methoxyphenyl)-6-[2,4-dichlorophenyl]pyrimidine;
(148) 2-(3,4-difluorophenoxy)-4-methoxy-5-(4-trifluoromethylphenyl)-6-[2,4-dichlorophenyl]pyrimidine;
(149) 2-(3,4-difluorophenoxy)-4-methoxy-5-(3-chlorophenyl)-6-[2,4-dichlorophenyl]pyrimidine;

(150) 2-(3,4-difluorophenoxy)-4-methoxy-5-(3-methoxyphenyl)-6-[2,4-dichlorophenyl]pyrimidine;

and pharmaceutically acceptable salts thereof.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, imidazothiazolyl, and the like. The heteroaryl ring may be substituted on one or more carbon or nitrogen atoms "Cycloheteroalkyl" means mono- or bicyclic or bridged saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "cycloheteroalkyl" include pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl,5,6-dihydroimidazo[2,1-b]thiazolyl, tetrahydrohydroquinolinyl, morpholinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl. The cycloheteroalkyl ring may be substituted on the ring carbons and/or the ring nitrogens.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

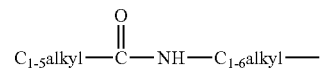

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxillary followed by separation by chromatography or crystallization, and fractional crystallization of diastereomeric salts.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor, inducing a conformational change in the receptor which, in turn, produces a response such as contraction, relaxation, secretion, change in enzyme activity, etc. similar to that elicited by the physiologically relevant agonist ligand(s) for that receptor. An "antagonist" is a compound which attenuates the effect of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of obesity or eating disorders associated with excessive food intake and complications associated therewith. The compounds are also useful for the treatment of constipation and chronic intestinal pseudo-obstruction. The compounds are also useful for the treatment of cirrhosis of the liver. The compounds are also useful for the treatment of asthma.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The utilities of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f)

reduction in opiate self-administration in mice (Sci. 1999, 283, 401404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282, 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm. Bulletin (Japan), 2000, 23(5), 657-9); j) neuropathology of paediatric chronic intestinal pseudo-obstruction and animal models related to the neuropathology of paediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for preventive use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 1000 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750 or 1000 milligrams of the active ingredient for the symptomatic adjustment of the dosage to the patient to be treated.

For the treatment of diseases of the eye, ophthalmic preparations for ocular administration comprising 0.001-1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. In particular, the term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art. To be administered in the form of a transdermal delivery system, the dosage administration will, of course, be continuous rather than intermittent throughout the dosage regimen.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from 0.01 to 1,000 mg, particularly 0.01, 0.05, 0.1, 0.5, 1, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated, and each cachet or capsule contains from about 0.01 to 1,000 mg, particularly 0.01, 0.05, 0.1, 0.5, 1.0, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |

Water for injection to a total volume of 1 mL

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |

-continued

| Aerosol | Per canister |
|---|---|
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, axiolytics, anti-Parkinson's agents, anti-epileptics, anorectic agents, and serotonin reuptake inhibitors, and other anti-obesity agents which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention also provides a method for the treatment or prevention of obesity, which method comprises administration to a patient in need of such treatment an amount of a compound of the present invention and an amount of an SSRI, such that together they give effective relief.

Suitable selective serotonin reuptake inhibitors of use in combination with a compound of the present invention include: fluoxetine, fluvoxamine, paroxetine, sertraline, and imipramine, and pharmaceutically acceptable salts thereof.

It will be appreciated that for the treatment or prevention of obesity, the compounds of the present invention may also be used in combination with an opioid antagonist.

The present invention also provides a method for the treatment or prevention of obesity, which method comprises administration to a patient in need of such treatment an amount of a compound of the present invention and an amount of an opioid antagonist, such that together they give effective relief.

Suitable opioid antagonists of use in combination with a compound of the present invention include: naltrexone, 3-methoxynaltrexone, naloxone and nalmefene, and pharmaceutically acceptable salts thereof.

It will be appreciated that for the treatment or prevention of obesity, the compounds of the present invention may also be used in combination with inhibitors of the enzyme 11Θ-HSD1. Generally, glucocorticoid concentrations are modulated by tissue-specific 11β-hydroxysteroid dehydrogenase enzymes. The 11β-hydroxysteroid dehydrogenase type 1 enzyme (11Θ-HSD1) is a low affinity enzyme that generally uses NADP+ as a cofactor rather than NAD+ (Agarwal et al., 1989). In vitro studies have shown that 11Θ-HSD1 is capable of acting as both a reductase and a dehydrogenase. However, 11Θ-HSD1 in vivo generally acts as a reductase, converting 11-ketoglucocorticoids, such as cortisone, to 11Θ-hydroxyglucocorticoids such as cortisol.

Excessive levels of cortisol have been associated with obesity, perhaps due to increased hepatic gluconeogenesis. Thus, the administration of an effective amount of an 11Θ-HSD1 inhibitor in combination with a CB1 antagonist of the present invention may be useful in the treatment or control of obesity. Particular inhibitors of 11Θ-HSD1 useful in combination with the compounds of the present invention include: 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, and 3-adamantanyl-4,5,6,7,8,9,10,11,12,3a-decahydro-1,2,4-triazolo[4,3-a][11]annulene.

It will be appreciated that for the treatment or prevention of obesity, the compounds of the present invention may also be used in combination with another anti-obesity agent.

The present invention also provides a method for the treatment or prevention of obesity, which method comprises administration to a patient in need of such treatment an amount of a compound of the present invention and an amount of another anti-obesity agent, such that together they give effective relief.

Suitable anti-obesity agents of use in combination with a compound of the present invention, include, but are not limited to: 1) growth hormone secretagogues, such as those disclosed and specifically described in U.S. Pat. No. 5,536,716; 2) growth hormone secretagogue receptor agonists/antagonists, such as NN703, hexarelin, MK-0677, SM-130686, CP424,391, L-692,429 and L-163,255, and such as those disclosed in U.S. Pat. No. 6,358,951, U.S. patent application Nos. 2002/049196 and 2002/022637, and PCT Application Nos. WO 01/56592 and WO 02/32888; 3) melanocortin agonists, such as Melanotan II or those described in WO 99/64002 and WO 00/74679; 4) Mc4r (melanocortin 4 receptor) agonists, such as CHIR86036 (Chiron), ME-10142, and ME-10145 (Melacure), and those disclosed in PCT Application Nos. WO 01/991752, WO 01/74844, WO 02/12166, WO 02/11715, and WO 02/12178; 5) β-3 agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. Nos. 5,705,515, and 5,451,677 and PCT Patent Publications WO94/18161, WO95/29159, WO97/46556, WO98/04526 and WO98/32753, WO 01/74782, and WO 02/32897; 6) 5HT-2 agonists; 7) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; 8) orexin antagonists, such as SB-334867-A, and those disclosed in PCT Patent Application Nos. WO 01/96302, WO 01/68609, WO 02/51232, and WO 02/51838; 9) melanin concentrating hormone antagonists; 10) melanin-concentrating hormone 1 receptor (MCH1R) antagonists, such as T-226296 (Takeda), and those disclosed in PCT Patent Application Nos. WO 01/82925, WO 01/87834, WO 02/06245, WO 02/04433, and WO 02/51809, and Japanese Patent Application No. JP 13226269; 11) melanin-concentrating hormone 2 receptor (MCH2R) agonist/antagonists; 12) galanin antagonists; 13) CCK agonists; 14) CCK-A (cholecystokinin-A) agonists, such as AR-R 15849, GI 181771, JMV-180, A-71378, A-71623 and SR146131, and those discribed in U.S. Pat. No. 5,739,106; 15) GLP-1 agonists; 16) corticotropin-releasing hormone agonists; 17) NPY 5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,140,354, 6,191,160, 6,313,298, 6,337,332, 6,329,395, 6,326,375, 6,335,345, and 6,340,683, European Patent Nos. EP-01010691, and EP-01044970, and PCT Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; 18) NPY 1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; 19) histamine receptor-3 (H3) modulators; 20) histamine receptor-3 (H3) antagonists/inverse agonists, such as hioperamide, 3-(1H-imidazol-4-yl) propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazolyl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); 21) β-hydroxy steroid dehydrogenase-1 inhibitors (β-HSD-1); 22) PDE (phosphodiesterase) inhibitors, such as theophylline, pentoxifylline, zaprinast, sildenafil, amrinone, milrinone, cilostamide, rolipram, and cilomilast; 23) phosphodiesterase-3B (PDE3B) inhibitors; 24) NE (norepinephrine) transport inhibitors, such as GW 320659, despiramine, talsupram, and nomifensine; 25) non-selective serotonin/norepinephrine transport inhibitors, such as sibutramine or fenfluramine; 26) ghrelin antagonists, such as those disclosed in PCT Application Nos. WO 01/87335, and WO 02/08250; 27) leptin, including recombinant human leptin (PEG-OB, Hoffman La Roche) and recombinant methionyl human leptin (Amgen); 28) leptin derivatives, such as those disclosed in U.S. Pat. Nos. 5,552,524, 5,552,523, 5,552, 522, 5,521,283, and PCT International Publication Nos. WO 96/23513, WO 96/23514, WO 96/23515, WO 96/23516, WO 96/23517, WO 96/23518, WO 96/23519, and WO 96/23520; 29) BRS3 (bombesin receptor subtype 3) agonists; 30) CNTF (Ciliary neurotrophic factors), such as GI-181771 (GlaxoSmithKiine), SR146131 (Sanofi Synthelabo), butabindide, PD170,292, and PD 149164 (Pfizer); 31) CNTE derivatives, such as axokine (Regeneron), and those disclosed in PCT Application Nos. WO 94/09134, WO 98/22128, and WO 99/43813; 32) monoamine reuptake inhibitors, such as those disclosed in PCT Application Nos. WO 01/27068, and WO 01/62341; 33) UCP-1 (uncoupling protein-1), 2, or 3 activators, such as phytanic acid, 4-[(E)-2-(5,6,7,8-tetrahydro-5,5, 8,8-tetramethyl-2-napthalenyl)-1-propenyl]benzoic acid (TTNPB), retinoic acid, and those disclosed in PCT Patent Application No. WO 99/00123; 34) thyroid hormone β agonists, such as KB-2611 (KaroBioBMS), and those disclosed in PCT Application No. WO 02/15845, and Japanese Patent Application No. JP 2000256190; 35) FAS (fatty acid synthase) inhibitors, such as Cerulenin and C75; 36) DGAT1 (diacylglycerol acyltransferase 1) inhibitors; 37) DGAT2 (diacylglycerol acyltransferase 2) inhibitors; 38) ACC2 (acetyl-CoA carboxylase-2) inhibitors; 39) glucocorticoid antagonists; 40) acyl-estrogens, such as oleoyl-estrone, disclosed in del Mar-Grasa, M. et al., Obesity Research, 9:202-9 (2001); 41) lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; 42) fatty acid transporter inhibitors; 43) dicarboxylate transporter inhibitors; 44) glucose transporter inhibitors; 45) phosphate transporter inhibitors; 46) serotonin reuptake inhibitors, such as those disclosed in U.S. Pat. No. 6,365,633, and PCT Patent Application Nos. WO 01/27060, and WO 01/162341; 47) Metformin (Glucophage®); and/or 48) Topiramate (Topimax (®).

Specific NPY5 antagonists of use in combination with a compound of the present invention are selected from the group consisting of:
  (1) 3-oxo-N-(5-phenyl-2-pyrazinyl)-spiro[isobenzofuran-1(3H),4'-piperidine]-1'-carboxamide,
  (2) 3-oxo-N-(7-trifluoromethylpyrido[3,2-b]pyridin-2-yl)spiro-[isobenzofuran-1(3H),4'-piperidine]-1'-carboxamide,
  (3) N-[5-(3-fluorophenyl)-2-pyrimidinyl]-3-oxospiro-[isobenzofuran-1(3H),4'-piperidine]-1'-carboxamide,
  (4) trans-3'-oxo-N-(5-phenyl-2-pyrimidinyl)spiro[cyclohexane-1,1'(3'H)-isobenzofuran]-4-carboxamide,
  (5) trans-3'-oxo-N-[1-(3-quinolyl)-4-inidazolyl]spiro[cyclohexane-1,1'(3'H)-isobenzofuran]-4-carboxamide,
  (6) trans-3-oxo-N-(5-phenyl-2-pyrazinyl)spiro[4-azaisobenzofuran-1(3H),1'-cyclohexane]-4'-carboxamide,
  (7) trans-N-[5-(3-fluorophenyl)-2-pyrimidinyl]-3-oxospiro[5-azaisobenzofuran-1(3H),1'-cyclohexane]-4'-carboxamide,
  (8) trans-N-[5-(2-fluorophenyl)-2-pyrimidinyl]-3-oxospiro[5-azaisobenzofuran-1(3H),1'-cyclohexane]-4'-carboxamide,
  (9) trans-N-[1-(3,5-difluorophenyl)-4-imidazolyl]-3-oxospiro[7-azaisobenzofuran-1(3H),1'-cyclohexane]-4'-carboxamide,
  (10) trans-3-oxo-N-(1-phenyl-4-pyrazolyl)spiro[4-azaisobenzofuran-1(3H),1'-cyclohexane]-4'-carboxamide,
  (11) trans-N-[1-(2-fluorophenyl)-3-pyrazolyl]-3-oxospiro[6-azaisobenzofuran-1(3H),1'-cyclohexane]-4'-carboxamide,
  (12) trans-3-oxo-N-(1-phenyl-3-pyrazolyl)spiro[6-azaisobenzofuran-1(3H),1'-cyclohexane]-4'-carboxamide,
  (13) trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk for obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asian countries, a "subject at risk for obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds or compositions of the present invention to reduce or maintain the body weight of an obese subject. One outcome of treatment may be reducing the body weight of an obese subject relative to that subject's body weight immediately before the administration of the compounds or compositions of the present invention. Another outcome of treatment may be preventing regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds or compositions of the present invention to reduce or maintain the body weight of a subject at risk for obesity. One outcome of prevention may be reducing the body weight of a subject at risk for obesity relative to that subject's body weight immediately before the administration of the compounds or compositions of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk for obesity. Another outcome of prevention may be decreasing the occurrence and/or severity of obesity-related disorders if the treatment is administered prior to the onset of obesity in a subject at risk for obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

Obesity-related disorders are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventiflation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compositions of the present invention are also useful for reducing the risk of secondary outcomes of obesity, such as reducing the risk of left ventricular hypertrophy.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes. Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds and compositions of the present invention are useful for treating both Type I and Type II diabetes. The compounds and compositions are especially effective for treating Type II diabetes. The compounds and compositions of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable neurokinin-1 receptor antagonists may be peptidal or non-peptidal in nature, however, the use of a non-peptidal neurokinin-1 receptor antagonist is preferred. In a preferred embodiment, the neurokinin-1 receptor antagonist is a CNS-penetrant neurokinin-1 receptor antagonist. In addition, for convenience the use of an orally active neurokinin-1 receptor antagonist is preferred. To facilitate dosing, it is also preferred that the neurokinin-1 receptor antagonist is a long acting neurokinin-1 receptor antagonist. An especially preferred class of neurokinin-1 receptor antagonists of use in the present invention are those compounds which are orally active and long acting.

Neurokinin-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913,0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, 97/49710, 98/24438-98/24441, 98/24442-98/24445, 02/16343, and 02/16344; and in British Patent Publication Nos. 2 266 529, 2 268 931, 2 269 170, 2 269 590, 2 271 774, 2 292 144, 2 293 168, 2 293 169, and 2 302 689.

Specific neurokinin-1 receptor antagonists of use in the present invention include:

(±)-(2R3R,2S3S)-N-{[2-cyclopropoxy-5-(trifluoromethoxy)-phenyl]methyl}-2-phenylpiperidin-3-amine; 2-(S)-(3,5-bis(trifluoromethyl)benzyloxy)-3(S)-(4-fluorophenyl)-4-(3-(5-oxo-1H,4H-1,2,4-triazolo)methyl)morpholine; 2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine; 2-(S)-(3,5-bis(trifluoromethyl)benzyloxy)-4-(3-(5-oxo-1H,4H-1,2,4-triazolo)methyl)-3-(S)-phenyl-morpholine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; 2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine; 2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine; (3S,5R,6S)-3-[2-cyclopropoxy-5-(trifluoromethoxy)phenyl]-6-phenyl-1-oxa-7-aza-spiro[4.5]decane; (3R,5R,6S)-3-[2-cyclopropoxy-5-(trifluoromethoxy)phenyl]-6-phenyl-1-oxa-7-aza-spiro[4.5]decane; 2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine; 2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine; 2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine; 2-(R)-(1-R)-(3,5-bis(trifluoromethyl)phenyl)ethoxy)-3-(S)-(4-fluorophenyl)H4-(3-(2-monophosphoryl-5-oxo-1H-1,2,4-triazolo)methyl)morpholine; 2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine; 2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine; 2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine; or a pharmaceutically acceptable salt thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and 5-HT$_{1A}$ agonists or antagonists, especially 5-HT$_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof.

Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the 5-HT$_{2A}$ receptor antagonists, examples of which include MDL100907 and fananserin. Also of use in combination with a CB1 receptor modulator are the serotonin dopamine antagonists (SDAs)

which are believed to combine 5-HT$_{2A}$ and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described in European Patent Specification No. 0 577 394, and International Patent Specification Nos. 95/08549, 95/18124, 95/23798, 96/05181, and 98/49710 (Application No. PCT/GB97/01630). The preparation of such compounds is fully described in the aforementioned publications.

Particularly preferred NK-1 receptor antagonists of use in the present invention include: (3S,5R,6S)-3-[2-cyclopropoxy-5-(trifluoromethoxy)phenyl]-6-phenyl-1-oxa-7-aza-spiro[4.5]decane; (3R,5R,6S)-3-[2-cyclopropoxy-5-(trifluoromethoxy)phenyl]-6-phenyl-1-oxa-7-aza-spiro[4.5]decane; (±)-(2R3R,2S3S)-N-{[2-cyclopropoxy-5-(trifluoromethoxy)phenyl]methyl}-2-phenylpiperidin-3-amine; 2-(S)-(3,5-bis(trifluoromethyl)benzyloxy)-3(S)-(4-fluorophenyl)-4-(3-(5-oxo-1H,4H-1,2,4-triazolo)methyl)morpholine; 2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine; 2-(S)-(3,5-bis(trifluoromethyl)benzyloxy)-4-(3-(5-oxo-1H,4H-1,2,4-triazolo)methyl)-3-(S)-phenyl-morpholine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; 2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine; 2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine; 2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4triazolo)methyl)morpholine; 2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine; 2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine; 2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine; 2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4triazolo)methyl)morpholine; 2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine; 2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine or a pharmaceutically acceptable salt thereof.

It will be appreciated that a combination of a conventional anti-asthmatic drug with a CB1 receptor modulator may provide an enhanced effect in the treatment of asthma.

Thus, according to a further aspect of the present invention there is provided the use of a CB1 receptor modulator and an anti-asthmatic agent for the manufacture of a medicament for the treatment or prevention of asthma.

The present invention also provides a method for the treatment or prevention of asthma, which method comprises administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); (f) antagonists of the chemokine receptors, especially CCR-1, CCR-2, and CCR-3; (g) immunosuppressants such as cyclosporin, tacrolimus, rapamycin and other FK-506 type immunosuppressants; (h) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (i) cyclooxygenase-2 (COX-2) inhibitors such as celecoxib; (j) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (k) preparations of interferon beta (interferon beta-1a, interferon beta-1b); (l) other compounds such as 5-aminosalicylic acid and prodrugs thereof, and pharmaceutically acceptable salts thereof.

It will be appreciated that a combination of a conventional anti-constipation drug with a CB1 receptor modulator may provide an enhanced effect in the treatment of constipation.

Thus, according to a further aspect of the present invention there is provided the use of a CB1 receptor modulator and an anti-constipation agent for the manufacture of a medicament for the treatment or prevention of constipation.

The present invention also provides a method for the treatment or prevention of constipation, which method comprises administration to a patient in need of such treatment an amount of a compound of the present invention and an amount of an anti-constipation agent, such that together they give effective relief.

It will be appreciated that a combination of a conventional anti-constipation drug with a CB1 receptor modulator may provide an enhanced effect in the treatment of chronic intestinal pseudo-obstruction.

Thus, according to a further aspect of the present invention there is provided the use of a CB1 receptor modulator and an anti-constipation agent for the manufacture of a medicament for the treatment or prevention of chronic intestinal pseudo-obstruction.

The present invention also provides a method for the treatment or prevention of chronic intestinal pseudo-obstruction, which method comprises administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof.

A particularly suitable class of osmotic agents include, but are not limited to sorbitol, lactulose, polyethylene glycol, magnesium, phosphate,and sulfate; and pharmaceutically acceptable salts thereof.

A particularly suitable class of laxatives and detergent laxatives, include, but are not limited to, magnesium, and docusate sodium; and pharmaceutically acceptable salts thereof.

A particularly suitable class of bulking agents include, but are not limited to, psyllium, methylcelulose, and calcium polycarbophil; and pharmaceutically acceptable salts thereof.

A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment of cirrhosis of the liver.

Thus, according to a further aspect of the present invention there is provided the use of a CB1 receptor modulator and an anti-cirrhosis agent for the manufacture of a medicament for the treatment or prevention of cirrhosis of the liver.

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples:

aq.: aqueous
API-ES: atmospheric pressure ionization-electrospray (mass spectrum term)
DCM: dichloromethane
DMAP: 4-dimethylaminopyridine
DMF: dimethylformamide
DMSO: dimethylsulfoxide
g: gram
h: hours
HPLC: high pressure liquid chromatography
HPLC/MS: high pressure liquid chromatography/mass spectrum
$HR_f$: higher $R_f$ material (compound moved faster on TLC)
in vacuo: rotoevaporation
LC: Liquid chromatography
LC/MS, LC-MS: liquid chromatography-mass spectrum
$LR_f$: lower $R_f$ material (compound moved slower on TLC)
M: molar
mCPBA: meta-chloroperbenzoic acid
Me: methyl
MeOH: methanol
MHz: megahertz
min: minute
mL: milliliter
mmol: millimole MR$_f$: middle-R$_f$ material (compound moved intermediate relative to two others on TLC)

MS or ms: mass spectrum

N: normal

NMR: nuclear magnetic resonance

R$_f$: in TLC, the displacement of the compound divided by the displacement of the solvent front R$_t$: retention time rt or RT: room temperature TFA: trifluoroacetic acid THF: tetrahydrofuran TLC: thin layer chromatography Compounds of the present invention may be prepared by procedures illustrated in the accompanying schemes.

Scheme 1 illustrates a synthetic method for the preparation of compounds of general Formula I when it is desired that the 2-position substituent on the pyrimidine ring bear a substituted heteroatom substituent. An aryl benzyl ketone of general formula C is the starting point for the synthesis. Arylbenzyl ketones of general formula C may be available commercially or they can be synthesized using one of several methods known in organic synthesis. For example, reaction a nitrile of general formula B with a benzyl grignard reagent derived from a benzyl halide of general formula A followed by acidic hydrolysis of the intermediate imine, affords an arylbenzyl ketone of general formula C. The arylbenzyl ketone of general formula C is then converted to a vinylogous amide of general formula E by reaction with an amide acetal of general formula D. The condensation reaction can be conducted using the amide acetal as the reaction solvent or a suitable polar aprotic solvent such as DMF may be used. The reaction is conducted at elevated temperature, typically between room temperature and 150° C. for periods of 1-8 hours. Condensation of the resulting vinylogous amide E with a substituted pseudothiourea of the general formula F then affords a 2-thiomethylpyrimidyl derivative of general formula G. The reaction is usually conducted in a polar aprotic solvent such as DMF in the presence of an organic base such as triethylamine with heating (80-100°). The resulting 2-methylthio-pyrimidine G is derivatized depending on the heteroatom substitution. The 2-methylthio-pyrimidyl derivative G is treated in a polar aprotic solvent such as DMF at room temperature with the sodium alkoxide of an benzylic alcohol H to give the 2-oxyalkaryl pyrimidine I.

SCHEME 1

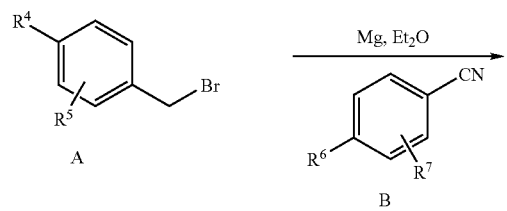

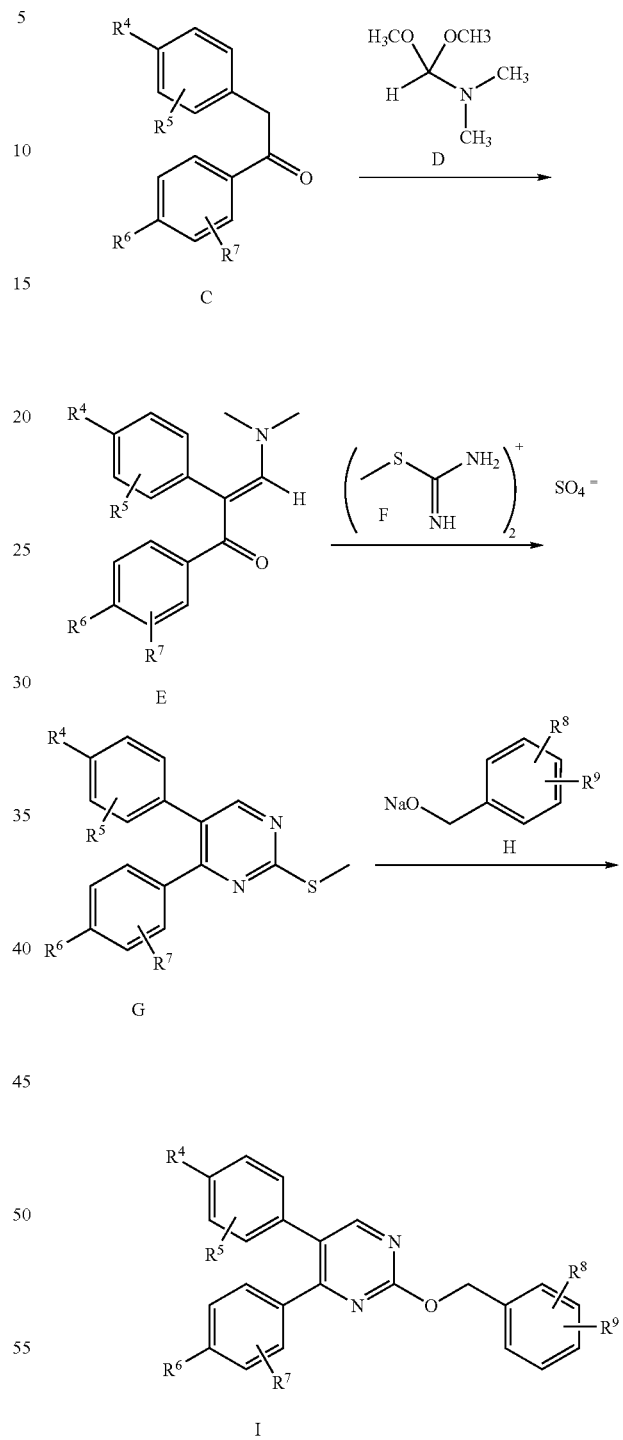

In Scheme 2, nucleophilic displacement of the methylthio group in pyrimidine G (from Scheme 1) with sodium or potassium cyanide gives the 2-cyano derivative J while displacement with an amine such as substituted amine K or benzylamine L gives the 2-amino derivatives of M and N, respectively.

SCHEME 2

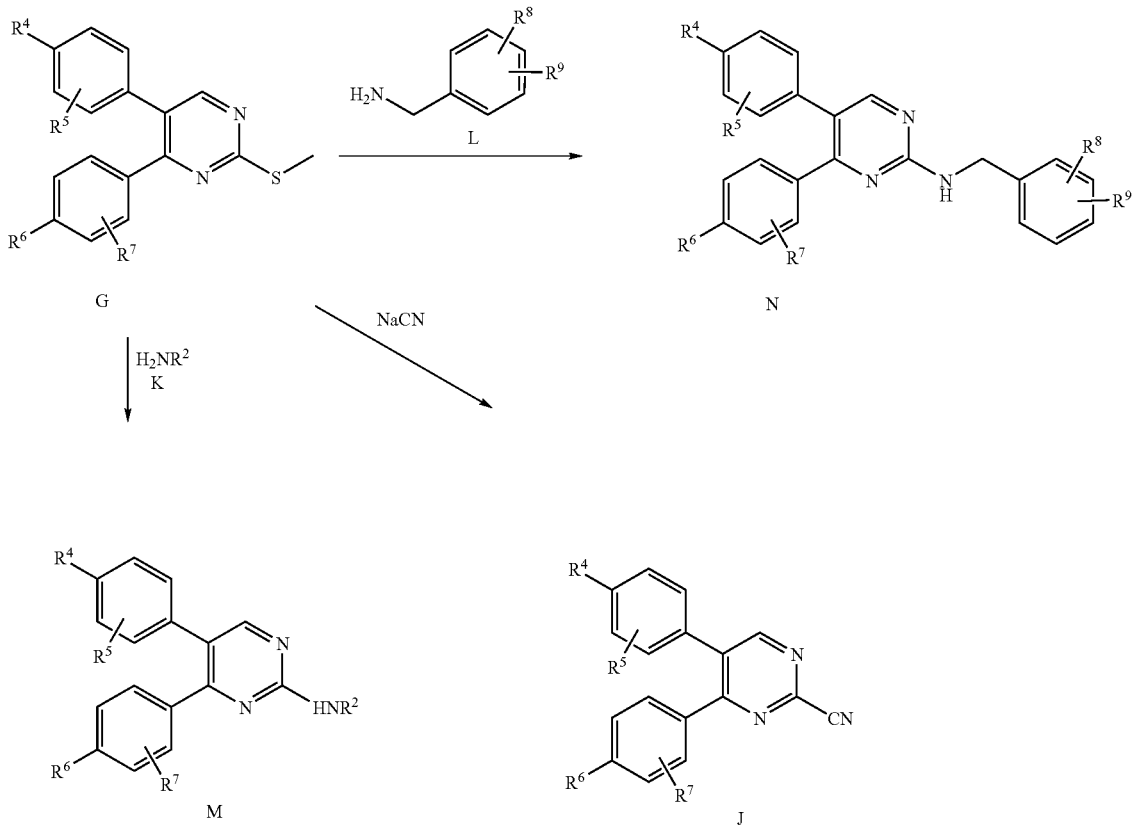

Scheme 3 illustrates a synthetic method for the preparation of compounds of general formula Q when it is desired that the 2 and 4-position substituents on the pyrimidine ring bear an easily and selectively substituted leaving group. An aryl benzyl ketone of general formula O is the starting point for the synthesis. Arylbenzyl ketones of general formula O may be available commercially or they can be synthesized using one of several methods known in organic synthesis. The arylbenzyl ketone of general formula O is then converted to 2,4-bis methylthio 5,6-biarylpyrimidine of the general formula P by reaction with of methyl isocyanaate (2 equivalents), triflic anhydride (1.1 equivalents) and the arylbenzyl ketone O (1 equivalent) in a solvent like DCM or 1,2-dichloroethane at 25° to 70° from 18 h to 96 h. Specifically, we effect the synthesis of 4-[2,4-dichlorophenyl]-5-[4-chlorophenyl]-2,4-bis(methylthio)pyrimidine by the reaction of 2-[4-chlorophenyl]-aceto-[2,4-dichlorophenone with triflic anhydride and methyl thiocyanate by the method of A. Garcia Martinez et al (*Synlett,* 1994, (7) 559. The bis sulfide P was oxidized to 6-[2,4-dichlorophenyl]-5-[4-chlorophenyl]-2,4-bis(methylsulfonyl)-pyrimidine Q with m-chloroperbenzoic acid according to the method of A. Garcia Martinez et al. (*Tetrahedron,* 1996, 52 (23) 7973).

SCHEME 3

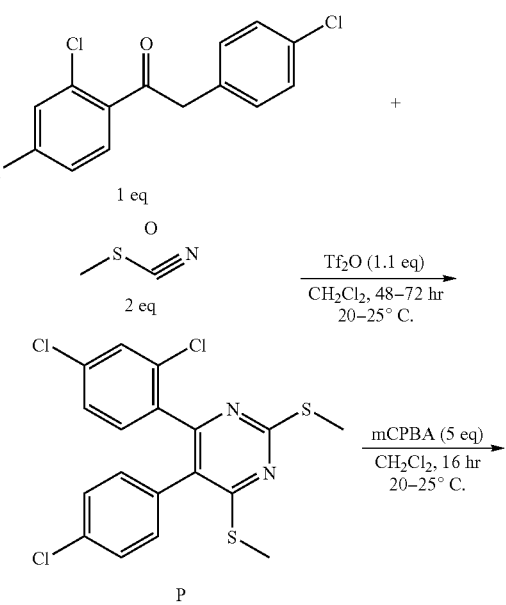

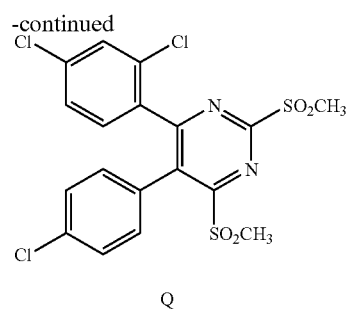

Q

The derivative Q in Scheme 3 is selectively substituted by nucleophilic reagents in a stepwise fashion (Scheme 4)

wherein, in general, the sodium or lithium phenoxide displaces the 4-methylsulfone preferentially over the 2-methylsulfone to afford R. Lithium alkoxy or benyloxy reagents generally displace both the 2- and the 4-sulfone substituents to yield isomers S and T. Excess alkoxide will, in general, substitute both positions. Primary free amines will, in general, displace the 4-methylsulfone preferentially over the 2-methyl sulfone. Secondary free amines will, in general, displace the 2-methylsulfone preferentially over the 4-methyl sulfone to afford U. The lithium amide of secondary amines will, in general, displace the 4-methyl sulfone preferentially over the 2-methyl sulfone to give V. The treatment of Q with Grignard reagents will generally afford both isomers W and X.

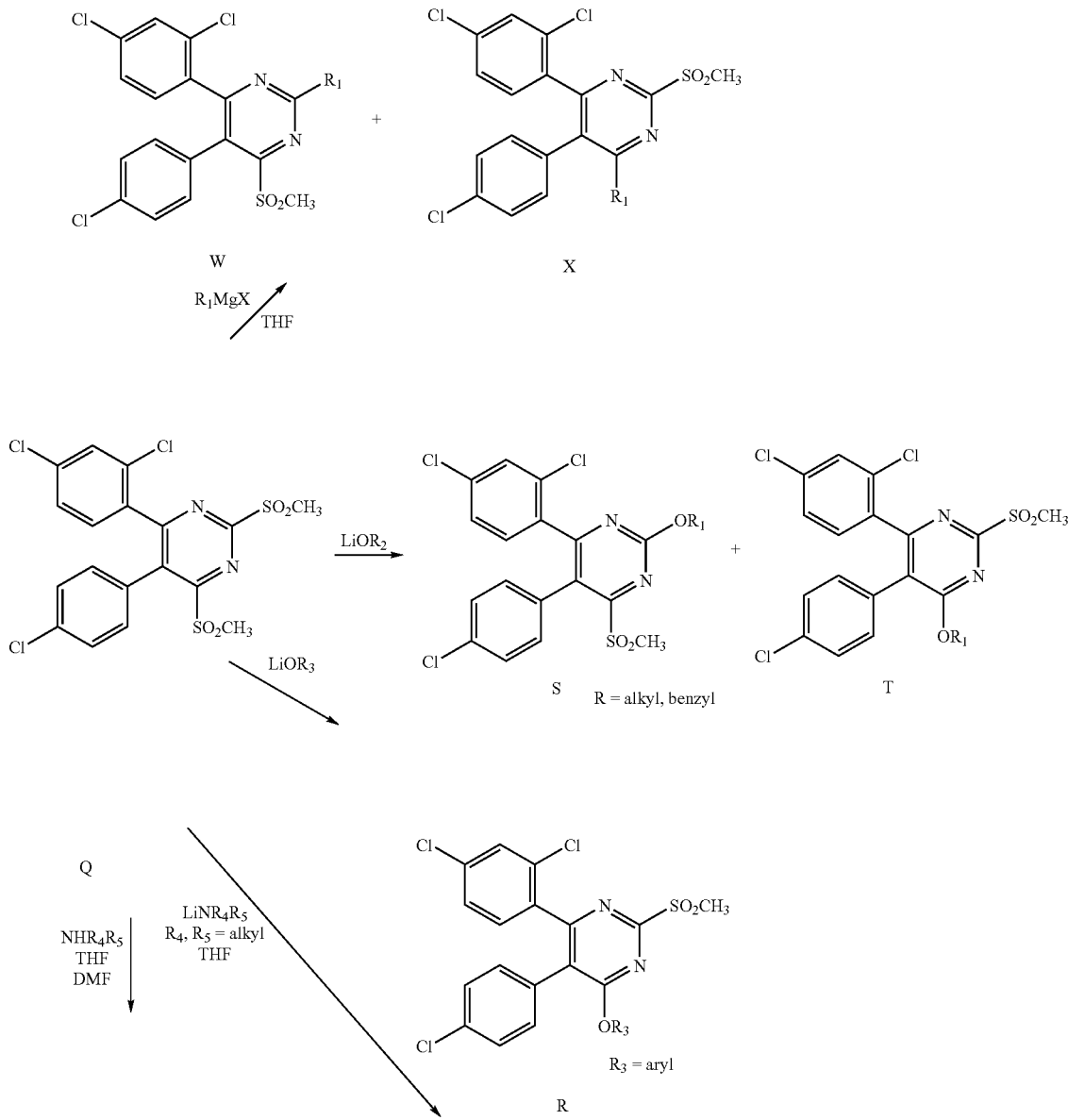

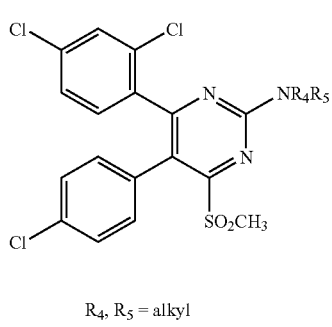

U
R4, R5 = alkyl

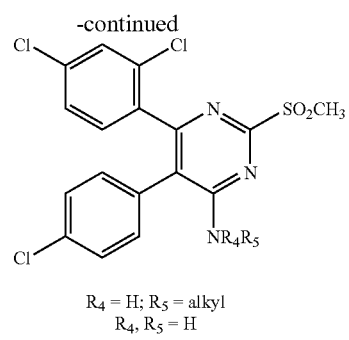

-continued

V
R4 = H; R5 = alkyl
R4, R5 = H

Scheme 5 illustrates a synthetic method for the preparation of compounds of the general formula EE for where it is desired that the 2, 4 and 5-position substituents on the pyrimidine ring bear an easily and selectively substituted leaving group. An aryl methyl ketone of general formula AA is the starting point for the synthesis. Aryl methyl ketones of general formula AA are available commercially or they can be synthesized using one of several methods known in organic synthesis. The aryl methyl ketone of general formula AA is then first converted to the 2-bromo aryl methyl ketone BB with 2 equivalents of bromine in acetic acid, and, after removale of the acetic acid and neutralization of hydrogen bromide, reacted with potassium acetated in refluxing acetone to give CC. After column chromatography, the aryl-2-acetoxy ketone is converted to 2,4-bis methylthio 5-acetoxy 6-arylpyrimidine of the general formula DD by reaction with methyl isocyanaate (2 equivalents), triflic anhydride (1.1 equivalents) and the aryl ketone CC (1 equivalent) in a solvent like dichloromethane or 1,2-dichloroethane at 25° to 70° from 18 h to 96 h. Specifically, we effect the synthesis of 6-[2,4-dichlorophenyl]-5-[acetoxyl]-2,4-bis(methylthio)pyrimidine by the reaction of 2-[4-chlorophenyl]-aceto-[2,4-dichloro]phenone with triflic anhydride and methyl thiocyanate by the method of A. Garcia Martinez et al (*Synlett*, 1994, (7) 559. The bis-sulfide DD is oxidized to 6-[2,4-dichlorophenyl]-5-[acetoxy]-2,4-bis(methylsulfonyl)-pyrimidine EE with m-chloroperbenzoic acid according to the method of A. Garcia Martinez et al (*Tetrahedron*, 1996, 52 (23) 7973).

SCHEME 5

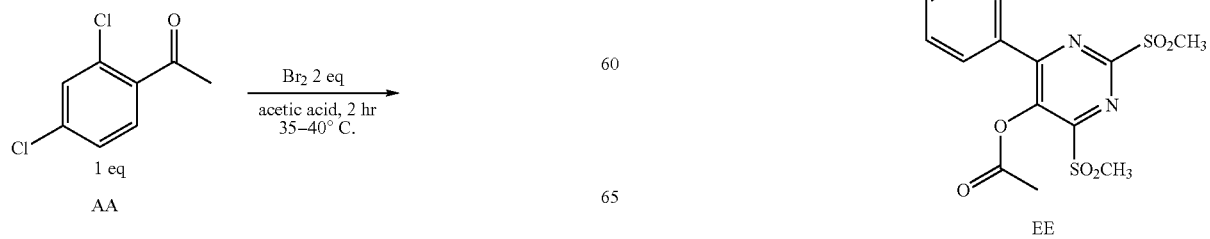

The derivative EE is selectively substituted by nucleophilic reagents in a stepwise fashion (Scheme 6) wherein, in general, a lithium alkoxide or phenoxide displaces the 4-methylsulfone preferentially over the 2-methylsulfone to afford FF. Hydrolysis of the acetate is effected by treating with excess sodium hydroxide in either water/ethanol or water/THF mixture to give a filterable precipitate GG. This is in turn treated with trifluoromethanesulfonic anhydride with pyridine in dichloromethane to give the triflate HH. Treating HH with a lithium phenoxide displaces the 2-sulphone in THF solvent in 2-4 hr at 0° to give II. This derivative in turn can be displaced with and aryl or heteroarylboronic acid via the Suzuki reaction to give the 5-aryl(heteroary) derivatives.

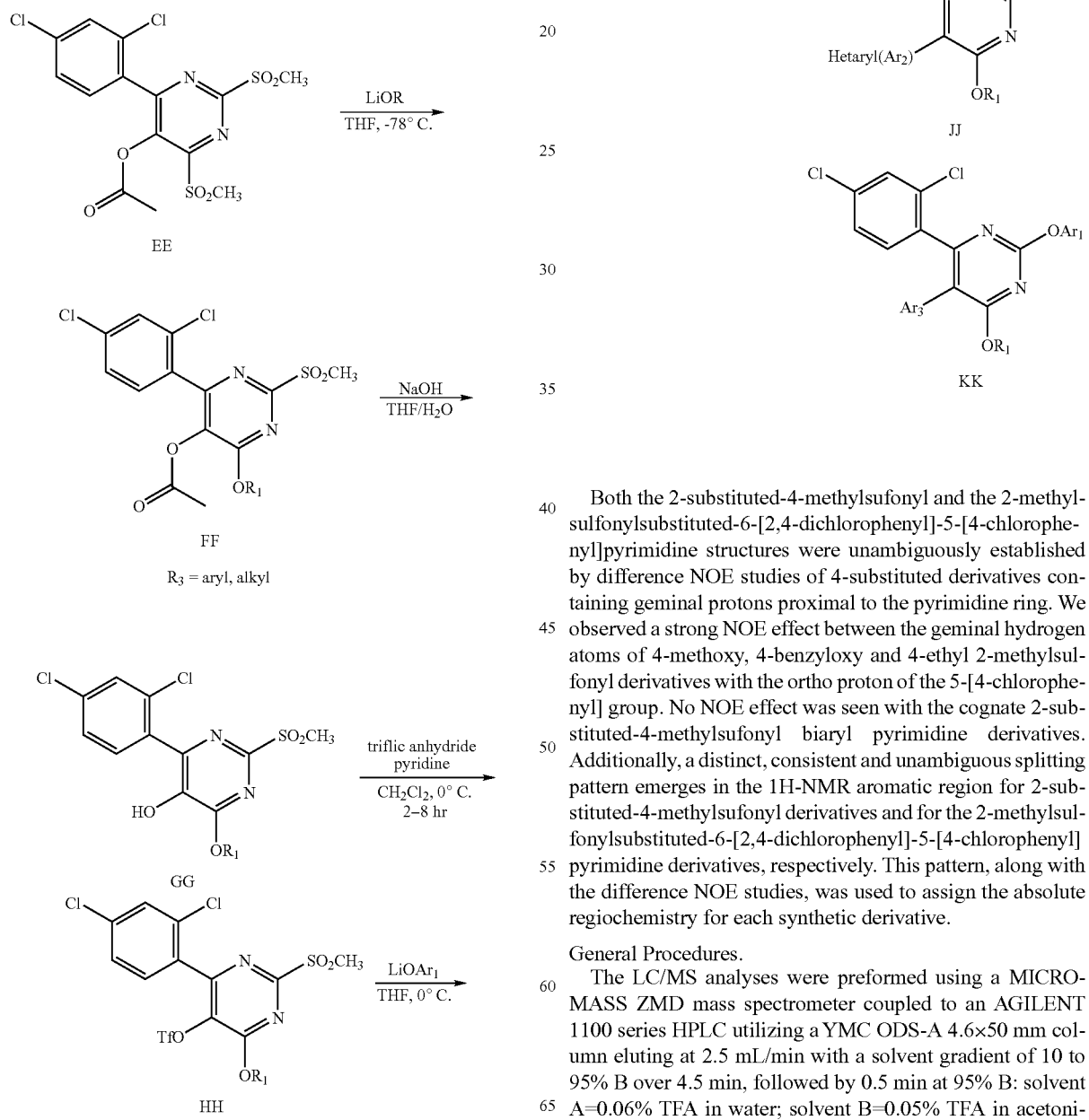

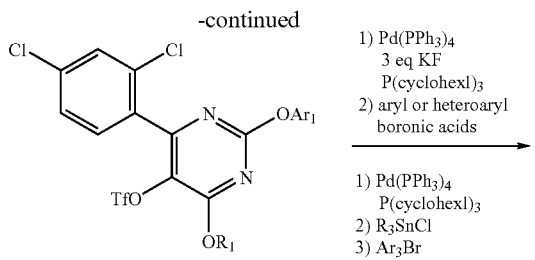

Both the 2-substituted-4-methylsufonyl and the 2-methylsulfonylsubstituted-6-[2,4-dichlorophenyl]-5-[4-chlorophenyl]pyrimidine structures were unambiguously established by difference NOE studies of 4-substituted derivatives containing geminal protons proximal to the pyrimidine ring. We observed a strong NOE effect between the geminal hydrogen atoms of 4-methoxy, 4-benzyloxy and 4-ethyl 2-methylsulfonyl derivatives with the ortho proton of the 5-[4-chlorophenyl] group. No NOE effect was seen with the cognate 2-substituted-4-methylsufonyl biaryl pyrimidine derivatives. Additionally, a distinct, consistent and unambiguous splitting pattern emerges in the 1H-NMR aromatic region for 2-substituted-4-methylsufonyl derivatives and for the 2-methylsulfonylsubstituted-6-[2,4-dichlorophenyl]-5-[4-chlorophenyl] pyrimidine derivatives, respectively. This pattern, along with the difference NOE studies, was used to assign the absolute regiochemistry for each synthetic derivative.

General Procedures.

The LC/MS analyses were preformed using a MICROMASS ZMD mass spectrometer coupled to an AGILENT 1100 series HPLC utilizing a YMC ODS-A 4.6×50 mm column eluting at 2.5 mL/min with a solvent gradient of 10 to 95% B over 4.5 min, followed by 0.5 min at 95% B: solvent A=0.06% TFA in water; solvent B=0.05% TFA in acetonitrile. $^1$H-NMRspectra were obtained on a 500 mHZ varian spectrometer in CDCl₃ or CD₃OD as indicated and chemical shifts are reported as δ using the solvent peak as reference and coupling constants are reported in hertz (HZ).

REFERENCE EXAMPLE 1

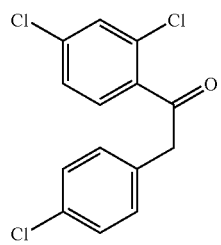

4-Chlorobenzyl 2,4-dichlorophenyl ketone

A solution of 4-chlorobenzyl bromide (Lancaster Chemical) (10.0 g, 48.6 mmol) in 40 mL ether was added under nitrogen to a suspension of magnesium turnings (Alpha Chemical Inc.) in ether (60 mL) over 10 minutes. The suspension was stirred for 2 h and the supernatant was cannulated under nitrogen into another round bottom flask fitted with a magnetic stirrer bar. Then 2,4-dichlorobenzonitrile (7.0 g, 40.5 mmol) in 65 mL ether was slowly added under nitrogen to the Grignard solution and the mixture was stirred over night at room temperature. The imine precipitated out of solution and the mixture was refluxed for 3 h. The reaction mixture was cooled and poured into a flask containing 50 mL ethyl acetate and 50 mL 2N HCl. Stirred vigorously to hydrolyze the imine, separated the organic layer and dried it over anhydrous magnesium sulfate. The desiccant was filtered off and the solvent volume reduced under reduced pressure. The crude product was flash chromatographed on silica gel (92/8 hexanes/ethyl acetate) to give product. $^1$H NMR 500 MHz (CDCl₃): δ 4.40 (s, 2H), 7.2-7.6 (m, 7H).

REFERENCE EXAMPLE 2

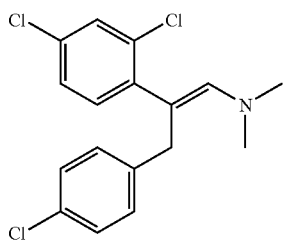

3-Dimethylamino-1-(4-dichlorophenyl)-2-(2,4-dichlorophenyl)prop-2-en

To a solution of 4-chlorobenzyl 2,4-dichlorophenyl ketone (600 mg, 2 mmol) from Step A in DMF (8 mL) was added dimethylformamide dimethylacetal (1.05 mL, 8 mmol) over several minutes. The reaction was heated to 80° C. for 18 h. The DMF and excess acetal was removed under reduced pressure and the product used without further purification.

REFERENCE EXAMPLE 3

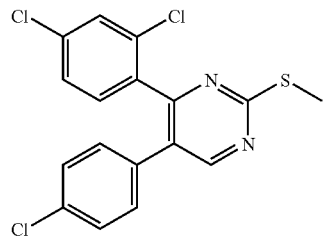

2-Methylthio-4-(2,4-dichlorophenyl)-5-(4-chlorophenyl)pyrimidine

The crude product from Reference Example 2 was added to 5 mL pyridine and 1 mL water, along with 1.1 mmole (310 mg, 2.2 equivalents) pseudothiourea sulfate and triethylamine (460 μL, 2.8 mmol). The reaction mixture was heated to 80° C. for 4 h. The solvents were removed in vacuo and the reaction mixture dissolved in water. Extraction with ether gave crude product. Flash column chromatography on silica gel (eluted with 98/2 hexanes/ethyl acetate) yielded the desired product. HPLC/MS: m/e=382 (M⁺), 384 (M+2); $R_t$=3.48 min; $^1$H-NMR 500 MHz (CDCl₃): δ 2.63 (s, 3H), 7.04 (d, J=8 Hz, 1H), 7.27 (d over multiplet, J=8 Hz, 4H), 8.59 (s, 1H).

REFERENCE EXAMPLE 4

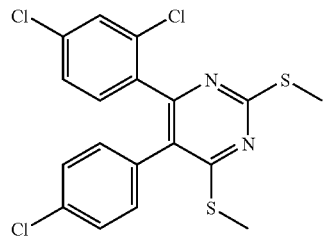

2,6-Bis(methylthio)-4-[2,4-dichlorophenyl]-5-[4-chlorophenyl]pyrimidine

To a well-stirred solution of triflic anhydride (5.0 g, 17.7 mmol) and methylthiocyanate (2.44 mL, 36 mmol) in anhydrous dichloromethane (40 mL) was slowly added a solution of 4-chlorobenzyl 2,4-dichlorophenyl ketone from Reference Example 1 (5.3 g, 17.7 mmol) in 20 mL DCM. The flask was flushed with nitrogen, stoppered and stirred for 4 days at room temperature. The reaction mixture was then washed with saturated sodium bicarbonate (3×100 mL), the organic layer separated and dried over MgSO₄. The solution was filtered, the solvent removed under reduced pressure and the product flash chromatographed (90/10 hexanes/ethyl acetate) to give 4-[2,4-dichlorophenyl]-5-[4-chlorophenyl]-2,6-bis(methylthio)pyrimidine. MPLC/ms: m/e=429 (m+1); $R_t$=5.12 min; $^1$H-NMR 500 mHZ (CDCl₃): δ 2.57 (s, 3H), 2.66 (s, 3H), 7.16-7.11 (m, 4H), 7.16-7.32 (m, 3H).

REFERENCE EXAMPLE 5

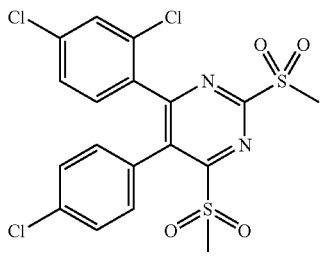

2,6-Bis(methylsulfonyl)-4-[2,4-dichlorophenyl]-5-[4-chlorophenyl]-pyrimidine

In a 250 mL round bottom flask fitted with a magnetic stirrer bar was added 2,4-bis(methylthio)-5-[4-chlorophenyl]-6-[2,4-dichlorophenyl]pyrimidine (Reference Example 4, 5.5 g, 12.8 mmol) and 100 mL DCM. The reaction flask was cooled in an ice bath and mCPBA (70%, 13.3 g, 58 mmol) was added portion wise over 10 minutes. The ice bath was removed and the reaction stirred overnight. The next day, the precipitated acid was filtered off and the precipitate was washed with 20 mL cold DCM. The organic layers were combined and washed with 1M NaHSO$_4$, (2×20 mL), then saturated NaHCO$_3$ (2×30 mL). The organic layer was dried over MgSO$_4$, filtered and the solvent removed under reduced pressure. The desired product precipitated out of solution and was washed with 80/20 hexanes/ethyl acetate. The mother liquor was saved for further recovery. HPLC/MS: m/e=493 (M+1); R$_f$=3.93 min; $^1$H-NMR 500 MHz (CDCl$_3$): δ 3.36 (s, 3H), 3.38 (s, 3H), 7.16-7.11 (m, 4H), 7.16-7.32 (m, 3H).

REFERENCE EXAMPLES 6 AND 7

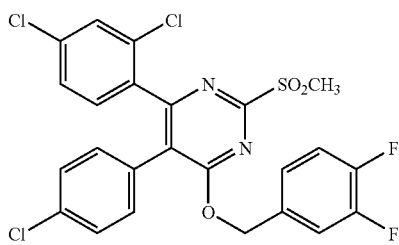

Reference Example 6
2-(Methylsulfonyl)-4-(3,4-difluorobenzyloxy)-5-(4-chlorophenyl)-6-(2,4-dichlorophenyl)pyrimidine

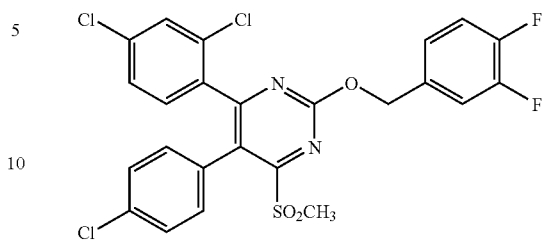

Reference Example 7
2-(3,4-Difluorobenzyloxy)-4-(methylsulfonyl)-5-(4-chlorophenyl)-6-(2,4-dichlorophenyl)pyrimidine 2-(Methylsulfonyl)-4-(3,4-difluorobenzyloxy)-5-(4-chlorophenyl)-6-(2,4-dichlorophenyl)pyrimidine and 2-(3,4-Difluorobenzyloxy)-4-(methylsulfonyl)-5-(4-chlorophenyl)-6-(2,4-dichlorophenyl)pyrimidine In a 50 mL round bottom flask fitted with a magnetic stirrer bar and rubber septum was added 20 mL anhydrous THF (Aldrich) and 2,4-bis(methyl-sulfonyl)-5-[4-chlorophenyl]-6-[2,4-dichlorophenyl]pyrimidine (Reference Example 5) (1.47 g, 3 mmol). The flask was flushed with nitrogen and cooled to −78° C. In a separate flask, also fitted with a magnetic stirrer bar and rubber septum, is added 10 mL anhydrous THF and 3,4-difluorobenzyl alcohol (345 μL, 3.0 mmol). This flask was flushed with nitrogen and cooled to 0° C. Then n-butyl lithium (1.5 mL, 3 mmol) (Aldrich, 2M solution in hexane) was added via syringe and the solution stirred for several minutes. The lithium alkoxide solution was then withdrawn by syringe and slowly added to the first reaction flask at a rate such that the solution temperature does not rise above −60° C. The solution was stirred at −78° C. for 1 h, slowly warmed to room temperature (90 minutes), quenched with saturated sodium bicarbonate and the reaction products extracted with DCM. The organic layer was dried over MgSO$_4$, filtered, and the solvent removed under reduced pressure. Flash column chromatography on silica gel (eluted with 85/15 hexanes/ethyl acetate) afforded a higher Rf product and a lesser quantity of a lower Rf product. Both gave MS: m/e=555 (M$^+$+1). The higher Rf product (TLC), which does not show an NOE effect, is 2-(3,4-difluorobenzyloxy)-4-(methylsulfonyl)-5-(4-chlorophenyl)-6-(2,4-dichloro-phenyl) pyrimidine (Reference Example 7): MS: m/e=555 (M$^+$+1); $^1$H-NMR 500 MHz (CDCl$_3$): δ 3.36 (s, 3H), 5.49 (s, 2H), 6.99 (d, J=8 Hz, 1 H), 7.18-7.30 (m, 7H), 7.38 (m, 1H), 7.39 (d, J=2 Hz, 1H).

By difference NOE (a strong NOE between the benzylic protons and the ortho hydrogen on 5-(4-chlorophenyl) ring on the pyrimidine), we determined that the lower Rf product (TLC) is 2-(methylsulfonyl)-4-(3,4-difluorobenzyloxy)-5-(4-chlorophenyl)-6-(2,4-dichlorophenyl)pyrimidine (Reference Example 6): MS: m/e=555 (M$^+$+1); $^1$H-NMR 500 MHz (CDCl$_3$): δ 3.40 (s, 3H), 5.57 (s, 2H), 7.07-7.11 (m, 3H), 7.18-7.30 (m, 6H), 7.39 (d, J=2 Hz, 1H).

In general, the 2-(alkyl, alkoxy, aryloxy, arylalkoxy or amino)-4-(methylsulfonyl)-5-(4-chlorophenyl)-6-(2,4-dichlorophenyl)pyrimidines were the higher Rf product while almost all of the 2-(methylsulfonyl)-4-(alkyl, alkoxy, aryloxy, arylalkoxy or amino)-5-(4-chlorophenyl)-6-(2,4-dichlorophenyl)pyrimidines proved to be the lower Rf product of reaction in the nucleophilic substitution reactions on the bis-methylsulfonyl pyrimidine (Reference Example 5). Within the group of 2-(alkyl, alkoxy, aryloxy, arylalkoxy or amino)-4-(methylsulfonyl)-5-(4-chlorophenyl)-6-(2,4-dichlorophenyl)pyrimidines, there are observed similar shifts and splitting patterns in the aromatic region of the $^1$H-NMR's. The 2-(methylsulfonyl)-4-(alkyl, alkoxy, aryloxy, arylalkoxy or amino)-5-(4-chlorophenyl)-6-(2,4-dichlorophenyl)pyrimidines displayed a distinctly different set of shifts and splitting patterns in the aromatic region of the $^1$H-NMR's. This observation facilitated the regiochemical assignments in the nucleophilic displacement reactions of Reference Example 5.

REFERENCE EXAMPLES 8 AND 9

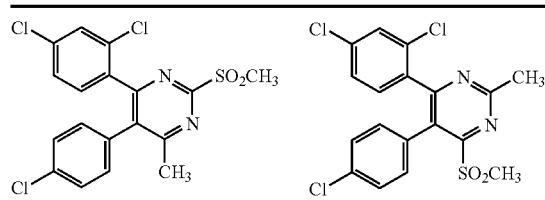

| Reference Example 8 | Reference Example 9 |
|---|---|
| 2-Methylsulfonyl-4-methyl-5-(4-chlorophenyl)-6-(2,4-dichlorophenyl)pyrimidine | 2-Methyl-4-methylsulfonyl-5-(4-chlorophenyl)-6-(2,4-dichlorophenyl)pyrimidine |

2-Methylsulfonyl-4-methyl-5-(4-chlorophenyl)-6-(2,4-dichlorophenyl)pyrimidine and 2-Methyl-4-methylsulfonyl-5-(4-chlorophenyl)-6-(2,4-dichlorophenyl)pyrimidine In a small round bottom flask fitted with a magnetic stirrer bar and rubber septum was added 2,4-bis(methylsulfonyl)-5-[4-chlorophenyl]-6-[2,4-dichlorophenyl]pyrimidine (Reference Example 5, 200 mg, 0.38 mmol) and 5 mL THF. The flask was flushed with nitrogen and cooled to −78° C. Then 1 equivalent of methyl magnesium bromide (390 μL, 1 M in ether (Aldrich)) was added to the solution via syringe. The solution was stirred 30 min, brought to room temperature and quenched with NHCl$_4$. Extraction with ether, drying over MgSO$_4$, filtering, reducing the solvent volume and flash chromatography (75/25 hexanes/ethyl acetate) afforded a higher Rf product and a lower Rf product. The $^1$H-NMR of 2-methyl-4-methylsulfonyl-5-(4-chlorophenyl)-6-(2,4-dichlorophenyl)pyrimidine is as follows: $^1$H-NMR 500 MHz (CDCl$_3$): δ 2.93 (s, 3H (2-methyl proton)), 3.40 (s, 3H (4-methylsulfonyl proton)), 7.02 (d, J=8 Hz, 1H), 7.18-7.20 (m, 3H), 7.21-7.29 (m, 2H), 7.39 (d, J=2 Hz, 1H). An difference NOE study was performed on the methyl protons attached to the pyrimidine ring for this isomer and no NOE signal was detected. The NMR of 2-methylsulfonyl-4-methyl-5-(4-chlorophenyl)-6-(2,4-dichlorophenyl)pyrimidine is as follows: $^1$H-NMR 500 MHz (CDCl$_3$): δ 2.57 (s, 3H (4-methyl proton)), 3.41 (s, 3H (2-methylsulfonyl proton)), 7.05 (m, J=9 Hz, 3H), 7.19 dd, J=8 Hz, J=2 Hz, 1H), 7.30-7.35 (m, 3H). A difference NOE study was performed on the methyl protons of this isomer attached to the pyrimidine ring and a strong NOE signal was observed with the ortho proton on the 5-(4 chlorophenyl) ring (δ=7.05).

REFERENCE EXAMPLE 10

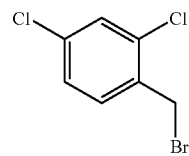

2,4-Dichlorobenzyl bromide

To a 500 mL round bottom flask fitted with a Teflon magnetic stirrer was added 2,4-dichlorotoluene (Aldrich) (14.4 g, 90 mmol) in 300 mL glacial acetic acid. To this was added sodium bromide (9.4 g, 92 mmol) and anhydrous ceric ammonium nitrate (100 g, 182 mmol) and the reaction mixture was heated at 80° C. for 2.5 h. The reaction mixture was then poured into 1000 g of ice and water. The slurry was extracted with ether (3×200 mL) and the combined ether layers were washed with saturated aqueous sodium bicarbonate. The organic layer was dried over MgSO$_4$, filtered, and the solvent removed under reduced pressure. The crude product was chromatographed by flash column chromatography on silica gel (eluted with 100% hexanes) and the desired product obtained. $^1$H-NMR 500 MHz (CDCl$_3$): δ 4.58 (s, 2H), 7.28 (m, 1H), 7.43 (m, 2H),

REFERENCE EXAMPLE 11

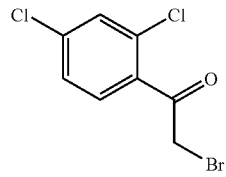

2-(O-Acetyl)-2',4'-dichlorophenyl ketone

Step A: 2-Bromo-2',4'-dichlorophenyl ketone

A solution of 2',4'-dichloroacetophenone (Lancaster)(100 g, 528 mmol) in 500 mL glacial acetic acid was poured into a 1 L round bottom flask filled with a large TEFLON coated stir bar. A pressure equalizing glass addition funnel was attached to the flask and bromine (85 g, 575 mmol) was added to it. The bromine was slowly added to the flask over a period of 1 h, and the temperature was maintained at 35-40° C. during the addition. Stirring was continued for an additional 1 h. Then the reaction mixture was stripped, under reduced pressure, of the acetic acid and the remaining product was taken up in 300 mL DCM and washed with saturated sodium bicarbonate (3×100 mL), saturated brine (2×100 mL) and dried over MgSO$_4$ before filtration. Removal of the solvent under reduced pressure gave essentially pure product (<5% of the dibromo derivative). HPLC/MS: m/e=269 (M$^+$+1); R$_t$=3.9 min.

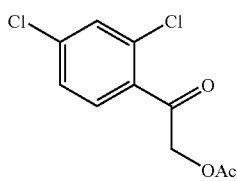

Step B: 2-(O-Acetyl)-2',4'-dichlorophenyl ketone

A solution of 2-bromo-2',4'-dichloroacetophenone (97 g, 254 mmol) in 400 mL reagent grade acetone was poured into a 1 L round bottom flask filled with anhydrous potassium acetate (50 g, 510 mmol). A reflux condenser was attached to the flask and the reaction mixture was refluxed for 2 h. The flask was then cooled to room temperature and the precipitate filtered off. The solvent was stripped off under reduced pressure and the product chromatographed in several batches with ethyl acetate/hexane (95/5 to 85/15 gradient). HPLC/MS: m/e=232 (M$^+$+1); R$_t$=3.3 min.

REFERENCE EXAMPLE 12

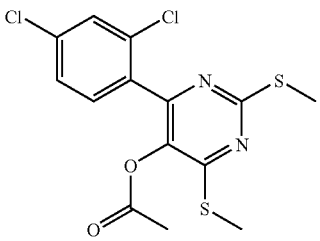

2,4-Bis(methylthio)-5-[O-acetyl]-6-[2,4-dichlorophenyl]pyrimidine

The title compound was synthesized by the procedure described in Reference Example 4. Triflic anhydride (20.0 g, 71 mmol) and methylthiocyanate (8.7 mL, 128 mmol) in anhydrous DCM (125 mL) was slowly added a solution of 2-(O-acetyl)-2',4'-dichlorophenyl ketone from Reference Example 11 (16 g, 64 mmol) in 20 mL DCM. The product was flash chromatographed (97/3 hexanes/ethyl acetate) to give the desired product. MPLC/ms: m/e=374 (m−1); R$^t$=4.3 min; $^1$H-NMR 500 mHZ (CDCl$_3$): δ 2.14 (s, 3H), 2.63 (s, 3H), 2.64 (s, 3H), 7.35 (s, 2H), 7.51 (s, 1H).

REFERENCE EXAMPLE 13

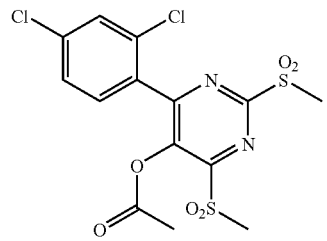

2,4-Bis(methylsulfonyl)-5-[O-acetyl]-6-[2,4-dichlorophenyl]pyrimidine

This compound was synthesized by the procedure described in Reference Example 5 where 2,4-bis(methylthio)-5-[O-acetyl]-6-[2,4-dichlorophenyl]pyrimidine (Reference Example 12 (3.1 g, 8.3 mmol) in 60 mL DCM was cooled in an ice bath and mCPBA (68%, 8.4 g, 34 mmol, 4.1 eq) was added portion wise over 30 minutes. The ice bath was removed and the reaction stirred overnight. The next day, the precipitated acid was filtered off. The organic layer was washed with 1M NaHSO$_4$, (2×20 mL), saturated NaHCO$_3$ (2×30 mL) and dried over MgSO$_4$. The solution was filtered and the solvent removed under reduced pressure. The desired product was used without further purification. HPLC R$_t$=3.93 min; $^1$H-NMR 500 MHz (CDCl$_3$): δ 2.25 (s, 3H), 3.46 (s, 3H), 3.49 (s, 3H), 7.42 (m, 2H), 7.61 (s, 3H).

REFERENCE EXAMPLE 14

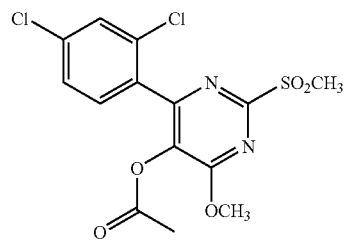

2-Methylsulfonyl-4-methoxy-5-(O-acetyl)-6-[2,4-dichlorophenyl]pyrimidine 2,4-Bis(methylsulfonyl)-5-(O-acetyl)-6-[2,4-dichlorophenyl]pyrimidine from Reference Example 13 (880 mg, 2.0 mmol) was reacted with 1.0 equivalent each of n-butyl lithium and methanol by the procedure described in Reference Example 6 and 7 to afford exclusively the title product. HPLC/MS: m/e=391 (M$^+$−1); R$_t$=3.42 min. $^1$H-NMR 500 MD (CDCl$_3$): δ 2.21 (s, 3H), 3.39 (s, 3H), 4.23 (s, 3H), 7.29 (d, J=8 Hz, 1H), 7.40 (d, J=8 Hz, 1H), 7.55 (d, J=2 Hz, 1H).

REFERENCE EXAMPLE 15

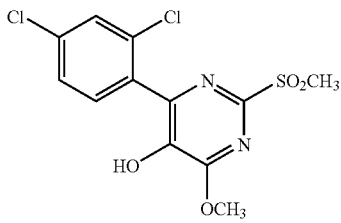

2-Methylsulfonyl-4-methoxy-5-hydroxy-6-[2,4-dichlorophenyl]pyrimidine

2-Methylsulfonyl-4-methoxy-5-(O-acetyl)-6-[2,4-dichlorophenyl]pyrimidine (290 mg, 0.77 mmol) from Reference Example 14 is dissolved in 3 mL THF. To this was added 1 mL water and 3 equivalents of 2 N NaOH. The reaction mixture was stirred at room temperature for 3 h. Then the reaction mixture was treated with 4 eq of 2 N HCl and the solvents removed under reduced pressure. The precipitate was resuspended in ice water and filtered. The product is insoluble in methanol or chloroform. HPLC/MS: m/e=350 (M$^+$−1); $R_t$=3.04 min.

REFERENCE EXAMPLE 16

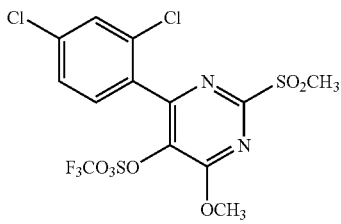

2-Methylsulfonyl-4-methoxy-5-trifluoromethansulfonyl-6-[2,4-dichlorophenyl]pyrimidine 2-Methylsulfonyl-4-methoxy-5-hydroxy-6-[2,4-dichlorophenyl]pyrimidine (700 mg, 2.0 mmol) prepared as described in Reference Example 15 was suspended in DCM (10 mL) in a round bottom flask fitted with a magnetic stir bar and rubber septum. The reaction mixture was cooled to 0° C. and pyridine (200 μL 5 mmol), followed by trifluoromethanesulfonyl anhydride (360 μL, 2.2 mmol) were added to the reaction mixture via syringe. The mixture was brought to room temperature, stirred for 2 h and worked up by adding 20 mL DCM and 20 mL ice cold 0.3 M NaOH. The organic layer was separated and subsequently washed with 1.0 M citric acid (2×5 mL). The organic layer was dried over MgSO$_4$, filtered and the solvent removed under reduced pressure. Flash chromatography (85/15 hexanes/ethyl acetate) afforded the desired product. HPLC $R_t$=3.91 min. $^1$H-NMR 500 MHz (CDCl$_3$): δ 2.21 (s, 3H), 3.39 (s, 3H), 4.23 (s, 3H), 7.32 (d, J=8 Hz, 1H), 7.39 (dd, J=8 Hz, J=2 Hz, 1H), 7.56 (d, J=2 Hz, 1H).

REFERENCE EXAMPLE 17

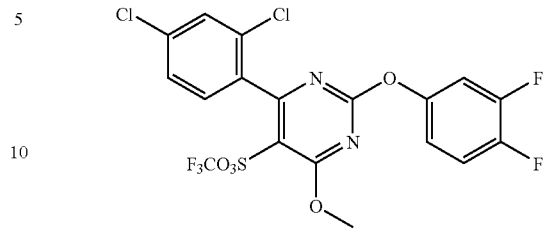

2-(3,4-Difluorophenoxy)-4-methoxy-5-trifluoromethansulfonyl-6-[2,4-dichlorophenyl]-pyrimidine 2-Methylsulfonyl-4-methoxy-5-trifluoromethansulfonyl-6-[2,4-dichlorophenyl]pyrimidine (93 mg, 0.19 mmol), prepared as described in Reference Example 16, was suspended in THF (500 μL) in a vial fitted with a magnetic stir bar and rubber septum. The reaction mixture was cooled to −78° and 3,4-difluorolithium phenoxide, prepared by adding n-butyl lithium (100 μL, 2M solution) to 3,4-difluorophenol (26 mg, 0.19 mmol) in 500 μL THF at 0° C., was added by syringe. The mixture was brought to room temperature, stirred for 1 h and worked up by adding 2 mL DCM and 1 mL saturated ammonium chloride. The organic layer was separated, dried over MgSO$_4$, filtered and the solvent removed under reduced pressure. HPLC analysis showed the product to be 95% pure and it was used in the next step without further purification. $R_t$=4.51 min. $^1$H-NMR 500 MHz (CDCl$_3$): δ 4.12 (s, 3H), 7.02 (m, 1H), 7.15 (m, 1H), 7.20-7.45 (m, 3H), 7.54 (d, J=2 Hz).

EXAMPLE 1

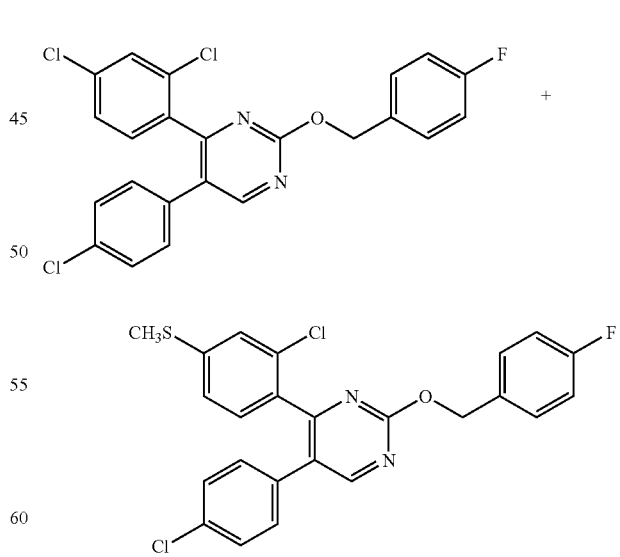

2-(4-Fluorobenzyloxy)-4-(2,4-dichlorophenyl)-5-(4-chlorophenyl)pyrimidine and 2-(4-Fluorobenzyloxy)-4-(2-chloro-4-methylthiophenyl)-5-(4-chlorophenyl)pyrimidine In a 5 mL round bottom flask fitted with a stir bar was added 1 mL DMF, 4-fluorobenzyl alcohol (65 uL, 0.6 mmol) and sodium hydride (60% in oil, 24 mg, 0.6 mmol). The solution was flushed with $N_2$, stoppered with a rubber septum and 2-methylthio-4-(2,4-dichlorophenyl)-5-(4-chlorophenyl)pyrimidine from Reference Example 3 (78 mg, 0.2 mmole) was added via syringe in 500 uL DMF over 90 min. The reaction was worked up with aqueous ammonium chloride, extracted with DCM and the organic layer was dried over $MgSO_4$. The solution was filtered and the volume reduced. Flash column chromatography on silica gel (eluted with 92/8 hexanes/ethyl acetate) afforded a major higher Rf and minor lower Rf product. The higher Rf product is 2-(4-fluorobenzyloxy)-4-(2,4-dichlorophenyl)-5-(4-chlorophenyl)pyrimidine. HPLC/MS: m/e=459 ($M^+$); $R_t$=4.65 min; $^1$H-NMR 500 MHz ($CDCl_3$): δ 5.49 (s, 2H), 7.0-7.12 (m, 4H), 7.22 (d J=8 Hz, 1H), 7.24-7.30 (m, 3H), 7.38 (s, 1H), 7.50 (m, 2H), 8.60 (s, 1H).

The minor lower Rf product is the by-product of the thiomethyl anion displacement of the 4-chloro substituent on the 4-(2,4-dichlorophenyl) ring, 2-(4-fluorobenzyloxy)-4-(2-chloro-4-methylthiophenyl)-5-(4-chlorophenyl)pyrimidine. HPLC/MS: m/e=471 ($M^+$); $R_t$=4.55 min; $^1$H-NMR 500 MHz ($CDCl_3$): δ 2.52 (s, 3H), 5.49 (s, 2H), 7.0-7.10 (m, 4H), 7.12-7.18 (m, 3H), 7.24-7.28 (m, 2H), 7.48-7.53 (m, 2H), 8.58 (s, 1H).

EXAMPLE 2

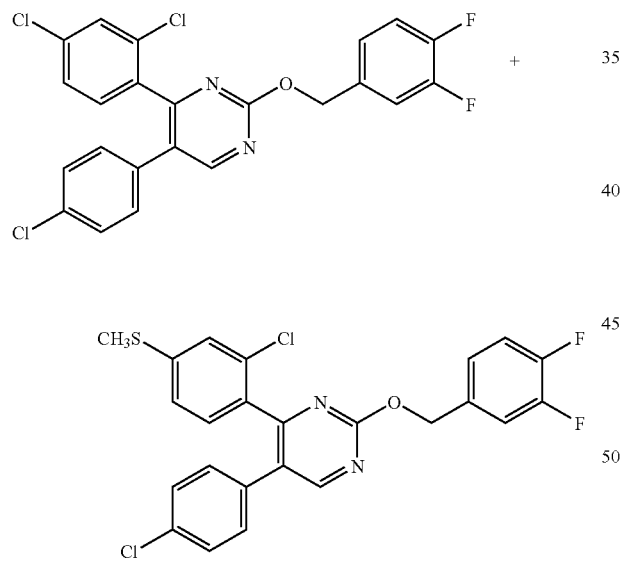

2-(3,4-Difluorobenzyloxy)-4-(2,4-dichlorophenyl)-5-(4-chlorophenyl)pyrimidine and 2-(3,4-Difluorobenzyloxy)-4-(2-chloro-4-methylthiophenyl)-5-(4-chlorophenyl)pyrimidine 2-Methylthio-4-(2,4-dichlorophenyl)-5-(4-chlorophenyl) pyrimidine (from Reference Example 3) was reacted with 3,4-difluorobenzyl alcohol according to the procedures described in Example 1 to afford 2-(3,4-difluorobenzyloxy)-4-(2,4-dichlorophenyl)-5-(4-chlorophenyl)pyrimidine as the higher Rf product (95/5 hexane/ethyl acetate TLC. HPLC/MS: m/e=478 ($M^+$); $R_t$=4.69 min; $^1$H-NMR 500 ($CDCl_3$): δ 5.47 (s, 2H), 7.07 (d, J=9 Hz, 1H), 7.18-7.22 (m, 3H), 7.22-7.30 (m, 5H), 7.40 (d, J=2 Hz, 1H), 8.62 (s, 1H). 2-(3,4-Difluorobenzyloxy)-4-(2-chloro-4-thiomethylphenyl)-5-(4-chlorophenyl)pyrimidine was obtained as the lower Rf product which was the by-product of the thiomethyl anion displacement of the 4-chloro substituent on the 4-(2,4-dichlorophenyl) ring. HPLC/MS: m/e=489 (M+1); $R_t$=4.59 min; $^1$H-NMR 500 MHz ($CDCl_3$): δ 2.52 (s, 3H), 5.47 (s, 2H), 7.0-7.10 (m, 2H), 7.15-7.21 (m, 3H), 7.24-7.30 (m, 3H), 7.40 (m, 2H), 8.60 (s, 1H).

EXAMPLE 3

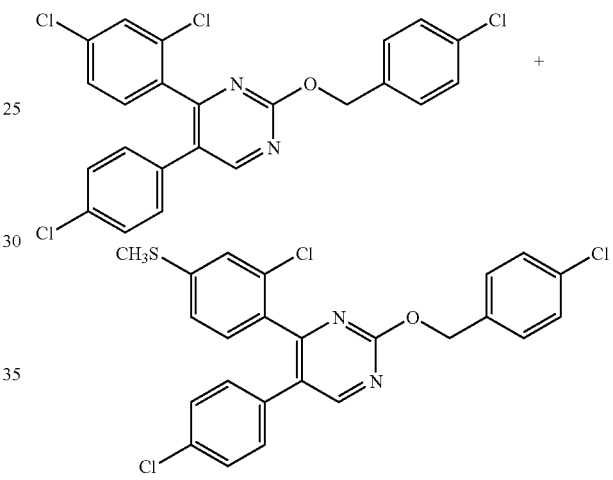

2-(4-Chlorobenzyloxy)-4-(2,4-dichlorophenyl)-5-(4-chlorophenyl)pyrimidine and 2-(4-Chlorobenzyloxy)-4-(2-chloro-4-methylthio-phenyl)-5-(4-chlorophenyl)pyrimidine 2-Methylthio-4-(2,4-dichlorophenyl)-5-(4-chlorophenyl) pyrimidine (from Reference Example 3) was reacted with 4-chlorobenzyl alcohol according to the procedures described in Example 1 to afford 2-(4-chlorobenzyloxy)-4-(2,4-dichlorophenyl)-5-(4-chlorophenyl)pyrimidine as the higher Rf product (95/5 hexane/ethyl acetate TLC). HPLC/MS: m/e=477 (M+1); $R_t$=4.91 min; $^1$H-NMR 500 MHz ($CDCl_3$): δ 5.50 (s, 2H), 7.02 (d, J=9 Hz, 2H), 7.22 (d, J=9 Hz, 1H), 7.22-7.30 (m, 4H), 7.40 (d, J=9 Hz, 2H), 7.50 (d, J=9 Hz, 2H), 8.62 (s, 1H). 2-(4-Chlorobenzyloxy)-4-(2-chloro-4-thiomethyl phenyl)-5-(4-chlorophenyl)pyrimidine was obtained as the lower Rf by-product of the thiomethyl anion displacement of the 4-chloro substituent on the 4-(2,4-dichlorophenyl) ring. HPLC/MS: m/e=489 (M+1); $R_t$=4.81 min; $^1$H-NMR 500 MHz ($CDCl_3$): δ 2.52 (s, 3H), 5.50 (s, 2H), 7.03 (m, 2H), 7.10-7.20 (m, 2H), 7.24-7.30 (m, 3H), 7.38 (d, J=9 Hz, 2H), 7.50 (d, J=9 Hz, 2H), 8.60 (s,1H).

EXAMPLE 4

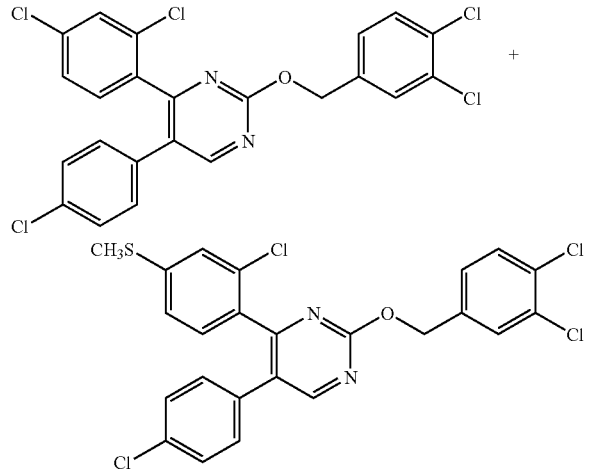

2-(3,4-Dichlorobenzyloxy)-4-(2,4-dichlorophenyl)-
5-(4-chlorophenyl)pyrimidine and 2-(3,4-Dichlo-
robenzyloxy)-4-(2-chloro-4-methylthio-phenyl)-5-
(4-chlorophenyl)pyrimidine 2-Methylthio-4-(2,4-dichlorophenyl)-5-(4-chlorophenyl) pyrimidine (from Reference Example 3) was reacted with 3,4-dichlorobenzyl alcohol according to the procedures described in Example 1 to afford 2-(3,4-dichlorobenzyloxy)-4-(2,4-dichlorophenyl)-5-(4-chlorophenyl)pyrimidine as the higher Rf product (95/5 hexane/ethyl acetate TLC). HPLC/MS: m/e=511 (M+); $R_t$=5.07 min; $^1$H-NMR 500 MHz (CDCl$_3$): δ 5.47 (s, 2H), 7.04 (d, J=9 Hz, 2H), 7.21 (d, J=9 Hz,1H), 7.22-7.30 (m, 3H), 7.38 (m, 2H), 7.43 (d, J=9 Hz, 1H), 7.66 (d, J=2 Hz,1H), 8.61 (s, 1H). 2-(3,4-Dichlorobenzyloxy)-4-(2-chloro-4-thiomethyl-phenyl)-5-(4-chlorophenyl)pyrimidine was obtained as the lower Rf product which was the by-product of the thiomethyl anion displacement of the 4-chloro substituent on the 4-(2,4-dichlorophenyl) ring. HPLC/MS: m/e=523 (M+1); $R_t$=4.93 min; $^1$H-NMR 500 MHz (CDCl$_3$): δ 2.52 (s, 3H), 5.48 (s, 2H), 7.0-7.10 (m, 1H), 7.15-7.21 (m, 2H), 7.24-7.30 (m, 3H), 7.40-7.60 (m, 3H), 7.68 (d, J=2 Hz,1H), 860 (s, 1H).

EXAMPLE 5

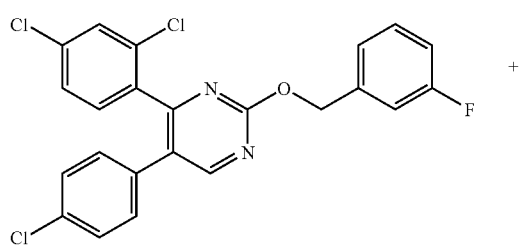

2-(3-Fluorobenzyloxy)-4-(2,4-dichlorophenyl)-5-(4-
chlorophenyl)pyrimidine and 2-(3-Fluorobenzy-
loxy)-4-(2-chloro-4-methylthio-phenyl)-5-(4-chlo-
rophenyl)pyrimidine 2-Methylthio-4-(2,4-dichlorophenyl)-5-(4-chlorophenyl) pyrimidine (from Reference Example 3) was reacted with 3-fluorobenzyl alcohol according to the procedures described in Example 1 to afford 2-(3-fluorobenzyloxy)-4-(2,4-dichlorophenyl)-5-(4-chlorophenyl)pyrimidine as the higher Rf product.(95/5 hexane/ethyl acetate TLC. HPLC/MS: 460 (M+); $R_t$=4.66 min; $^1$H-NMR 500 MHz (CDCl$_3$): δ 5.53 (s, 2H), 7.04 (d over m, J=9 Hz, 3H), 7.2-7.3 (m, 6H), 7.36-7.4 (m, 2H), 8.61 (s, 1H).

2-(3-Fluorobenzyloxy)-4-(2-chloro-4-thiomethylphenyl)-5-(4-chlorophenyl)pyrimidine was obtained as the lower Rf product which was the by-product of the thiomethyl anion displacement of the 4-chloro substituent on the 4-(2,4-dichlorophenyl) ring. HPLC/MS: m/e=471 (M+); $R_t$=4.56 min; $^1$H-NMR 500 MHz (CDCl$_3$): δ 2.52 (s, 3H), 5.53 (s, 2H), 7.0-7.10 (m, 3H), 7.15-7.21 (m, 2H), 7.21-7.30 (m, 4H), 7.31-7.4 (m, 2H), 8.60 (s, 1H).

EXAMPLE 6

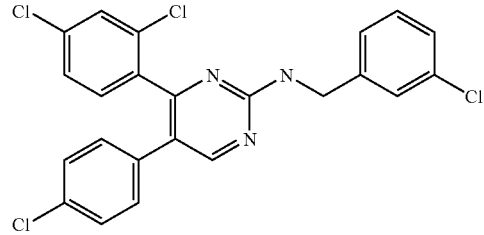

2-(3-Chlorobenzylamino)-4-(2,4-dichlorophenyl)-5-
(4-chlorophenyl)pyrimidine

Step A: 2-Methylsulfonyl-4-(2,4-dichlorophenyl)-5-
(4-chlorophenyl)pyrimidine

In a 25 mL round bottom flask fitted with a stir bar was added 2-methylthio-4-(2,4-dichlorophenyl)-5-(4-chlorophenyl)pyrimidine (Reference Example 3) (762 mg, 2 mmol) and 10 mL DCM. The flask was cooled to 0° and a slight excess of m-chloroperbenzoic acid (70%) (1.0 g, 4 mmol) was slowly added and stirred overnight at room temperature. The reaction was worked up by adding 1.0M sodium bisulfite (3 mL), 25 mL more of DCM and the reaction was stirred vigorously to destroy any excess peracid. After washing with 1.0 M sodium bicarbonate, the DCM layer was dried over MgSO$_4$. Filtering the mixture and reducing the solvent volume under reduced pressure gave the desired product which was 97% pure by LC. This was used without further purification. HPLC/MS: m/e=415 (M$^+$); R$_t$=3.68 min; $^1$H-NMR 500 MHz (CDCl$_3$): δ 3.46 (s, 3H), 7.08 (d, J=9 Hz, 2H), 7.31-7.4 (m, 5H), 9.00 (s, 1H).

Step B: 2-(3-Chlorobenzylamino)-4-(2,4-dichlorophenyl)-5-(4-chlorophenyl)pyrimidine To a 5 mL round bottom flask fitted with a stirrer bar and rubber septum was added 1 mL DMF and 2-methylsulfonyl-4-(2,4-dichlorophenyl)-5-(4-chlorophenyl)pyrimidine (103 mg, 0.2 mmol) from Step A. Then 3-chlorobenzyl amine (2 eq, 50 μL, 0.4 mmol) was added vial syringe and the mixture heated at 100° C. for 4 h. HPLC/MS, showed that the starting material had been converted to the desired product. The product was extracted from 10 mL water with 20 mL ether, dried over MgSO$_4$, filtered and the solvent removed under reduced pressure. Flash column chromatography on silica gel (eluted with 92/8 hexanes/ethyl acetate) afforded the desired product. HPLC/MS: m/e=476 (M+1); R$_t$=4.70 min; $^1$H-NMR 500 MHz (CDCl$_3$): δ 5.46 (s, 2H), 7.08 (d, J=9 Hz, 2H), 7.31-7.4 (m, 5H), 7.41-7.53 (m, 4H), 9.00 (s, 1H).

EXAMPLE 7

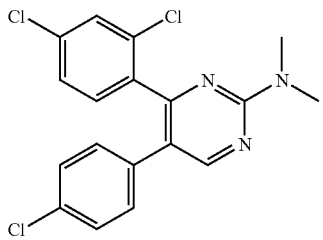

2-(N,N-Dimethylamino)-4-(2,4-dichlorophenyl)-5-(4-chlorophenyl)pyrimidine

To a 25 mL thick glass wall pressure tube was added a stirrer bar, 4 mL DMF and 2-methylsulfonyl-4-(2,4-dichlorophenyl)-5-(4-chlorophenyl)pyrimidine (42 mg 0.1 mmol). Then excess dimethylamine in ether (2M) was added, the tube sealed and heated at 100° C. for 18 h. The solvents were removed under high vacuum, and product was obtained. HPLC/MS: m/e=379 (M+1); R$_t$=3.79 min; $^1$H-NMR 500 MHz (CDCl$_3$): δ 3.18 (s, 6H), 7.40 (d, J=9 Hz, 1H), 7.5-7.6 (m, 3H), 7.8 (m, 2H), 8.20 (s, 1H).

EXAMPLE 8

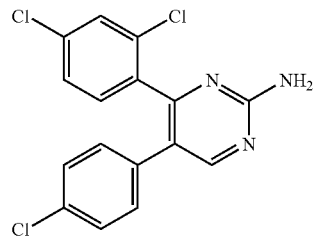

2-Amino-4-(2,4-dichlorophenyl)-5-(4-chlorophenyl)pyrimidine

In a 75 mL stainless steel pressure vessel was added 5 mL DMF and 2-methylsulfonyl-4-(2,4-dichlorophenyl)-5-(4-chlorophenyl)pyrimidine (420 mg, 1.0 mmol). Then excess ammonia gas was introduced into the vessel, and the vessel was sealed with a stainless steel nut. The vessel was heated at 120° C. for 18 h. The solvent was removed under high vacuum and product was obtained. HPLC/MS: m/e=351 (M+1); R$_t$=3.42 min; $^1$H-NMR 500 MHz (CDCl$_3$): δ 4.8 (bs, 2H), 7.42 (d, J=9 Hz, 1H), 7.5-7.6 (m, 3H), 7.8 (m, 2H), 8.18 (s, 1H).

EXAMPLE 9

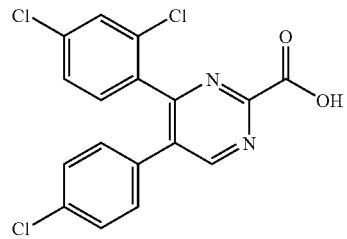

2-Carboxy-4-(2,4-dichlorophenyl)-5-(4-chlorophenyl)pyrimidine

Step A: 2-Cyano-4-(2,4-dichlorophenyl)-5-(4-chlorophenyl)pyrimidine

To a 25 mL round bottom flask fitted with a stirrer bar and rubber septum was added 2-methylsulfonyl-4-(2,4-dichlorophenyl)-5-(4-chlorophenyl)pyrimidine (1.45 g, 3.5 mmol) and 10 mL DCM. The solution was cooled to 0° C. and tetra-N-butyl ammonium cyanide (1.9 g, 7.0 mmol) was added portion-wise. Within 10 minutes, no starting material was seen. The reaction mixture was worked up with 2×10 mL water and the aqueous layer was disposed of in the toxic waste container. The organic layer was dried over MgSO$_4$, filtered and the solvent was removed under reduced pressure. The crude product was chromatographed by flash column chromatography on silica gel (eluted with 95/5 hexanes/ethyl acetate) to give the desired product. HPLC/MS: m/e=367 (M+7). $R_t$=4.13 min; $^1$H-NMR 500 MHz (CDCl$_3$): δ 7.10 (d, J=9 Hz, 2H), 7.3-7.41 (m, 4H), 8.92 (s, 1H).

Step B: 2-Carboxy-4-(2,4-dichlorophenyl)-5-(4-chlorophenyl)pyrimidine

To a 25 mL round bottom flask fitted with a stirrer bar and rubber septum was added 2-cyano-4-(2,4-dichlorophenyl)-5-(4-chlorophenyl)pyrimidine (800 mg, 2.2 mmol) and 3 mL concentrated sulfuric acid. The mixture was heated at 80° C. for 1 h. By LC/MS, the material was converted to the carboxamide HPLC/MS: m/e=378 (M$^+$). $R_t$=3.25 min. Further heating at 120° C. for 3 h gave clean conversion of the amide intermediate to the carboxylic acid. The reaction mixture was poured into ice water and the product was extracted with DCM. No further purification was necessary. HPLC/MS: m/e=335 (M$^+$-CO$_2$). $R_t$=3.74; $^1$H-NMR 500 MHz (CDCl$_3$): δ 7.10 (d, J=9 Hz, 2H), 7.3-7.41 (m, 4H), 8.92 (bs, 1H), 9.38 (bs, 1H). For comparison purposes, treatment of 2-cyano-4-(2,4-dichlorophenyl)-5-(4-chlorophenyl)pyrimidine in water with KOH gave 2-hydroxy-4-(2,4-dichlorophenyl)-5-(4-chlorophenyl)pyrimidine (HPLC/MS: m/e=351 (M$^+$). $R_t$=2.90.

EXAMPLE 10

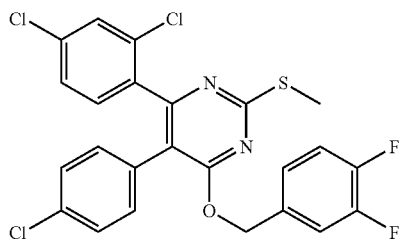

2-Methylthio-4-(3,4-difluorobenzyloxy)-5-(4-chlorophenyl)-6-(2,4-dichlorophenyl)pyrimidine To a round bottom flask fitted with a magnetic stir bar and rubber septum was added 1 mL DMF, 3,4-difluorobenzyl alcohol (23 µL, 0.120 mmol) and sodium hydride (60% in oil, 8 mg, 0.20 mmol). The flask was flushed with nitrogen, The product of Reference Example 4, (84 mg, 0.2 mmol) in 500 µL DMF was added by syringe. The reaction was heated at 100° C. for 1 hour and then poured into ice water and the product extracted with ether. The ether layer was dried (MgSO$_4$), filtered and the solvent removed under reduced pressure. Flash column chromatography on silica gel (eluted with 75/25 hexanes/ethyl acetate) gave starting material and the desired product. HPLC/MS: m/e=525 (M$^+$+1); $R_t$=4.97 min; $^1$H-NMR 500 MHz (CDCl$_3$): δ 2.60 (s, 3H), 4.69 (s, 2H), 7.09-7.23 (m, 9H), 7.38 (d, J=2 Hz, 1H).

EXAMPLE 11

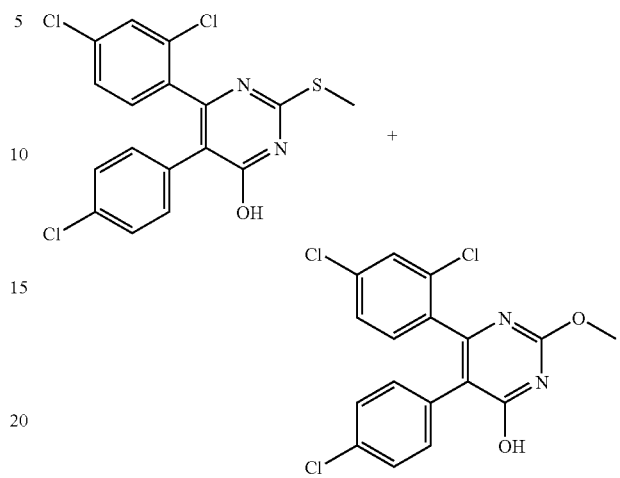

2-Methylthio-4-hydroxy-5-(4-chlorophenyl)-6-(2,4-dichlorophenyl)pyrimidine and 2-Methoxy-4-hydroxy-5-(4-chlorophenyl)-6-(2,4-dichlorophenyl)pyrimidine To a round bottom flask fitted with a magnetic stir bar and small reflux condenser was added 0.25 mL methanol, and sodium metal (23 mg, 1.0 mmol), and the flask was flushed with nitrogen. When the sodium dissolved, the starting material (Reference Example 4, 215 mg, 0.5 mmol) in 500 µL methanol was added by syringe. No reaction occurred after reflux for 1 h. The methanol was blown off with nitrogen and 2 mL DMF added to the mixture. After heating for at 80° C. for 5 h, two major products were observed by LC. The product eluting at Rt=3.49 min was 2-methoxy-4-hydroxy-5-(4-chlorophenyl)-6-(2,4-dichlorophenyl)pyrimidine, m/e=382 (M$^{+-}$1) and that at Rt=3.75 min was 2-methylthio-4-hydroxy-5-(4-chlorophenyl)-6-(2,4-dichlorophenyl)pyrimidine, m/e=399 (M$^+$+1). The reaction mixture was poured into aqueous NH$_4$Cl and the products precipitated out of solution. The precipitate was washed with water, dried under reduced pressure and re-dissolved in DCM. Soon thereafter, a precipitate fell out of this organic layer and was filtered off. By TLC (75/25 hexanes/ethyl acetate-Rf=0.15) and LC/MS, this product is 2-methylthio-4-hydroxy-5-(4-chlorophenyl)-6-(2,4-dichlorophenyl)pyrimidine (78 mg); m/e=399 (M$^+$+1). Rt=3.75 min; $^1$H-NMR 500 MHz (CDCl$_3$): δ 2.58 (s, 3H), 7.08-7.23 (m, 6H), 7.37 (d, J=2 Hz, 1H).

The organic filtrate was chromatographed (65/35 hexanes/ethyl acetate) and 2-methoxy-4-hydroxy-5-(4-chlorophenyl)-6-(2,4-dichlorophenyl)pyrimidine was isolated: m/e=382 (M$^+$−1). Rt=3.49 min; $^1$H-NMR 500 MHz (CDCl$_3$): δ 4.0 (s, 3H), 7.04-7.23 (m, 6H), 7.37 (d, J=2 Hz, 1H).

EXAMPLE 12

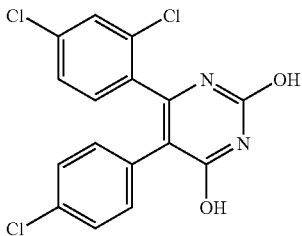

2,4-Dihydroxy-5-(4-chlorophenyl)-6-(2,4-dichlorophenyl)pyrimidine

To a 10 mL round bottom flask fitted with a magnetic stirrer bar was added 2-methylthio-4-hydroxy-5-(4-chlorophenyl)-6-(2,4-dichlorophenyl)pyrimidine from Example 11 (40 mg, 0.1 mmol) and 1.0 mL DCM. The reaction flask was cooled in an ice bath and mCPBA (70%, 50mg, 0.22 mmol) was added all at once. After 2 h, two new products were observed by LC. The product eluting at $R_t$=3.38 min was 2-methylsulfonyl-4-hydroxy-5-(4-chlorophenyl)-6-(2, 4-dichlorophenyl)pyrimidine, m/e=431 ($M^+$+1) and that at $R_t$=2.91 min is 2,4-dihydroxy-5-(4-chlorophenyl)-6-(2,4-dichlorophenyl) pyrimidine: m/e=367 ($M^+$). The mixture was poured into 2 N NaOH and heated briefly. The precipitate that formed was filtered, washed with water and dried under reduced pressure. The title product was recovered. m/e=367 ($M^+$). Rt=2.91 min; $^1$H-NMR 500 MHz (CDCl$_3$): δ 6.98 (d, J=8 Hz, 2H), 7.08 (d, J=8 Hz, 1H), 7.17 (d, J=8 Hz, 3H), 7.38 (d, J=2 Hz, 1H), 9.8 (bs, 1H), 10.1 (bs 1H).

EXAMPLE 13

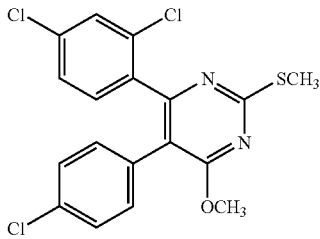

2-Methylthio-4-methoxy-5-(4-chlorophenyl)-6-(2,4-dichlorophenyl)pyrimidine

To a round bottom flask fitted with a magnetic stir bar and small reflux condenser was added 0.25 mL methanol, sodium metal (23 mg, 1.0 mmol). The flask was flushed with nitrogen. When the sodium dissolved, 2,4-bis(methylthio)-5-[4-chlorophenyl]-6-[2,4-dichlorophenyl]-pyrimidine (Reference Example 4, 215 mg, 0.5 mmol) in 500 μL methanol was added by syringe. The methanol was removed under high vacuum and 2 mL scrupulously dried DMF (15X sieve and 3A sieve, respectively) added to the mixture. The mixture was stirred for 5 h, quenched in aqueous NH$_4$Cl and immediately extracted with ether. Starting material and product were observed by LC. The organic layer was dried over MgSO$_4$ and filtered. The solvent removed under reduced pressure. Flash column chromatography on silica gel (eluted with 98/2 hexanes/ethyl acetate) gave pure product and mixed starting material/product fraction. The title compound eluted by LC at Rt=4.62 min, m/e=313 ($M^+$+1). $^1$H-NMR 500 MHz (CDCl$_3$): δ 2.64 (s, 3H), 4.05 (s, 3M), 7.08 (d, J=8 Hz, 2H), 7.13 (d, J=8 Hz, 1H), 7.19-7.24 (m, 3H), 7.34 (d, J=2 Hz, 1H).

EXAMPLE 14

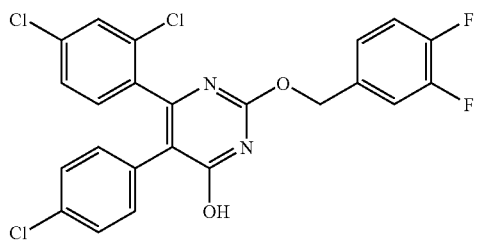

2-(3,4-Difluorobenyloxy)-4-hydroxy-5-(4-chlorophenyl)-6-(2,4-dichlorophenyl)pyrimidine Step A: 2-Methylsulfonyl-4-hydroxy-5-(4-chlorophenyl)-6-(2,4-dichlorophenyl)pyrimidine To a round bottom flask fitted with a magnetic stir bar and rubber septum was added 2 mL DMF, 6-[2,4-dichlorophenyl]-5-[4-chlorophenyl]-2,4-bis(methylsulfonyl)pyrimidine (Reference Example 5) (98 mg, 0.2 mmol) and potassium cyanide (15 mg, 0.22 mmol). The mixture was heated for 30 min at 80°. By LC, all starting material was consumed (Rt=3.59 min) and a new peak appeared (Rt=3.50 min). The molecular weight corresponded not to the cyano derivative, but to 2-methylsulfonyl-4-hydroxy-5-(4-chlorophenyl)-6-(2,4-dichlorophenyl)pyrimidine. (HPLC/MS: m/e=430 ($M^+$)) probably due to the fact that the solvent was not anhydrous.

Step B: 2-(3,4-Difluorobenyloxy)-4-hydroxy-5-(4-chlorophenyl)-6-(2,4-dichlorophenyl)pyrimidine To a round bottom flask fitted with a magnetic stir bar and rubber septum was added 2 mL DMF, 3,4-difluorobenzyl alcohol (14 μl, 0.11 mmol) and sodium hydride (60% in oil, 4.5 mg, 0.12 mmol). The flask was flushed with nitrogen and 2-methylsulfonyl-4-hydroxy-5-(4-chlorophenyl)-6-(2,4-dichlorophenyl)pyrimidine (from Step A) (43 mg, 0.1 mmol) in 500 μL DMF was added by syringe. After 1 h, the reaction was quenched with aqueous NH$_4$Cl. A precipitate fell out of solution and it was filtered, washed with water and dried under reduced pressure. HPLC/MS: m/e=494 ($M^+$); $R_t$=4.28 min; $^1$H-NMR 500 MHz (CDCl$_3$): δ 5.39 (s, 2H), 7.04 (d, J=9 Hz, 2H), 7.09 (d, J=9 Hz, 2H), 7.15-7.22 (m, 4H), 7.22-7.28 (m, 1H), 7.41 (d, J=2 Hz, 1H).

EXAMPLE 15

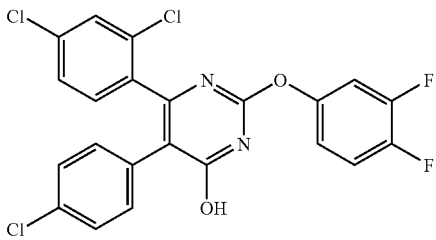

2-(3,4-Difluorolphenloxy)-4-hydroxy-5-(4-chlorophenyl)-6-(2,4-dichlorophenyl)pyrimidine To a round bottom flask fitted with a magnetic stir bar and rubber septum was added 1 mL DMF, 3,4-difluorophenol (28 mg, 0.2 mmol) and sodium hydride (60% in oil, 8 mg, 0.2 mmol). The flask was flushed with nitrogen and 2-methylsulfonyl-4-hydroxy-5-(4-chlorophenyl)-6-(2,4-dichlorophenyl)pyrimidine (Step A, Example 14) (43 mg, 0.1 mmol) in 500 μL DMF was added by syringe. The mixture was heated at 90° C. for 10 h. The reaction was poured into ice water and the product extracted with ether. The ether layer was dried (MgSO$_4$), filtered and the solvent removed under reduced pressure. Flash column chromatography on silica gel (eluted with 75/25 hexanes/ethyl acetate) gave desired product. (HPLC/MS: m/e=494 (M$^+$); R$_t$=4.01 min; $^1$H-NMR 500 MHz (CDCl$_3$): δ 6.94 (d, J=9 Hz, 1H), 7.0 (m, 1H), 7.08-7.22 (m, 7H), 7.34 (d, J=2 Hz, 1H).

EXAMPLE 16

2,4-bis-(3,4-Difluorobenyloxy)-5-(4-chlorophenyl)-6-(2,4-dichlorophenyl)pyrimidine To a round bottom flask fitted with a magnetic stir bar and rubber septum was added 10 mL DMF, 3,4-difluorobenzyl alcohol (130 μL, 1.0 mmol) and sodium hydride (60% in oil, 20 mg, 1.0 mmol). The flask was cooled to 0° C., flushed with nitrogen and 2,4-bis(methylsulfonyl)-5-[4-chlorophenyl]-6-[2,4-dichloro-phenyl]-pyrimidine (Reference Example 5, 43 mg, 0.1 mmol) in 500 μL DMF was added by syringe. After 1 h, the reaction was warmed to room temperature and stirred overnight. The next day, the solution was quenched with aqueous NH$_4$Cl and extracted with ether. The ether layer was then washed with brine, the organic layer dried over MgSO$_4$, filtered and the solvent removed under reduced pressure. TLC (95/5 hexanes/ethyl acetate) showed two products. 2,4-bis-(3,4-Difluorobenyloxy)-5-(4-chlorophenyl)-6-(2,4-dichlorophenyl)pyrimidine is the higher R$_f$ material (R$_f$=0.5). The lower R$_f$ material was not identified. HPLC/MS: m/e=619 (M$^+$); R$_t$=5.07 min; $^1$H-NMR 500 MHz (CDCl$_3$): δ 5.42 (s, 2H), 5.44 (s, 2H), 7.04-7.10 (m, 3H), 7.11-7.15 (m, 8H), 7.41 (s, 2H).

In Examples 17-19, the procedure described in Example 16 was followed but with substitution of the appropriate sodium alkoxide (2 eq) for sodium-3,4-difluorobenzyloxide in the reaction with 2,4-bis(methylsulfonyl)-5-[4-chlorophenyl]-6-[2,4-dichlorophenyl]pyrimidine (Reference Example 5) to afford the following compounds:

EXAMPLE 17

2,4-Dimethoxy-5-(4-chlorophenyl)-6-(2,4-dichlorophenyl)pyrimidine

HPLC/MS: m/e=396 (M$^+$); R$_t$=4.28 min; $^1$H-NMR 500 MHz (CDCl$_3$): δ 4.04 (s, 3H), 4.12 (s, 3H), 7.06 (d, J=8 Hz, 2H), 7.12 (d, J=8 Hz, 1H), 7.18-7.24 (m, 3H), 7.34 (d, J=2 Hz, 1H).

EXAMPLE 18

2,4-Diethoxy-5-(4-chlorophenyl)-6-(2,4-dichlorophenyl)pyrimidine

HPLC/MS: m/e=424 (M$^+$); R$_t$=4.6 min; $^1$H-NMR 500 MHz (CDCl$_3$): δ 1.37 (t, J=7 Hz, 3H), 1.48 (t, J=7 Hz, 3H), 4.50 (m, 4H), 7.04 (d, J=8 Hz, 2H), 7.11 (d, J=8 Hz, 1H), 7.17-7.24 (m, 3H), 7.33 (d, J=2 Hz, 1H).

EXAMPLE 19

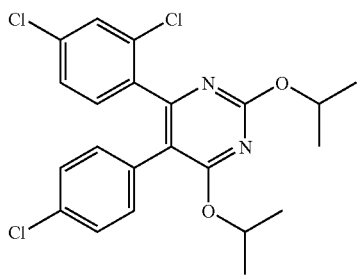

2,4-Diisopropoxy-5-(4-chlorophenyl)-6-(2,4-dichlorophenyl)pyrimidine

HPLC/MS: m/e=452 (M+); $R_t$=4.89 min; $^1$H-NMR 500 MHz (CDCl$_3$): δ 1.35 (d, J=6 Hz, 6H), 1.45 (d, J=6 Hz, 6H), 5.32 (m, 1H), 5.50 (m, 1H), 7.04 (d, J=8 Hz, 2H), 7.09 (d, J=8 Hz, 1H), 7.17-7.21 (m, 3H), 7.38 (d, J=2 Hz, 1H).

EXAMPLE 20

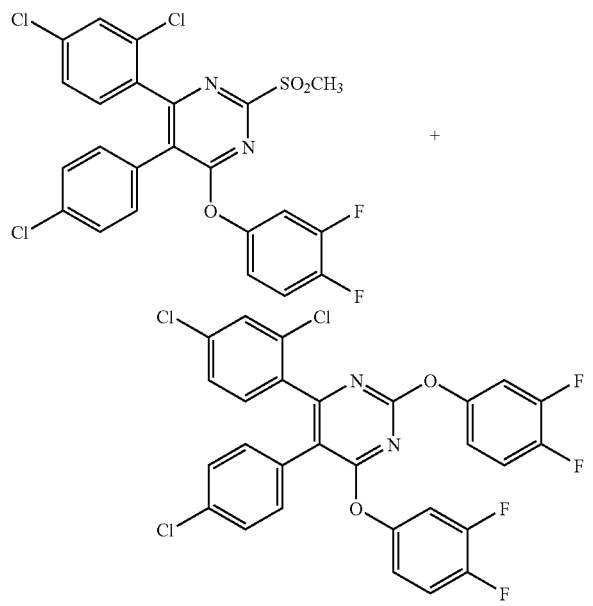

2-Methylsulfonyl-4-(3,4-difluorophenoxy)-5-(4-chlorophenyl)-6-(2,4-dichlorophenyl)pyrimidine and 2,4-bis(3,4-Difluorophenoxy)-5-(4-chlorophenyl)-6-(2,4-dichlorophenyl)pyrimidine Starting with 2,4-bis(methylsulfonyl)-5-[4-chlorophenyl]-6-[2,4dichlorophenyl]pyrimidine (Reference Compound 5), (124 mg, 0.25 mmol), the title compound was obtained by the same general procedure described in Example 10. Workup and flash column chromatography on silica gel (eluted with 75/25 hexanes/ethyl acetate) afforded 2-methylsulfonyl-4-(3,4-difluorophenoxy)-5-(4-chlorophenyl)-6-(2,4-dichlorophenyl)pyrimidine: HPLC/MS: m/e=543 (M++1)); $R_t$=4.33 min; $^1$H-NMR 500 MHz (CDCl$_3$): δ 3.27 (s, 3H), 7.0 (m, 1H), 7.1 (m, 1H), 7.20 (dd, J=8 Hz, J=1.6 Hz, 2H), 7.23-7.32 (m, 3H), 7.38 (m, 2H), 7.40 (d, J=2 Hz, 1H). 2,4-bis(3,4-difluorophenoxy)-5-(4-chlorophenyl)-6-(2,4-dichlorophenyl)pyrimidine was also isolated: HPLC/MS: m/e=592 (M+); $R_t$=4.89 min; $^1$H-NMR 500 MHz (CDCl$_3$): δ 6.87-6.90 (m, 2H), 7.0-7.08 (dm, 2H), 7.09-7.21 (m, 8H), 7.36 (d, J=8 Hz, 2H), 7.48 (d, J=2 Hz, 1H).

EXAMPLE 21

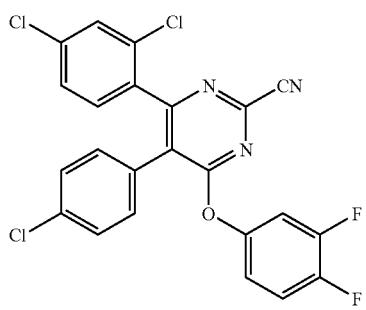

2-Cyano-4-(3,4-difluorophenoxy)-5-(4-chlorophenyl)-6-(2,4-dichlorophenyl)pyrimidine The product was obtained by treating 2-methylsulfonyl-4-(3,4-difluorophenoxy)-5-(4-chlorophenyl)-6-(2,4-dichlorophenyl)pyrimidine from Example 20 by the same general procedure described in Example 8, Step A. Workup and flash column chromatography on silica gel (eluted with 80/20 hexanes/ethyl acetate) afforded the title compound: HPLC $R_t$=4.15 min; $^1$H-NMR 500 MHz (CDCl$_3$): δ 6.58 (m, 1H), 6.70 (m, 1H), 7.10 (m, 4H), 7.23-7.32 (m, 2H), 7.38 (m, 2H).

EXAMPLE 22

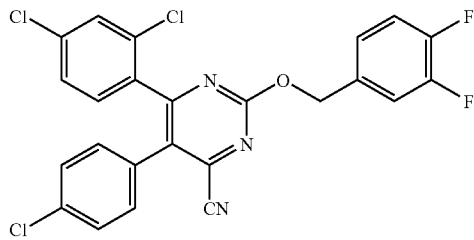

2-(3,4-Difluorobenzyloxy)-4-cyano-5-(4-chlorophenyl)-6-(2,4-dichlorophenyl)pyrimidine The title compound was obtained by treating 2-(3,4-difluorobenzyloxy)-4-(methylsulfonyl)-5-(4-chlorophenyl)-6-(2,4-dichlorophenyl)pyrimidine (Reference Example 7) compound, (80 mg, 0.14 mmol) by the same general procedure described in Example 8, Step A. Workup and flash column chromatography on silica gel (eluted with 80/20 hexanes/ethyl acetate) afforded the desired compound. HPLC $R_t$=4.71 min; ¹H-NMR 500 MHz (CDCl₃): δ 5.53 (s, 2H), 7.10-7.12 (d, J=8 Hz, 2H), 7.21-7.24 (m, 2H), 7.24-7.26 (m, 2H), 7.30-7.41 (m, 4H).

EXAMPLE 23

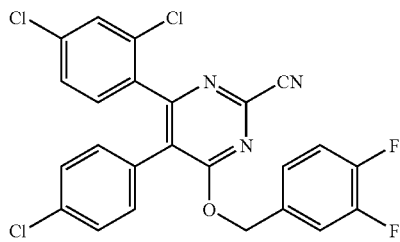

2-Cyano-4-(3,4-difluorobenzyloxy)-5-(4-chlorophenyl)-6-(2,4-dichlorophenyl)pyrimidine The title compound was obtained by treating 2-(methylsulfonyl)-4-(3,4-difluorobenzyloxy)-5-(4-chlorophenyl)-6-(2,4-dichlorophenyl)pyrimidine (Reference Example 6) compound, (55 mg, 0.11 mmol) by the same general procedure described in Example 8, Step A. Workup and flash column chromatography on silica gel (eluted with 80/20 hexanes/ethyl acetate) afforded desired product. ¹H-NMR 500 MHz (CDCl₃): δ 5.50 (s, 2H), 7.07-7.11 (d, J=8 Hz, 2H), 7.14-7.17 (d, J=8 Hz, 2H), 7.18-7.23 (m, 2H), 7.23-7.30 (m, 3H). 3.39 (d, J=2 Hz, 1H).

EXAMPLE 24

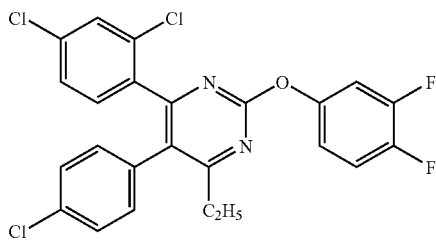

2-(3,4-Difluorophenoxy)-4-ethyl-5-(4-chlorophenyl)-6-(2,4-dichlorophenyl)pyrimidine The title compound is obtained by treating 2-methylsulfonyl-4-ethyl-5-(4-chlorophenyl)-6-(2,4-dichlorophenyl)pyrimidine (Reference Example 8, 37 mg, 0.09 mmol) with ethylmagnesium chloride by the general procedure described in Reference Examples 8 and 9. Workup and flash column chromatography on silica gel (eluted with 80/20 hexanes/ethyl acetate) affords title compound.

EXAMPLE 25

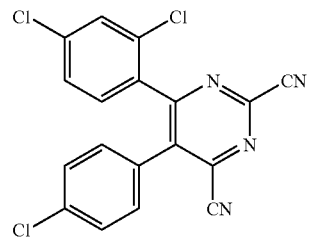

2,4-Bis(cyano)-5-(4-chlorophenyl)-6-(2,4-dichlorophenyl)pyrimidine

The title compound was obtained by treating 2,4-bis(methylsulfonyl)-5-[4-chlorophenyl]-6-[2,4-dichlorophenyl]pyrimidine (Reference Example 5, 100 mg, 0.19 mmol) by the same general procedure described in Example 9, Step A. Workup and flash column chromatography on silica gel (eluted with 85:15 hexanes:ethyl acetate) afforded the desired product. HPLC R$_t$=4.16 min; ¹H-NMR 500 MHz (CDCl₃): δ 7.20 (d, J=8 Hz, 1H), 7.22 (d, J=8 Hz, 2H), 7.37 (dd, J=20 Hz, J=2 Hz, 1H), 7.41 (m, 3H).

EXAMPLE 26

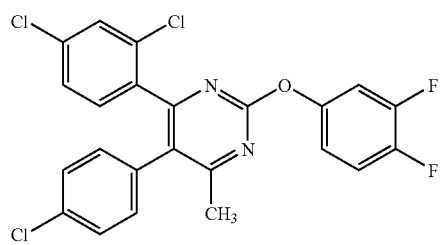

2-(3,4-Difluorophenoxy)-4-methyl-5-(4-chlorophenyl)-6-(2,4-dichlorophenyl)pyrimidine The title compound was obtained by treating 2-methylsulfonyl-4methyl-5-(4-chlorophenyl)-6-(2,4-dichlorophenyl)pyrimidine (Reference Example 8, 34 mg, 0.08 mmol) by the same general procedure described in Reference Examples 8 and 9. Workup and flash column chromatography on silica gel (eluted with 80/20 hexanes/ethyl acetate) afforded the desired product. HPLC/MS: m/e=478 (M⁺)

EXAMPLE 27

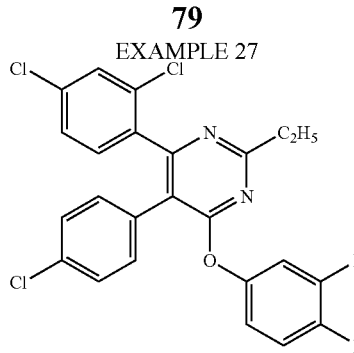

2-Ethyl 4-(3,4-difluorophenoxy)-5-(4-chlorophenyl)-6-(2,4-dichlorophenyl)pyrimidine The title compound was obtained by treating 2-methylsulfonyl-4-(3,4-difluorophenoxy)-5-(4-chlorophenyl)-6-(2,4-dichlorophenyl)pyrimidine (Example 20, 107 mg, 0.2 mmol) by the same general procedure described in Reference Examples 8 and 9 but substituting ethyl magnesium bromide for methyl magnesium bromide. Workup and flash column chromatography on silica gel (eluted with 85/15 hexanes/ethyl acetate) afforded the desired product. HPLC/MS: m/e=493 (M$^+$+1); R$_t$=4.90 min. $^1$H-NMR 500 MHz (CDCl$_3$): δ 1.31 (t, J=8 Hz, 3H), 2.91 (q, J=8 Hz, 2H), 6.95 (m, 1H), 7.12 (m, 4H), 7.19 (d, J=8 Hz, 1H), 7.20-7.30 (m, 3H), 7.38 (d, J=2 Hz, 1H).

EXAMPLE 28

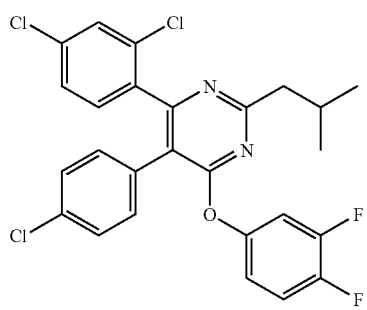

2-Isopropy-4-(3,4-difluorophenoxy)-5-(4-chlorophenyl)-6-(2,4-dichlorophenyl)pyrimidine The title compound was obtained by treating 2-methylsulfonyl -4-(3,4-difluorophenoxy)-5-(4-chlorophenyl)-6-(2,4-dichlorophenyl)pyrimidine (Example 20, 128 mg, 0.25 mmol) by the same general procedure described in Reference Examples 8 and 9 but substituting isobutyl magnesium bromide for methyl magnesium bromide. Workup and flash column chromatography on silica gel (eluted with 85/15 hexanes/ethyl acetate) afforded desired product. HPLC/MS: m/e=505 (M$^+$); R$_t$=5.02 min. $^1$H-NMR 500 MHz (CDCl$_3$): δ 1.28 (d, J=8 Hz, 6H), 3.15 (qn, J=8 Hz, 1H), 6.95 (m, 1H), 7.12 (m, 4H), 7.18-7.30 (m, 4H), 7.39 (d, J=2 Hz, 1H).

EXAMPLE 29

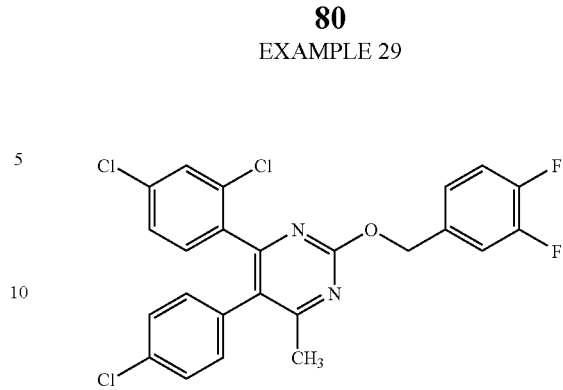

2-(3,4-Difluorobenzyloxy)-4-methyl-5-(4-chlorophenyl)-6-(2,4-dichlorophenyl)pyrimidine The title compound was obtained by treating 2-(3,4-difluorobenzyloxy)-4-(methylsulfonyl)-5-(4-chlorophenyl)-6-(2,4-dichlorophenyl)pyrimidine (Reference Example 7) (40 mg, 0.075 mmol) by the same general procedure described in Reference Examples 8 and 9. Workup and flash column chromatography on silica gel (eluted with 83/17 hexanes/ethyl acetate) afforded the desired product. HPLC/MS: m/e=493 (M$^+$+1); R$_t$=4.80 min. $^1$H-NMR 500 MHz (CDCl$_3$): δ 2.39 (s, 3H), 5.44 (s, 2H), 7.02 (m, 2H), 7.17 (m, 2H), 7.25 (m, 2H), 7.35-7.41 (m, 4H).

EXAMPLE 30

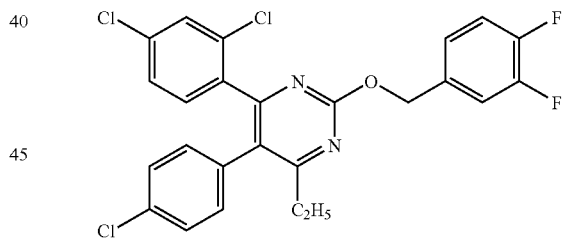

2-(3,4-Difluorobenzyloxy)-4-ethyl-5-(4-chlorophenyl)-6-(2,4-dichlorophenyl)pyrimidine The title compound was obtained by treating 2-(3,4-difluorobenzyloxy)-4-(methylsulfonyl)-5-(4-chlorophenyl)-6-(2,4-dichlorophenyl)pyrimidine (Reference Example 7) (40 mg, 0.075 mmol) by the same general procedure described in Reference Examples 8 and 9 but substituting ethyl magnesium bromide for methyl magnesium bromide. Workup and flash column chromatography on silica gel (eluted with 85/15 hexanes/ethyl acetate) afforded title compound. HPLC/MS: m/e=507 (M$^+$+1); R$_t$=4.97 min. $^1$H-NMR 500 MHz (CDCl$_3$): δ 1.24 (t, J=8 Hz), 2.63 (q, J=8 Hz), 5.46 (s, 2H), 7.02 (m, 2H), 7.17-7.21 (m, 5H), 7.25 (d, J=9 Hz, H), 7.38-7.42 (m,1H).

EXAMPLE 31

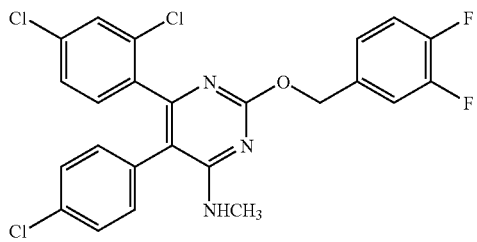

2-(3,4-Difluorobenzyloxy)-4-(N-methylamino)-5-(4-chlorophenyl)-6-(2,4-dichlorophenyl)pyrimidine

Step A: 2-(Methylsulfonyl)-4-(aminomethyl)-5-(4-chlorophenyl)-6-(2,4-dichlorophenyl)pyrimidine To a round bottom flask fitted with a magnetic stirrer bar and rubber septum was added 2,4-bis(methylsulfonyl)-5-[4-chlorophenyl]-6-[2,4-dichlorophenyl]-pyrimidine (Reference Example 5, Step A, 50 mg, 0.1 mmol), and 1 mL each of ethanol and acetonitrile. The mixture was cooled to 0° and methylamine (2 eq., 400 μL, 1M in THF) was added via syringe. The mixture was stirred for 1 h, the solvents removed under reduced pressure and the product chromatographed (77/23 hexanes/ethyl acetate) to give two products: a higher Rf product (unidentified) and 2-(3,4-difluorobenzyloxy)-4-(N-methylamino)-5-(4-chlorophenyl)-6-(2,4-dichlorophenyl)pyrimidine as the lower Rf product. HPLC/MS: m/e=442 (M$^+$−1); R$_t$=3.58 min. $^1$H-NMR 500 MHz (CDCl$_3$): δ 3.13 (d, J=5 Hz, 3H), 3.37 (s, 3H), 7.07 (d, J=8 Hz 1H), 7.10 (d, J=8 Hz, 2H), 7.18 (d, J=8 Hz, 1H), 7.38-7.40 (m, 3H).

Step B: 2-(3,4-Difluorobenzyloxy)-4-(N-methylamino)-5-(4-chlorophenyl)-6-(2,4-dichlorophenyl)pyrimidine The title compound was obtained by treating 2-(methylsulfonyl)-4-(aminomethyl)-5-(4-chlorophenyl)-6-(2,4-dichlorophenyl)pyrimidine (Example 31, Step A) (21 mg, 0.048 mmol) by the same general procedure described in Reference Examples 6 and 7. Workup and flash column chromatography on silica gel (eluted with 60/40 hexanes/ethyl acetate) afforded 2-(3,4-difluorobenzyloxy)-4-(N-methylamino)-5-(4-chlorophenyl)-6-(2,4-dichlorophenyl)pyrimidine. HPLC/MS: m/e=508 (M$^+$+1); R$_t$=3.50 min. $^1$H-NMR 500 MHz (CDCl$_3$): δ 3.02 (d, J=5 Hz, 3H), 4.83 (bd, J=2 Hz, 1H) 5.40 (s, 2H), 7.07-7.42 (m, 10H).

EXAMPLE 32

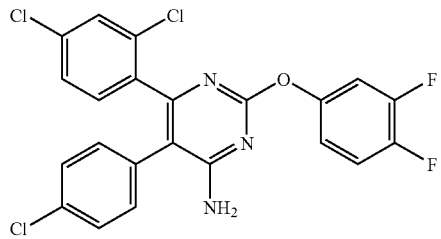

2-(3,4-Difluorophenoxy)-4-amino-5-(4-chlorophenyl)-6-(2,4-dichlorophenyl)pyrimidine

Step A: 2-(Methylsulfonyl)-4-(amino)-5-(4-chlorophenyl)-6-(2,4-dichlorophenyl)pyrimidine The title compound was obtained by treating 2,4-bis(methylsulfonyl)-5-[4-chlorophenyl]-6-[2,4-dichlorophenyl]pyrimidine (Reference Example 5, Step A, 325 mg, 0.70 mmol), by the same general procedure described in Example 31 (Step A) but using excess ammonia gas in methanol. Based on the relative retention times and the results from Example 31, the only product was 2-methylsulfonyl-4-(amino)-5-(4-chlorophenyl)-6-(2,4-dichlorophenyl)pyrimidine: HPLC/MS: m/e=430 (M$^+$+1); R$_t$=3.47 min. The solvent was removed and the crude reaction mixture used without further purification or characterization.

Step B: 2-(3,4-Difluorophenoxy)-4-(amino)-5-(4-chlorophenyl)-6-(2,4-dichlorophenyl)pyrimidine The title compound was obtained by treating 2-(methylsulfonyl)-4-(amino)-5-(4-chlorophenyl)-6-(2,4-dichlorophenyl)pyrimidine (Example 32, Step A,) with 3,4-difluorophenol by the same general procedure described in Reference Examples 6 and 7. Workup and flash column chromatography on silica gel (eluted with 80/20 hexanes/ethyl acetate) afforded starting material and 2-(3,4-difluorophenoxy)-4-(amino)-5-(4-chlorophenyl)-6-(2,4-dichlorophenyl)pyrimidine. HPLC/MS: m/e=480 (M$^+$+1); R$_t$=4.21 min. $^1$H-NMR 500 MHz (CDCl$_3$): δ 5.10 (bs, 2H), 7.0-7.10 (m, 2H), 7.11-7.25 (m, 4H), 7.15-7.19 (m, 4H).

EXAMPLE 33

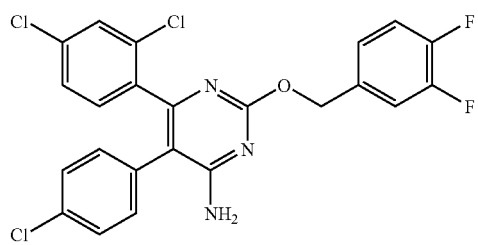

2-(3,4-Difluorobenzyloxy)-4-(amino)-5-(4-chlorophenyl)-6-(2,4-dichlorophenyl)pyrimidine The title compound obtained by treating 2-(methylsulfonyl)-4-(amino)-5-(4-chlorophenyl)-6-(2,4-dichlorophenyl)pyrimidine (Example 32, Step A,) with 3,4-difluorobenzyl alcohol by the same general procedure described in Reference Examples 6 and 7. Workup and flash column chromatography on silica gel (eluted with 80/20 hexanes/ethyl acetate) afforded 2-(3,4-difluorobenzyloxy)-4-(amino)-5-(4-chlorophenyl)-6-(2,4-dichlorophenyl)pyrimidine. HPLC/MS: m/e=494 (M$^+$+1); R$_t$=3.91 min. $^1$H-NMR 500 MHz (CDCl$_3$): δ 5.10 (bs, 2H), 5.38 (s, 2H), 7.0-7.10 (m, 2H), 7.11-7.23 (m, 6H), 7.15-7.19 (m, 2H).

EXAMPLE 34

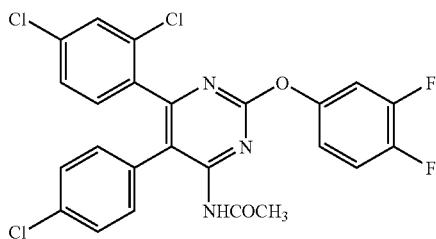

2-(3,4-Difluorophenoxy)-4-(acetylamino)-5-(4-chlorophenyl)-6-(2,4-dichlorophenyl)-pyrimidine To a round bottom flask fitted with a magnetic stirrer bar and rubber septum was added 2-(3,4-difluorophenoxy)-4-amino-5-(4-chlorophenyl)-6-(2,4-dichlorophenyl)pyrimidine (Example 32) (20 mg, 0.04 mmol), 500 μL acetic anhydride and 10 mg of 4-(N,N-dimethylamino)pyridine (DMAP). The mixture was heated at reflux for 10 minutes and then worked up by removing the solvent/reagent under high vacuum. Flash chromatography on silica gel (70/30 hexanes/ethyl acetate) afforded the desired product. $^1$H-NMR 500 MHz (CDCl$_3$): δ 2.41 (s, 3H), 7.06-7.67(m, 10H), 8.03 (bs, 1H).

EXAMPLE 35

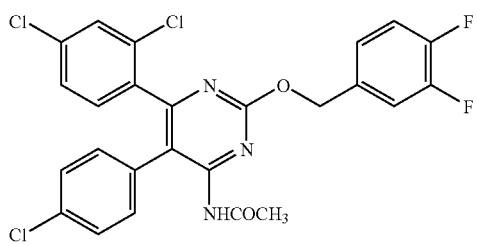

2-(3,4-Difluorobenzyloxy)-4-(acetylamino)-5-(4-chlorophenyl)-6-(2,4-dichlorophenyl)-pyrimidine The title compound was obtained by treating 2-(3,4-difluorobenzyloxy)-4-amino-5-(4-chlorophenyl)-6-(2,4-dichlorophenyl)pyrimidine (Example 33) with acetic anhydride and catalytic DMAP by the same general procedure described in Example 34. Workup and flash column chromatography on silica gel (eluted with 80/20 hexanes/ethyl acetate) afforded the desired product. HPLC/MS: m/e=536 (M$^+$+1); R$_t$=4.5 min. $^1$H-NMR 500 MHz (CDCl$_3$): δ 2.56 (s, 3H), 5.45 (s, 2H), 7.03-7.27 (m, 9H), 7.38 (d, J=2 Hz, 1H), 8.05 (bs, 1H).

EXAMPLE 36

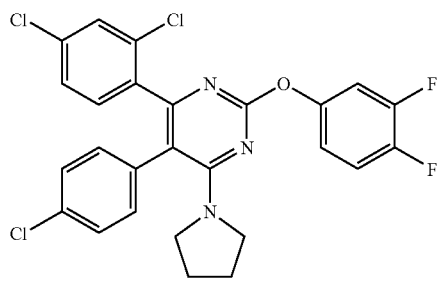

2-(3,4-Difluorophenoxy)-4-(N-pyrrolidinyl)-5-[4-chlorophenyl]-6-[2,4-dichlorophenyl]-pyrimidine Step A: 2-(Methylsulfonyl)-4-(N-pyrrolidinyl)-5-(4-chlorophenyl)-6-(2,4-dichlorophenyl)pyrimidine To a 5 mL round bottom flask fitted with a magnetic stir bar and rubber septum was added 1 mL dry hexane and pyrrolidine (25 μL, 0.3 mmol). The flask was cooled to 0°, flushed with nitrogen, and n-butyl lithium (150 μL, 0.3 mmol, (2M solution)) was added via syringe to the solution. To a separate round bottom flask fitted with a magnetic stir bar and rubber septum was added 2,4-bis(methylsulfonyl)-5-[4-chlorophenyl]-6-[2,4-dichlorophenyl]pyrimidine (Reference Example 5, 150 mg, 0.3 mmol) and 1 mL THF. This flask was cooled to −78° C. and the pyrrolidine lithium amide solution was added slowly to this flask via syringe. The reaction mixture was stirred 2 h at −78° C. then brought to room temperature. The reaction mixture was washed with saturated NaHCO$_3$, dried over MgSO$_4$, and filtered. The solvent removed under reduced pressure. Flash column chromatography on silica gel (eluted with 75/25 to 60/40 hexanes/ethyl acetate gradient) afforded higherRf material, identified by NMR as 2-(N-pyrrolidinyl)-4-(methylsulfonyl)-5-[4-chlorophenyl]-6-[2,4-dichlorophenyl]pyrimidine: HPLC/MS: m/e=482 (M−1); R$_t$=4.3 min; $^1$H-NMR 500 MHz (CDCl$_3$): δ 2.09 (bs, 4H), 3.34 (s, 3H), 3,67 (bd, J=6 Hz, 4H), 7.0 (d, J=8 Hz, 2H), 7.16 (d, J=8 Hz, 3H), 7.21 (d, J=8 Hz, 1H), 7.34 (d, J=2 Hz, 1H) and a lowerRf material identified as 2-(methylsulfonyl) 4-(N-pyrrolidinyl)-5-[4-chlorophenyl]-6-[2,4-dichlorophenyl]pyrimidine: HPLC/MS: m/e=482 (M−1); R$_t$=4.0 min; $^1$H-NMR 500 MHz (CDCl$_3$): δ 1.90 (bs, 4H), 2.8-3.6 (bs, 4H), 3.34 (s, 3H), 6.85 (d, J=8 Hz, 1H), 7.16 (d over bs, J=8 Hz, 3H), 7.21 (d, J=8 Hz, 2H7.34 (d, J=2 Hz, 1H).

Step B: 2-(3,4-Difluorophenoxy)-4-(N-pyrrolidinyl)-5-[4-chlorophenyl]-6-[2,4-dichlorophenyl]pyrimidine 2-(Methylsulfonyl)-4-(N-pyrrolidinyl)-5-(4-chlorophenyl)-6-(2,4-dichlorophenyl)pyrimidine (24 mg, 0.05 mmol)

was treated with 3,4-difluorophenol by the same general procedure described in Reference Examples 6 and 7. Workup and flash column chromatography on silica gel (eluted with 70/30 hexanes/ethyl acetate) afforded the title compound. HPLC/MS: m/e=534 (M$^+$+1); R$_t$=4.39 min. $^1$H-NMR 500 MHz (CDCl$_3$): δ 1.80 (bs, 4H), 3.2 (bs, 4H), 6.85-7.28 (m, 10H).

EXAMPLE 37

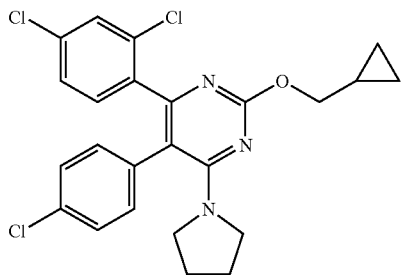

2-(Cyclopropylmethoxy)-4-(N-pyrrolidinyl)-5-[4-chlorophenyl]-6-[2,4-dichlorophenyl]-pyrimidine 2-(Methylsulfonyl)-4-(N-pyrrolidinyl)-5-(4-chlorophenyl)-6-(2,4-dichlorophenyl)pyrimidine (Example 36, Step A, 48 mg, 0.1 mmol) was treated with cyclopropyl methanol by the same general procedure described in Reference Examples 6 and 7. Workup and flash column chromatography on silica gel (eluted with 70/30 hexanes/ethyl acetate) afforded the title compound. HPLC: R$_t$=3.46 min. $^1$H-NMR 500 MHz (CDCl$_3$): δ 0.37 (d, J=4 Hz, 2H), 0.61 (dd, J=8 Hz, J=1 Hz, 2H), 1.38 (m, 1H), 1.80 (bs, 4H), 3.2 (bs, 4H), 4.17 (m, 1H), 4.25 (m, 1H), 6.85 (d, J=8 Hz, 1H), 7.08 (d over bs, J=8 Hz, 3H), 7.12 (d, J=8 Hz, 2H) 7.24 (d, J=2 Hz, 1H).

EXAMPLE 38

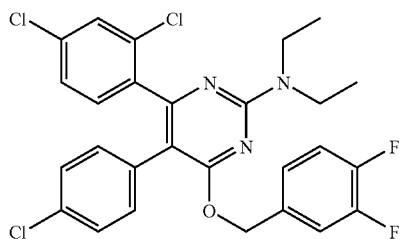

2-(N,N-Diethylamino)-4-(3,4-difluorobenzyloxy)-5-(4-chlorophenyl)-6-(2,4-dichlorophenyl)pyrimidin 2-(Methylsulfonyl)-4-(3,4-difluorobenzyloxy)-5-[4-chlorophenyl]-6-[2,4-dichlorophenyl]pyrimidine (Reference Example 6, 55 mg, 0.10 mmol) was treated with excess diethylamine in THF according to the same general procedure described in Example 31, Step A. Workup (solvent removal under reduced pressure) and flash column chromatography on silica gel (eluted with 87/13 hexanes/ethyl acetate) afforded the title compound. HPLC/MS: m/e=550 (M$^+$+1); R$_t$=4.48 min. $^1$H-NMR 500 MHz (CDCl$_3$): δ 1.23 (t, J=7 Hz, 3H), 3.65 (q, J=7 Hz, 2H), 5.39 (s, 2H), 7.04 (d, J=8 Hz, 2H), 7.08 (d, J=8 Hz, 2H), 7.13-7.22 (m, 5H), 7.34 (d, J=2 Hz, 1H).

EXAMPLE 39

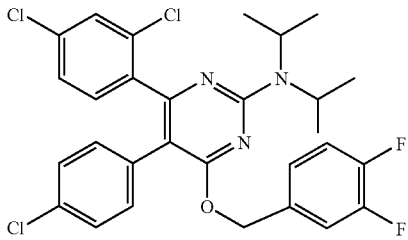

2-(N,N-Diisopropylamino)-4-(3,4-difluorobenzyloxy)-5-(4-chlorophenyl)-6-(2,4-dichlorophenyl) pyrimidine 2-(Methylsulfonyl)-4-(3,4-difluorobenzyloxy)-5-[4-chlorophenyl]-6-[2,4-dichlorophenyl]pyrimidine (Reference Example 6, 55 mg, 0.10 mmol) was reacted in neat diisopropyl amine heated at 150° C. overnight in a stainless steel pressure bottle by the general procedure described in Example 31, Step A. Workup (excess isopropyl amine removed under reduced pressure) and flash column chromatography on silica gel (eluted with 97/3 hexanes/ethyl acetate) afforded the title compound. HPLC: R$_t$=4.22 min. $^1$H-NMR 500 MHz (CDCl$_3$): δ 1.28 (d, J=6 Hz, 6H), 4.217 (q, J=6 Hz, 1H), 5.39 (s, 2H), 7.04 (d, J=8 Hz, 2H), 7.08-7.14 (m, J=2H), 7.17 (m, 5H), 7.31 (d, J=2 Hz, 1H).

EXAMPLE 40

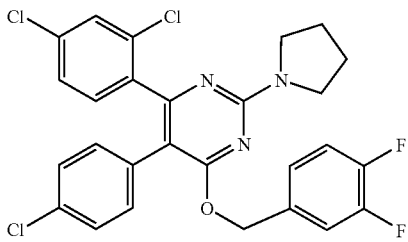

2(N-Pyrrolidinyl)-4-(3,4-difluorobenzyloxy)-5-(4-chlorophenyl)-6-(2,4-dichlorophenyl)pyrimidine 2-(Methylsulfonyl)-4-(3,4-difluorobenzyloxy)-5-[4-chlorophenyl]-6-[2,4-dichlorophenyl]pyrimidine (Reference Example 6, 55 mg, 0.10 mmol) was reacted in excess neat pyrrolidine at 80° C. overnight by the general procedure described in Example 31, Step A. Workup (solvent removal under reduced pressure) and flash column chromatography on silica gel (eluted with 92/8 hexanes/ethyl acetate) afforded the title compound. HPLC/MS: m/e=548 (M$^+$+1); R$_t$=4.76 min. $^1$H-NMR 500 MHz (CDCl$_3$): δ 2.02 (bs, J=4H), 3.63 (bs, 4H), 5.40 (s, 2H), 7.04 (d, J=8 Hz, 2H), 7.08-7.20 (m, 7H), 7.34 (d, J=2 Hz, 1H).

EXAMPLE 41

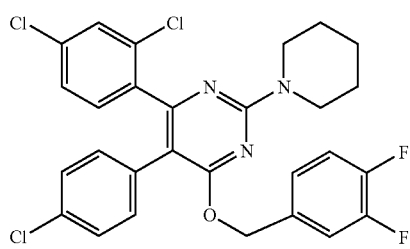

2-(N-Piperidyl)-4-(3,4-difluorobenzyloxy)-5-(4-chlorophenyl)-6-(2,4-dichlorophenyl)pyrimidine 2-(Methylsulfonyl)-4-(3,4-difluorobenzyloxy)-5-[4-chlorophenyl]-6-[2,4-dichlorophenyl]pyrimidine (Reference Example 6, 48 mg, 0.085 mmol) was reacted in excess neat piperidine at 80° C. overnight by the general procedure described in Example 31, Step A. Workup (solvent removal under reduced pressure, then toluene azeotrope) and flash column chromatography on silica gel (eluted with 90/10 hexanes/ethyl acetate) afforded the title compound. HPLC $R_f$=5.36 min. $^1$H-NMR 500 MHz (CDCl$_3$): δ 1.63 (m, 4H), 1.71 (m, 2H), (bs, 4H), 3.83 (m, 4H), 5.36 (s, 2), 7.02 (d, J=8 Hz, 2H), 7.08-7.20 (m, 7H), 7.31(d, J=1 Hz, 1H).

EXAMPLE 42

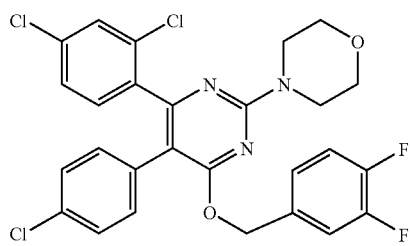

2-(N-Morpholinyl)-4-(3,4-difluorobenzyloxy)-5-(4-chlorophenyl)-6-(2,4-dichlorophenyl)pyrimidine 2-(Methylsulfonyl)-4-(3,4-difluorobenzyloxy)-5-[4-chlorophenyl]-6-[2,4-dichlorophenyl]pyrimidine (Reference Example 6, 48 mg, 0.085 mmol) was reacted in excess neat morpholine at 80° for 3 h by the general procedure described in Example 31, Step A. Workup (solvent removal under reduced pressure, then toluene azeotrope) and flash column chromatography on silica gel (eluted with 88/12 hexanes/ethyl acetate) afforded the title product. HPLC/MS: m/e=564 (M$^+$+1); $R_f$=5.00 min 1H-NMR 500 MHz (CDCl$_3$): δ 3.80 (m, 4H), 3.86 (m, 4H), 5.38 (s, 2H), 7.02 (d, J=8 Hz, 2H), 7.08-7.20 (m, 7H), 7.31(d, J=1 Hz, 1H).

EXAMPLE 43

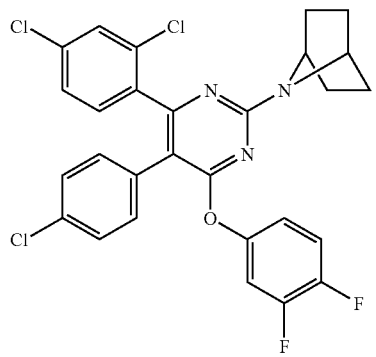

2-(7-N-[2.2.1]-Azabicycloheptyl)-4-(3,4-difluorophenoxy)-5-(4-chlorophenyl)-6-(2,4-dichlorophenyl)pyrimidine The title compound was obtained by treating 2-(methylsulfonyl)-4-(3,4-difluorophenoxy)-5-[4-chlorophenyl]-6-[2,4-dichlorophenyl]pyrimidine (Example 20, 55 mg, 0.1 mmol) was reacted with three equivalents of [2.2.1]-7-azabicycloheptane (39 mg, 0.3 mmol) (Tyger Chemical) in DMF at 125° C. for 3 h by the general procedure described in Example 31, Step A. Workup and flash column chromatography on silica gel (eluted with 93/7 hexanes/ethyl acetate) afforded the desired product. HPLC $R_f$=5.33 min $^1$H-NMR 500 MHz (CDCl$_3$): δ 1.47 (m, 4H), 1.79 (m, 4H), 4.4 (bs, 2H), 6.9 (m, 1H), 7.02-7.30 (m, 9H).

EXAMPLE 44

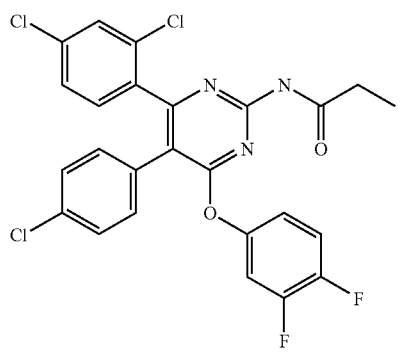

2-(N-n-Propionamide)-4-(3,4-difluorophenoxy)-5-(4-chlorophenyl)-6-(2,4-dichlorophenyl)-pyrimidine Step A: 2-(Amino)-4-(3,4-difluorophenoxy)-5-(4-chlorophenyl)-6-(2,4-dichlorophenyl)pyrimidine To a 5 mL round bottom flask fitted with a magnetic stir bar and rubber septum was added 1 mL THF and excess ammonia gas. The flask was cooled to 0°. 2-(methylsulfonyl)-4-(3,4- difluorophenoxy)-5-[4-chlorophenyl]-6-[2,4-dichlorophenyl]pyrimidine (Example 20, 270 mg, 0.5 mmol) was added. The reaction mixture was stirred overnight at room temperature. The reaction mixture was washed with saturated NaHCO$_3$, dried over MgSO$_4$, filtered and the solvent removed under reduced pressure. Flash column chromatography on silica gel (eluted with 60/40 hexanes/ethyl acetate) afforded 2-(amino)-4-(3,4-difluorophenoxy)-5-(4-chlorophenyl)-6-(2,4-dichlorophenyl)pyrimidine. HPLC/MS: m/e=480 (M+1); R$_t$=4.2 min; $^1$H-NMR 500 MHz (CD$_3$OD): δ 6.95 (m, 1H), 7.20 (m, 4H), 7.28 (m, 4H), 7.41 (d, J=2 Hz, 1H).

Step B: 2-(N-n-Propionamide)-4-(3,4-difluorophenoxy)-5-(4-chlorophenyl)-6-(2,4-dichlorophenyl)pyrimidine 2-(Amino)-4-(3,4-difluorophenoxy)-5-(4-chlorophenyl)-6-(2,4-dichlorophenyl)pyrimidine (Step A), (30 mg, 0.06 mmol) was reacted with propionic anhydride by the same general procedure described in Example 34. Workup and flash column chromatography on silica gel (eluted with 75/25 hexanes/ethyl acetate) afforded 2-(N-n-propionamide)-4-(3, 4-difluorophenoxy)-5-(4-chlorophenyl)-6-(2,4-dichlorophenyl)pyrimidine. HPLC/MS: m/e=480 (M$^+$-acetyl); R$_t$=4.54 min vs R$_t$=4.2 min for starting material. $^1$H-NMR 500 MHz (CDCl$_3$): δ 1.09 (t, J=9 Hz, 3H), 2.60 (q, J=9 Hz, 2H), 6.95 (m, 1H), 7.16 (m, 4H), 7.26 (m, 4H), 7.39 (d, J=2 Hz, 1H).

EXAMPLE 45

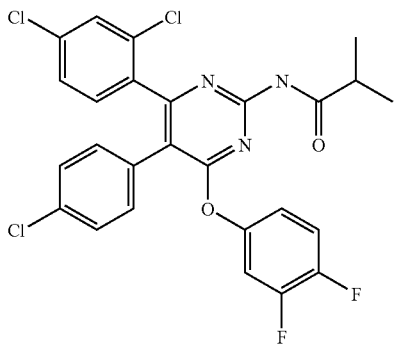

2-(N-(2-Methyl)propioamide)-4-(3,4-difluorophenoxy)-5-(4-chlorophenyl)-6-(2,4-dichlorophenyl)pyrimidine 2-(Amino)-4-(3,4-difluorophenoxy)-5-(4-chlorophenyl)-6-(2,4-dichlorophenyl)pyrimidine (Example 44, Step A), (25 mg, 0.05 mmol) was reacted with isobutyric anhydride by the same general procedure described in Example 34. Workup and flash column chromatography on silica gel (eluted with 75/25 hexanes/ethyl acetate) afforded the title compound. HPLC/MS: m/e=550 (M$^+$+1); R$_t$=4.59 min vs R$_t$=4.2 min for starting material. $^1$H-NMR 500 MHz (CDCl$_3$): δ 1.10 (d, J=7 Hz, 6H), 3.14 (m, J=7 Hz, 1H), 7.0 (m, 1H), 7.17 (m, 4H), 7.27 (m, 4H), 7.37 (d, J=2 Hz, 1H), 7.85 (bs, 1H (NH).

EXAMPLE 46

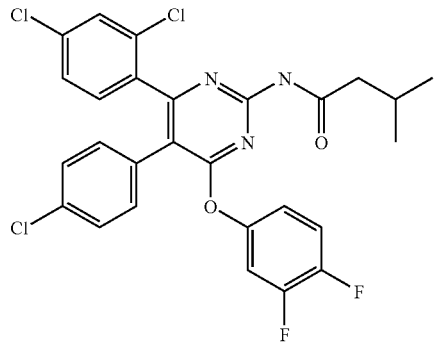

2-(N-(3-Methyl)butyramide)-4-(3,4-difluorophenoxy)-5-(4-chlorophenyl)-6-(2,4-dichlorophenyl)pyrimidine 2-(Amino)-4-(3,4-difluorophenoxy)-5-(4-chlorophenyl)-6-(2,4-dichlorophenyl)pyrimidine (Example 44, Step A), (25 mg, 0.05 mmol) was reacted with isoamyl anhydride by the general procedure described in Example 34. Workup and flash column chromatography on silica gel (eluted with 75/25 hexanes/ethyl acetate) afforded the title compound. HPLC/MS: m/e=562 (M$^+$-1); R$_t$=4.65 min vs R$_t$=4.2 min for starting material. $^1$H-NMR 500 MHz (CDCl$_3$): δ 0.89 (d, J=7 Hz, 3H), 1.0 (d, J=7 Hz, 3H), 2.17 (m, J=7 Hz, 1H), 2.24 (d, J=7 Hz, 1H), 2.47 (d, J=7 Hz, 1H), 7.0 (m, 1H), 7.17 (m, 4H), 7.27 (m, 4H), 7.32 (d, J=2 Hz, 1H), 7.32 (bs, 1H (NH)).

EXAMPLE 47

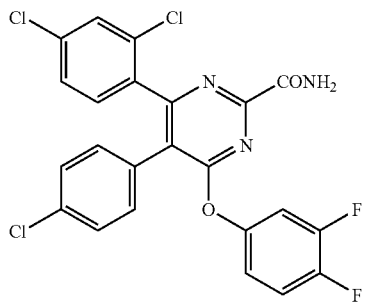

2-(Aminocarbonyl)-4-(3,4-difluorophenoxy)-5-(4-chlorophenyl)-6-(2,4-dichlorophenyl)pyrimidine The title compound was obtained by treating 2-(cyano)-4-(3,4-difluorophenoxy)-5-(4-chlorophenyl)-6-(2,4-dichlorophenyl)pyrimidine (Example 22, 410 mg, 0.8 mmol) with sulfuric acid (2 h, 80° C.) by the general procedure described in Example 8, Step B. Workup and flash column chromatography on silica gel (eluted with 50/50 hexanes/ethyl acetate) afforded the desired product. HPLC/MS: m/e=508 (M$^+$+1); R$_t$=3.97 min.

EXAMPLE 48

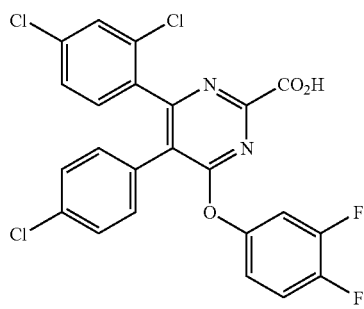

2-(Carboxy)-4-(3,4-difluorophenoxy)-5-(4-chlorophenyl)-6-(2,4-dichlorophenyl)pyrimidine 2-(Aminocarbonyl)-4-(3,4-difluorophenoxy)-5-(4-chlorophenyl)-6-(2,4-dichloro-phenyl)pyrimidine (Example 47, 228 mg, 0.5 mmol) was reacted with sulfuric acid (3 h, 125° C.) by the same general procedure described in Example 8, Step B. Workup (ice water) afforded a white precipitate which was washed with water and dried under high vacuum to give the title compound. HPLC/MS: m/e=353; $R_f$=3.02 min.

EXAMPLE 49

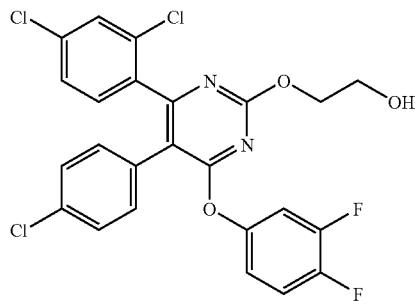

2-(2-Hydroxyethyleneoxy)-4-(3,4-difluorophenoxy)-5-(4-chlorophenyl)-6-(2,4-dichlorophenyl)pyrimidine 2-(Methylsulfonyl)-4-(3,4-difluorophenoxy)-5-(4-chlorophenyl)-6-(2,4-dichlorophenyl)-pyrimidine (Example 20, 54 mg, 0.1 mmol) was reacted with 1 equivalent of n-butyl lithium and ethylene glycol by the general procedure described in Reference Examples 6 and 7. Workup and flash column chromatography on silica gel (eluted with 60/40 hexanes/ethyl acetate) afforded the title compound. HPLC/MS: m/e=379 ($M^+$−45 (ethyleneoxy)); $R_f$=4.25 min. $^1$H-NMR 500 MHz (CDCl$_3$): δ 3.93 (t, J=5 Hz, 2H), 4.42 (t, J=5 Hz, 2H), 6.90 (m, 1H), 7.08 (m, 2H), 7.17 (m, 2H), 7.27 (m, 4H), 7.32 (d, J=2 Hz, 1H).

EXAMPLE 50

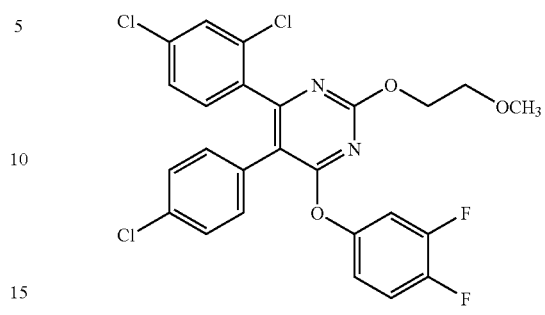

2-(2-Methoxyethyleneoxy)-4-(3,4-difluorophenoxy)-5-(4-chlorophenyl)-6-(2,4-dichlorophenyl)pyrimidine 2-(Methylsulfonyl)-4-(3,4-difluorophenoxy)-5-(4-chlorophenyl)-6-(2,4-dichlorophenyl)pyrimidine (Example 20, 54 mg, 0.1 mmol) was reacted with 1 equivalent of n-butyl lithium and 2-methoxyethanol by the general procedure described in Reference Examples 6 and 7. Workup and flash column chromatography on silica gel (eluted with 80/20 hexanes/ethyl)acetate afforded the title compound. HPLC/MS: m/e=439 ($M^+$+1); $R_f$=5.38 min. $^1$H-NMR 500 MHz (CDCl$_3$): δ 3.41 (s, 3H), 3.73 (t, J=5 Hz, 2H), 4.42 (t, J=5 Hz, 2H), 6.90 (m, 1H), 7.10 (m, 1H), 7.14 (dd J=8 Hz, J=2 Hz, 2H), 7.17-7.26 (m, 5H), 7.36 (d, J=2 Hz, 1H).

EXAMPLE 51

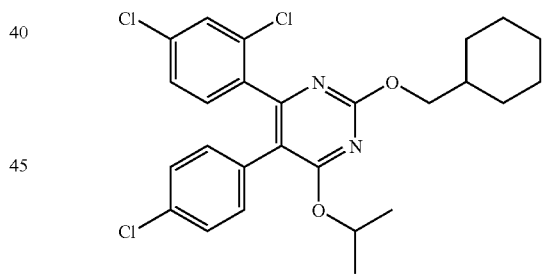

2-(Cyclohexylmethyloxy)-4-isopropoxy-5-(4-chlorophenyl)-6-(2,4-dichlorophenyl)pyrimidine Step A: 2-Cyclohexyloxy-4-(methylsulfonyl)-5-(4-chlorophenyl)-6-(2,4-dichlorophenyl)pyrimidine (HRf) product)

2,4-bis(Methylsulfonyl)-5-[4-chlorophenyl]-6-[2,4-dichlorophenyl]pyrimidine (Reference Example 5) (98 mg, 0.2 mmol) was reacted with 1 equivalent each of n-butyl lithium and cyclohexyl methanol by the procedure described in Reference Examples 6 and 7. Workup and flash column chromatography on silica gel eluted with 85/15 hexanes/ethyl acetate afforded 2-(cyclohexylmethoxy)-4-(methyl-sulfonyl)-5-(4-chlorophenyl)-6-(2,4-dichlorophenyl)pyrimidine (HRf product): $^1$H-NMR 500 MHz (CDCl$_3$): δ 0.9-1.1 (m, 1H), 1.10-1.2 (m, 2H), 1.2-1.4 (m, 3H); 1.67-1.88 (m, 3H), 1.9-2.0 (m, 2H), 3.38 (s, 3H), 4.29 (d, J=6 Hz, 2H), 7.0 (d, J=7 Hz, 1H), 7.18-7.22 (m, 3H), 7.24-7.28 (m, 2H), 7.36 (d, J=2 Hz, 1H) and 28 mg of 2-(methylsulfonyl)-4-(cyclohexylmethyloxy)-5-(4-chlorophenyl)-6-(2,4-dichloro-phenyl)pyrimidine (LRf product): $^1$H-NMR 500 MHz (CDCl$_3$): δ 0.87-0.9 (m, 1H), 0.95-1.07 (m, 2H), 1.1-1.3 (m, 2H), 1.33 (m, 2H), 1.7-1.82 (m, 4H), 3.40 (s, 3H), 4.37 (d, J=6 Hz, 2H), 7.08-7.12 (m, 2H), 7.22-7.30 (m, 4H), 7.36 (d, J=2 Hz, 1H).

Step B: 2-Cyclohexylmethyloxy-4-isopropoxy-5-(4-chlorophenyl)-6-(2,4-dichlorophenyl)pyrimidine 2-Cyclohexyloxy-4-methylsulfonyl-5-(4-chlorophenyl)-6-(2,4-dichlorophenyl)pyrimidine (HRf product, Example 51, Step A),(24 mg, 0.1 mmol) was reacted with 1 equivalent each of n-butyl lithium and isopropanol by the procedure described in Reference Examples 6 and 7. Workup and flash column chromatography on silica gel (eluted with 95/5 hexanes/ethyl acetate) afforded 2-cyclohexylmethyloxy-4-isopropoxy-5-(4-chlorophenyl)-6-(2,4-dichlorophenyl)pyrimidine. HPLC/R$_t$=5.47 min. $^1$H-NMR 500 MHz (CDCl$_3$): δ 0.8 (m, 1H), 1.1 (m, 2H), 1.20-1.35 (m, 3H), 1.37 (d, J=6 Hz, 6H), 1.7-1.8 (m, 3H), 1.90 (m, 2H). 4.20 (d, J=6 Hz, 1H), 5.50 (qn, J=6 Hz, 1H), 7.03 (d, J=7 Hz, 1H), 7.10 (d, J=8 Hz, 1H), 7.18 (m, 4H), 7.32 (d, J=2 Hz, 1H).

EXAMPLE 52

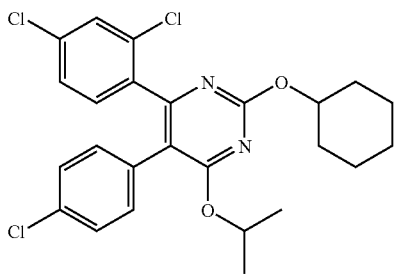

2-Cyclohexyloxy-4-isopropoxy-5-(4-chlorophenyl)-6-(2,4-dichlorophenyl)pyrimidine Step A: 2-Cyclohexyloxy-4-methylsulfonyl-5-(4-chlorophenyl)-6-(2,4-dichlorophenyl)pyrimidine (Higher Rf) product)

2,4-Bis(methylsulfonyl)-5-[4-chlorophenyl]-6-[2,4-dichlorophenyl]pyrimidine (Reference Example 5) (196 mg, 0.4 mmol) was reacted with 1 equivalent each of n-butyl lithium and cyclohexanol by the procedure described in Reference Examples 6 and 7. Workup and flash column chromatography on silica gel (eluted with 90/10 hexanes/ethyl acetate) afforded 2-cyclohexyloxy-4-(methylsulfonyl)-5-(4-chlorophenyl)-6-(2,4-dichlorophenyl)pyrimidine (Higher Rf product): $^1$H-NMR 500 MHz (CDCl$_3$): δ 1.30 (m, 5H), 1.45 (m, 1H), 1.55 (m, 1H), 1.64 (m, 1H), 1.75 (m, 1H), 1.90 (m, 1H), 2.15 (m, 1H), 3.38 (s, 3H), 5.09 (m, 1H), 7.0 (d, J=7 Hz, 1H), 7.18-7.22 (m, 4H), 7.36 (d over m, J=2 Hz, 2H); and 2-methylsulfonyl-4-cyclohexyl-oxy-5-(4chlorophenyl)-6-(2,4-dichlorophenyl)pyrimidine (Lower Rf product): $^1$H-NMR 500 MHz (CDCl$_3$): δ 0.87-0.9 (m, 1H), 0.95-1.07 (m, 2H), 1.1-1.3 (m, 2H), 1.33 (m, 2H), 1.7-1.82 (m, 4H), 3.40 (s, 3H), 4.37 (d, J=6 Hz, 2H), 7.08 (d, J=8 Hz, 2H), 7.12 (d, J=8 Hz, 1H), 7.22-7.30 (m, 3H), 7.37 (d, J=2 Hz, 1H).

Step B: 2-Cyclohexyloxy-4-isopropoxy-5-(4-chlorophenyl)-6-(2,4-dichlorophenyl)pyrimidine 2-Cyclohexyloxy-4-(methylsulfonyl)-5-(4-chlorophenyl)-6-(2,4-dichlorophenyl)pyrimidine (Higher Rf product) (Example 52, Step A), (26 mg, 0.05 mmol) was reacted with 1 equivalent each of n-butyl lithium and isopropanol by the procedure described in Reference Examples 6 and 7. Workup and flash column chromatography on silica gel (eluted with 95/5 hexanes/ethyl acetate) afforded 2-isopropoxy-4-methylsulfonyl-5-(4-chlorophenyl)-6-(2,4-dichlorophenyl)pyrimidine and 2-cyclohexyloxy)-4-isopropoxy-5-(4-chlorophenyl)-6-(2,4-dichlorophenyl)pyrimidine (HRf product): HPLC/MS: m/e=493 (M$^+$+1); R$_t$=5.26 min. $^1$H-NMR 500 MHz (CDCl$_3$): δ 0.9 (m, 1H), 1.30 (m, 1H), 1.35) d, J=6 Hz, 6H), 1.42 (m, 2H), 1.65 (m, 3H), 1.90 (m, 2H), 2.15 (m, 2H), 5.03 (m, J=4 Hz, 1H), 5.47 (qn, J=6 Hz, 1H), 7.03 (d, J=7 Hz, 1H), 7.10 (d, J=8 Hz, 1H), 7.18 (m, 4H), 7.32 (d, J=2 Hz, 1H).

EXAMPLE 53

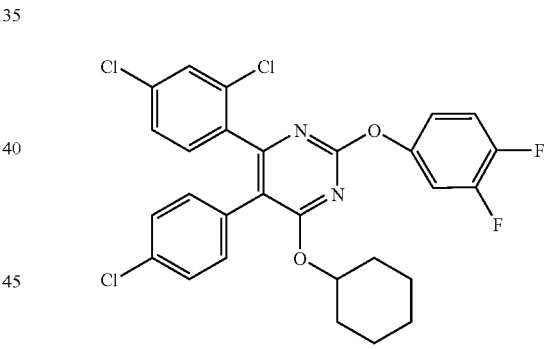

2-(3,4-Difluorophenoxy)-4-cyclohexyloxy-5-(4-chlorophenyl)-6-(2,4-dichlorophenyl)pyrimidine 2-(Methylsulfonyl)-4-(cyclohexyloxy)-5-(4-chlorophenyl)-6-(2,4-dichloro-phenyl)pyrimidine (Lower Rf product) (Example 52, Step A), (26 mg, 0.05 mmol) was reacted with 1 equivalent each of n-butyl lithium and 3,4-difluorophenol by the procedure described in Reference Examples 6 and 7. Workup and flash column chromatography on silica gel (eluted with 95/5 hexanes/ethyl acetate) afforded title compound. HPLC/MS: m/e=563 (M$^+$+1); R$_t$=5.25 min. $^1$H-NMR 500 MHz (CDCl$_3$): 1.28-1.40 (m, 4H), 1.55 (m, 3H), 1.65 (m, 2H), 1.90 (m, 2H), 5.03 (m, J=4 Hz, 1H), 7.05 (m, 4H), 7.10 (m, 5H), 7.34 (d, J=2 Hz, 1H).

EXAMPLE 54

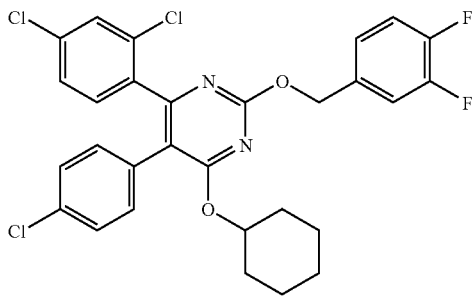

2-(3,4-Difluorobenzyloxy)-4-cyclohexyloxy-5-(4-chlorophenyl)-6-(2,4-dichlorophenyl)pyrimidine 2-(Methylsulfonyl)-4-(cyclohexyloxy)-5-(4-chlorophenyl)-6-(2,4-dichlorophenyl)pyrimidine (LRf product) (Example 52, Step A), (24 mg, 0.045 mmol) was reacted with 1 equivalent each of n-butyl lithium and 3,4-difluorobenzyl alcohol by the procedure described in Reference Examples 6 and 7. Workup and flash column chromatography on silica gel (eluted with 93/7 hexanes/ethyl acetate) afforded the title compound. HPLC/MS: m/e=577 (M$^+$+1); R$_f$=5.34 min; $^1$H-NMR 500 MHz (CDCl$_3$): 1.28-1.40 (m, 3H), 1.40-1.55 (m, 2M), 1.50-1.60 (m, 2H), 1.60-1.70 (m, 2H), 1.8-1.90 (m, 2H), 5.26 (m, J=4 Hz, 1H), 5.40 (s, 2H), 7.03 (d, J=8 Hz, 2H), 7.05 (d, J=1 Hz), 7.15-7.27 (m, 5H), 7.34 (d over multiplet, J=2 Hz, 2H).

EXAMPLE 55

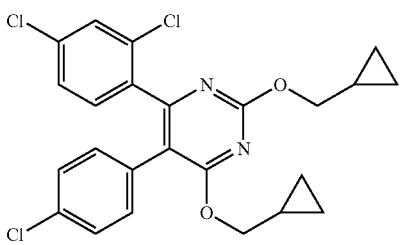

2,4-bis(Cyclopropylmethyloxy)-5-(4-chlorophenyl)-6-(2,4-dichlorophenyl)pyrimidine 2,4-bis(methylsulfonyl)-5-[4-chlorophenyl]-6-[2,4-dichlorophenyl]pyrimidine (Reference Example 5) (98 mg, 0.25 mmol) was reacted with 1.1 equivalent each of n-butyl lithium and cyclopropylmethanol by the procedure described in Reference Examples 6 and 7. Workup and flash column chromatography on silica gel (eluted with 90/10, then 70/30 hexanes/ethyl acetate) afforded the following products: 2,4-bis(cyclopropyloxy)-5-(4-chlorophenyl)-6-(2,4-dichlorophenyl)pyrimidine (Higher Rf product): $^1$H-NMR 500 MHz (CDCl$_3$): δ 0.34 (m, 2H), 0.41 (m, 2H), 0.60 (m, 2H), 0.65 (m, 2H), 1.30 (m, 1H), 1.40 (m, 1H), 4.24 (d, J=7 Hz, 2H), 4.35 (d, J=7 Hz, 2H), 7.05-7.15 (m, 3H), 7.20-7.28 (m, 3H), 7.35 (d, J=2 Hz, 1H); and 2-cyclopropyloxy-4-methylsulfonyl-5-(4-chlorophenyl)-6-(2,4-dichloro-phenyl)pyrimidine (Middle Rf product): $^1$H-NMR 500 MHz (CDCl$_3$): δ 0.41 (d, J=5 Hz, 2H), 0.69 (d, J=5 Hz, 2H), 1.40 (m, 1H), 3.77 (d, J=1 Hz, 2H), 4.31 (d, J=7 Hz, 2H), 6.98 (d, J=8 Hz, 1H), 7.18 (m, 3H), 7.25 (m, 2H), 7.35 (d, J=2 Hz, 1H); and
2-methylsulfonyl-4-cyclopropyloxy-5-(4-chlorophenyl)-6-(2,4-dichlorophenyl)pyrimidine (Lower Rf product): $^1$H-NMR 500 MHz (CDCl$_3$): δ 0.41 (m, 2H), 0.65 (m, 2H), 1.35 (m, 1H), 3.41 (s, H), 4.43 (d, J=7 Hz, 2H), 7.12 (m, 3H), 7.26 (m, 1H), 7.30 (m, 2H), 7.39, (d, J=2 Hz, 1H).

EXAMPLE 56

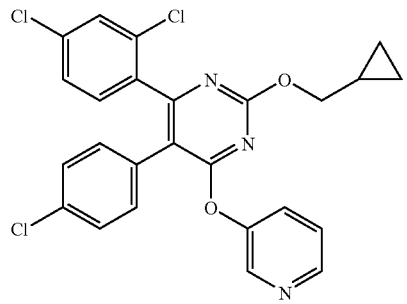

2-Cyclopropyloxy-4-(3-pyridyloxy)-5-(4-chlorophenyl)-6-(2,4-dichlorophenyl)pyrimidine 2-Cyclopropyloxy-4-methylsulfonyl-5-(4-chlorophenyl)-6-(2,4-dichlorophenyl)pyrimidine (Middle Rf product) (Example 55, Step A), (28 mg, 0.06 mmol) was reacted with 1 equivalent each of n-butyl lithium and 3-hydroxypyridine by the procedure described in Reference Examples 6 and 7. Workup and flash column chromatography on silica gel (eluted with 80/20 hexanes/ethyl acetate) afforded the title compound. HPLC/MS: m/e=498 (M$^+$−1); R$_f$=4.30 min. $^1$H-NMR 500 MHz (CDCl$_3$): δ 0.30 (m, 2H), 0.59 (m, 2H), 1.26 (m, J=5 Hz, 1H), 4.09 (s, 2H), 7.18-7.30 (m, 6H), 7.36 (d, J=2 Hz, 1H), 7.40 (dd, J=7 Hz, J=5 Hz, 1H), 7.57 (d, J=7 Hz, 1H), 8.53 (d, J=5 Hz, 2H).

EXAMPLE 57

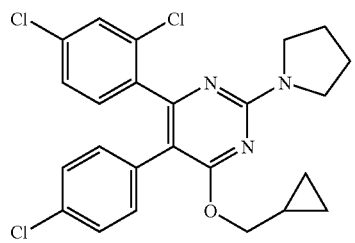

2-(N-Pyrrolidinyl)-4-cyclopropyloxy-5-(4-chlorophenyl)-6-(2,4-dichlorophenyl)pyrimidine 2-Methylsulfonyl-4-cyclopropyloxy-5-(4-chlorophenyl)-6-(2,4-dichlorophenyl)pyrimidine (LowerRf product). (Example 55, Step A), (12 mg, 0.024 mmol) was reacted by the procedure described in Example 31, Step A overnight with excess pyrrolidine at room temperature. Workup by removing excess pyrrolidine under vacuum and flash column chromatography on silica gel (eluted with 85/15 hexanes/ethyl acetate) afforded the title compound. HPLC/MS: m/e=476 (M$^+$+1); R$_t$4.29 min. $^1$H-NMR 500 MHz (CDCl$_3$): δ 0.33 (m, 2H), 0.59 (m, 2H), 1.30 (m, J=5 Hz, 1H), 2.02 (bs, 4H) 3.64 (bs, 4H), 4.24 (s, 2H), 7.03 (d, J=7 Hz, 2H), 7.16 (m, 4H), 7.30 (m, 1H).

EXAMPLE 58

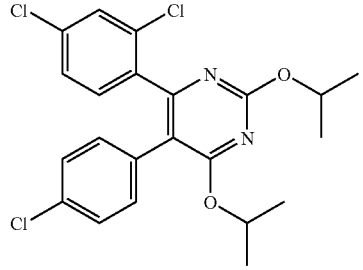

2,4-bis(Isopropyloxy)-5-(4-chlorophenyl)-6-(2,4-dichlorophenyl)pyrimidine

The title compound was obtained by treating 2,4-bis(methylsulfonyl)-5-[4-chlorophenyl]-6-[2,4-dichlorophenyl]pyrimidine (Reference Example 5) (250 mg, 0.5 mmol) with 1.1 equivalent each of n-butyl lithium and isopropanol by the procedure described in Reference Examples 6 and 7. Workup and flash column chromatography on silica gel (eluted with 90/10, then 70/30 hexanes/ethyl acetate) afforded the following products: the desired 2,4-bis(isopropyloxy)-5-(4-chlorophenyl)-6-(2,4-dichlorophenyl)pyrimidine (HigherRf product): $^1$H-NMR 500 MHz (CDCl$_3$): δ 0.94 (d, J=7 Hz, 6H), 1.05 (d, J=7 Hz, 6H), 2.05 (qn, J=7 Hz, 1H), 2.18 (qn, J=7 Hz, 1H), 4.17 (d, J=7 Hz, 2H), 4.19 (d, J=7 Hz, 2H), 7.05 (d, J=7 Hz, 2H), 7.12 (d, J=7 Hz, 1H), 7.17-7.21 (m, 3H), 7.35 (d, J=2 Hz, 1H); 2-isopropyloxy-4-methylsulfonyl-5-(4-chlorophenyl)-6-(2,4-dichlorophenyl)pyrimidine (Middle Rf product): $^1$H-NMR 500 MHz (CDCl$_3$): δ 1.12 (d, J=7 Hz, 6H), 2.25 (qn, J=7 Hz, 1H), 3.41 (s, 3H), 4.27 (d, J=7 Hz, 2H), 7.03 (d, H=7 Hz,1H), 7.20 (m, 3H), 7.27 (m, 2H), 7.39 (d, J=2 Hz, 1H); 2-methylsulfonyl-4-isopropyloxy-5-(4-chlorophenyl)-6-(2,4-dichlorophenyl)pyrimidine (Lower Rf product): 1H-NMR 500 MHz (CDCl$_3$): δ 0.96 (d, J=7 Hz, 6H), 2.07 (qn, J=7 Hz, 1H), 3.41 (s, 3H), 4.34 (d, J=7 Hz, 2H), 7.08-7.12 (m, 3H), 7.22 (d, J=7 Hz, 1H), 7.28 (m, 2H), 7.39 (d, J=2 Hz, 1H).

EXAMPLE 59

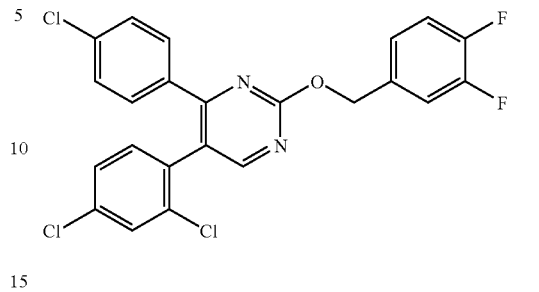

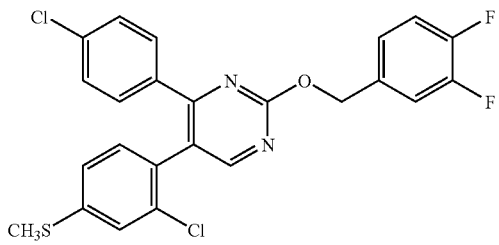

2-(3,4-Difluorobenzyloxy)-4-(4-chlorophenyl)-5-(2,4-dichlorophenyl)pyrimidine

To a 25 mL round bottom flask fitted with a stirrer bar was added 3 mL DMF, 3,4-difluorobenzyl alcohol (113.3 mg, 0.79 mmol) and sodium hydride (60% in oil, 52.4 mg, 1.31 mmol). The flask was flushed with N$_2$, stoppered with a rubber septum and 2-methylthio-4-(4-chlorophenyl)-5-(2,4-dichlorophenyl)pyrimidine (100 mg, 0.26 mmole) from Reference Example 3 was added via syringe in 500 μL of DMF for 90 min. Aqueous ammonium chloride was added, the mixture extracted with ethyl acetate (3×) and the combined organics dried over anhydrous MgSO$_4$. The solution was filtered and the volume reduced by rotoevaporation. Flash column chromatography on silica gel (eluted with 96/4 hexanes/ethyl acetate) afforded 2-(3,4-difluorobenzyloxy)-4-(4-chlorophenyl)-5-(2,4-dichlorophenyl)pyrimidine (HRf): HPLC/MS: m/e=478 (M$^+$+1); R$_t$=4.85 min; $^1$H-NMR 400 MHz (CDCl$_3$): 5.49 (s, 2H), 7.1-7.12 (d, J=9 Hz, 2H), 7.14-7.25 (m, 5H), 7.26-7.40 (m, 2H), 7.43 (s, 1H), 8.48 (s, 1H) and 2-(3,4-difluorobenzyloxy)-4-(4-chlorophenyl)-5-(2-chloro-4-thiomethylphenyl)-pyrimidine (LRf): HPLC/MS: m/e=489 (M$^+$+1); R$_t$=4.74 min; $^1$H-NMR 400 MHz (CDCl$_3$): δ 2.45 (s, 3H), 5.55 (s, 2H), 7.1-7.18 (d, 2H), 7.2-7.6 (m, 8H), 8.42 (s, 1H).

EXAMPLE 60

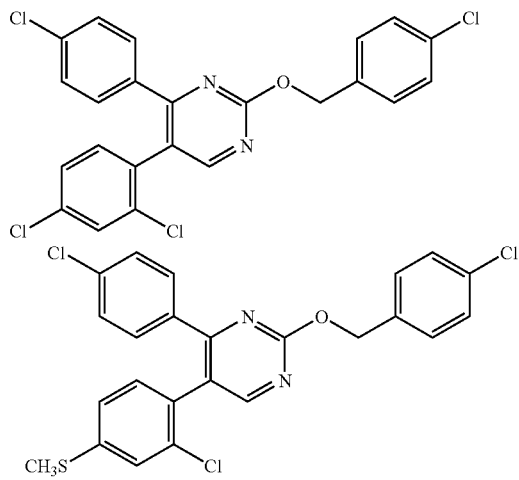

2-(4-Chlorobenzyloxy)-4-(4-chlorophenyl)-5-(2,4-dichlorophenyl)pyrimidine

2-Methylthio-4-(4-chlorophenyl)-5-(2,4-dichlorophenyl) pyrimidine from Reference Example 3 was reacted with 4-chlorobenzyl alcohol according to the procedure described in Example 59 to afford 2-(4-chlorobenzyloxy)-4-(4-chlorophenyl)-5-(2,4-dichlorophenyl)pyrimidine (HRf): HPLC/MS: m/e=475 (M$^+$+1); R$_f$=5.01 min; $^1$H-NMR 400 MHz (CDCl$_3$): 5.55 (s, 2H), 7.1 (d, J=9 Hz, 1H), 7.25-7.3 (m, 4H), 7.15-7.20 (m, 3H), 7.43 (m, 3H), 8.45 )s, 1H) and 2-(4-chlorobenzyloxy)-4-(4-chlorophenyl)5-(2-chloro-4-thiomethylphenyl)pyrimidine (LRf): HPLC/MS: m/e=487 (M$^+$+1); R$_f$=4.91 min; $^1$H-NMR 400 MHz (CDCl$_3$): δ 2.52 (s, 3H), 5.55 (s, 2H), 7.15 (d, J=6 Hz, 2H), 7.25-7.30 (m, 3H), 7.55-7.40 (m, 4H), 7.45 (m, 2H), 8.42 (s, 1H).

EXAMPLE 61

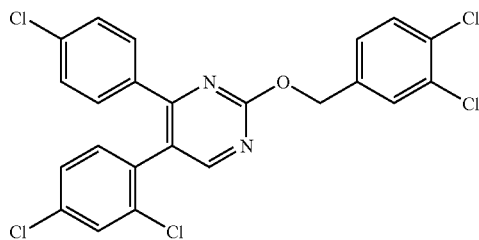

2-(3,4-Dichlorobenzyloxy)-4-(4-chlorophenyl)-5-(2,4-dichlorophenyl)pyrimidine

2-Methylthio-4-(4-chlorophenyl)-5-(2,4-dichlorophenyl) pyrimidine from Reference Example 3 was reacted with 3,4-dichlorobenzyl alcohol according to the procedure described in Example 59 to afford 2-(3,4-dichlorobenzyloxy)-4-(4-chlorophenyl)-5-(2,4-dichlorophenyl)pyrimidine (HRf): HPLC/MS: m/e=509 (M$^+$+1); R$_f$=5.14 min; $^1$H-NMR 400 MHz (CDCl$_3$): δ 5.56 (s, 2H), 7.12 (d, J=9 Hz, 1H), 7.22-7.25 (m, 4H), 7.27-7.40 (m, 3H), 7.28 (m, 1H), 7.68 (d, J=2 Hz, 1H), 8.45 (s, 1H).

EXAMPLE 62

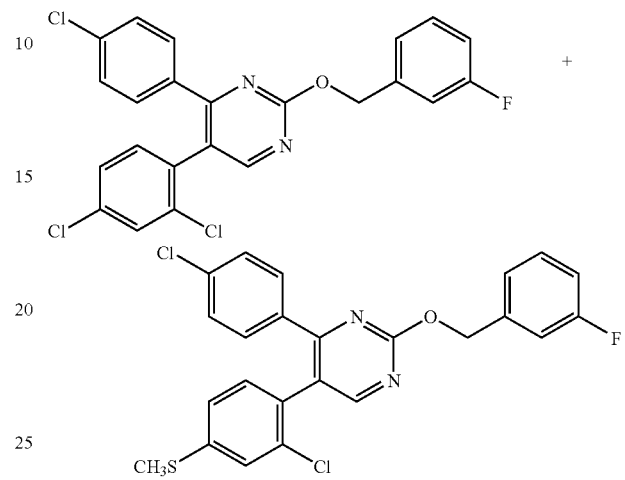

2-(3-Fluorobenzyloxy)-4-(4-chlorophenyl)-5-(2,4-dichlorophenyl)pyrimidine

2-Methylthio-4-(4-chlorophenyl)-5-(2,4-dichlorophenyl) pyrimidine from Reference Example 3 was reacted with 3-fluorobenzyl alcohol according to the procedure described in Example 59 to afford 2-(3-fluorobenzyloxy)-4-(4-chlorophenyl)-5-(2,4-dichlorophenyl)pyrimidine(HRf): HPLC/MS: m/e=459 (M$^+$+1); R$_f$=4.77 min; $^1$H-NMR 500 MHz (CDCl$_3$): δ 5.58 (s, 2H), 7.15 (d, J=9 Hz, 1H), 7.29-7.4 (m, 10H), 8.48 (s, 1H) and 2-(3-fluorobenzyloxy)-4-(4-chlorophenyl)-5-(2-chloro-4-thiomethylphenyl)pyrimidine (LRf): HPLC/MS: m/e=471 (M$^+$+1); R$_f$=4.63 min; $^1$H-NMR 500 MHz (CDCl$_3$): δ 2.50 (s, 3H), 5.60 (s, 2H), 7.15 (d, J=7 Hz, 2H), 7.26-7.40 (m, 6H), 7.50 (m, 2H), 7.58-7.40 (m, 1H), 8.42 (s, 1H).

EXAMPLE 63

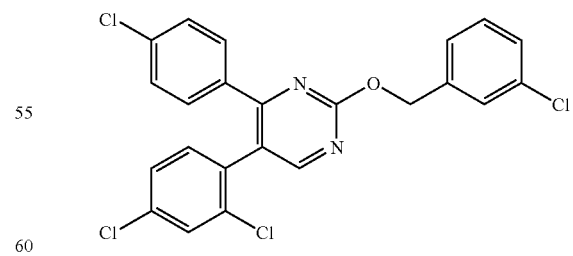

2-(3-Chlorobenzyloxy)-4-(4-chlorophenyl)-5-(2,4-dichlorophenyl)pyrimidine

2-Methylthio-4-(4-chlorophenyl)-5-(2,4-dichlorophenyl) pyrimidine from Reference Example 3 was reacted with 3-chlorobenzyl alcohol according to the procedure described in Example 59 to afford 2-(3-chlorobenzyloxy)-4-(4-chlorophenyl)-5-(2,4-dichlorophenyl)pyrimidine (HRf): HPLC/MS: m/e=475 (M⁺+1); $R_t$=4.92 min; 1H-NMR 400 MHz (CDCl₃): δ 5.58 (s, 2H), 7.15 (d, J=9 Hz, 1H), 7.25-7.38 (m, 7H), 7.40-7.50 (m, 2H), 7.58 (s, 1H), 8.48 (s, 1H).

EXAMPLE 64

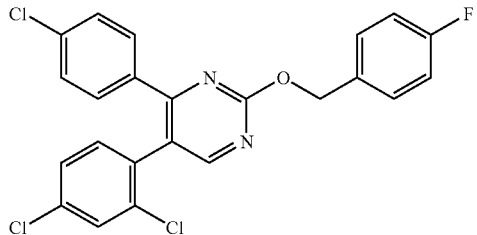

2-(4-Fluorobenzyloxy)-4-(4-chlorophenyl)-5-(2,4-dichlorophenyl)pyrimidine

2-Methylthio-4-(4-chlorophenyl)-5-(2,4-dichlorophenyl)pyrimidine from Reference Example 3 was reacted with 4-fluorobenzyl alcohol according to the procedure described in Example 59 to afford 2-(4-fluorobenzyloxy)-4-(4-chlorophenyl)-5-(2,4-dichlorophenyl)pyrimidine (HRf): HPLC/MS: m/e=459 (M⁺30 1); $R_t$=4.80 min; ¹H-NMR 500 MHz (CDCl₃): δ 5.58 (s, 2H), 7.05-7.15 (m, 3H), 7.23-7.30 (m, 3H), 7.39 (d, J=9 Hz, 2H), 7.41-7.49 (m, 1H), 7.50-7.58 (m, 2H), 8.48 (s, 1H).

EXAMPLE 65

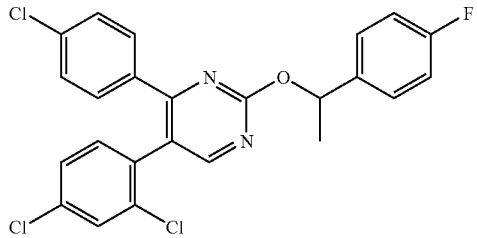

2-(α-methyl-4-fluorobenzyloxy-)-4-(4-chlorophenyl)-5-(2,4-dichlorophenyl)pyrimidine 2-Methylthio-4-(4-chlorophenyl)-5-(2,4-dichlorophenyl)pyrimidine from Reference Example 3 was reacted with α-methyl-4-fluorobenzyl alcohol according to the procedure described in Example 59 to afford 2-(α-methyl-4-fluorobenzyloxy-)-4-(4-chlorophenyl)-5-(2,4-dichlorophenyl)pyrimidine. (HRf): HPLC/MS: m/e=473 (M⁺+1); R′=4.91 min; ¹H-NMR 400 MHz (CDCl₃): δ 1.78 (d, J=9 Hz, 3H), 6.22-6.30 (dd, J=6 Hz, J=9 Hz, 1H), 7.02 (m, 3H), 7.20-7.25 (m, 5H), 7.50-7.59 (m, 3H), 8.40 (m, 1H).

EXAMPLE 66

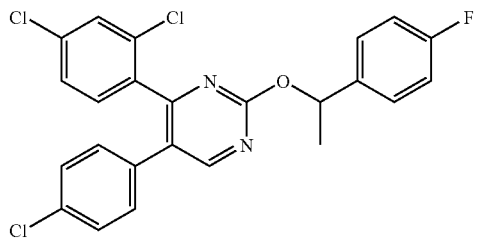

2-(α-Methyl-4-fluorobenzyloxy)-4-(2,4-dichlorophenyl)-5-(4-chlorophenyl)pyrimidine 2-Methylthio-5-(4-chlorophenyl)-4-(2,4-dichlorophenyl)pyrimidine from Reference Example 3 was reacted with α-methyl-4-fluorobenzyl alcohol according to the procedure described in Example 59 to afford 2-(α-methyl-4-fluorobenzyloxy)-4-(2,4-dichlorophenyl)-5-(4-chlorophenyl)pyrimidine (HRf): HPLC/MS: m/e=473 (M⁺+1); $R_t$=4.80 min; ¹H-NMR 400 MHz (CDCl₃): δ 1.76 (d, J=9 Hz, 3H), 6.22-6.30 (dd, J=6 Hz, J=9 Hz, 1H), 6.90-7.05 (m, 4H), 7.15-7.18 (d, J=9 Hz, 2H), 7.21-7.23 (m, 3H), 7.38 (d, 1H), 7.45-7.52 (m, 2H), 8.58 (m, 1H).

EXAMPLE 67

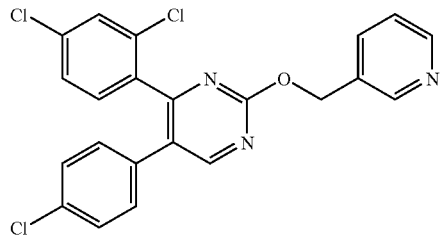

2-(3-Pyridylmethoxy)-4-(2,4-dichlorophenyl)-5-(4-chlorophenyl)pyrimidine

2-Methylthio-5-(4-chlorophenyl)-4-(2,4-dichlorophenyl)pyrimidine from Reference Example 3 was reacted with 3-pyridinemethanol according to the procedure described in Example 59 to afford 2-(3-pyridylmethoxy)-4-(2,4-dichlorophenyl)-5-(4-chlorophenyl)pyrimidine (HRf): HPLC/MS: m/e=442 (M⁺+1); $R_t$=3.01 min; 1H-NMR 500 MHz (CDCl₃): δ 5.61 (s, 2H), 7.05 (d, J=9 Hz, 2H), 7.15-7.22 (m, 1H), 7.24-7.32 (m, 4H), 7.50-7.58 (m, 1H), 7.60 (m, 1H), 7.62-7.63 (m, 1H), 8.45 (m, 1H), 8.83 (s, 1H).

EXAMPLE 68

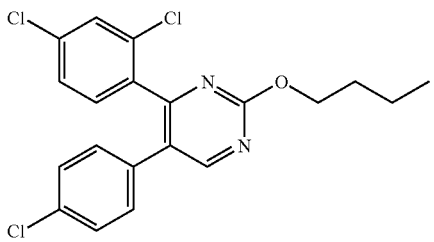

2-(n-Butyloxy)-4-(2,4-dichlorophenyl)-5-(4-chlorophenyl)pyrimidine

2-Methylthio-5-(4-chlorophenyl)-4-(2,4-dichlorophenyl)pyrimidine from Reference Example 3 was reacted with n-butanol according to the procedure described in Example 59 to afford 2-(n-butyloxy)-4-(2,4-dichlorophenyl)-5-(4-chlorophenyl)pyrimidine (HRf): HPLC/MS: m/e=407 (M$^+$+1); R$_t$=4.80 min; $^1$H-NMR 400 MHz (CDCl$_3$): δ 1.00 (t, 3H), 1.50-1.6 (m,2H), 1.80-1.85 (m, 2H), 4.41-4.44 (t, 2H), 7.01 (d, J=9 Hz, 2H), 7.21-7.25 (m, 5H), 8.58 (s, 1H).

EXAMPLE 69

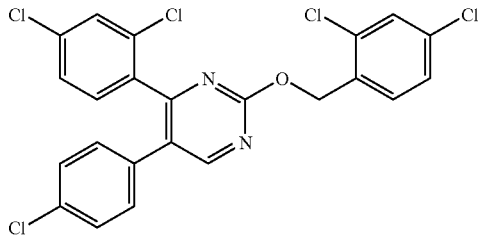

2-(2,4-Dichlorobenzyloxy)-4-(2,4-dichlorophenyl)-5-(4-chlorophenyl)pyrimidine

2-Methylthio-5-(4-chlorophenyl)-4-(2,4-dichlorophenyl)pyrimidine from Reference Example 3 was reacted with 2,4-dichlorobenzyl alcohol according to the procedure described in Example 59 to afford 2-(2,4-dichlorobenzyloxy)-4-(2,4-dichlorophenyl)-5-(4-chlorophenyl)pyrimidine (HRf): HPLC/MS: m/e=509 (M$^+$+1); R$_t$=5.07 min; $^1$H-NMR 400 MHz (CDCl$_3$): δ 5.60 (s, 2H), 7.04 (d, J=9 Hz, 2H), 7.21 (m, 6H), 7.38-7.42 (m, 1H), 7.60 (d, J=9 Hz, 1H), 8.60 (s, 1H).

EXAMPLE 70

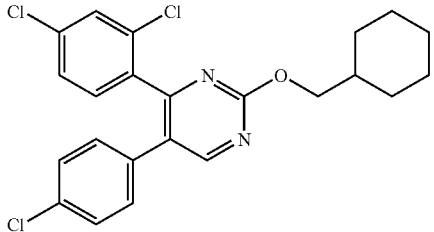

2-(Cyclohexylmethoxy)-4-(2,4-dichlorophenyl)-5-(4-chlorophenyl)pyrimidine

2-Methylthio-5-(4-chlorophenyl)-4-(2,4-dichlorophenyl)pyrimidine from Reference Example 3 was reacted with cyclohexylmethanol according to the procedure described in Example 59 to afford 2-(cyclohexylmethoxy)-4-(2,4-dichlorophenyl)-5-(4-chlorophenyl)pyrimidine (HRf): HPLC/MS: m/e=447 (M$^+$+1); R$_t$=5.17 min; $^1$H-NMR 400 MHz (CDCl$_3$): δ 1.02-1.20 (m, 2H), 1.20-1.40 (m, 4H), 1.64-1.80 (m, 3H), 1.81-1.98 (m, 2H), 4.23 (d, J=9 Hz, 2H), 7.01 (d, J=9 Hz, 2H), 7.22-7.30 (m, 4H), 7.38 (d, J=2 Hz,1H), 8.58 (s, 1H).

EXAMPLE 71

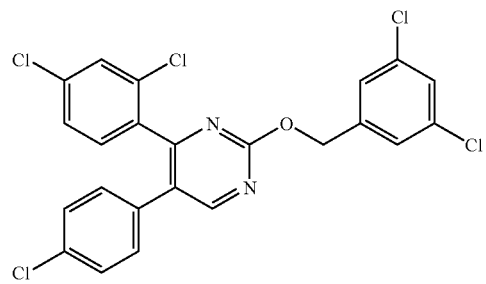

2-(3,5-Dichlorobenzyloxy)-4-(2,4-dichlorophenyl)-5-(4-chlorophenyl)pyrimidine

2-Methylthio-5-(4-chlorophenyl)-4-(2,4-dichlorophenyl)pyrimidine from Reference Example 3 was reacted with 3,5-dichlorobenzyl alcohol according to the procedure described in Example 59 to afford 2-(3,5-dichlorobenzyloxy)-4-(2,4-dichlorophenyl)-5-(4-chlorophenyl)pyrimidine (HRf): HPLC/MS: m/e=510 (M$^+$+1); R$_t$=5.12 min; $^1$H-NMR 400 MHz (CDCl$_3$): δ 5.45 (s, 2H), 7.03 (d, J=9 Hz, 2H), 7.21-7.40 (m, 6H), 7.42 (d, J=2 Hz, 2H), 8.60 (s, 1H).

EXAMPLE 72

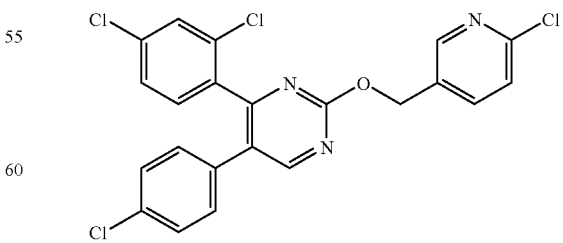

2-(6-Chloro-3-pyridylmethoxy)-4-(2,4-dichlorophenyl)-5-(4-chlorophenyl)pyrimidine 2-Methylthio-5-(4-chlorophenyl)-4-(2,4-dichlorophenyl) pyrimidine from Reference Example 3 was reacted 6-chloro-3-pyridinemethanol according to the procedure described in Example 59 to afford 2-(6-chloro-3-pyridylmethoxy)-4-(2,4-dichlorophenyl)-5-(4-chlorophenyl)pyrimidine (HRf): HPLC/MS: m/e=476 (M$^+$+1); R$_t$=4.45 min; $^1$H-NMR 400 MHz (CDCl$_3$): δ 5.51 (s, 2H), 7.05 (d, J=9 Hz, 2H), 7.20 (d, J=9Hz, 1H), 7.25-7.30 (m, 4H), 7.38-7.40 (m, 1H), 7.85 (m, 1H), 8.55 (d, J=2 Hz, 1H), 8.60 (s, 1H).

EXAMPLE 73

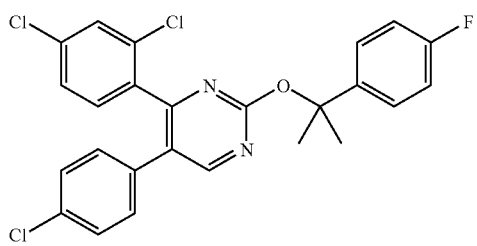

2-(α,α-dimethyl-4-fluorobenzyloxy)-4-(2,4-dichlorophenyl)-5-(4-chlorophenyl)pyrimidine 2-Methylthio-5-(4-chlorophenyl)-4-(2,4-dichlorophenyl) pyrimidine from Reference Example 3 was reacted with α,α-dimethyl-4-fluorobenzyl alcohol according to the procedure described in Example 59 to afford 2-(α,α-dimethyl-4-fluorobenzyloxy)-4-(2,4-dichlorophenyl)-5-(4-chlorophenyl) pyrimidine (HRf): $^1$H-NMR 500 MHz (CDCl$_3$): δ 1.91 (s, 6H), 6.90-7.00 (m, 5H), 7.20-7.25 (m, 3H), 7.30 (s, 1H), 7.41-7.45 (m, 2H), 8.40 (s, 1H).

EXAMPLE 74

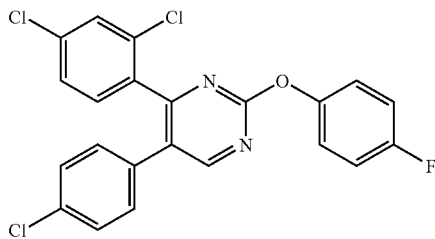

2-(4-Fluorophenyloxy)-4-(2,4-dichlorophenyl)-5-(4-chlorophenyl)pyrimidine

To a 5 mL round bottom flask fitted with a stirrer bar and septum was added 2 mL CH$_3$CN and 2-methylsulfonyl-4-(2,4-dichlorophenyl)-5-(4-chlorophenyl)pyrimidine from from Reference Example 3 (100 mg, 0.24 mmol). Then 4-fluorophenol (10 eq., 269 mg, 2.4 mmol), K$_2$CO$_3$ (2 eq., 66.3 mg, 0.48 mmol) and a drop of tris[2-(2-methoxyethoxy)-ethyl] amine were added via syringe and the mixture heated at 70° C. for 2 h. By HPLC/MS, the starting material was converted to the desired product. The product was extracted from 10 mL water with 20 mL ethyl acetate, dried over anhydrous MgSO$_4$, filtered and the solvent removed under reduced pressure. Flash column chromatography on silica gel (eluted with 90/10 hexanes/ethyl acetate) afforded 2-(4-fluorophenyloxy)-4-(2,4-dichlorophenyl)-5-(4-chlorophenyl)pyrimidine: HPLC/MS: m/e=445 (M$^+$+1); R$_t$=4.53 min; $^1$H-NMR 400 MHz (CDCl$_3$): δ 7.02 (d, J=9 Hz, 2H), 7.20-7.40 (m, 9H), 8.80 (s, 1H).

EXAMPLE 75

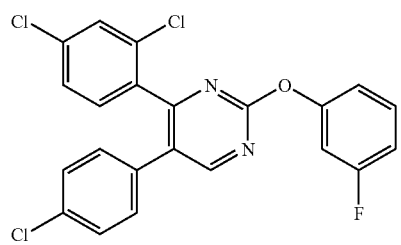

2-(3-Fluorophenyloxy)-4-(2,4-dichlorophenyl)-5-(4-chlorophenyl)pyrimidine

2-Methylsulfonyl-4-(2,4-dichlorophenyl)-5-(4-chlorophenyl)pyrimidine from Reference Example 3 was reacted with 3-fluorophenol according to the procedure described in Example 74 to afford 2-(3-fluorophenyloxy)-4-(2,4-dichlorophenyl)-5-(4-chlorophenyl)pyrimidine: HPLC/MS: m/e=445 (M$^+$+1); R$_t$=4.50 min; $^1$H-NMR 400 MHz (CDCl$_3$): δ 7.05. (m, 3H), 7.21-7.30 (m, 6H), 7.38-7.42 (m, 2H), 8.60 (s, 1H).

EXAMPLE 76

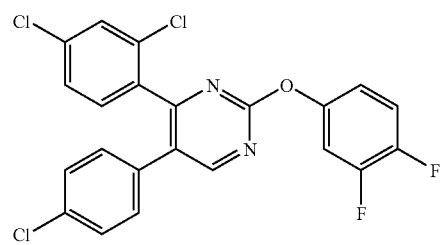

2-(3,4-Difluorophenyloxy)-4-(2,4-dichlorophenyl)-5-(4-chlorophenyl)pyrimidine

2-Methylsulfonyl-4-(2,4-dichlorophenyl)-5-(4-chlorophenyl)pyrimidine from Reference Example 3 was reacted with 3,4-difluorophenol according to the procedure described in Example 74 to afford 2-(3,4-difluorophenyloxy)-4-(2,4-dichlorophenyl)-5-(4-chlorophenyl)pyrimidine: HPLC/MS: m/e=463 (M$^+$+1); R$_t$=4.60 min; $^1$H-NMR 400 MHz (CDCl$_3$): δ 7.05. (m, 3H), 7.19-7.30 (m, 6H), 7.39 (d, J=2 Hz, 1H), 8.60 (s, 1H).

EXAMPLE 77

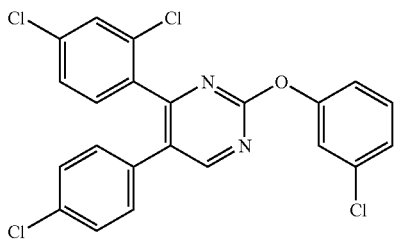

2-(3-Chlorophenyloxy)-4-(2,4-dichlorophenyl)-5-(4-chlorophenyl)pyrimidine

2-Methylsulfonyl-4-(2,4-dichlorophenyl)-5-(4-chlorophenyl)pyrimidine from Reference Example 3 was reacted with 3-chlorophenol according to the procedure described in Example 74 to afford 2-(3-chlorophenyloxy)-4-(2,4-dichlorophenyl)-5-(4-chlorophenyl)pyrimidine: HPLC/MS: m/e=461 (M$^+$+1); R$_t$=4.72 min; $^1$H-NMR 400 MHz (CDCl$_3$): δ 7.00-7.12. (m, 2H), 7.11-7.18 (m, 2H), 7.20-7.30 (m, 7H), 8.60 (s, 1H).

EXAMPLE 78

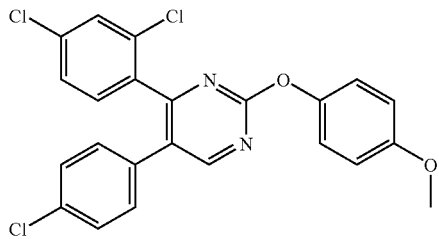

2-(4-Methoxyphenyloxy)-4-(2,4-dichlorophenyl)-5-(4-chlorophenyl)pyrimidine

2-Methylsulfonyl-4-(2,4-dichlorophenyl)-5-(4-chlorophenyl)pyrimidine from Reference Example 3 was reacted with 4-methoxyphenol according to the procedure described in Example 74 to afford 2-(4-methoxyphenyloxy)-4-(2,4-dichlorophenyl)-5-(4-chlorophenyl)pyrimidine: HPLC/MS: m/e=457 (M$^+$+1); R$_t$=4.50 min; $^1$H-NMR 500 MHz (CDCl$_3$): δ 3.85 (s, 3H), 6.95 (d, J=9 Hz, 2H), 7.05. (d, J=9 Hz, 2H), 7.21 (d, J=9 Hz, 2H), 7.25-7.30 (m, 4H), 7.39 (d, J=2 Hz, 1H), 8.60 (s, 1H).

EXAMPLE 79

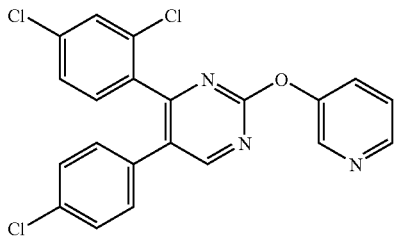

2-(3-Pyridyloxy)-4-(2,4-dichlorophenyl)-5-(4-chlorophenyl)pyrimidine

2-Methylsulfonyl-4-(2,4-dichlorophenyl)-5-(4-chlorophenyl)pyrimidine from Reference Example 3 was reacted with 3-hydroxypyridine according to the procedure described in Example 74 to afford 2-(3-pyridyloxy)-4-(2,4-dichlorophenyl)-5-(4-chlorophenyl)pyrimidine: HPLC/MS: m/e=428 (M$^+$+1); R$_t$=3.49 min; $^1$H-NMR 400 MHz (CDCl$_3$): δ 7.05 (d, J=9 Hz, 2H), 7.19-7.30 (m, 4H), 7.38-7.42 (m, 2H), 7.65 (m, 1H), 8.55 (d, J=6 Hz, 1H), 8.60 (s, 1H), 8.65 (d, J=2 Hz, 1H).

EXAMPLE 80

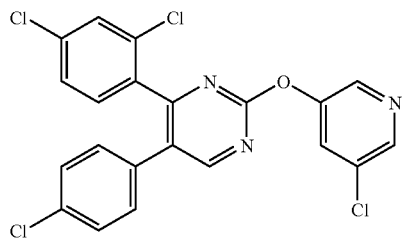

2-(5-Chloro-3-pyridyloxy)-4-(2,4-dichlorophenyl)-5-(4-chlorophenyl)pyrimidine

2-Methylsulfonyl-4-(2,4-dichlorophenyl)-5-(4-chlorophenyl)pyrimidine from Reference Example 3 was reacted with 5-chloro-3-hydroxypyridine according to the procedure described in Example 74 to afford 2-(5-chloro-3-pyridyloxy)-4-(2,4-dichlorophenyl)-5-(4-chlorophenyl)pyrimidine: HPLC/MS: m/e=462 (M$^+$+1); R$_t$=4.40 min; $^1$H-NMR 400 MHz (CDCl$_3$): δ 7.05. (d, J=9 Hz, 2H), 7.21 (d, J=10 Hz, 1H), 7.25-7.31 (m, 3H), 7.41 (s, 1H), 7.75 (s, 1H), 8.50 (s, 1H), 8.55 (s, 1H), 8.62 (s, 1H).

EXAMPLE 81

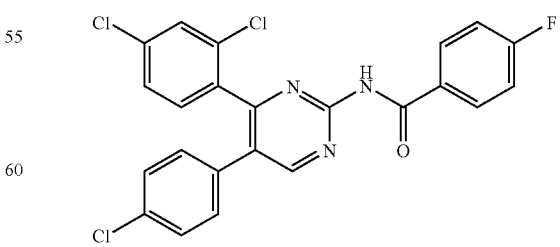

2-(N-(4-Fluorobenzamido)-4-(2,4-dichlorophenyl)-5-(4-chlorophenyl)pyrimidine

To a 25 mL round bottom flask fitted with a stirrer bar and rubber septum was added 2-amino-4-(2,4-dichlorophenyl)-5-(4-chlorophenyl)pyrimidine from Example 8 (100 mg, 0.28 mmol) and 3 mL pyridine. 4-Fluorobenzoyl chloride was added to the reaction. The reaction mixtures were heated to 70° C. for overnight. Ethyl acetate and water were added. The organic layer was washed with water and brine and then dried over anhydrous MgSO$_4$, filtered, and the solvent removed under reduced pressure. The crude product was chromatographed by flash column chromatography on silica gel (eluted with 80/20 hexanes/ethyl acetate) to afford 2-(N-(4-fluorobenzamido))-4-(2,4-dichlorophenyl)-5-(4-chlorophenyl)pyrimidine: HPLC/MS: m/e=472 (M$^+$+1). R$_f$=3.79 min; $^1$H-NMR 400 MHz (CDCl$_3$): δ 7.10 (d, J=9 Hz, 2H), 7.15-7.31 (m, 5H), 8.02-8.15 (m, 4H), 8.80 (s, 1H), 8.98 (s, 1H).

EXAMPLE 82

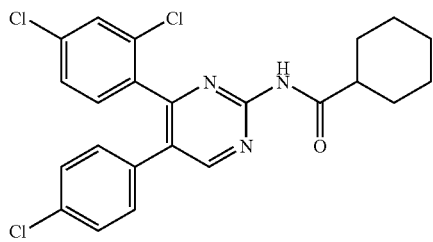

2-(N-(Cyclohexylcarboxamido))-4-(2,4-dichlorophenyl)-5-(4-chlorophenyl)pyrimidine 2-Amino-4-(2,4-dichlorophenyl)-5-(4-chlorophenyl)pyrimidine from Example 8 was reacted with cyclohexane-carbonyl chloride according to the procedure described in Example 81 to afford 2-(N-(cyclohexylcarbox-amido))-4-(2,4-dichlorophenyl)-5-(4-chlorophenyl)pyrimidine: HPLC/MS: m/e=460 (M$^+$+1). R$_f$=4.24 min; $^1$H-NMR 400 MHz (CDCl$_3$): δ 1.35-1.40 (m, 2H), 1.55-2.05 (m, 7H), 2.27 (m, 1H), 7.05 (d, J=9 Hz, 2H), 7.15-7.31 (m, 5H), 8.15 (s, 1H), 8.70 (s, 1H).

EXAMPLE 83

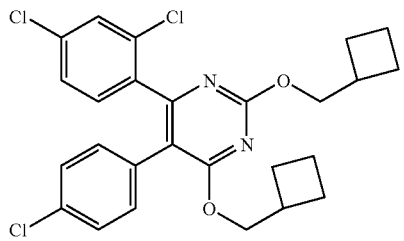

2,4-bis(Cyclobutylmethoxy)-5-(4-chlorophenyl)-6-(2,4-dichlorophenyl)pyrimidine 2,4-Bis(methylsulfonyl)-5-[4-chlorophenyl]-6-[2,4-dichlorophenyl]pyrimidine (Reference Example 5) (600 mg, 1.22 mmol) was reacted with 1.1 equivalent each of n-butyl lithium and cyclobutanemethanol by the procedure described in Example 55 to afford 2,4-bis-(cyclobutylmethyloxy)-5-(4-chlorophenyl)-6-(2,4-dichlorophenyl)pyrimidine (HRf product): $^1$H-NMR 400 MHz (CDCl$_3$): 1.80-2.20 (m, 12H), 2.61-2.80 (m, 1H), 2.80-2.90 (m, 1H), 4.20 (m, 4H), 7.02 (d, J=9 Hz, 2H), 7.10-7.20 (m, 4H), 7.31 (s, 1H); 2-cyclobutylmethoxy-4-methylsulfonyl-5-(4-chlorophenyl)-6-(2,4-dichlorophenyl)pyrimidine (MRf product): $^1$H-NMR 400 MHz (CDCl$_3$):1.90-2.00 (m, 4H), 2.18-2.20 (m, 2H), 2.80-2.95 (m, 1H), 3.37 (s, 3H), 4.45 (d, J=7 Hz, 2H), 7.00 (d, J=8 Hz, 2H), 7.18-7.25 (m, 4H), 7.35 (s, 1H); and 2-methylsulfonyl-4-cyclobutylmethoxy-5-(4-chlorophenyl)-6-(2,4-dichlorophenyl)pyrimidine (LRf product): $^1$H-NMR 400 MHz (CDCl$_3$): δ 1.60-2.00 (m, 4H), 2.05-2.10 (m, 2H), 2.70-2.80 (m, 1H), 3.40 (s, 2H), 4.58 (d, J=7 Hz, 2H), 7.02-7.15 (m, 3H), 7.20 (m, 3H), 7.30 (m, 2H), 7.39 (d, J=2 Hz, 1H).

EXAMPLE 84

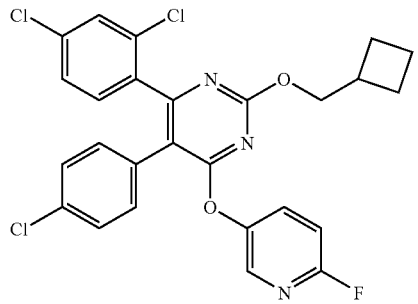

2-Cyclobutylmethoxy-4-(6-fluoro-3-pyridyloxy)-5-(4-chlorophenyl)-6-(2,4-dichlorophenyl)pyrimidine 2-Cyclobutylmethoxy-4-methylsulfonyl-5-(4-chlorophenyl)-6-(2,4-dichlorophenyl)pyrimidine (the MRf product from Example 83), (30 mg, 0.06 mmol) was reacted with 2 equivalents each of n-butyl lithium and 3-hydroxy-6-fluoropyridine according to the procedure described in Reference Examples 6 and 7 to afford 2-cyclobutylmethoxy-4-(6-fluoro-3-pyridyloxy)-5-(4-chlorophenyl)-6-(2,4-dichlorophenyl)pyrimidine: HPLC/MS: m/e=530 (M$^+$+1); R$_f$=5.01 min. $^1$H-NMR 400 MHz (CDCl$_3$): δ 1.80-1.98 (m, 4H), 2.10-2.11(m, 2H), 2.74 (m, 1H), 4.20 (d, J=7 Hz, 2H), 7.00 (m, 1H), 7.13-7.18 (m, 2H), 7.20-7.30 (m, 5H), 7.63-7.68 (m, 1H), 8.11 (m, 1H).

EXAMPLE 85

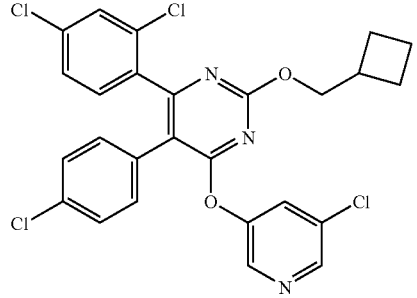

2-Cyclobutylmethoxy-4-(5-chloro-3-pyridyloxy)-5-(4-chlorophenyl)-6-(2,4-dichlorophenyl)pyrimidine 2-Cyclobutylmethoxy-4-methylsulfonyl-5-(4-chlorophenyl)-6-(2,4-dichlorophenyl)pyrimidine (the Mrf product from Example 83), (40 mg, 0.08 mmol) was reacted with 2 equivalents each of n-butyl lithium and 3-hydroxy-5-chloropyridine according to the procedure described in Reference Examples 6 and 7 to afford 2-cyclobutylmethoxy-4-(5-chloro-3-pyridyloxy)-5-(4-chlorophenyl)-6-(2,4-dichlorophenyl)pyrimidine: HPLC/MS: m/e=546 (M$^+$+1); R$_f$=5.20 min. $^1$H-NMR 400 MHz (CDCl$_3$): δ 1.80-1.98 (m, 4H), 2.10-2.11(m, 2H), 2.74 (m, 1H), 4.20 (d, J=7 Hz, 2H), 7.10-7.18 (m, 3H), 7.20-7.28 (m, 3H), 7.35 (d, J=2 Hz, 1H), 7.63 (m, 1H), 8.05 (d, J=2 Hz, 1H), 8.10 (d, J=2 Hz, 1H).

EXAMPLE 86

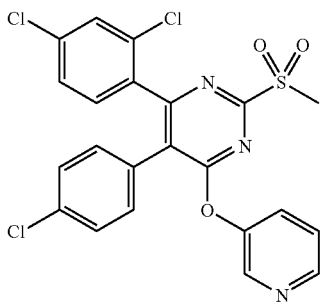

2-Methylsulfonyl-4-(3-pyridyloxy)-5-(4-chlorophenyl)-6-(2,4-dichlorophenyl)pyrimidine To a 50 mL round bottom flask fitted with a magnetic stirrer bar and rubber septum was added 20 mL anhydrous THF (Aldrich) and 2,4-bis(methyl-sulfonyl)-5-(4-chlorophenyl)-6-(2,4-dichlorophenyl)pyrimidine (Reference Example 5) (1.0 g, 2 mmol). The flask was flushed with nitrogen and cooled to 0° C. In a separate flask, also fitted with a magnetic stirrer bar and rubber septum, was added 10 mL anhydrous THF and 3-hydroxypyridine (213 mg, 2.24 mmol), This flask was flushed with nitrogen and cooled to 0° C. Then n-butyl lithium (1.12 mL, 2.24 mmol) (Aldrich-2M solution in hexane) was added via syringe and the solution stirred for several minutes. The lithium alkoxide solution was then withdrawn by syringe and slowly added to the first reaction flask. The solution was stirred at 0° C. for 1 h, quenched with saturated sodium bicarbonate and the reaction products extracted with ethyl acetate. The organic layer was dried over anhydrous MgSO$_4$, filtered and the solvent removed under reduced pressure. Flash column chromatography on silica gel (eluted with 35/65 hexanes/ethyl acetate) afforded 2-methylsulfonyl-4-(3-pyridyloxy)-5-(4-chlorophenyl)-6-(2,4-dichlorophenyl)pyrimidine: $^1$H-NMR 500 MHz (CDCl$_3$): δ 3.20 (s, 3H), 7.20-7.25 (m, 4H), 7.30-7.38 (m, 3H), 7.41 (m, 1H), 7.63-7.65 (m, 1H), 8.53-8.55 (m, 2H).

EXAMPLE 87

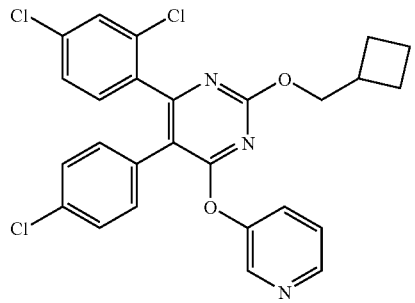

2-Cyclobutylmethoxy-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (50 mg, 0.1 mmol) was reacted with 2 equivalents each of n-butyl lithium and cyclobutylmethanol by the procedure described in Reference Examples 6 and 7 to afford 2-cyclobutylmethoxy-4-(3-pyridyloxy)-5-(4-chlorophenyl)-6-(2,4-dichlorophenyl)pyrimidine: HPLC/MS: m/e=512 (M$^+$+1); R$_f$=4.40 min. $^1$H-NMR 400 MHz (CDCl$_3$): δ 1.80-1.98 (m, 4H), 2.10-2.11(m, 2H), 2.74(m, 1H), 4.20 (d, J=7 Hz, 2H), 7.00 (m, 1H), 7.13-7.18 (m, 2H), 7.20-7.30 (m, 5H), 7.63-7.68 (m, 1H), 8.11 (m, 2H).

EXAMPLE 88

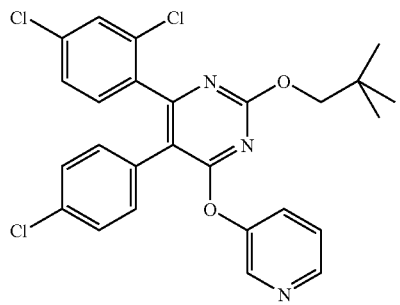

2-(2,2-Dimethylpropyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (30 mg, 0.06 mmol) was reacted with 2 equivalents each of n-butyl lithium and neopentyl alcohol by the procedure described in Reference Examples 6 and 7 to afford 2-(2,2-dimethylpropyloxy)-4-(3-pyridyloxy)-5-(4-chlorophenyl)-6-(2,4-dichlorophenyl)pyrimidine: HPLC/MS: m/e=514 (M$^+$+1); R$_f$4.48 min. $^1$H-NMR 400 MHz (CDCl$_3$): δ 1.20-1.30 (s, 9H), 3.88 (s, 2H), 7.15-7.28 (m, 7H), 7.40-7.43 (m, 1H), 7.58-7.61 (m, 1H), 8.52-8.56 (m, 2H).

EXAMPLE 89

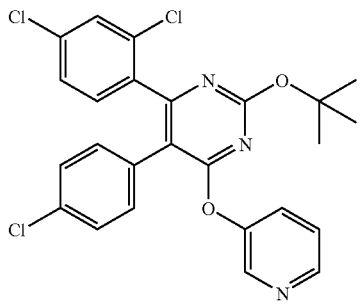

2-(2-t-Butyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (30 mg, 0.06 mmol) was reacted with 2 equivalents each of n-butyl lithium and t-butyl alcohol by the procedure described in Reference Examples 6 and 7 to afford 2-(2-t-Butyloxy)-4-(3-pyridyloxy)-5-(4-chloro-phenyl)-6-(2,4-dichlorophenyl)pyrimidine: HPLC/MS: m/e=500 (M$^+$+1); R$_f$4.11 min. $^1$H-NMR 400 MHz (CDCl$_3$): δ 1.22-1.28 (s, 9H), 7.18-7.28 (m, 7H), 7.40-7.43 (m, 1H), 7.56-7.59 (m, 1H), 8.53-8.56 (m, 2H).

EXAMPLE 90

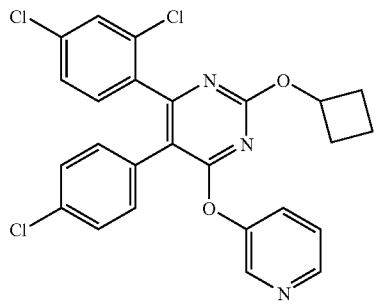

2-(2-Cyclobutyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (30 mg, 0.06 mmol) with 2 equivalents each of n-butyl lithium and cyclobutyl alcohol by the procedure described in Reference Examples 6 and 7 to afford 2-(2-cyclobutyloxy-4-(3-pyridyloxy)-5-(4-chlorophenyl)-6-(2,4-dichlorophenyl)pyrimidine: HPLC/MS: m/e=498 (M$^+$+1); R$_f$4.16 min. $^1$H-NMR 400 MHz (CDCl$_3$): δ 1.70-1.85 (m, 2H), 2.16-2.28 (m, 4H), 4.93 (m, 1H), 7.14-7.38 (m, 7H), 7.40-7.42 (m, 1H), 7.55-7.58 (m, 1H), 8.52-8.54 (m, 2H).

EXAMPLE 91

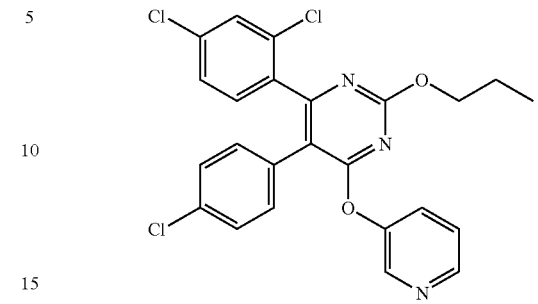

2-(n-Propyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (50 mg, 0.1 mmol) was reacted with 2 equivalents each of n-butyl lithium and n-propanol by the procedure described in Reference Examples 6 and 7 to afford 2-(2-n-propyloxy-4-(3-pyridyloxy)-5-(4-chlorophenyl)-6-(2,4-dichlorophenyl)pyrimidine. HPLC/MS: m/e=486 (M$^+$+1); R$_f$4.13 min. 1H-NMR 500 MHz (CDCl$_3$): δ 0.96 (t, 3H), 1.73-1.79 (m, 2H), 4.13-4.18 (m, 2H), 7.18-7.30 (m, 7H), 7.40-7.43 (m, 1H), 7.60 (m, 1H), 8.55 (s, 2H).

EXAMPLE 92

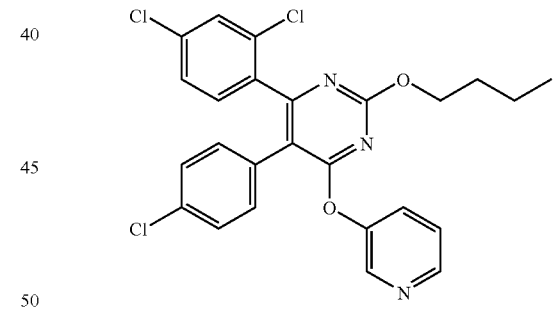

2-(n-butyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (50 mg, 0.1 mmol) with 2 equivalents each of n-butyl lithium and n-butanol by the procedure described in Reference Examples 6 and 7 to afford 2-(2-n-butyloxy-4-(3-pyridyloxy)-5-(4-chlorophenyl)-6-(2,4-dichlorophenyl)pyrimidine. HPLC/MS: m/e=500 (M$^+$+1); R$_f$=4.34 min. $^1$H-NMR 500 MHz (CDCl$_3$): δ 0.93 (t, 3H), 1.40-1.46 (m, 2H), 1.70-1.75 (m, 2H), 4.22-4.26 (t, 2H), 7.18-7.30 (m, 7H), 7.40-7.42 (m, 1H), 7.57-7.60 (m, 1H), 8.54-8.55 (m, 2H).

EXAMPLE 93

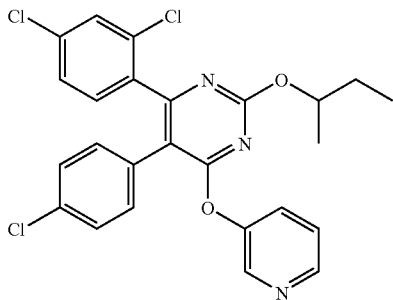

2-(sec-Butyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (50 mg, 0.1 mmol) was reacted with 2 equivalents each of n-butyl lithium and sec-butanol by the procedure described in Reference Examples 6 and 7 to afford 2-(sec-butyloxy)-4-(3-pyridyloxy)-5-(4-chloro-phenyl)-6-(2,4-dichlorophenyl)pyrimidine: HPLC/MS: m/e=500 (M$^+$+1); R$_t$=4.26 min. $^1$H-NMR 500 MHz (CDCl$_3$): δ 0.91 (t, 3H), 1.29 (d, J=6 Hz, 3H), 1.56-1.64 (m, 1H), 1.71-1.80 (m, 1H), 4.81-4.88 (m, 1H), 7.18-7.30 (m, 6H), 7.36-7.38 (t, 1H), 7.40-7.43 (m, 1H), 7.60 (m, 1H), 8.52-8.56 (m, 2H).

EXAMPLE 94

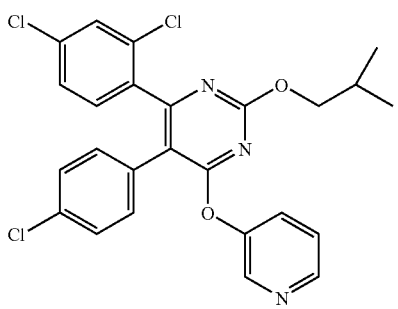

2-(iso-Butyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (100 mg, 0.2 mmol) with 2 equivalents each of n-butyl lithium and iso-butyl alcohol by the procedure described in Reference Examples 6 and 7 to afford the title compound: HPLC/MS: m/e=500 (M$^+$+1); R$_t$=4.31 min. $^1$H-NMR 500 MHz (CDCl$_3$): δ 0.96 (d, J=6 Hz, 6H), 2.02-2.10 (m, 1H), 4.01 (d, J=7 Hz, 2H), 7.18-7.30 (m, 6H), 7.39 (s, 1H), 7.40-7.43 (m, 1H), 7.58-7.60 (m, 1H), 8.55 (s, 2H).

EXAMPLE 95

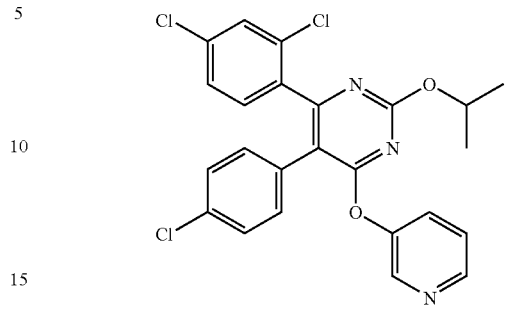

2-(Isopropyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (200 mg, 0.4 mmol) with 2 equivalents each of n-butyl lithium and isopropanol by the procedure described in Reference Examples 6 and 7 to afford the title compound: HPLC/MS: m/e=486 (M$^+$+1); R$_t$=4.11 min. $^1$H-NMR 400 MD (CDCl$_3$): δ 1.32 (d, J=6 Hz, 6H), 5.01-5.06 (m, 1H), 7.17-7.30 (m, 6H), 7.36-7.37 (d, J=2 Hz, 1H), 7.36-7.41 (m, 1H), 7.56-7.59 (m, 1H), 8.53-8.55 (m, 2H).

EXAMPLE 96

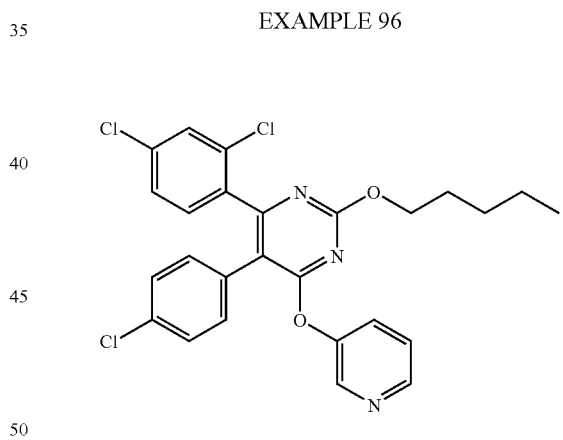

2-(n-Pentyloxy)-4-(3-pyridyloxy)-5-(4-chlorophenyl)-6-(2,4-dichlorophenyl)pyrimidine 2-Methylsulfonyl-4-(3-pyridyloxy)-5-(4-chlorophenyl)-6-(2,4-dichlorophenyl)pyrimidine from Example 86 (30 mg, 0.06 mmol) was reacted with 2 equivalents each of n-butyl lithium and n-pentanol by the procedure described in Reference Examples 6 and 7 to afford the title compound: HPLC/MS: m/e=514 (M$^+$+1); R$_t$'4.48 min. $^1$H-NMR 400 MHz (CDCl$_3$): δ 0.89-0.91 (t, 3H), 1.26-1.40 (m, 4H), 1.69-1.76 (m, 2H), 4.19-4.22 (t, 2H), 7.15-7.28 (m, 6H), 7.35 (d, J=2 Hz, 1H), 7.40-7.43 (m, 1H), 7.58-7.61 (m, 1H), 8.52-8.55 (m, 2H).

EXAMPLE 97

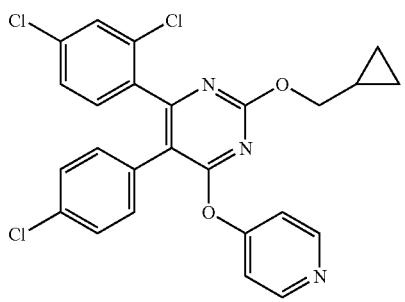

2-Cyclopropyloxy-4-(4-pyridyloxy)-5-(4-chlorophenyl)-6-(2,4-dichlorophenyl)pyrimidine 2-Cyclopropyloxy-4-methylsulfonyl-5-(4-chlorophenyl)-6-(2,4-dichlorophenyl)pyrimidine (MRf product) (Example 55, Step A), (25 mg, 0.05 mmol) was reacted with 1.1 equivalents each of sodium hydride (60% in oil, 2.5 mg, 0.06 mmol) and 4-hydroxypyridine (5.9 mg, 0.062 mmol) by the procedure described in Examples 16 to afford the title compound: HPLC/MS: m/e=498 ($M^+$+1); $R_t$=3.49 min. $^1$H-NMR 400 MHz (CDCl$_3$): δ 1.60-1.90 (m, 4H), 2.74 (m, 1H), 4.12 (d, J=7 Hz, 2H), 7.10-7.18 (m, 3H), 7.20-7.30 (m, 5H), 7.35 (d, J=2 Hz, 1H), 8.66 (d, J=6 Hz, 2H).

EXAMPLE 98

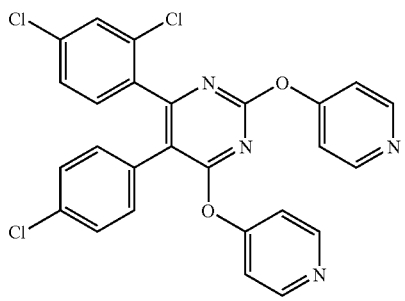

2,4-Bis-(4-pyridyloxy)-5-(4-chlorophenyl)-6-(2,4-dichlorophenyl)pyrimidine 2,4-Bis-(methylsulfonyl)-5-(4-chlorophenyl)-6-(2,4-dichlorophenyl)pyrimidine from Reference Example 5 (500 mg, 1.02 mmol) was reacted with 1.1 equivalents each of sodium hydride (60% in oil, 45 mg, 1.12 mmol) and 4-hydroxy-pyridine (106.4 mg, 1.12 mmol) by the general procedure described in Example 16 to afford the title compound: $^1$H-NMR 400 MHz (CDCl$_3$): δ 6.38 (d, J=8 Hz, 2H), 7.17-7.21 (m, 4H), 7.25-7.31 (m, 4H), 7.42 (d, J=2 Hz, 1H), 8.53 (d, J=8 Hz, 2H), 8.75 (d, J=5 Hz, 2H).

EXAMPLE 99

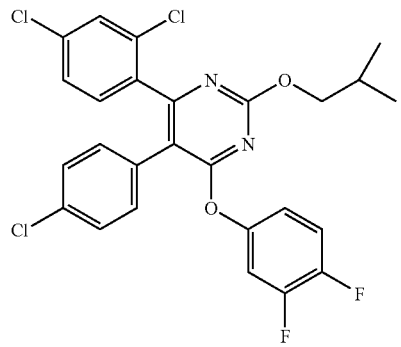

2-(Isobutyloxy)-4-(3,4-difluorophenoxy)-5-(4-chlorophenyl)-6-(2,4-dichlorophenyl)pyrimidine 2-Methylsulfonyl-4-(3,4-difluorophenoxy)-5-(4-chlorophenyl)-6-(2,4-dichlorophenyl)pyrimidine from Example 20 (65 mg, 0.12 mmol) was reacted with 2 equivalents each of n-butyl lithium and isobutyl alcohol by the procedure described in Reference Example 6 and 7 to yield the title compound: HPLC/MS: m/e=535 ($M^+$+1); $R_t$=5.28 min. $^1$H-NMR 400 MHz (CDCl$_3$): δ 0.97 (d, J=7 Hz, 6H), 2.07 (m, 1H), 4.01 (d, J=7 Hz, 2H), 6.90-6.94 (m, 1H), 7.05-7.10 (m, 1H), 7.12-7.28 (m, 7H), 7.34 (d, J=2 Hz, 1H).

EXAMPLE 100

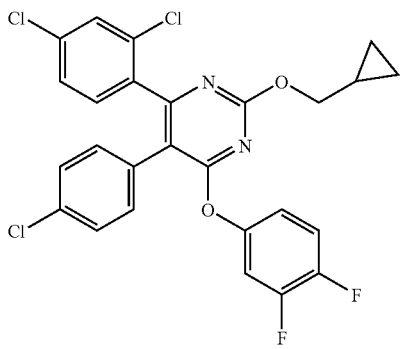

2-(Cyclopropylmethoxy)-4-(3,4-difluorophenoxy)-5-(4-chlorophenyl)-6-(2,4-dichlorophenyl)pyrimidine 2-Methylsulfonyl-4-(3,4-difluorophenoxy)-5-(4-chlorophenyl)-6-(2,4-dichlorophenyl)pyrimidine from Example 20 (65 mg, 0.12 mmol) was reacted with 2 equivalents each of n-butyl lithium and cyclopropylmethanol by the procedure described in Reference Example 6 and 7 to afford the title compound: HPLC/MS: m/e=533 ($M^+$+1); $R_t$=5.12 min. $^1$H-NMR 400 MHz (CDCl$_3$): δ 0.56-0.61 (m, 2H), 1.23-1.30 (m, 2H), 1.57 (s, 1H), 4.01 (d, J=7 Hz, 2H), 6.90-6.94 (m, 1H), 7.04-7.10 (m, 1H), 7.12-7.28 (m, 7H), 7.35 (d, J=2 Hz, 1H).

EXAMPLE 101

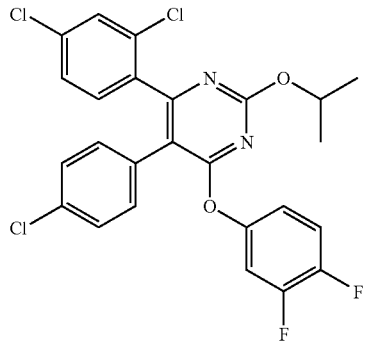

2-(Isopropyloxy)-4-(3,4-difluorophenoxy)-5-(4-chlorophenyl)-6-(2,4-dichlorophenyl)pyrimidine 2-Methylsulfonyl-4-(3,4-difluorophenoxy)-5-(4-chlorophenyl)-6-(2,4-dichlorophenyl)pyrimidine from Example 20 (30 mg, 0.06 mmol) with 2 equivalents each of n-butyl lithium and isopropyl alcohol by the procedure described in Reference Example 6 and 7 to afford the title compound: HPLC/MS: m/e=521 (M$^+$+1); R$_f$=4.93 min. $^1$H-NMR 400 MHz (CDCl$_3$): δ 1.33 (d, J=6 Hz, 6H), 5.02-5.09 (m, 1H), 6.90-6.94 (m, 1H), 7.04-7.10 (m, 1H), 7.12-7.28 (m, 7H), 7.35 (d, J=2 Hz, 1H).

EXAMPLE 102

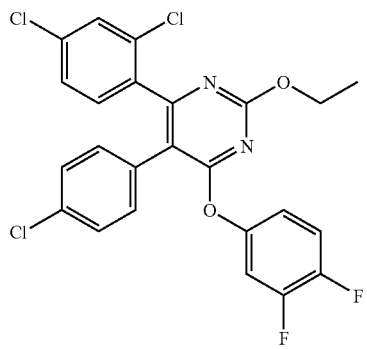

2-Ethoxy-4-(3,4-difluorophenoxy)-5-(4-chlorophenyl)-6-(2,4-dichlorophenyl)pyrimidine 2-Methylsulfonyl-4-(3,4-difluorophenoxy)-5-(4-chlorophenyl)-6-(2,4-dichlorophenyl)pyrimidine from Example 20 (30 mg, 0.06 mmol) was reacted with 2 equivalents each of n-butyl lithium and ethanol by the procedure described in Reference Example 6 and 7 to afford the title compound: HPLC/MS: m/e=507 (M$^+$+1); R$_f$=4.85 min. $^1$H-NMR 400 MHz (CDCl$_3$): δ 1.36-1.40 (t, 3H), 4.28-4.38 (dd, J=9 Hz, J=7 Hz, 2H), 6.90-6.94 (m, 1H), 7.04-7.10 (m, 1H), 7.12-7.28 (m, 7H), 7.35 (d, J=2 Hz, 1H).

EXAMPLE 103

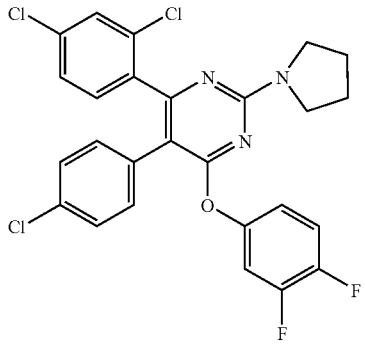

2-(N-Pyrrolidinyl)-4-(3,4-difluorophenoxy)-5-(4-chlorophenyl)-6-(2,4-dichlorophenyl)pyrimidine To a sealed tube fitted with a magnetic stirrer bar was added 2-methylsulfonyl-4-(3,4-difluorophenoxy)-5-(4-chlorophenyl)-6-(2,4-dichlorophenyl)pyrimidine (from Example 20) (30 mg, 0.06 mmol), 10 eq. of pyrrolidine and THF, flushed with nitrogen. The reaction was heated at 60° C. overnight in the sealed tube. The solvent was removed under reduced pressure. Flash column chromatography on silica gel (eluted with 90/10 hexanes/ethyl acetate) afforded the title compound: HPLC/MS: m/e=532 (M$^+$+1); R$_f$=4.9 min. $^1$H-NMR 500 MHz (CDCl$_3$): δ 1.91-2.00 (m, 4H), 3.23-3.40 (s, 2H1), 3.45-3.62 (s, 2H), 6.89-6.94 (m, 1H), 7.08-7.21 (m, 8H), 7.35 (s, 1H).

EXAMPLE 104

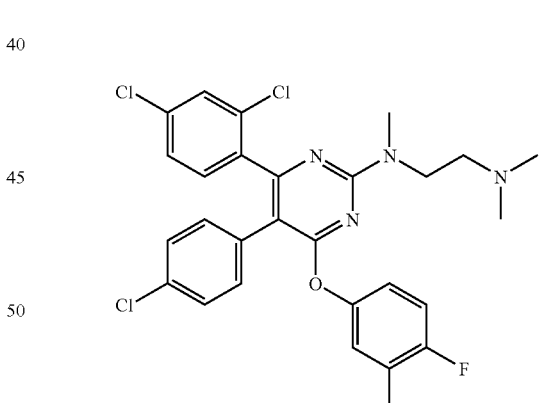

2-(N,N',N'-Trimethyl-ethylenediamino)-4-(3,4-difluorophenoxy)-5-(4-chlorophenyl)-6-(2,4-dichlorophenyl)pyrimidine 2-Methylsulfonyl-4-(3,4-difluorophenoxy)-5-(4-chlorophenyl)-6-(2,4-dichlorophenyl)pyrimidine (from Example 20) (30 mg, 0.06 mmol) was reacted with excess N,N',N'-trimethylethylenediamine (0.3 mL) in THF in a sealed tube at 60° C. overnight by general procedure described in Example 103 to afford the title compound: HPLC/MS: m/e=563 (M$^+$+

1); R,3.68 min. ¹H-NMR 500 MHz (CDCl₃): δ2.08-2.58 (m, 6H), 2.93-3.20 (m, 4H), 3.45-3.80 (m, 3H), 6.90-6.94 (m, 1H), 7.04-7.20 (m, 8H), 7.34 (d, J=2 Hz, 1H).

EXAMPLE 105

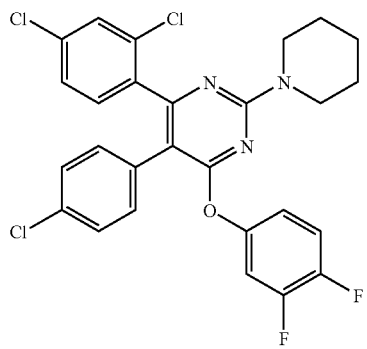

2-(N-Piperidinyl)-4-(3,4-difluorophenoxy)-5-(4-chlorophenyl)-6-(2,4-dichlorophenyl)pyrimidine 2-Methylsulfonyl-4-(3,4-difluorophenoxy)-5-(4-chlorophenyl)-6-(2,4-dichlorophenyl)pyrimidine (from Example 20) (30 mg, 0.06 mmol) was reacted with excess piperidine (0.5 mL) in THF in a sealed tube at 60° C. overnight by general procedure described in Example 103 to afford the title compound: HPLC/MS: m/e=546 (M⁺+1); R_f=5.36 min. ¹H-NMR 400 MHz (CDCl₃); δ 0.85-0.95 (m, 2H), 1.71-1.59 (m, 2H), 1.60-1.69 (m, 2H), 3.55-3.65 (s, 4H), 6.89-6.94 (m, 1H), 7.08-7.21 (m, 8H), 7.35 (d, J=2 Hz, 1H).

EXAMPLE 106

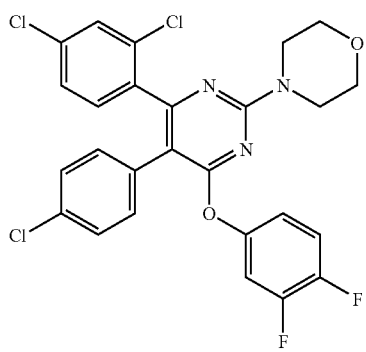

2-(N-morpholinyl)-ethylenediamino-4-(3,4-difluorophenoxy)-5-(4-chlorophenyl)-6-(2,4-dichlorophenyl)pyrimidine 2-Methylsulfonyl-4-(3,4-difluorophenoxy)-5-(4-chlorophenyl)-6-(2,4-dichlorophenyl)pyrimidine (from Example 20) (30 mg, 0.06 mmol) with excess morpholine (0.5 mL) in THF in a sealed tube at 60° C. overnight by general procedure described in Example 103 to afford the title compound: HPLC/MS: m/e=548 (M⁺+1); R_f=4.96 min. ¹H-NMR 400 MHz (CDCl₃): δ3.60-3.75 (m, 8H), 6.89-6.94 (m, 1H), 7.02-7.08 (m, 1H), 7.08-7.21 (m, 7H), 7.35 (d, J=2 Hz, 1H).

EXAMPLE 107

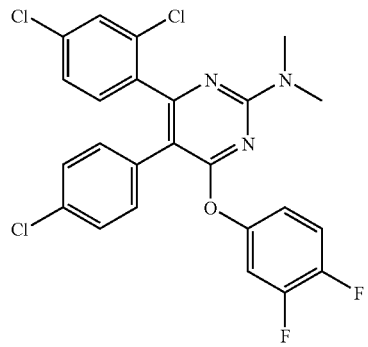

2-Dimethylamino-4-(3,4-difluorophenoxy)-5-(4-chlorophenyl)-6-(2,4-dichlorophenyl)pyrimidine 2-Methylsulfonyl-4-(3,4-difluorophenoxy)-5-(4-chlorophenyl)-6-(2,4-dichlorophenyl)pyrimidine (from Example 20) (100 mg, 0.19 mmol) was reacted with excess dimethylamine (0.14 mL, 0.28 mmol) in THF in a sealed tube at 60° C. overnight by general procedure described in Example 103 to afford the title compound: HPLC/MS: m/e=506 (M⁺+1); R_f=4.99 min. ¹H-NMR 400 MHz (CDCl₃); δ 3.00-3.20 (s, 6H), 6.89-6.94 (m, 1H), 7.08-7.21 (m, 8H), 7.35 (d, J=2 Hz, 1H).

EXAMPLE 108

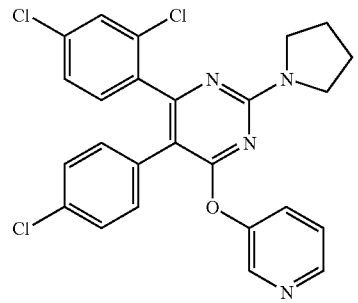

2-(N-Pyrrolidinyl)-4-(3-pyridyloxy)-5-(4-chlorophenyl)-6-(2,4-dichlorophenyl)pyrimidine 2-(N-pyrrolidinyl)-4-methylsulfonyl-5-(4-chlorophenyl)-6-(2,4-dichlorophenyl)pyrimidine (HRf product from Example 36, Step A (50 mg, 0.10 mmol) was reacted with 2 equivalents each of n-butyl lithium and 3-hydroxypyridine by the procedure described in Reference Example 6 and 7 to afford the title compound: HPLC/MS: m/e=497 (M⁺+1); R_f=3.84 min. ¹H-NMR 400 MHz (CDCl₃): δ 1.91-2.00 (m, 4H), 3.23-3.35 (s, 2H), 3.55-3.62 (s, 2H), 7.08-7.21 (m, 6H), 7.35-7.39 (m, 2H), 7.56-7.58 (m, 1H), 8.48 (d, J=6 Hz, 1H), 8.58 (s, 1H).

EXAMPLE 109

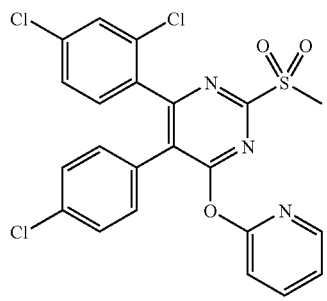

2-Methylsulfonyl-4-(2-pyridyloxy)-5-(4-chlorophenyl)-6-(2,4-dichlorophenyl)pyrimidine 2,4-Bis(methylsulfonyl)-5-(4-chlorophenyl)-6-(2,4-dichlorophenyl)pyrimidine from Reference Example 5 (200 mg, 0.41 mmol) was reacted with 1.0 equivalent of n-butyl lithium and 1.1 equivalent of 2-hydroxypyridine by the procedure described in Example 86 to afford the title compound: $^1$H-NMR 400 MHz (CDCl$_3$): δ 3.22 (s, 3H), 7.15-7.33 (m, 8H), 7.38 (d, J=2 Hz, 1H), 7.85-7.90 (m, 1H), 8.30-8.42 (m, 1H).

EXAMPLE 110

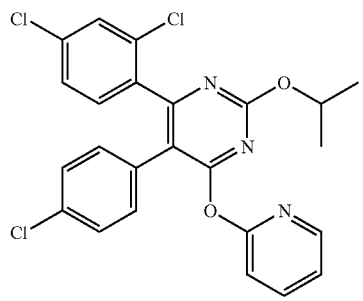

2-(2-Isopropyloxy)-4-(2-pyridyloxy)-5-(4-chlorophenyl)-6-(2,4-dichlorophenyl)pyrimidine 2-Methylsulfonyl-4-(2-pyridyloxy)-5-(4-chlorophenyl)-6-(2,4-dichlorophenyl)pyrimidine from Example 109 (50 mg, 0.1 mmol) with 2 equivalents each of n-butyl lithium and isopropanol by the procedure described in Reference Examples 6 and 7 to afford the title compound: HPLC/MS: m/e=486 (M$^+$+1); R$_t$=4.51 min. $^1$H-NMR 400 MHz (CDCl$_3$); δ 1.30 (d, J=6 Hz, 6H), 5.00-5.05 (m, 1H), 7.08-7.19 (m, 2H), 7.19-7.25 (m, 6H), 7.35 (d, J=2Hz, 1H), 7.79-7.83 (m, 1H), 8.42 (m, 1H).

EXAMPLE 111

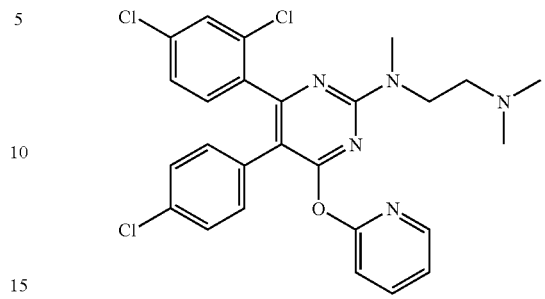

2-(N,N',N'-Trimethyl-ethylenediamino)-4-(2-pyridyloxy)-5-(4-chlorophenyl)-6-(2,4-dichlorophenyl) pyrimidine 2-Methylsulfonyl-4-(2-pyridyloxy)-5-(4-chlorophenyl)-6-(2,4-dichlorophenyl)pyrimidine from Example 109 (47 mg, 0.09 mmol) was reacted with with excess N,N',N'-trimethylethylenediamine (0.5 mL) in THF at a sealed tube 60° C. overnight by the general procedure described in Example 103 to afford the title compound HPLC/MS: m/e=528 (M$^+$+1); R$_t$=3.28 min. $^1$H-NMR 400 MHz (CDCl$_3$): δ 2.05-2.60 (m, 6H), 2.80-3.20 (m, 4H), 3.40-3.80 (m, 3H), 7.08-7.19 (m, 2H), 7.19-7.22 (m, 6H), 7.35 (d, J=2 Hz, 1H), 7.76-7.81 (m, 1H), 8.40-8.42 (m, 1H).

EXAMPLE 112

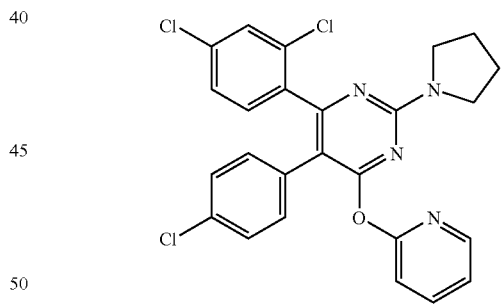

2-(2-Pyrrolidinyl)-4-(2-pyridyloxy)-5-(4-chlorophenyl)-6-(2,4-dichlorophenyl)pyrimidine 2-Methylsulfonyl-4-(2-pyridyloxy)-5-(4-chlorophenyl)-6-(2,4-dichlorophenyl)pyrimidine from Example 109 (45 mg, 0.09 mmol) was reacted with excess pyrrolidine (0.5 mL) in THF at a sealed tube 60° C. for overnight by general procedure Example 103 to afford the title compound: HPLC/MS: m/e=497 (M$^+$+1); R$_t$4.21 min. $^1$H-NMR 400 MHz (CDCl$_3$): δ 1.85-1.95 (s 4H), 3.20-3.60 (m, 4H), 7.00-7.19 (m, 8H), 7.31 (d, J=2 Hz, 1H), 7.75-7.80 (m, 1H), 8.38 (m, 1H).

EXAMPLE 113

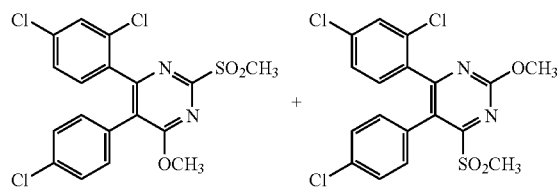

2-(Methylsulfonyl)-4-methoxy-5-(4-chlorophenyl)-6-(2,4-dichlorophenyl)pyrimidine 2-Methoxy-4-(methylsulfonyl)-5-(4-chlorophenyl)-6-(2,4-dichlorophenyl)pyrimidine 2,4-Bis(methylsulfonyl)-5-[4-chlorophenyl]-6-[2,4-dichlorophenyl]pyrimidine from Reference Example 5 (2.0 g, 4.1 mmol) was reacted with 1.0 equivalent each of n-butyl lithium and methanol by the procedure described in Reference Example 6 and 7 to afford 2-(methylsulfonyl)-4-methoxy-5-(4-chlorophenyl)-6-(2,4-dichlorophenyl)pyrimidine and 2-methoxy-4-(methylsulfonyl)-5-(4-chlorophenyl)-6-(2,4-dichloro-phenyl)pyrimidine as a mixture: HPLC/MS: m/e=443 (M$^+$+1); R$_t$=3.57-3.89 min.

EXAMPLE 114

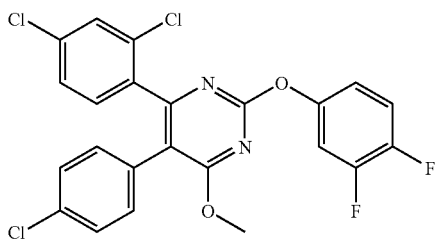

2-(3,4-Difluorophenyloxy)-4-methoxy-5-(4-chlorophenyl)-6-(2,4-dichlorophenyl)pyrimidine (HRf)

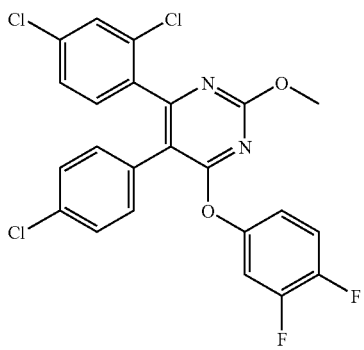

2-Methoxy-4-(3,4-difluorophenyloxy)-5-(4-chlorophenyl)-6-(2,4-dichlorophenyl)pyrimidine (LRf)

A mixture of 2-(methylsulfonyl)-4-methoxy-5-(4-chlorophenyl)-6-(2,4-dichlorophenyl)-pyrimidine and 2-methoxy-4-(methylsulfonyl)-5-(4-chloro-phenyl)-6-(2,4-dichlorophenyl)-pyrimidine (1.6 g, 3.6 mmol) from Example 113 was reacted with 2 equivalents each of sodium hydride (60% in oil, 0.29 g, 7.2 mmol) and 3,4-difluorophenol (0.94 g, 7.2 mmol) by the procedure described in Example 16 to afford a mixture of 2-(3,4-difluorophenyloxy)-4-methoxy-5-(4-chlorophenyl)-6-(2,4-dichlorophenyl)pyrimidine and 2-methoxy-4-(3,4-difluorophenyloxy)-5-(4-chlorophenyl)-6-(2,4-dichlorophenyl)pyrimidine which was separated by flash chromatography on silica gel. 2-(3,4-difluorophenyloxy)-4-methoxy-5-(4-chlorophenyl)-6-(2,4-dichlorophenyl)pyrimidine (HRf): HPLC/MS: m/e=493 (M$^+$+1); R$_t$=4.72 min. $^1$H-NMR 400 MHz (CDCl$_3$): δ 3.95 (s, 3H), 7.02-7.08 (m, 4H), 7.13-7.25 (m, 5H), 7.35 (d, J=2 Hz, 1 H). 2-methoxy-4-(3,4-difluorophenyl-oxy)-5-(4-chlorophenyl)-6-(2,4-dichlorophenyl)pyrimidine (LRf): HPLC/MS: m/e=493 (M$^+$+1); R$_t$=4.74 min. $^1$H-NMR 400 MHz (CDCl$_3$): δ 3.93 (s, 3H), 6.90-6.94 (m, 1H), 7.04-7.10 (m, 1H), 7.12-7.28 (m, 7H), 7.35 (d, J=2 Hz, 1H).

EXAMPLE 115

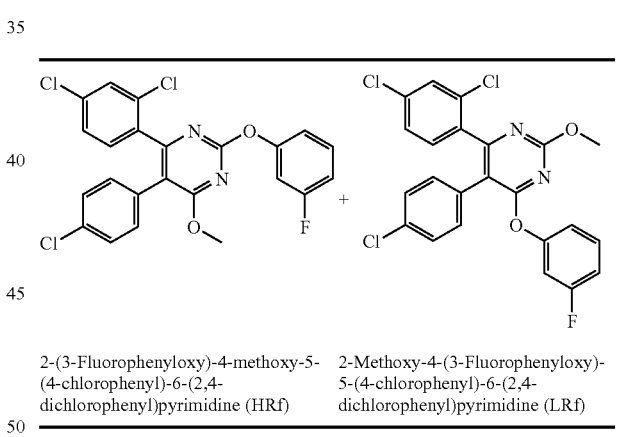

2-(3-Fluorophenyloxy)-4-methoxy-5-(4-chlorophenyl)-6-(2,4-dichlorophenyl)pyrimidine (HRf)

2-Methoxy-4-(3-Fluorophenyloxy)-5-(4-chlorophenyl)-6-(2,4-dichlorophenyl)pyrimidine (LRf)

A mixture of 2-(methylsulfonyl)-4-methoxy-5-(4-chlorophenyl)-6-(2,4-dichlorophenyl)-pyrimidine and 2-methoxy-4-(methylsulfonyl)-5-(4-chloro-phenyl)-6-(2,4-dichlorophenyl)-pyrimidine (Example 113) was reacted with 3 equivalents each of n-butyl lithium and 3-fluorophenol by the procedure described in Reference Example 6 and 7 to afford a mixture of 2-(3-fluorophenyloxy)-4-methoxy-5-(4-chlorophenyl)-6-(2,4-dichlorophenyl)pyrimidine and 2-methoxy-4-(3-fluoro-phenyloxy)-5-(4-chlorophenyl)-6-(2,4-dichlorophenyl)pyrimidine which was separated by flash column chromatography on silica gel. 2-(3-fluorophenyloxy)-4-methoxy-5-(4-chlorophenyl)-6-(2,4-dichlorophenyl)-pyrimidine (HRf): HPLC/MS: m/e=475 (M$^+$+1); R$_t$=4.82 min. $^1$H-NMR 400 MHz (CDCl$_3$): δ 3.93 (s, 3H), 6.90-6.94 (m, 1H), 7.04-7.19 (m, 5H), 7.12-7.40 (m, 5H);

2-methoxy-4-(3-fluorophenyl-oxy)-5-(4-chlorophenyl)-6-(2,4-dichlorophenyl)-pyrimidine (LRf): HPLC/MS: m/e=475 (M$^+$+1); R$_t$=4.74 min. $^1$H-NMR 400 MHz (CDCl$_3$): 3.90 (s, 3H), 6.55-6.65 (m, 1H), 6.95-7.00 (m, 1H), 7.12-7.40 (m, 9H).

EXAMPLE 116

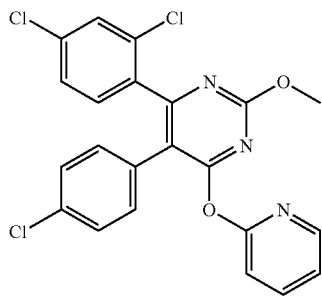

2-Methoxy-4-(2-pyridyloxy)-5-(4-chlorophenyl)-6-(2,4-dichlorophenyl)pyrimidine (HRf)

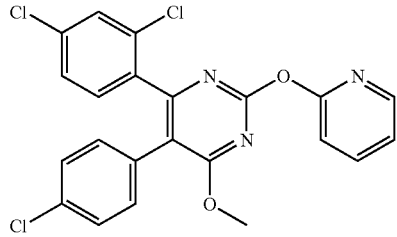

2-(2-Pyridyloxy)-4-methoxy-5-(4-chlorophenyl)-6-(2,4-dichlorophenyl)pyrimidine (LRf)

A mixture of 2-(methylsulfonyl)-4methoxy-5-(4-chlorophenyl)-6-(2,4-dichlorophenyl)-pyrimidine and 2-methoxy-4-(methylsulfonyl)-5-(4-chloro-phenyl)-6-(2,4-dichlorophenyl)-pyrimidine (Example 113) was reacted with 3 equivalents each of n-butyl lithium and 2-hydroxypyridine by the procedure described in Reference Example 6 and 7 to afford a mixture of 2-methoxy-4-(2-pyridyloxy)-5-(4-chlorophenyl)-6-(2,4-dichlorophenyl)pyrimidine and 2-(2-pyridyloxy)-4-methoxy-5-(4-chlorophenyl)-6-(2,4-dichlorophenyl)pyrimidine which was separated by flash column chromatography on silica gel. 2-methoxy-4-(2-pyridyloxy)-5-(4-chlorophenyl)-6-(2,4-dichlorophenyl)pyrimidine (HRf): HPLC/MS: m/e=458 (M$^+$+1); R$_t$=4.18 min. $^1$H-NMR 400 MHz (CDCl$_3$): δ 3.89 (s, 3H), 6.90-6.94 (m, 1H), 7.09-7.28 (m, 7H), 7.36 (m, 1H), 7.79-7.81 (m, 1H), 8.40-8.42 (m, 1H); 2-(2-pyridyloxy)-4-methoxy-5-(4-chlorophenyl)-6-(2,4-dichlorophenyl)pyrimidine (LRf): HPLC/MS: m/e=458 (M$^+$+1); R$_t$=3.70 min. $^1$H-NMR 400 MHz (CDCl$_3$): δ 4.07 (s, 3H), 6.25-6.29 (m, 1H), 6.67 (d, J=9 Hz, 1H), 7.09-7.28 (m, 6H), 7.35 (d, J=2 Hz, 1H), 7.38-7.43 (m, 1H), 7.68-7.70 (m, 1H).

EXAMPLE 117

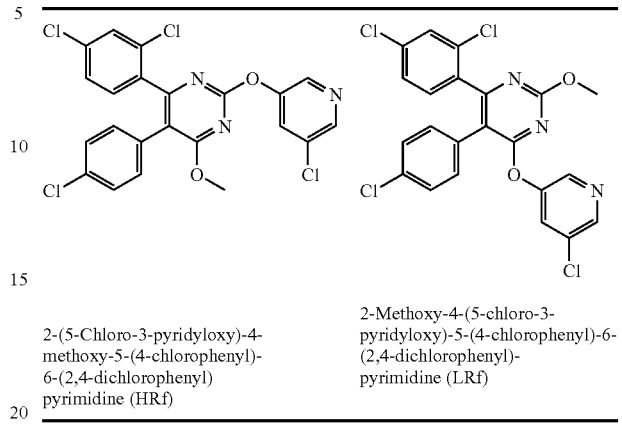

2-(5-Chloro-3-pyridyloxy)-4-methoxy-5-(4-chlorophenyl)-6-(2,4-dichlorophenyl) pyrimidine (HRf)

2-Methoxy-4-(5-chloro-3-pyridyloxy)-5-(4-chlorophenyl)-6-(2,4-dichlorophenyl)-pyrimidine (LRf)

A mixture of 2-(methylsulfonyl)-4-methoxy-5-(4-chlorophenyl)-6-(2,4-dichlorophenyl)-pyrimidine and 2-methoxy-4-(methylsulfonyl)-5-(4-chloro-phenyl)-6-(2,4-dichlorophenyl)-pyrimidine (Example 113) was reacted with 3 equivalents each of n-butyl lithium and 5-chloro-3-hydroxypyridine by the procedure described in Reference Example 6 and 7 to afford a mixture of 2-(5-chloro-3-pyridyloxy)-4-methoxy-5-(4-chlorophenyl)-6-(2,4-dichlorophenyl)pyrimidine and 2-methoxy-4-(5-chloro-3-pyridyloxy)-5-(4-chlorophenyl)-6-(2,4-dichlorophenyl)pyrimidine which was separated by flash column chromatography on silica gel. 2-(5-chloro-3-pyridyloxy)-4-methoxy-5-(4-chlorophenyl)-6-(2,4-dichlorophenyl)pyrimidine (HRf): HPLC/MS: m/e=492 (M$^+$=1); R$_t$4.90 min. $^1$H-NMR 400 MHz (CDCl$_3$): δ 3.98 (s, 3H), 7.00-7.06 (m, 3H), 7.13-7.15 (m, 1H), 7.22-7.24 (m, 2H), 7.33 (d, J=2 Hz, 1H), 7.73-7.74 (m, 1H), 8.46 (d, J=2 Hz, 1H), 8.56 (d, J=2 Hz, 1H); 2-methoxy-4-(5-chloro-3-pyridyloxy)-5-(4-chlorophenyl)-6-(2,4-dichloro-phenyl)pyrimidine (LRf): HPLC/MS: m/e=492 (M$^+$+1); R$_t$=4.70 min. $^1$H-NMR 400 MHz (CDCl$_3$): δ 3.93 (s, 3H), 7.14-7.17 (m, 3H), 7.21-7.28 (m, 3H), 7.36 (d, J=2 Hz, 1H), 7.62 (m, 1H), 8.43 (d, J=2 Hz, 1H), 8.49 (d, J=2 Hz, 1H).

EXAMPLE 118

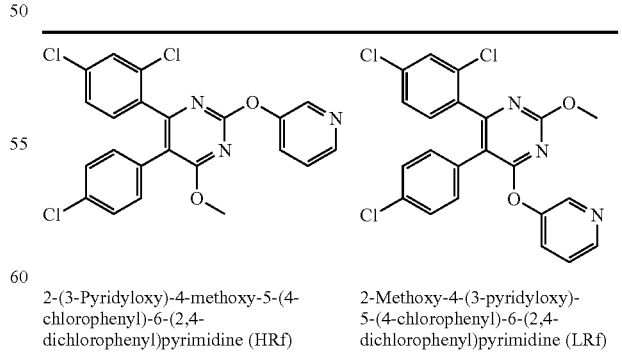

2-(3-Pyridyloxy)-4-methoxy-5-(4-chlorophenyl)-6-(2,4-dichlorophenyl)pyrimidine (HRf)

2-Methoxy-4-(3-pyridyloxy)-5-(4-chlorophenyl)-6-(2,4-dichlorophenyl)pyrimidine (LRf)

A mixture of 2-(methylsulfonyl)-4-methoxy-5-(4-chlorophenyl)-6-(2,4-dichlorophenyl)-pyrimidine and 2-methoxy-4-(methylsulfonyl)-5-(4-chlorophenyl)-6-(2,4-dichlorophenyl)-pyrimidine (Example 113) was reacted with 2 equivalents each of n-butyl lithium and 5-chloro-3-hydroxy-pyridine by the procedure described in Reference Example 6 and 7 to afford a mixture of 2-(3-pyridyloxy)-4-methoxy-5-(4-chlorophenyl)-6-(2,4-dichlorophenyl)pyrimidine and 2-methoxy-4-(3-pyridyloxy)-5-(4-chlorophenyl)-6-(2,4-dichlorophenyl)pyrimidine which was separated by flash column chromatography on silica gel. 2-(3-pyridyloxy)-4-methoxy-5-(4-chlorophenyl)-6-(2,4-dichlorophenyl)pyrimidine (HRf): HPLC/MS: m/e=458 (M$^+$+1); R$_t$=3.49 min. $^1$H-NMR 400 MHz (CDCl$_3$): δ 3.95 (s, 3H), 7.00-7.06 (m, 3H), 7.13-7.15 (m, 1H), 7.22-7.30 (m, 3H), 7.37-7.40 (m, 1H), 7.67-7.70 (m, 1H), 8.48-8.50 (m, 1H), 8.67 (d, J=3 Hz, 1H); 2-methoxy-4-(3-pyridyloxy)-5-(4-chlorophenyl)-6-(2,4-dichlorophenyl)pyrimidine (LRf): HPLC/MS: m/e=458 (M$^+$+1); R$_t$=3.63 min. $^1$H-NMR 400 MHz (CDCl$_3$): δ 3.90 (s, 3H), 7.15-7.28 (m, 6H), 7.35-7.40 (m, 2H), 7.56-7.59 (m, 1H), 8.51-8.53 (m, 2H).

EXAMPLE 119

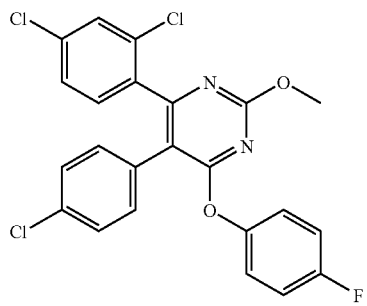

2-Methoxy-4-(4-fluorophenyloxy)-5-(4-chlorophenyl)-6-(2,4-dichlorophenyl)pyrimidine A mixture of 2-(methylsulfonyl)-4-methoxy-5-(4-chlorophenyl)-6-(2,4-dichlorophenyl)-pyrimidine and 2-methoxy-4-(methylsulfonyl)-5-(4-chloro-phenyl)-6-(2,4-dichlorophenyl)-pyrimidine (Example 113) was reacted with 1.1 equivalents each of n-butyl lithium and 4-fluorophenol by the procedure described in Reference Example 6 and 7 to afford a mixture of 2-(4-fluorophenyloxy)-4-methoxy-5-(4-chlorophenyl)-6-(2,4-dichlorophenyl) and 2-methoxy-4-(4-fluorophenyloxy)-5-(4-chlorophenyl)-6-(2,4-dichlorophenyl) pyrimidine which was separated by flash column chromatography on silica gel. Only the LRf was characterized. 2-methoxy-4-(4-fluorophenyloxy)-5-(4-chlorophenyl)-6-(2,4-dichlorophenyl)pyrimidine (LRf): HPLC/MS: m/e=475 (M$^+$+1); R$_t$=4.61 min. $^1$H-NMR 400 MHz (CDCl$_3$): 3.89 (s, 3H), 6.75-6.79 (m, 2H), 6.91-6.96 (m, 2H), 7.10-7.34 (m, 7H).

EXAMPLE 120

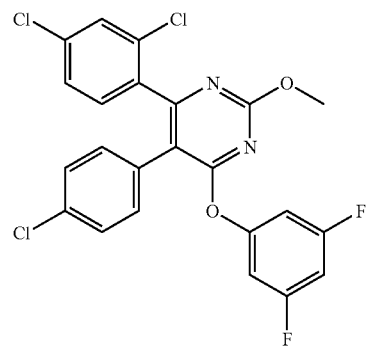

2-Methoxy-4-(3,5-difluorophenyloxy)-5-(4-chlorophenyl)-6-(2,4-dichlorophenyl)pyrimidine A mixture of 2-(methylsulfonyl)-4-methoxy-5-(4-chlorophenyl)-6-(2,4-dichlorophenyl)-pyrimidine and 2-methoxy-4-(methylsulfonyl)-5-(4-chloro-phenyl)-6-(2,4-dichlorophenyl)-pyrimidine Example 113) was reacted with 1.1 equivalents each of n-butyl lithium and 3,5-difluorophenol by the procedure described in Reference Example 6 and 7 to afford a mixture of 2-(3,5-difluorophenyloxy)-4-methoxy-5-(4-chlorophenyl)-6-(2,4-dichlorophenyl)pyrimidine and 2-methoxy-4-(3,5-difluorophenyloxy)-5-(4-chlorophenyl)-6-(2,4-dichlorophenyl)pyrimidine which was separated by flash column chromatography on silica gel. Only the LRf was characterized: 2-methoxy-4-(3,5-difluorophenyloxy)-5-(4-chlorophenyl)-6-(2,4-dichlorophenyl)pyrimidine (LRf): HPLC/MS: m/e=493 (M$^+$+1); R$_t$=4.77 min. $^1$H-NMR 400 MHz (CDCl$_3$): δ 3.94 (s, 3H), 6.33-6.42 (m, 3H), 6.70-6.80 (m, 2H), 7.12-7.28 (m, 5H), 7.34 (d, J=2Hz, 1H).

EXAMPLE 121

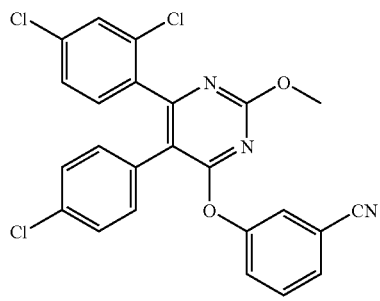

2-Methoxy-4-(3-cyanophenyloxy)-5-(4-chlorophenyl)-6-(2,4-dichlorophenyl)pyrimidine A mixture of 2-(methylsulfonyl)-4-methoxy-5-(4-chlorophenyl)-6-(2,4-dichlorophenyl)pyrimidine and 2-methoxy-4-(methylsulfonyl)-5-(4-chlorophenyl)-6-(2,4-dichlorophenyl)pyrimidine (Example 113) was reacted with 1.1 equivalents each of n-butyl lithium and 3-cyanophenol by the procedure described in Reference Example 6 and 7 to afford a mixture of 2-(3-cyanophenyloxy)-4-methoxy-5-(4-chlorophenyl)-6-(2,4-dichlorophenyl)pyrimidine and 2-methoxy-4-(3-cyanophenyloxy)-5-(4-chlorophenyl)-6-(2,4-dichlorophenyl)pyrimidine which was separated by flash column chromatography on silica gel. Only the LRf was characterized: 2-methoxy-4-(3-cyano-phenyloxy)-5-(4-chlorophenyl)-6-(2,4-dichlorophenyl)pyrimidine (HRf): HPLC/MS: m/e=482 (M$^+$+1); R$_f$=4.45 min. $^1$H-NMR 400 MHz (CDCl$_3$): δ 3.93 (s, 3H), 7.09-7.20 (m, 3H), 7.22-7.35 (m, 4H), 7.38-7.40 (m, 2H), 7.45-7.60 (m, 2H).

EXAMPLE 122

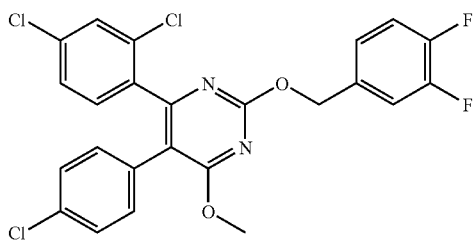

2-(3,4-Difluorobenzyloxy)-4-methoxy-5-(4-chlorophenyl)-6-(2,4-dichlorophenyl)pyrimidine (HRf)

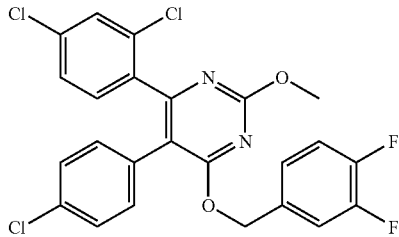

2-Methoxy-4-(3,4-difluorobenzyloxy)-5-(4-chlorophenyl)-6-(2,4-dichlorophenyl)pyrimidine (LRf)

A mixture of 2-(methylsulfonyl)-4-methoxy-5-(4-chlorophenyl)-6-(2,4-dichlorophenyl)-pyrimidine and 2-methoxy-4-(methylsulfonyl)-5-(4-chlorophenyl)-6-(2,4-dichlorophenyl)-pyrimidine (Example 113) was reacted with 1.1 equivalents each of n-butyl lithium and 3,4-difluorobenzyl alcohol by the procedure described in Reference Example 6 and 7 to afford a mixture of 2-(3,4-difluorobenzyl-oxy)-4-methoxy-5-(4-chlorophenyl)-6-(2,4-dichlorophenyl)pyrimidine and 2-methoxy-4-(3,4-difluorobenzyloxy)-5-(4-chlorophenyl)-6-(2,4-dichlorophenyl)pyrimidine which was separated by flash column chromatography on silica gel. 2-(3,4-difluorobenzyloxy)-4-methoxy-5-(4-chlorophenyl)-6-(2,4-dichlorophenyl)pyrimidine (HRf): HPLC/MS: m/e=507 (M$^+$+1). $^1$H-NMR 400 MHz (CDCl$_3$): δ 4.00 (s, 3H), 5.44 (s, 2H), 7.02-7.15 (m, 4H), 7.15-7.25 (m, 5H), 7.35 (d, J=2 Hz, 1H). 2-methoxy-4-(3,4-difluorobenzyloxy)-5-(4-chlorophenyl)-6-(2,4-dichlorophenyl)pyrimidine (LRf): HPLC/MS: m/e=507 (M$^+$+1). $^1$H-NMR 500 MHz (CDCl$_3$): δ 4.15 (s, 3H), 5.45 (s, 2H), 7.02-7.22 (m, 9H), 7.35 (d, J=2 Hz, 1H).

EXAMPLE 123

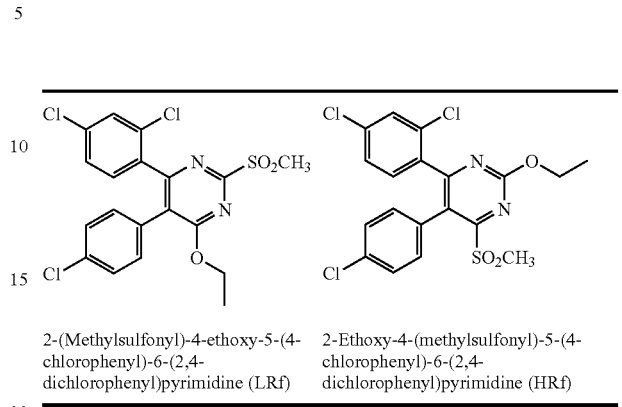

| 2-(Methylsulfonyl)-4-ethoxy-5-(4-chlorophenyl)-6-(2,4-dichlorophenyl)pyrimidine (LRf) | 2-Ethoxy-4-(methylsulfonyl)-5-(4-chlorophenyl)-6-(2,4-dichlorophenyl)pyrimidine (HRf) |
|---|---|

2,4-bis(methylsulfonyl)-5-[4-chlorophenyl]-6-[2,4-dichlorophenyl]pyrimidine (Reference Example 5) (100 mg, 0.2 mmol) was reacted with 1.5 equivalents of sodium hydride (60% in oil, 12.2 mg, 0.31 mmol) and 1.0 equivalent of ethanol (9.4 mg, 0.204 mmol) by the procedure described in Example 16 to afford a mixture of 2-(methylsulfonyl)-4-ethoxy-5-(4-chlorophenyl)-6-(2,4-dichlorophenyl)pyrimidine and 2-ethoxy-4-(methylsulfonyl)-5-(4-chlorophenyl)-6-(2,4-dichloro-phenyl)pyrimidine which was separated by flash column chromatography on silica gel. 2-ethoxy-4-(methylsulfonyl)-5-(4-chlorophenyl)-6-(2,4-dichlorophenyl)pyrimidine (HRf): HPLC/MS: m/e=457 (M$^+$+1); R$_t$=4.00 min. $^1$H-NMR 400 MHz (CDCl$_3$): δ 1.55 (t, 3H), 3.38 (s, 3H), 4.55-4.58 (dd, J=9 Hz, J=7 Hz, 2H), 6.95 (d, J=9 Hz, 1H), 7.15-7.19 (m, 2H), 7.25-7.29 (m, 3H), 7.35 (d, J=2 Hz, 1H). 2-(methyl-sulfonyl)-4-ethoxy-5-(4-chlorophenyl)-6-(2,4-dichlorophenyl)pyrimidine (LRf): HPLC/MS: m/e=457 (M$^+$+1); R$_t$=3.84 min. $^1$H-NMR 400 MHz (CDCl$_3$): δ 1.40 (t, 3H), 3.40(s, 3H), 4.60-4.69 (dd, J=9 Hz, J=7 Hz, 2H), 7.15-7.26 (m, 6H), 7.35 (d, J=2 Hz, 1H).

EXAMPLE 124

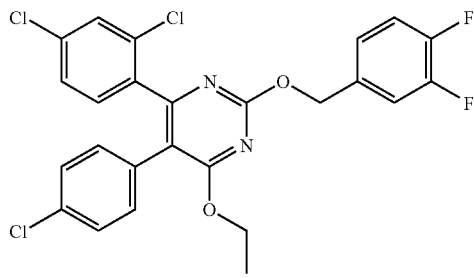

2-(3,4-Difluorobenzyloxy)-4-ethoxy-5-(4-chlorophenyl)-6-(2,4-dichlorophenyl)pyrimidine 2-(Methylsulfonyl)-4-ethoxy-5-(4-chlorophenyl)-6-(2,4-dichloro-phenyl)pyrimidine (LRf from Example 123) was reacted with 2 equivalents each of sodium hydride and 3,4-difluorobenzyl alcohol by the procedure described in Example 16 to afford the title compound: HPLC/MS: m/e=521 (M$^+$+1); R$_f$=4.90 min. $^1$H-NMR 400 MHz (CDCl$_3$): δ 1.35 (t, 3H), 4.45-4.55 (dd, J=9 Hz, J=7 Hz, 2H), 5.20 (s, 2H), 7.02-7.21 (m, 9H), 7.35 (d, J=2 Hz, 1H).

EXAMPLE 125

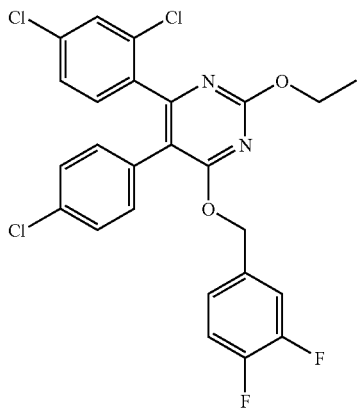

2-Ethoxy-4-(3,4-difluorophenyloxy)-5-(4-chlorophenyl)-6-(2,4-dichlorophenyl)pyrimidine 2-Ethoxy-4-(methylsulfonyl)-5-(4-chlorophenyl)-6-(2,4-dichloro-phenyl)pyrimidine (HRf from Example 123) was reacted with 2 equivalents each of sodium hydride and 3,4-difluorobenzyl alcohol by the procedure described in Example 16 to afford the title compound: HPLC/MS: m/e=498 (M$^+$+1); R$_f$=4.30 min. $^1$H-NMR 400 MHz (CDCl$_3$): δ 1.45 (t, 3H), 4.45-4.55 (dd, J=9 Hz, J=7 Hz, 2H), 5.22 (s, 2H), 7.01-7.21 (m, 9H), 7.35 (d, J=2 Hz, 1H).

EXAMPLE 126

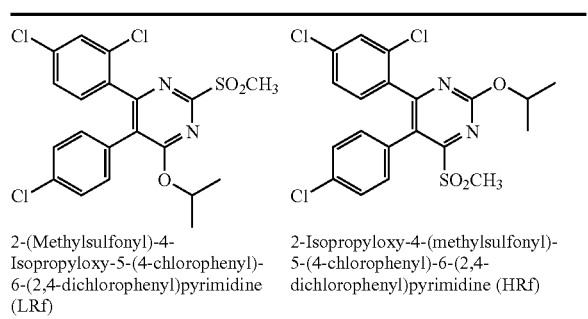

2-(Methylsulfonyl)-4-Isopropyloxy-5-(4-chlorophenyl)-6-(2,4-dichlorophenyl)pyrimidine (LRf)

2-Isopropyloxy-4-(methylsulfonyl)-5-(4-chlorophenyl)-6-(2,4-dichlorophenyl)pyrimidine (HRf)

2,4-bis(methylsulfonyl)-5-[4-chlorophenyl]-6-[2,4-dichlorophenyl]pyrimidine (Reference Example 5) (100 mg, 0.2 mmol) was reacted with 1.1 equivalents of isopropanol and 1.5 equivalents of sodium hydride by the procedure described in Example 16 to afford a mixture of 2-isopropoxy-4-(methylsulfonyl)-5-(4-chlorophenyl)-6-(2,4-dichlorophenyl)pyrimidine and 2-(methylsulfonyl)-4-isopropoxy-5-(4-chlorophenyl)-6-(2,4-dichlorophenyl)pyrimidine which was separated by flash column chromatography on silica gel. 2-isopropoxy-4-(methylsulfonyl)-5-(4-chlorophenyl)-6-(2, 4-dichlorophenyl)pyrimidine (HRf): $^1$H-NMR 400 MHz (CDCl$_3$): δ 1.50 (d, J=8 Hz, 6H), 3.38 (s, 3H), 5.35-5.40 (m, 1H), 6.95 (d, J=9 Hz, 1H), 7.17-7.19 (m, 3H), 7.25-7.29 (m, 2H), 7.35 (d, J=2 Hz, 1H); 2-(methylsulfonyl)-4-isopropoxy-5-(4-chlorophenyl)-6-(2,4-dichlorophenyl)pyrimidine (LRf): $^1$H-NMR 400 MHz (CDCl$_3$): δ 1.40 (d, J=8 Hz, 6H), 3.39(s, 3H), 5.59-5.67 (m, 1H), 7.15-7.26 (m, 6H), 7.35 (d, J=2 Hz, 1H).

EXAMPLE 127

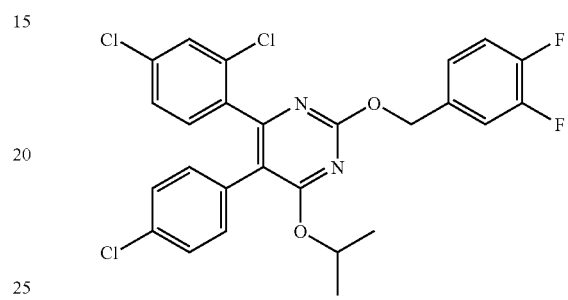

2-(3,4-Difluorobenzyloxy)-4-isopropyloxy-5-(4-chlorophenyl)-6-(2,4-dichlorophenyl)pyrimidine 2-(Methylsulfonyl)-4-isopropyloxy-5-(4-chlorophenyl)-6-(2,4-dichlorophenyl)pyrimidine (LRf from Example 126) was reacted with 2 equivalents each of sodium hydride and 3,4-difluorobenzyl alcohol by the procedure described in Example 16 to afford the title compound: HPLC/MS: m/e=535 (M$^+$+1); R$_f$=4.99 min. $^1$H-NMR 500 MHz (CDCl$_3$): δ 1.45 (d, J=8 Hz, 6H), 5.28-5.35 (m, 1H), 5.22 (s, 2H), 7.02-7.21 (m, 9H), 7.35 (d, J=2 Hz, 1H).

EXAMPLE 128

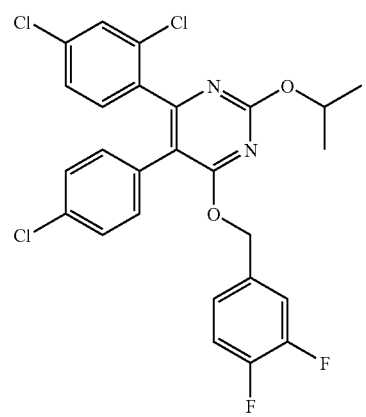

2-Isopropyloxy-4-(3,4-difluorophenyloxy)-5-(4-chlorophenyl)-6-(2,4-dichlorophenyl)pyrimidine 2-Isopropyloxy-4-(methylsulfonyl)-5-(4-chlorophenyl)-6-(2,4-dichlorophenyl)pyrimidine (HRf from Example 126)

was reacted with 2 equivalents each of sodium hydride and 3,4-difluorobenzyl alcohol by the procedure described in Example 16 to afford the title compound: HPLC/MS: m/e=535 (M$^+$+1); R$_t$=5.04 min. $^1$H-NMR 400 MHz (CDCl$_3$): δ 1.32 (d, J=4 Hz, 6H), 5.20 (s, 2H), 5.25-5.50 (m, 1H), 7.01-7.11 (m, 4H), 7.17-7.21 (m, 5H), 7.35 (d, J=2 Hz, 1H).

EXAMPLE 129

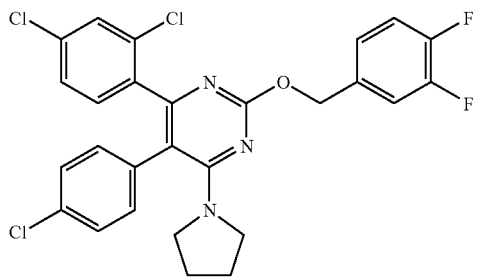

2-(3,4-Difluorobenzyloxy)-4-pyrrolidinyl-5-(4-chlorophenyl)-6-(2,4-dichlorophenyl)pyrimidine 2-(3,4-Difluorobenzyloxy)-4-(methylsulfonyl)-5-(4-chlorophenyl)-6-(2,4-dichlorophenyl)-pyrimidine (Reference Example 7) (30 mg, 0.05 mmol) was reacted with pyrrolidine (37.7 mg, 0.53 mmol) by the same general procedure described in Example 103 to afford the title compound after flash column chromatography on silica gel (eluted with 90/10 hexanes/ethyl acetate): HPLC/MS: m/e=546 (M$^+$+1); R$_t$=3.70 min. $^1$H-NMR 400 MHz (CDCl$_3$): δ 1.75-1.80 (br, 4H), 3.10-3.20 (br, 4H), 5.32-5.42 (m, 2H), 6.95 (d, J=9 Hz, 1H), 7.05-7.21 (m, 8H), 7.35-7.40 (m, 1H).

EXAMPLE 130

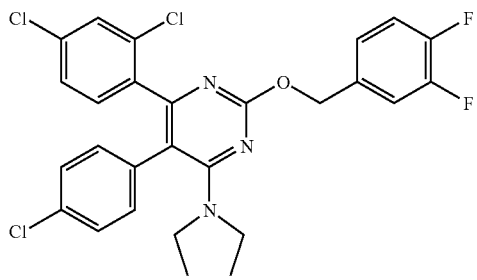

2-(3,4-Difluorobenzyloxy)-4-diethylamino-5-(4-chlorophenyl)-6-(2,4-dichlorophenyl)pyrimidine 2-(3,4-Difluorobenzyloxy)-4-(methylsulfonyl)-5-(4-chlorophenyl)-6-(2,4-dichlorophenyl)-pyrimidine (Reference Example 7) (29 mg, 0.05 mmol) was reacted with diethylamine (38.0 mg, 0.52 mmol) by the same general procedure described in Example 103 to afford the title compound: HPLC/MS: m/e=548 (M$^+$+1); R$_t$=3.84 min. $^1$H-NMR 400 MHz (CDCl$_3$): δ 0.96-1.00 (m, 6H), 3.20-3.30 (m, 4H), 5.30-5.40 (m, 2H), 6.90 (d, J=9 Hz, 1H), 7.01-7.21 (m, 8H), 7.35-7.40 (m, 1H).

EXAMPLE 131

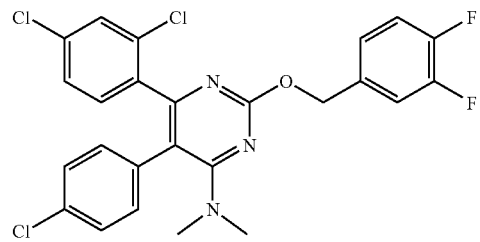

2-(3,4-Difluorobenzyloxy)-4-dimethylamino-5-(4-chlorophenyl)-6-(2,4-dichlorophenyl)pyrimidine 2-(3,4-Difluorobenzyloxy)-4-(methylsulfonyl)-5-(4-chlorophenyl)-6-(2,4-dichlorophenyl)-pyrimidine (Reference Example 7) (29 mg, 0.05 mmol) was reacted with 2 equivalents of dimethylamine by the same general procedure described in Example 103 to afford the title compound: HPLC/MS: m/e=520 (M$^+$+1); R$_t$=3.68 min. $^1$H-NMR 400 MHz (CDCl$_3$): δ 2.80 (s, 6H), 5.28-5.42 (m, 2H), 6.90 (d, J=9 Hz, 1H), 7.01-7.21 (m, 8H), 7.35-7.40 (m, 1H).

EXAMPLE 132

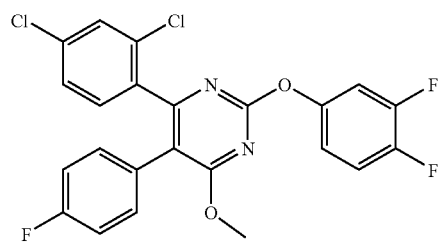

2-(3,4-Difluorophenoxy)-4-methoxy-5-(4-fluorophenyl)-6-[2,4-dichlorophenyl]pyrimidine To a 5 mL round bottom flask fitted with a stir bar and septum was added 2-(3,4-difluorophenoxy)-4-methoxy-5-trifluoromethansulfonyl-6-[2 4-dichlorophenyl]pyrimidine (85 mg, 0.16 mmol) as described in Reference Example 17, anhydrous potassium carbonate (66 mg, 0.48 mmol) and 4-fluorobenzeneboronic acid (44 mg, 0.32 mmol) in 1 mL 80/20 toluene/ethanol. The mixture was degassed under nitrogen with three freeze-thaw cycles and tetrakis(triphenylphosphine) palladium (27 mg, 0.024 mmol) was added to the reaction mixture and the mixture was heated between 75-90° C. for 4 h. The solvent was removed under reduced pressure and the residue flash chromatographed with 95/5 hexane/ethyl acetate to recover the desired product. HPLC/MS: m/e=477 (M$^+$−1); R$_t$=4.54 min. $^1$H-NMR 500 MHz (CDCl$_3$): δ 3.97 (s, 3H), 6.96 (m, 2H), 7.02-7.20 (m, 7H), 7.33 (d, J=2 Hz, 1H).

EXAMPLE 133

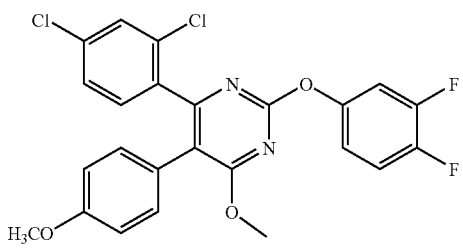

2-(3,4-Difluorophenoxy)-4-methoxy-5-(4-methoxyphenyl)-6-[2,4-dichlorophenyl]pyrimidine This derivative was prepared by the method described in Example 132 using 2-(3,4-difluorophenoxy)-4-methoxy-5-trifluoromethansulfonyl-6-[2,4-dichlorophenyl]pyrimidine (54 mg, 0.1 mmol) as described in Reference Example 17 and 4-methoxy-benzeneboronic acid (Lancaster, 16 mg, 0.11 mmol). HPLC/MS: m/e=488 (M$^+$–1); R$_t$=4.62 min. $^1$H-NMR 500 MHz (CDCl$_3$): δ 3.86 (s, 3H), 4.09 (s, 3H), 6.66 (m, 1H), 6.78 (m, 1H), 6.87 (dd, J=6 Hz, J=2 Hz, 2H), 7.08 (dd over m, J=6 Hz, J=2 Hz, 3H), 7.40 (d, J=1 Hz, 2H), 7.45 (d, J=2 Hz, 1H).

EXAMPLE 134

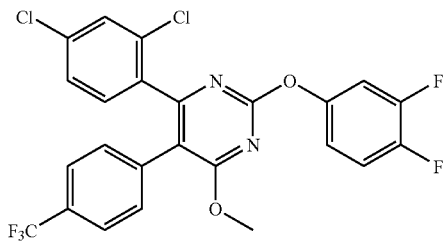

2-(3,4-Difluorophenoxy)-4-methoxy-5-(4-trifluoromethylphenyl)-6-[2,4-dichlorophenyl]pyrimidine This derivative was prepared by the method described in Example 132 using 2-(3,4-difluorophenoxy)-4-methoxy-5-trifluoromethansulfonyl-6-[2,4-dichlorophenyl]pyrimidine (60 mg, 0.11 mmol) as described in Reference Example 17 and 4-trifluoromethylbenzeneboronic acid (Lancaster, 24 mg, 0.13 mmol HPLC R$_t$=4.76 min. $^1$H-NMR 500 MHz (CDCl$_3$): 4.13 (s, 3H), 6.55 (m, 1H), 6.68 (m, 1H), 7.07 (q, J=10 Hz, 1H), 7.28 (m, 3H), (7.50 m, 3H), 7.61 (d, J=10 Hz, 2H).

EXAMPLE 135

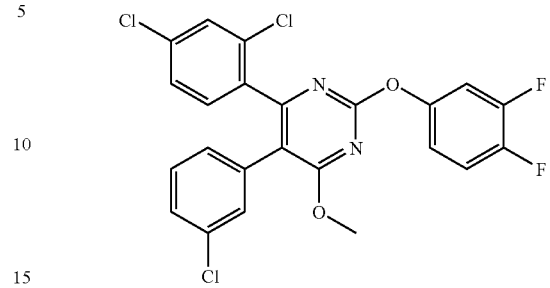

2-(3,4-Difluorophenoxy)-4-methoxy-5-(3-chlorophenyl)-6-[2,4-dichlorophenyl]pyrimidine This derivative was prepared by the method described in Example 132 using 2-(3,4-difluorophenoxy)-4-methoxy-5-trifluoromethansulfonyl-6-[2,4-dichlorophenyl]pyrimidine (27 mg, 0.05 mmol) as described in Reference Example 17 and 3-chlorobenzeneboronic acid (Lancaster, 16 mg, 0.1 mmol). HPLC R$_t$=4.82 min. $^1$H-NMR 500 MHz (CDCl$_3$): 3.88 (s, 3H), 6.45 (d, J=8 Hz, 1H), 6.51 (s, 1H), 6.67 (d, J=8 Hz, 1H), 6.71 (s, 1H), 6.95 (m, 1H), 7.05 (t, J=9 Hz, 1H), 7.8 (m, 2H), (7.39 s, 2H).

EXAMPLE 136

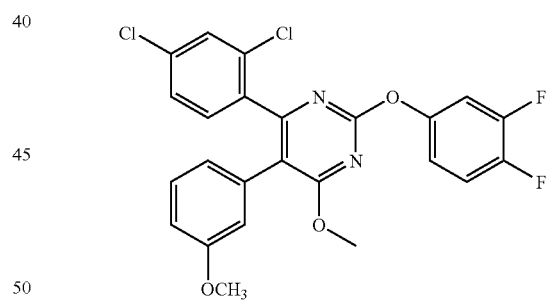

2-(3,4-Difluorophenoxy)-4-methoxy-5-(3-methoxyphenyl)-6-[2,4-dichlorophenyl]pyrimidine This derivative was prepared by the method described in Example 132 using 2-(3,4-difluorophenoxy)-4-methoxy-5-trifluoromethansulfonyl-6-[2,4-dichlorophenyl]pyrimidine (53 mg, 0.1 mmol) as described in Reference Example 17 and 3-methoxybenzeneboronic acid (Lancaster, 16 mg, 0.1 mmol). HPLC R$_t$=4.63 min. $^1$H-NMR 500 MHz (CDCl$_3$): 3.77 (s, 3H), 4.12 (s, 3H), 6.51 (m, 1H), 6.72 (m, 2H), 6.75 (m, 1H), 6.90 (dd, J=8 Hz, J=2 Hz, 1H), 7.07 (q, J=9 Hz, 1H), 7.25 (t, J=4 Hz, 1H), 7.43 (d, J=2 Hz, 2H), 7.49 (d, J=2 Hz, 1H).

EXAMPLE 137

Cannabinoid Receptor-1 (CB1) Binding Assay

Binding affinity determination is based on recombinant human CB1 receptor expressed in Chinese Hamster Ovary (CHO) cells (Felder et al, Mol. Pharmacol. 48: 443-450, 1995). Total assay volume is 250 μl (240 μl CB1 receptor membrane solution plus 5 μl test compound solution plus 5 μl [3H]CP-55940 solution). Final concentration of [3H]CP-55940 is 0.6 nM. Binding buffer contains 50 mM Tris-HCl, pH7.4, 2.5 mM EDTA, 5 mM $MgCl_2$, 0.5 mg/mL fatty acid free bovine serum albumin and protease inhibitors (Cat#P8340, from Sigma). To initiate the binding reaction, 5 μl of radioligand solution is added, the mixture is incubated with gentle shaking on a shaker for 1.5 hours at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from IC50 values (DeBlasi et al., Trends Pharmacol Sci 10: 227-229, 1989).

The binding assay for CB2 receptor is done similarly with recombinant human CB2 receptor expressed in CHO cells.

EXAMPLE 138

Cannabinoid Receptor-1 (CB1) Functional Activity Assay

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 μl of CB1-CHO cell suspension are mixed with test compound and 70 ul assay buffer containing 0.34 mM 3-isobutyl-1-methylxanthine and 5.1 uM of forskolin in 96-well plates. The assay buffer is comprised of Earle's Balanced Salt Solution supplemented with 5 mM $MgCl_2$, 1 mM glutamine, 10 mM HEPES, and 1 mg/mL bovine serum albumin. The mixture is incubated at room temperature for 30 minutes, and terminated by adding 30 ul/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

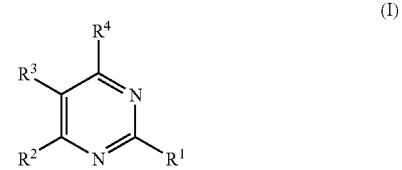

(I)

or a pharmaceutically acceptable salt thereof, wherein:
$R^1$ is selected from:
(1) —$OC_{1-6}$alkyl, unsubstituted or substituted with one to three $R^c$ substituents,
(2) cycloalkyloxy-, unsubstituted or substituted with one to three $R^c$ substituents,
(3) cycloalkyl-$C_{1-4}$alkyloxy-, unsubstituted or substituted with one to three $R^c$ substituents,
(4) cycloheteroalkyloxy-, unsubstituted or substituted with one to three $R^c$ substituents,
(5) cycloheteroalkyl-$C_{1-4}$alkyloxy, unsubstituted or substituted with one to three $R^c$ substituents,
(6) phenyloxy, unsubstituted or substituted with one to three $R^c$ substituents,
(7) heteroaryloxy, unsubstituted or substituted with one to three $R^c$ substituents,
(8) phenyl-$C_{1-4}$alkyloxy, unsubstituted or substituted with one to three $R^c$ substituents,
(9) heteroaryl-$C_{1-4}$alkyloxy, unsubstituted or substituted with one to three $R^c$ substituents,
(10) —$NR^aR^b$,
(11) —$NR^bC(O)R^a$,
(12) —$CO_2H$,
(13) $C_{1-6}$alkyloxycarbonyl-, unsubstituted or substituted with one to three $R^c$ substituents,
(14) cycloalkyloxycarbonyl-, unsubstituted or substituted with one to three $R^c$ substituents,
(15) cycloalkyl-$C_{1-4}$alkyloxycarbonyl-, unsubstituted or substituted with one to three $R^c$ substituents,
(16) phenyloxycarbonyl, unsubstituted or substituted with one to three $R^c$ substituents,
(17) heteroaryloxycarbonyl, unsubstituted or substituted with one to three $R^c$ substituents,
(18) phenyl-$C_{1-4}$alkyloxycarbonyl, unsubstituted or substituted with one to three $R^c$ substituents,
(19) heteroaryl-$C_{1-4}$alkyloxycarbonyl, unsubstituted or substituted with one to three $R^c$ substituents,
(20) —$C(O)NR^aR^b$,
(21) cyano,
(22) —$SO_2C_{1-6}$alkyl, unsubstituted or substituted with one to three $R^c$ substituents;
provided that $R^1$ is not $NH_2$;

$R^2$ is selected from:
 (1) hydrogen,
 (2) $C_{1-10}$alkyl,
 (3) —$OR^a$,
 (4) —$NR^aR^b$,
 (5) —$NR^aC(O)R^b$,
 (6) —$CO_2R^a$,
 (7) —$C(O)NR^aR^b$,
 (8) cyano,
 (9) —$SR^a$, and
 (10) —$SO_2R^a$;
wherein $R^3$ and $R^4$ are each independently selected from:

(1)
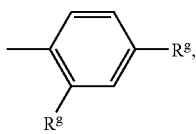

(2)
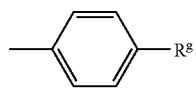

(3)
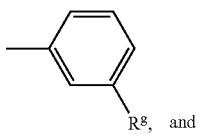

(4)
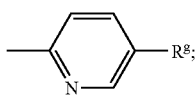

each $R^a$ is independently selected from:
 (1) hydrogen,
 (2) $C_{1-10}$alkyl,
 (3) $C_{2-10}$alkenyl,
 (4) cycloalkyl,
 (5) cycloalkyl-$C_{1-10}$alkyl;
 (6) cycloheteroalkyl,
 (7) cycloheteroalkyl-$C_{1-10}$alkyl;
 (8) aryl,
 (9) heteroaryl,
 (10) aryl-$C_{1-10}$alkyl, and
 (11) heteroaryl-$C_{1-10}$alkyl; and
 each $R^b$ is independently selected from:
 (1) hydrogen,
 (2) $C_{1-10}$alkyl,
 (3) $C_{2-10}$alkenyl,
 (4) cycloalkyl,
 (5) cycloalkyl-$C_{1-10}$alkyl;
 (6) cycloheteroalkyl,
 (7) cycloheteroalkyl-$C_{1-10}$ alkyl;
 (8) aryl,
 (9) heteroaryl,
 (10) aryl-$C_{1-10}$alkyl, and
 (11) heteroaryl-$C_{1-10}$alkyl, or
 $R^a$ and $R^b$ together with the nitrogen atom to which they are attached form a bridged or unbridged heterocyclic ring of 4 to 7 members containing 0-2 additional heteroatoms independently selected from oxygen, sulfur and N—$R^d$,
 each $R^a$ and $R^b$ may be unsubstituted or substituted with one to three substituents selected from $R^c$;
 each $R^c$ is independently selected from:
 (1) $C_{1-10}$alkyl,
 (2) —$OR^d$,
 (3) —$NR^eS(O)_mR^d$,
 (4) halogen,
 (5) —$SR^d$,
 (6) —$S(O)_mNR^dR^e$,
 (7) —$NR^dR^e$,
 (8) —$C(O)R^d$,
 (9) —CN,
 (10) —$C(O)NR^dR^e$,
 (11) —$NR^eC(O)R^d$,
 (12) —$NR^eC(O)ORd^e$,
 (13) —$NR^eC(O)NR^dR^e$,
 (14) —$CF_3$,
 (15) —$OCF_3$,
 (16) cycloheteroalkyl,
 (17) aryl,
 (18) aryl$C_{1-4}$alkyl,
 (19) heteroaryl, and
 (20) heteroaryl$C_{1-4}$alkyl;
 $R^d$ and $R^e$ are independently selected from:
 (1) hydrogen,
 (2) $C_{1-10}$alkyl,
 (3) $C_{2-10}$ alkenyl,
 (4) cycloalkyl,
 (5) cycloalkyl-$C_{1-10}$alkyl;
 (6) cycloheteroalkyl,
 (7) cycloheteroalkyl-$C_{1-10}$ alkyl;
 (8) aryl,
 (9) heteroaryl,
 (10) aryl-$C_{1-10}$alkyl, and
 (11) heteroaryl-$C_{1-10}$alkyl, or
 $R^d$ and $R^e$ together with the nitrogen atom to which they are attached form a bridged or unbridged heterocyclic ring of 4 to 7 members containing 0-2 additional heteroatoms independently selected from oxygen, sulfur and N—$R^f$,
 each $R^d$ and $R^e$ may be unsubstituted or substituted with one to three substituents selected from $R^f$;
 $R^f$ is independently selected from:
 (1) halogen,
 (2) $C_{1-10}$alkyl,
 (3) —O—$C_{1-4}$alkyl,
 (4) —S—$C_{1-4}$alkyl,
 (5) —CN,
 (6) —$CF_3$, and
 (7) —$OCF_3$;
 each $R^g$ is independently selected from:
 (1) halogen,
 (2) $C_{1-10}$alkyl,
 (3) —O—$C_{1-4}$alkyl,
 (4) —S—$C_{1-4}$alkyl,
 (5) —CN,
 (6) —$CF_3$, and
 (7) —$OCF_3$; and
 m is selected from 1 and 2.

2. The compound according to claim 1, wherein:
 $R^a$ and $R^b$ are each selected from:
 (1) hydrogen,
 (2) $C_{1-6}$alkyl, unsubstituted or substituted with one to three $R^c$ substituents,
 (3) cycloalkyl, unsubstituted or substituted with one to three $R^c$ substituents,
 (4) cycloalkyl-$C_{1-4}$alkyl, unsubstituted or substituted with one to three $R^c$ substituents, (5) phenyl, unsubstituted or substituted with one to three $R^c$ substituents,
(6) heteroaryl, unsubstituted or substituted with one to three $R^c$ substituents,
(7) phenyl-$C_{1-4}$alkyl, unsubstituted or substituted with one to three $R^c$ substituents, or
(8) heteroaryl-$C_{1-4}$alkyl, unsubstituted or substituted with one to three $R^c$ substituents, or when bonded to nitrogen, $R^a$ and $R^b$ together with the nitrogen atom to which they are attached form a bridged or unbridged heterocyclic ring of 4 to 7 members containing 0-2 additional heteroatoms independently selected from oxygen, sulfur and N—$R^d$, unsubstituted or substituted on carbon with one to three $R^c$ substituents;

or a pharmaceutically acceptable salt thereof.

3. The compound according to claim 2, wherein $R^1$ is selected from:
(1) —$OC_{1-6}$alkyl, unsubstituted or substituted with one to three $R^c$ substituents,
(2) $C_{4-7}$cycloalkyloxy-, unsubstituted or substituted with one to two $R^c$ substituents,
(3) cycloalkyl-$C_{1-3}$alkyloxy-, unsubstituted or substituted with one to two $R^c$ substituents,
(4) phenyloxy, unsubstituted or substituted with one to two $R^c$ substituents,
(5) pyridyloxy, unsubstituted or substituted with one to two $R^c$ substituents,
(6) phenyl-$C_{1-3}$alkyloxy, unsubstituted or substituted with one to two $R^c$ substituents,
(7) pyridyl-$C_{1-3}$alkyloxy, unsubstituted or substituted with one to two $R^c$ substituents,
(8) —$NR^aR^b$, wherein:
  $R^a$ is selected from:
  (a) $C_{1-6}$alkyl, unsubstituted or substituted with one to three $R^c$ substituents,
  (b) cycloalkyl, unsubstituted or substituted with one to two $R^c$ substituents,
  (c) cycloalkyl-$C_{1-4}$alkyl, unsubstituted or substituted with one to two $R^c$ substituents,
  (d) phenyl, unsubstituted or substituted with one to two $R^c$ substituents,
  (e) heteroaryl, unsubstituted or substituted with one to two $R^c$ substituents,
  (f) benzyl, unsubstituted or substituted with one to two $R^c$ substituents,
  $R^b$ is selected from:
  (a) hydrogen,
  (b) $C_{1-6}$alkyl, unsubstituted or substituted with one to three $R^c$ substituents, or
  $R^a$ and $R^b$ together with the nitrogen atom to which they are attached form a bridged or unbridged heterocyclic ring of 4 to 7 members containing 0-2 additional heteroatoms independently selected from oxygen, sulfur and N—$R^d$, unsubstituted or substituted on carbon with one to two $R^c$ substituents,
(9) —$NR^bC(O)R^a$, wherein:
$R^a$ is selected from:
  (a) hydrogen,
  (b) $C_{1-6}$alkyl, unsubstituted or substituted with one to three $R^c$ substituents,
  (c) cycloalkyl, unsubstituted or substituted with one to two $R^c$ substituents,
  (d) cycloalkyl-$C_{1-4}$alkyl, unsubstituted or substituted with one to two $R^c$ substituents,
  (e) phenyl, unsubstituted or substituted with one to two $R^c$ substituents,
  (f) pyridyl, unsubstituted or substituted with one to three $R^c$ substituents,
  (g) benzyl, unsubstituted or substituted with one to two $R^c$ substituents,
  (h) pyridylmethyl-, unsubstituted or substituted with one to three $R^c$ substituents,
  $R^b$ is selected from:
  (a) hydrogen,
  (b) $C_{1-6}$alkyl, unsubstituted or substituted with one to three $R^c$ substituents,
(11) —$CO_2H$,
(12) $C_{1-6}$alkyloxycarbonyl-, unsubstituted or substituted with one to three $R^c$ substituents,
(13) —$C(O)NR^aR^b$, wherein:
  $R^a$ is selected from:
  (a) hydrogen,
  (b) $C_{1-6}$alkyl, unsubstituted or substituted with one to three $R^c$ substituents,
  $R^b$ is selected from:
  (a) hydrogen, and
  (b) $C_{1-6}$alkyl, unsubstituted or substituted with one to three $R^c$ substituents,
(14) cyano
(15) —$SC_{1-6}$alkyl, unsubstituted or substituted with one to three $R^c$ substituents, and
(16) —$SO_2C_{1-6}$alkyl, unsubstituted or substituted with one to three $R^c$ substituents;

each $R^c$ is independently selected from:
(1) $C_{1-3}$alkyl,
(2) hydroxy,
(3) —$OC_{1-3}$alkyl,
(4) halogen,
(5) —$SCH_3$,
(6) —$SH$,
(7) —$NR^dR^e$,
(8) —$C(O)C_{1-3}$alkyl,
(9) —$CN$,
(10) —$CF_3$,
(11) —$OCF_3$,
(12) cycloheteroalkyl,
(13) phenyl,
(14) benzyl, and
(15) pyridyl;

or a pharmaceutically acceptable salt thereof.

4. The compound according to claim 2, wherein $R^2$ is selected from:
(1) hydrogen,
(2) $C_{1-6}$alkyl,
(3) —OH,
(4) —$OC_{1-6}$alkyl, unsubstituted or substituted with one to three $R^c$ substituents,
(5) cycloalkyloxy-, unsubstituted or substituted with one to three $R^c$ substituents,
(6) cycloalkyl-$C_{1-4}$alkyloxy-, unsubstituted or substituted with one to three $R^c$ substituents,
(7) cycloheteroalkyloxy-, unsubstituted or substituted with one to three $R^c$ substituents,
(8) cycloheteroalkyl-$C_{1-4}$alkyloxy, unsubstituted or substituted with one to three $R^c$ substituents,
(9) phenyloxy, unsubstituted or substituted with one to three $R^c$ substituents,
(10) heteroaryloxy, unsubstituted or substituted with one to three $R^c$ substituents,
(11) phenyl-$C_{1-4}$alkyloxy, unsubstituted or substituted with one to three $R^c$ substituents,
(12) heteroaryl-$C_{1-4}$alkyloxy, unsubstituted or substituted with one to three $R^c$ substituents,

(13) —NR$^a$R$^b$,
(14) —NR$^b$C(O)R$^a$,
(15) —CO$_2$H,
(16) C$_{1-6}$alkyloxycarbonyl-, unsubstituted or substituted with one to three R$^c$ substituents,
(17) cycloalkyloxycarbonyl-, unsubstituted or substituted with one to three R$^c$ substituents,
(18) cycloalkyl-C$_{1-4}$alkyloxycarbonyl-, unsubstituted or substituted with one to three R$^c$ substituents,
(19) phenyloxycarbonyl, unsubstituted or substituted with one to three R$^c$ substituents,
(20) heteroaryloxycarbonyl, unsubstituted or substituted with one to three R$^c$ substituents,
(21) phenyl-C$_{1-4}$alkyloxycarbonyl, unsubstituted or substituted with one to three R$^c$ substituents,
(22) heteroaryl-C$_{1-4}$alkyloxycarbonyl, unsubstituted or substituted with one to three R$^c$ substituents,
(23) —C(O)NR$^a$R$^b$,
(24) cyano,
(25) —SC$_{1-6}$alkyl, unsubstituted or substituted with one to three R$^c$ substituents, and
(26) —SO$_2$C$_{1-6}$alkyl, unsubstituted or substituted with one to three R$^c$ substituents,
or a pharmaceutically acceptable salt thereof.

5. The compound according to claim 1, wherein:
R$^2$ is selected from:
(1) hydrogen,
(2) C$_{1-6}$alkyl,
(3) —OH,
(4) —OC$_{1-6}$alkyl, unsubstituted or substituted with one to three R$^c$ substituents,
(5) C$_{4-7}$cycloalkyloxy-, unsubstituted or substituted with one to two R$^c$ substituents,
(6) C$_{4-7}$cycloalkyl-C$_{1-3}$alkyloxy-, unsubstituted or substituted with one to two R$^c$ substituents,
(7) phenyloxy, unsubstituted or substituted with one to two R$^c$ substituents,
(8) pyridyloxy, unsubstituted or substituted with one to two R$^c$ substituents,
(9) phenyl-C$_{1-3}$alkyloxy, unsubstituted or substituted with one to two R$^c$ substituents,
(10) pyridyl-C$_{1-3}$alkyloxy, unsubstituted or substituted with one to two R$^c$ substituents,
(11) —NR$^a$R$^b$, wherein:
R$^a$ is selected from:
(a) hydrogen,
(b) C$_{1-6}$alkyl, unsubstituted or substituted with one to three R$^c$ substituents,
(c) cycloalkyl, unsubstituted or substituted with one to two R$^c$ substituents,
(d) cycloalkyl-C$_{1-4}$alkyl, unsubstituted or substituted with one to two R$^c$ substituents,
(e) phenyl, unsubstituted or substituted with one to two R$^c$ substituents,
(f) heteroaryl, unsubstituted or substituted with one to two R$^c$ substituents,
(g) benzyl, unsubstituted or substituted with one to two R$^c$ substituents,
R$^b$ is selected from:
(a) hydrogen,
(b) C$_{1-6}$alkyl, unsubstituted or substituted with one to three R$^c$ substituents, or
R$^a$ and R$^b$ together with the nitrogen atom to which they are attached form a bridged or unbridged heterocyclic ring of 4 to 7 members, unsubstituted or substituted on carbon with one to two R$^c$ substitutents,
(12) —NHC(O)R$^a$, wherein:
R$^a$ is selected from:
(a) hydrogen,
(b) C$_{1-6}$alkyl, unsubstituted or substituted with one to three R$^c$ substituents,
(c) cycloalkyl, unsubstituted or substituted with one to two R$^c$ substituents,
(d) cycloalkyl-C$_{1-4}$alkyl, unsubstituted or substituted with one to two R$^c$ substituents,
(e) phenyl, unsubstituted or substituted with one to two R$^c$ substituents,
(f) pyridyl, unsubstituted or substituted with one to three R$^c$ substituents,
(g) benzyl, unsubstituted or substituted with one to two R$^c$ substituents,
(h) pyridylmethyl-, unsubstituted or substituted with one to three R$^c$ substituents,
(13) cyano, and
(14) —SO$_2$C$_{1-6}$alkyl, unsubstituted or substituted with one to three R$^c$ substituents;
or a pharmaceutically acceptable salt thereof.

6. The compound according to claim 1, wherein:
R$^1$ is selected from:
(1) methoxy, ethyloxy, isopropyloxy, n-butyloxy, sec-butyloxy, isobutyloxy, tert.-butyloxy, n-pentyloxy, or 2,2-dimethylpropyloxy, unsubstituted or substituted with one to three halo, hydroxy, or methoxy substituents,
(2) cyclopropyloxy, cyclobutyloxy, cyclopentyloxy, cyclohexyloxy, or cycloheptyloxy,
(3) cyclopropylmethoxy, cyclobutylmethoxy, cyclopentylmethoxy, cyclohexylmethoxy, or cycloheptylmethoxy,
(4) 4-fluorophenyloxy, 4-chlorophenyloxy, 4-methoxyphenyloxy, 3-fluorophenyloxy, 3-chlorophenyloxy, 3,4-difluorophenyloxy, 3,4-dichlorophenyloxy, 3,5-difluorophenyloxy, 3,5-dichlorophenyloxy or phenyloxy,
(5) 4-pyridyloxy, 3-pyridyloxy, 2-pyridyloxy, 6-chloro-3-pyridyloxy, or 5-chloro-3-pyridyloxy,
(6) benzyloxy, 3-fluorobenzyloxy, 3-chlorobenzyloxy, 4-fluorobenzyloxy, 4-chlorobenzyloxy, 3,4-difluorobenzyloxy, 3,4-dichlorobenzyloxy, 3,5-difluorobenzyloxy, 3,5-dichlorobenzyloxy, 2,4-fluorobenzyloxy, 2,4-dichlorobenzyloxy, alpha-methyl-4-fluorobenzyloxy, alpha-methyl-4-chlorobenzyloxy, alpha,alpha-dimethyl-4-fluorobenzyloxy, or alpha,alpha-dimethyl-4-chlorobenzyloxy,
(7) 2-pyridylmethyloxy 3,-pyridylmethyloxy, or 4-pyridylmethyloxy,
(8) N-methylamino, N,N-dimethyamino, N,N-diisopropylamino, or —N(CH$_3$)CH$_2$CH$_2$N(CH$_3$)$_2$, or N-containing heterocycloalkyl bonded via nitrogen selected from: morpholinyl, thiomorpholinyl, pyrrolidnyl, piperidinyl, and [2.2.1]azabicycloheptyl,
(9) —NHCOR$^a$ wherein R$^a$ is selected from:
(a) hydrogen,
(b) C$_{1-4}$alkyl,
(c) C$_{4-6}$cycloalkyl, and
(d) phenyl, 4-fluorophenyl, 4-chlorophenyl, 3,4-difluorophenyl, or 3,4-dichlorophenyl,
(10) —CO$_2$H,
(11) —C(O)NH$_2$,
(12) —CN, and
(13) —SO$_2$CH$_3$;

147

R² is selected from:
(1) hydrogen,
(2) methyl, ethyl, propyl, isopropyl, n-butyl, sec-butyl, isobutyl, tert.-butyl, n-pentyl, or 2,2-dimethylpropyloxy,
(3) —OH,
(4) methoxy, ethyloxy, isopropyloxy, n-butyloxy, sec-butyloxy, isobutyloxy, tert.-butyloxy, n-pentyloxy, or 2,2-dimethylpropyloxy, unsubstituted or substituted with one to three halo, hydroxy, or methoxy substituents,
(5) cyclopropyloxy, cyclobutyloxy, cyclopentyloxy, cyclohexyloxy, or cycloheptyloxy,
(6) cyclopropylmethoxy, cyclobutylmethoxy, cyclopentylmethoxy, cyclohexylmethoxy, or cycloheptylmethoxy,
(7) 4-fluorophenyloxy, 4-chlorophenyloxy, 3-fluorophenyloxy, 3-chlorophenyloxy, 3-cyanophenyloxy, 3,4-difluorophenyloxy, 3,4-dichlorophenyloxy, 3,5-difluorophenyloxy, 3,5-dichlorophenyloxy, or phenyloxy,
(8) benzyloxy, 3-fluorobenzyloxy, 3-chlorobenzyloxy, 4-fluorobenzyloxy, 4-chlorobenzyloxy, 3,4-difluorobenzyloxy, 3,4-dichlorobenzyloxy, 3,5-difluorobenzyloxy, 3,5-dichlorobenzyloxy, 2,4-fluorobenzyloxy, or 2,4-dichlorobenzyloxy,
(9) 4-pyridyloxy, 3-pyridyloxy, 2-pyridyloxy, 6-chloro-3-pyridyloxy, or 5-chloro-3-pyridyloxy,
(10) amino, N-methylamino, N-ethylamino, N,N-dimethyamino, N,N-diethylamino, N,N-diisopropylamino, or N-containing heterocycloalkyl bonded via nitrogen selected from: pyrrolidinyl, and piperidinyl,
(11) —NHCOR$^a$ wherein R$^a$ is selected from:
(a) hydrogen, and
(b) C$_{1-4}$alkyl,
(12) —CN, and
(14) —SO$_2$CH$_3$;
R³ and R⁴ are each independently selected from:
(1) 4-chlorophenyl,
(2) 4-methoxyphenyl,
(3) 4-fluorophenyl,
(4) 4-trifluoromethylphenyl,
(5) 3-chlorophenyl,
(6) 3-methoxyphenyl,
(7) 2,4-dichlorophenyl, and
(8) 2-chloro-4-methylthiophenyl;
or a pharmaceutically acceptable salt thereof.

7. The compound according to claim 6, wherein:
R³ is 4-chlorophenyl and R⁴ is 2,4-dichlorophenyl, or a pharmaceutically acceptable salt thereof.

8. A method of treating a disease mediated by the Cannabinoid-1 receptor selected from: substance abuse disorders and eating disorders associated with excessive food intake, comprising administration to a patient in need of such treatment of a therapeutically effective amount of a compound of structural formula I:

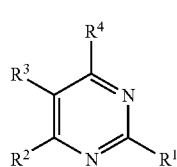

(I)

or a pharmaceutically acceptable salt thereof, wherein:

148

R¹ is selected from:
(1) C$_{1-10}$alkyl,
(2) —OR$^a$,
(3) —NR$^a$R$^b$,
(4) —NR$^b$C(O)R$^a$,
(5) —CO$_2$R$^a$,
(6) —C(O)NR$^a$R$^b$,
(7) cyano, and
(8) —SO$_2$R$^b$,
provided that R¹ is not —NH$_2$;
R² is selected from:
(1) hydrogen,
(2) C$_{1-10}$alkyl,
(3) —OR$^a$,
(4) —NR$^a$R$^b$,
(5) —NR$^a$C(O)R$^b$,
(6) —CO$_2$R$^a$,
(7) —C(O)NR$^a$R$^b$,
(8) cyano,
(9) —SR$^a$, and
(10) —SO$_2$R$^a$;
wherein R³ and R⁴ are each independently selected from:

(1) 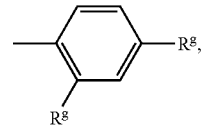

(2) 

(3) 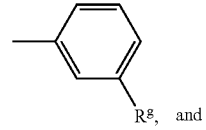

(4) 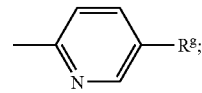

each R$^a$ is independently selected from:
(1) hydrogen,
(2) C$_{1-10}$alkyl,
(3) C$_{2-10}$ alkenyl,
(4) cycloalkyl,
(5) cycloalkyl-C$_{1-10}$alkyl;
(6) cycloheteroalkyl,
(7) cycloheteroalkyl-C$_{1-10}$ alkyl;
(8) aryl,
(9) heteroaryl,
(10) aryl-C$_{1-10}$alkyl, and
(11) heteroaryl-C$_{1-10}$alkyl; and
each R$^b$ is independently selected from:
(1) hydrogen,
(2) C$_{1-10}$alkyl,
(3) C$_{2-10}$alkenyl,
(4) cycloalkyl,
(5) cycloalkyl-C$_{1-10}$alkyl;
(6) cycloheteroalkyl, (7) cycloheteroalkyl-$C_{1-10}$ alkyl;
(8) aryl,
(9) heteroaryl,
(10) aryl-$C_{1-10}$alkyl, and
(11) heteroaryl-$C_{1-10}$alkyl, or $R^a$ and $R^b$ together with the nitrogen atom to which they are attached form a bridged or unbridged heterocyclic ring of 4 to 7 members containing 0-2 additional heteroatoms independently selected from oxygen, sulfur and N—$R^d$, each $R^a$ and $R^b$ may be unsubstituted or substituted with one to three substituents selected from $R^c$;

each $R^c$ is independently selected from:
(1) $C_{1-10}$alkyl,
(2) —$OR^d$,
(3) —$NR^eS(O)_mR^d$,
(4) halogen,
(5) —$SR^d$,
(6) —$S(O)_mNR^dR^e$,
(7) —$NR^dR^e$,
(8) —$C(O)R^d$,
(9) —$CO_2R^d$,
(10) —CN,
(11) —$C(O)NR^dR^e$,
(12) —$NR^eC(O)R^d$,
(13) —$NR^eC(O)ORd^e$,
(14) —$NR^eC(O)NR^dR^e$,
(15) —$CF_3$,
(16) —$OCF_3$,
(17) cycloheteroalkyl,
(18) aryl,
(19) aryl$C_{1-4}$alkyl,
(20) heteroaryl, and
(21) heteroaryl$C_{1-4}$alkyl;

$R^d$ and $R^e$ are independently selected from:
(1) hydrogen,
(2) $C_{1-10}$alkyl,
(3) $C_{2-10}$ alkenyl,
(4) cycloalkyl,
(5) cycloalkyl-$C_{1-10}$alkyl;
(6) cycloheteroalkyl,
(7) cycloheteroalkyl-$C_{1-10}$ alkyl;
(8) aryl,
(9) heteroaryl,
(10) aryl-$C_{1-10}$alkyl, and
(11) heteroaryl-$C_{1-10}$alkyl, or $R^d$ and $R^e$ together with the nitrogen atom to which they are attached form a bridged or unbridged heterocyclic ring of 4 to 7 members containing 0-2 additional heteroatoms independently selected from oxygen, sulfur and N—$R^f$, each $R^d$ and $R^e$ may be unsubstituted or substituted with one to three substituents selected from $R^f$;

$R^f$ is independently selected from:
(1) halogen,
(2) $C_{1-10}$alkyl,
(3) —O—$C_{1-4}$alkyl,
(4) —S—$C_{1-4}$alkyl,
(5) —CN,
(6) —$CF_3$, and
(7) —$OCF_3$;

each $R^g$ is independently selected from:
(1) halogen,
(2) $C_{1-10}$alkyl,
(3) —O—$C_{1-4}$alkyl,
(4) —S—$C_{1-4}$alkyl,
(5) —CN,
(6) —$CF_3$, and
(7) —$OCF_3$; and m is selected from 1 and 2.

9. The method according to claim 8 wherein the disease mediated by the Cannabinoid-1 receptor is an eating disorder associated with excessive food intake.

10. The method according to claim 9 wherein the eating disorder associated with excessive food intake is selected from obesity, bulimia nervosa, and compulsive eating disorders.

11. The method according to claim 10 wherein the eating disorder associated with excessive food intake is obesity.

12. A composition comprising a compound according to claim 1 and a pharmaceutically acceptable carrier.

13. The method according to claim 8 for treating substance abuse disorders, wherein the abused substance is nicotine in a person dependent on nicotine.

14. The compound according to claim 1, selected from:
(1) 2-(4-fluorobenzyloxy)-4-(2,4-dichlorophenyl)-5-(4-chlorophenyl)pyrimidine;
(2) 2-(4-fluorobenzyloxy)-4-(2-chloro-4-methylthiophenyl)-5-(4-chlorophenyl)-pyrimidine;
(3) 2-(3,4-difluorobenzyloxy)-4-(2,4-dichlorophenyl)-5-(4-chlorophenyl)pyrimidine;
(4) 2-(3,4-difluorobenzyloxy)-4-(2-chloro-4-methylthiophenyl)-5-(4-chlorophenyl)-pyrimidine;
(5) 2-(4-chlorobenzyloxy)-4-(2,4-dichlorophenyl)-5-(4-chlorophenyl)pyrimidine;
(6) 2-(4-chlorobenzyloxy)-4-(2-chloro-4-methylthio-phenyl)-5-(4-chlorophenyl)-pyrimidine;
(7) 2-(3,4-dichlorobenzyloxy)-4-(2,4-dichlorophenyl)-5-(4-chlorophenyl)pyrimidine;
(8) 2-(3,4-dichlorobenzyloxy)-4-(2-chloro-4-methylthiophenyl)-5-(4-chlorophenyl)-pyrimidine;
(9) 2-(3-fluorobenzyloxy)-4-(2,4-dichlorophenyl)-5-(4-chlorophenyl)pyrimidine;
(10) 2-(3-fluorobenzyloxy)-4-(2-chloro-4-methylthiophenyl)-5-(4-chlorophenyl)-pyrimidine;
(11) 2-(3-chlorobenzylamino)-4-(2,4-dichlorophenyl)-5-(4-chlorophenyl)-pyrimidine;
(12) 2-(N,N-dimethylamino)-4-(2,4-dichlorophenyl)-5-(4-chlorophenyl)pyrimidine;
(13) 2-carboxy-4-(2,4-dichlorophenyl)-5-(4-chlorophenyl)pyrimidine;
(14) 2-methoxy-4-hydroxy-5-(4-chlorophenyl)-6-(2,4-dichlorophenyl)pyrimidine;
(15) 2-(3,4-difluorobenzyloxy)-4-hydroxy-5-(4-chlorophenyl)-6-(2,4-dichlorophenyl)pyrimidine;
(16) 2-(3,4-difluorobenzyloxy)-4-hydroxy-5-(4-chlorophenyl)-6-(2,4-dichlorophenyl)pyrimidine;
(17) 2,4-bis-(3,4-difluorobenyloxy)-5-(4-chlorophenyl)-6-(2,4-dichlorophenyl)pyrimidine;
(18) 2,4-dimethoxy-5-(4-chlorophenyl)-6-(2,4-dichlorophenyl)pyrimidine;
(19) 2,4-diethoxy-5-(4-chlorophenyl)-6-(2,4-dichlorophenyl)pyrimidine;
(20) 2,4-diisopropoxy-5-(4-chlorophenyl)-6-(2,4-dichlorophenyl)pyrimidine;
(21) 2-methylsulfonyl-4-(3,4-difluorophenoxy)-5-(4-chlorophenyl)-6-(2,4-dichlorophenyl)pyrimidine;
(22) 2,4-bis(3,4-difluorophenoxy)-5-(4-chlorophenyl)-6-(2,4-dichlorophenyl)pyrimidine;
(23) 2-cyano-4-(3,4-difluorophenoxy)-5-(4-chlorophenyl)-6-(2,4-dichlorophenyl)pyrimidine;
(24) 2-(3,4-difluorobenzyloxy)-4-cyano-5-(4-chlorophenyl)-6-(2,4-dichlorophenyl)pyrimidine;

(25) 2-cyano-4-(3,4-difluorobenzyloxy)-5-(4-chlorophenyl)-6-(2,4-dichlorophenyl)pyrimidine;
(26) 2,4-bis(cyano)-5-(4-chlorophenyl)-6-(2,4-dichlorophenyl)pyrimidine;
(27) 2-(3,4-difluorophenoxy)-4-methyl-5-(4-chlorophenyl)-6-(2,4-dichlorophenyl)pyrimidine;
(28) 2-ethyl-4-(3,4-difluorophenoxy)-5-(4-chlorophenyl)-6-(2,4-dichlorophenyl)pyrimidine;
(29) 2-isopropy-4-(3,4-difluorophenoxy)-5-(4-chlorophenyl)-6-(2,4-dichlorophenyl)pyrimidine;
(30) 2-(3,4-difluorobenzyloxy)-4-methyl-5-(4-chlorophenyl)-6-(2,4-dichlorophenyl)pyrimidine;
(31) 2-(3,4-difluorobenzyloxy)-4-ethyl-5-(4-chlorophenyl)-6-(2,4-dichlorophenyl)pyrimidine;
(32) 2-(3,4-difluorobenzyloxy)-4-(N-methylamino)-5-(4-chlorophenyl)-6-(2,4-dichlorophenyl)pyrimidine;
(33) 2-(3,4-difluorophenoxy)-4-amino-5-(4-chlorophenyl)-6-(2,4-dichlorophenyl)pyrimidine;
(34) 2-(3,4-difluorobenzyloxy)-4-(amino)-5-(4-chlorophenyl)-6-(2,4-dichlorophenyl)pyrimidine;
(35) 2-(3,4-difluorophenoxy)-4-(acetylamino)-5-(4-chlorophenyl)-6-(2,4-dichlorophenyl)pyrimidine;
(36) 2-(3,4-difluorobenzyloxy)-4-(acetylamino)-5-(4-chlorophenyl)-6-(2,4-dichlorophenyl)pyrimidine;
(37) 2-(3,4-difluorophenoxy)-4-(N-pyrrolidinyl)-5-[4-chlorophenyl]-6-[2,4-dichlorophenyl]pyrimidine;
(38) 2-(cyclopropylmethoxy)-4-(N-pyrrolidinyl)-5-[4-chlorophenyl]-6-[2,4-dichlorophenyl]pyrimidine;
(39) 2-(N,N-diethylamino)-4-(3,4-difluorobenzyloxy)-5-(4-chlorophenyl)-6-(2,4-dichlorophenyl)pyrimidine;
(40) 2-(N,N-diisopropylamino)-4-(3,4-difluorobenzyloxy)-5-(4-chlorophenyl)-6-(2,4-dichlorophenyl)pyrimidine;
(41) 2-(N-pyrrolidinyl)-4-(3,4-difluorobenzyloxy)-5-(4-chlorophenyl)-6-(2,4-dichlorophenyl)pyrimidine;
(42) 2-(N-piperidyl)-4-(3,4-difluorobenzyloxy)-5-(4-chlorophenyl)-6-(2,4-dichlorophenyl)pyrimidine;
(43) 2-(N-morpholinyl)-4-(3,4-difluorobenzyloxy)-5-(4-chlorophenyl)-6-(2,4-dichlorophenyl)pyrimidine;
(44) 2-(7-N-[2.2.1]-azabicycloheptyl)-4-(3,4-difluorophenoxy)-5-(4-chlorophenyl)-6-(2,4-dichlorophenyl)pyrimidine;
(45) 2-(n-propionyl)-4-(3,4-difluorophenoxy)-5-(4-chlorophenyl)-6-(2,4-dichlorophenyl)pyrimidine;
(46) 2-(N-(2-methyl)propionyl)-4-(3,4-difluorophenoxy)-5-(4-chlorophenyl)-6-(2,4-dichlorophenyl)pyrimidine;
(47) 2-(N-(3-methyl)butyryl)-4-(3,4-difluorophenoxy)-5-(4-chlorophenyl)-6-(2,4-dichlorophenyl)pyrimidine;
(48) 2-(aminocarbonyl)-4-(3,4-difluorophenoxy)-5-(4-chlorophenyl)-6-(2,4-dichlorophenyl)pyrimidine;
(49) 2-(carboxy)-4-(3,4-difluorophenoxy)-5-(4-chlorophenyl)-6-(2,4-dichlorophenyl)pyrimidine;
(50) 2-(2-hydroxyethyleneoxy)-4-(3,4-difluorophenoxy)-5-(4-chlorophenyl)-6-(2,4-dichlorophenyl)pyrimidine;
(51) 2-(2-methoxyethyleneoxy)-4-(3,4-difluorophenoxy)-5-(4-chlorophenyl)-6-(2,4-dichlorophenyl)pyrimidine;
(52) 2-(cyclohexylmethyloxy)-4-isopropoxy-5-(4-chlorophenyl)-6-(2,4-dichlorophenyl)pyrimidine;
(53) 2-cyclohexyloxy-4-isopropoxy-5-(4-chlorophenyl)-6-(2,4-dichlorophenyl)pyrimidine;
(54) 2-(3,4-difluorophenoxy)-4-cyclohexyloxy-5-(4-chlorophenyl)-6-(2,4-dichlorophenyl)pyrimidine;
(55) 2-(3,4-difluorobenzyloxy)-4-cyclohexyloxy-5-(4-chlorophenyl)-6-(2,4-dichlorophenyl)pyrimidine;
(56) 2,4-bis(cyclopropylmethyloxy)-5-(4-chlorophenyl)-6-(2,4-dichlorophenyl)pyrimidine;
(57) 2-cyclopropyloxy-4-(3-pyridyloxy)-5-(4-chlorophenyl)-6-(2,4-dichlorophenyl)pyrimidine;
(58) 2-(N-pyrrolidinyl)-4-cyclopropyloxy-5-(4-chlorophenyl)-6-(2,4-dichlorophenyl)pyrimidine;
(59) 2,4-bis(isopropyloxy)-5-(4-chlorophenyl)-6-(2,4-dichlorophenyl)pyrimidine;
(60) 2-(3,4-difluorobenzyloxy)-4-(4-chlorophenyl)-5-(2,4-dichlorophenyl)pyrimidine;
(61) 2-(4-chlorobenzyloxy)-4-(4-chlorophenyl)-5-(2,4-dichlorophenyl)pyrimidine;
(62) 2-(3-fluorobenzyloxy)-4-(4-chlorophenyl)-5-(2,4-dichlorophenyl)pyrimidine;
(63) 2-(3-chlorobenzyloxy)-4-(4-chlorophenyl)-5-(2,4-dichlorophenyl)pyrimidine;
(64) 2-(4-fluorobenzyloxy)-4-(4-chlorophenyl)-5-(2,4-dichlorophenyl)pyrimidine;
(65) 2-(α-methyl-4-fluorobenzyloxy-)-4-(4-chlorophenyl)-5-(2,4-dichlorophenyl)pyrimidine;
(66) 2-(α-methyl-4-fluorobenzyloxy)-4-(2,4-dichlorophenyl)-5-(4-chlorophenyl)pyrimidine;
(67) 2-(3-pyridylmethoxy)-4-(2,4-dichlorophenyl)-5-(4-chlorophenyl)pyrimidine;
(68) 2-(n-butyloxy)-4-(2,4-dichlorophenyl)-5-(4-chlorophenyl)pyrimidine;
(69) 2-(2,4-dichlorobenzyloxy)-4-(2,4-dichlorophenyl)-5-(4-chlorophenyl)pyrimidine;
(70) 2-(cyclohexylmethoxy)-4-(2,4-dichlorophenyl)-5-(4-chlorophenyl)pyrimidine;
(71) 2-(3,5-dichlorobenzyloxy)-4-(2,4-dichlorophenyl)-5-(4-chlorophenyl)pyrimidine;
(72) 2-(6-chloro-3-pyridylmethoxy)-4-(2,4-dichlorophenyl)-5-(4-chlorophenyl)pyrimidine;
(73) 2-(α,α-dimethyl-4-fluorobenzyloxy)-4-(2,4-dichlorophenyl)-5-(4-chlorophenyl)pyrimidine;
(74) 2-(4-fluorophenyloxy)-4-(2,4-dichlorophenyl)-5-(4-chlorophenyl)pyrimidine;
(75) 2-(3-fluorophenyloxy)-4-(2,4-dichlorophenyl)-5-(4-chlorophenyl)pyrimidine;
(76) 2-(3,4-difluorophenyloxy)-4-(2,4-dichlorophenyl)-5-(4-chlorophenyl)pyrimidine;
(77) 2-(3-chlorophenyloxy)-4-(2,4-dichlorophenyl)-5-(4-chlorophenyl)pyrimidine;
(78) 2-(4-methoxyphenyloxy)-4-(2,4-dichlorophenyl)-5-(4-chlorophenyl)pyrimidine;
(79) 2-(3-pyridyloxy)-4-(2,4-dichlorophenyl)-5-(4-chlorophenyl)pyrimidine;
(80) 2-(5-chloro-3-pyridyloxy)-4-(2,4-dichlorophenyl)-5-(4-chlorophenyl)pyrimidine;
(81) 2-(N-(4-fluorobenzamido))-4-(2,4-dichlorophenyl)-5-(4-chlorophenyl)pyrimidine;
(82) 2-(N-(cyclohexylcarboxamido))-4-(2,4-dichlorophenyl)-5-(4-chlorophenyl)pyrimidine;
(83) 2,4-bis(cyclobutylmethoxy)-5-(4-chlorophenyl)-6-(2,4-dichlorophenyl)pyrimidine;
(84) 2-cyclobutylmethoxy-4-(6-fluoro-3-pyridyloxy)-5-(4-chlorophenyl)-6-(2,4-dichlorophenyl)pyrimidine;
(85) 2-cyclobutylmethoxy-4-(5-chloro-3-pyridyloxy)-5-(4-chlorophenyl)-6-(2,4-dichlorophenyl)pyrimidine;
(86) 2-methylsulfonyl-4-(3-pyridyloxy)-5-(4-chlorophenyl)-6-(2,4-dichlorophenyl)pyrimidine;
(87) 2-cyclobutylmethoxy-4-(3-pyridyloxy)-5-(4-chlorophenyl)-6-(2,4-dichlorophenyl)pyrimidine;
(88) 2-(2,2-dimethylpropyloxy)-4-(3-pyridyloxy)-5-(4-chlorophenyl)-6-(2,4-dichlorophenyl)pyrimidine;
(89) 2-(2-t-butyloxy)-4-(3-pyridyloxy)-5-(4-chlorophenyl)-6-(2,4-dichlorophenyl)pyrimidine;

(90) 2-(2-cyclobutyloxy)-4-(3-pyridyloxy)-5-(4-chlorophenyl)-6-(2,4-dichlorophenyl)pyrimidine;

(91) 2-(n-propyloxy)-4-(3-pyridyloxy)-5-(4-chlorophenyl)-6-(2,4-dichlorophenyl)pyrimidine;

(92) 2-(n-butyloxy)-4-(3-pyridyloxy)-5-(4-chlorophenyl)-6-(2,4-dichlorophenyl)pyrimidine;

(93) 2-(sec-butyloxy)-4-(3-pyridyloxy)-5-(4-chlorophenyl)-6-(2,4-dichlorophenyl)pyrimidine;

(94) 2-(iso-butyloxy)-4-(3-pyridyloxy)-5-(4-chlorophenyl)-6-(2,4-dichlorophenyl)pyrimidine;

(95) 2-(isopropyloxy)-4-(3-pyridyloxy)-5-(4-chlorophenyl)-6-(2,4-dichlorophenyl)pyrimidine;

(96) 2-(n-pentyloxy)-4-(3-pyridyloxy)-5-(4-chlorophenyl)-6-(2,4-dichlorophenyl)pyrimidine;

(97) 2-cyclopropyloxy-4-(4-pyridyloxy)-5-(4-chlorophenyl)-6-(2,4-dichlorophenyl)pyrimidine;

(98) 2,4-bis-(4-pyridyloxy)-5-(4-chlorophenyl)-6-(2,4-dichlorophenyl)pyrimidine;

(99) 2-(isobutyloxy)-4-(3,4-difluorophenoxy)-5-(4-chlorophenyl)-6-(2,4-dichlorophenyl)pyrimidine;

(100) 2-(cyclopropylmethoxy)-4-(3,4-difluorophenoxy)-5-(4-chlorophenyl)-6-(2,4-dichlorophenyl)pyrimidine;

(101) 2-(isopropyloxy)-4-(3,4-difluorophenoxy)-5-(4-chlorophenyl)-6-(2,4-dichlorophenyl)pyrimidine;

(102) 2-ethoxy-4-(3,4-difluorophenoxy)-5-(4-chlorophenyl)-6-(2,4-dichlorophenyl)pyrimidine;

(103) 2-(N-pyrrolidinyl)-4-(3,4-difluorophenoxy)-5-(4-chlorophenyl)-6-(2,4-dichlorophenyl)pyrimidine;

(104) 2-(N,N',N'-trimethyl-ethylenediamino)-4-(3,4-difluorophenoxy)-5-(4-chlorophenyl)-6-(2,4-dichlorophenyl)pyrimidine;

(105) 2-(N-piperidinyl)-4-(3,4-difluorophenoxy)-5-(4-chlorophenyl)-6-(2,4-dichlorophenyl)pyrimidine;

(106) 2-(N-morpholinyl)-ethylenediamino-4-(3,4-difluorophenoxy)-5-(4-chlorophenyl)-6-(2,4-dichlorophenyl)pyrimidine;

(107) 2-dimethylamino-4-(3,4-difluorophenoxy)-5-(4-chlorophenyl)-6-(2,4-dichlorophenyl)pyrimidine;

(108) 2-(N-pyrrolidinyl)-4-(3-pyridyloxy)-5-(4-chlorophenyl)-6-(2,4-dichlorophenyl)pyrimidine;

(109) 2-methylsulfonyl-4-(2-pyridyloxy)-5-(4-chlorophenyl)-6-(2,4-dichlorophenyl)pyrimidine;

(110) 2-(2-isopropyloxy)-4-(2-pyridyloxy)-5-(4-chlorophenyl)-6-(2,4-dichlorophenyl)pyrimidine;

(111) 2-(2-N,N',N'-trimethyl-ethylenediamino)-4-(2-pyridyloxy)-5-(4-chlorophenyl)-6-(2,4-dichlorophenyl)pyrimidine;

(112) 2-(2-pyrrolindinyl)-4-(2-pyridyloxy)-5-(4-chlorophenyl)-6-(2,4-dichlorophenyl)pyrimidine;

(113) 2-(methylsulfonyl)-4-methoxy-5-(4-chlorophenyl)-6-(2,4-dichlorophenyl)pyrimidine;

(114) 2-methoxy-4-(methylsulfonyl)-5-(4-chlorophenyl)-6-(2,4-dichlorophenyl)pyrimidine;

(115) 2-(3,4-difluorophenyloxy)-4-methoxy-5-(4-chlorophenyl)-6-(2,4-dichlorophenyl)pyrimidine;

(116) 2-methoxy-4-(3,4-difluorophenyloxy)-5-(4-chlorophenyl)-6-(2,4-dichlorophenyl)pyrimidine;

(117) 2-(3-fluorophenyloxy)-4-methoxy-5-(4-chlorophenyl)-6-(2,4-dichlorophenyl)pyrimidine;

(118) 2-methoxy-4-(3-fluorophenyloxy)-5-(4-chlorophenyl)-6-(2,4-dichlorophenyl)pyrimidine;

(119) 2-methoxy-4-(2-pyridyloxy)-5-(4-chlorophenyl)-6-(2,4-dichlorophenyl)pyrimidine;

(120) 2-(2-pyridyloxy)-4-methoxy-5-(4-chlorophenyl)-6-(2,4-dichlorophenyl)pyrimidine;

(121) 2-(5-chloro-3-pyridyloxy)-4-methoxy-5-(4-chlorophenyl)-6-(2,4-dichlorophenyl)pyrimidine;

(122) 2-methoxy-4-(5-chloro-3-pyridyloxy)-5-(4-chlorophenyl)-6-(2,4-dichlorophenyl)pyrimidine;

(123) 2-(3-pyridyloxy)-4-methoxy-5-(4-chlorophenyl)-6-(2,4-dichlorophenyl)pyrimidine;

(124) 2-methoxy-4-(3-pyridyloxy)-5-(4-chlorophenyl)-6-(2,4-dichlorophenyl)pyrimidine;

(125) 2-methoxy-4-(4-fluorophenyloxy)-5-(4-chlorophenyl)-6-(2,4-dichlorophenyl)pyrimidine;

(126) 2-methoxy-4-(3,5-difluorophenyloxy)-5-(4-chlorophenyl)-6-(2,4-dichlorophenyl)pyrimidine;

(127) 2-methoxy-4-(3-cyanophenyloxy)-5-(4-chlorophenyl)-6-(2,4-dichlorophenyl)pyrimidine;

(128) 2-(3,4-difluorobenzyloxy)-4-methoxy-5-(4-chlorophenyl)-6-(2,4-dichlorophenyl)pyrimidine;

(129) 2-methoxy-4-(3,4-difluorobenzyloxy)-5-(4-chlorophenyl)-6-(2,4-dichlorophenyl)pyrimidine;

(130) 2-(methylsulfonyl)-4-ethoxy-5-(4-chlorophenyl)-6-(2,4-dichlorophenyl)pyrimidine;

(131) 2-ethoxy-4-(methylsulfonyl)-5-(4-chlorophenyl)-6-(2,4-dichlorophenyl)pyrimidine;

(132) 2-(3,4-difluorobenzyloxy)-4-ethoxy-5-(4-chlorophenyl)-6-(2,4-dichlorophenyl)pyrimidine;

(133) 2-ethoxy-4-(3,4-difluorophenyloxy)-5-(4-chlorophenyl)-6-(2,4-dichlorophenyl)pyrimidine;

(134) 2-(methylsulfonyl)-4-isopropyloxy-5-(4-chlorophenyl)-6-(2,4-dichlorophenyl)pyrimidine;

(135) 2-isopropyloxy-4-(methylsulfonyl)-5-(4-chlorophenyl)-6-(2,4-dichlorophenyl)pyrimidine;

(136) 2-(3,4-difluorobenzyloxy)-4-isopropyloxy-5-(4-chlorophenyl)-6-(2,4-dichlorophenyl)pyrimidine;

(137) 2-isopropyloxy-4-(3,4-difluorophenyloxy)-5-(4-chlorophenyl)-6-(2,4-dichlorophenyl)pyrimidine;

(138) 2-(3,4-difluorobenzyloxy)-4-pyrrolidinyl-5-(4-chlorophenyl)-6-(2,4-dichlorophenyl)pyrimidine;

(139) 2-(3,4-difluorobenzyloxy)-4-diethylamino-5-(4-chlorophenyl)-6-(2,4-dichlorophenyl)pyrimidine;

(140) 2-(3,4-difluorobenzyloxy)-4-dimethylamino-5-(4-chlorophenyl)-6-(2,4-dichlorophenyl)pyrimidine;

(141) 2-(3,4-difluorophenoxy)-4-methoxy-5-(4-fluorophenyl)-6-[2,4-dichlorophenyl]pyrimidine;

(142) 2-(3,4-difluorophenoxy)-4-methoxy-5-(4-methoxyphenyl)-6-[2,4-dichlorophenyl]pyrimidine;

(143) 2-(3,4-difluorophenoxy)-4-methoxy-5-(4-trifluoromethylphenyl)-6-[2,4-dichlorophenyl]pyrimidine;

(144) 2-(3,4-difluorophenoxy)-4-methoxy-5-(3-chlorophenyl)-6-[2,4-dichlorophenyl]pyrimidine; and (145) 2-(3,4-difluorophenoxy)-4-methoxy-5-(3-methoxyphenyl)-6-[2,4-dichlorophenyl]pyrimidine, or a pharmaceutically acceptable salt thereof.

* * * * *